US010647780B2

(12) United States Patent
Ewert et al.

(10) Patent No.: US 10,647,780 B2
(45) Date of Patent: May 12, 2020

(54) REVERSAL BINDING AGENTS FOR ANTI-FACTOR XI/XIA ANTIBODIES AND USES THEREOF

(71) Applicant: Novartis AG, Basel (CH)

(72) Inventors: Stefan Ewert, Geroldswill (DE); Yasser Khder, Hesingue (FR); Alexander Koch, Arlington, MA (US)

(73) Assignee: Novartis AG, Basel (CH)

( * ) Notice: Subject to any disclaimer, the term of this patent is extended or adjusted under 35 U.S.C. 154(b) by 166 days.

(21) Appl. No.: 15/604,556

(22) Filed: May 24, 2017

(65) Prior Publication Data

US 2018/0022825 A1 Jan. 25, 2018

Related U.S. Application Data

(60) Provisional application No. 62/341,574, filed on May 25, 2016, provisional application No. 62/438,754, filed on Dec. 23, 2016.

(51) Int. Cl.
*A61K 39/395* (2006.01)
*C07K 16/42* (2006.01)
*A61K 45/06* (2006.01)
*A61K 39/00* (2006.01)

(52) U.S. Cl.
CPC .... *C07K 16/4241* (2013.01); *A61K 39/39566* (2013.01); *A61K 45/06* (2013.01); *C07K 16/4208* (2013.01); *A61K 2039/505* (2013.01); *C07K 2317/21* (2013.01); *C07K 2317/51* (2013.01); *C07K 2317/515* (2013.01); *C07K 2317/55* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,399,216 | A | 8/1983 | Axel et al. |
| 4,439,196 | A | 3/1984 | Higuchi |
| 4,447,224 | A | 5/1984 | DeCant, Jr. et al. |
| 4,447,233 | A | 5/1984 | Mayfield |
| 4,486,194 | A | 12/1984 | Ferrara |
| 4,487,603 | A | 12/1984 | Harris |
| 4,596,556 | A | 6/1986 | Morrow et al. |
| 4,634,665 | A | 1/1987 | Axel et al. |
| 4,790,824 | A | 12/1988 | Morrow et al. |
| 4,816,397 | A | 3/1989 | Boss et al. |
| 4,816,567 | A | 3/1989 | Cabilly et al. |
| 4,941,880 | A | 7/1990 | Burns |
| 4,946,778 | A | 8/1990 | Ladner et al. |
| 4,963,657 | A | 10/1990 | Pixley |
| 5,064,413 | A | 11/1991 | McKinnon et al. |
| 5,179,017 | A | 1/1993 | Axel et al. |
| 5,223,409 | A | 6/1993 | Ladner et al. |
| 5,225,539 | A | 7/1993 | Winter |
| 5,312,335 | A | 5/1994 | McKinnon et al. |
| 5,383,851 | A | 1/1995 | McKinnon, Jr. et al. |
| 5,399,163 | A | 3/1995 | Peterson et al. |
| 5,403,484 | A | 4/1995 | Ladner et al. |
| 5,545,806 | A | 8/1996 | Lonberg et al. |
| 5,569,825 | A | 10/1996 | Lonberg et al. |
| 5,571,698 | A | 11/1996 | Ladner et al. |
| 5,585,089 | A | 12/1996 | Queen et al. |
| 5,624,821 | A | 4/1997 | Winter et al. |
| 5,625,126 | A | 4/1997 | Lonberg et al. |
| 5,633,425 | A | 5/1997 | Lonberg et al. |
| 5,648,260 | A | 7/1997 | Winter et al. |
| 5,661,806 | A | 8/1997 | Lonberg et al. |
| 5,959,083 | A | 9/1999 | Bosslet et al. |
| 6,005,091 | A | 12/1999 | Blackburn et al. |
| 7,217,794 | B2 | 5/2007 | Abdel-Meguid et al. |
| 7,300,922 | B2 | 11/2007 | Sullenger et al. |
| 7,459,564 | B2 | 12/2008 | Corte et al. |
| 7,501,404 | B2 | 3/2009 | Bannister et al. |
| 7,544,699 | B2 | 6/2009 | Mjalli et al. |
| 7,626,039 | B2 | 12/2009 | Pinto et al. |
| 7,645,799 | B2 | 1/2010 | Corte et al. |
| 7,842,708 | B2 | 11/2010 | Pinto et al. |
| 8,153,590 | B2 | 4/2012 | Lu et al. |
| 8,236,316 | B2 | 8/2012 | Gruber et al. |
| 8,268,783 | B2 | 9/2012 | Sinha et al. |
| 8,283,330 | B2 | 10/2012 | Sullenger et al. |
| 8,324,199 | B2 | 12/2012 | Corte et al. |
| 8,334,372 | B2 | 12/2012 | Freier et al. |
| 8,388,959 | B2 | 3/2013 | Gruber et al. |
| 8,389,488 | B2 | 3/2013 | Monia et al. |

(Continued)

FOREIGN PATENT DOCUMENTS

| | | |
|---|---|---|
| EP | 0 125 023 A1 | 11/1984 |
| EP | 0 171 496 A2 | 2/1986 |

(Continued)

OTHER PUBLICATIONS

US 9,023,796 B2, 05/2015, Lu et al. (withdrawn)

(Continued)

*Primary Examiner* — Michael Szperka

(74) *Attorney, Agent, or Firm* — Finnegan, Henderson, Farabow, Garrett & Dunner LLP.

(57) ABSTRACT

The present disclosure relates to reversal agents, which specifically bind to anti-Factor XI and/or anti-Factor XIa antibodies, and reverse one or more anticoagulant effects of the anti-Factor XI and/or anti-Factor XIa antibodies, as well as to methods of use thereof, such as methods for reversing anticoagulant effects of such anti-Factor XI and/or anti-Factor XIa antibodies, and to related methods for managing bleeding or bleeding risks.

17 Claims, 6 Drawing Sheets

Specification includes a Sequence Listing.

(56) References Cited

U.S. PATENT DOCUMENTS

| | | | |
|---|---|---|---|
| 8,399,648 | B2 | 3/2013 | Gruber et al. |
| 8,455,439 | B2 | 6/2013 | Lu et al. |
| 8,455,441 | B2 | 6/2013 | Lu et al. |
| 8,568,724 | B2 | 10/2013 | Hack |
| 8,586,524 | B2 | 11/2013 | Sullenger et al. |
| 8,735,370 | B2 | 5/2014 | Freier et al. |
| 8,889,129 | B2 | 11/2014 | Lu et al. |
| 8,940,833 | B2 | 1/2015 | Schmitt et al. |
| 9,056,106 | B2 | 6/2015 | Sinha et al. |
| 9,062,298 | B2 | 6/2015 | Lu et al. |
| 9,109,046 | B2 | 8/2015 | Sinha et al. |
| 9,125,895 | B2 | 9/2015 | Gruber et al. |
| 9,388,401 | B2 | 7/2016 | Lu et al. |
| 9,587,233 | B2 | 3/2017 | Sinha et al. |
| 9,636,399 | B2 | 5/2017 | Gruber et al. |
| 9,637,550 | B2 | 5/2017 | Gruber et al. |
| 9,783,614 | B2 | 10/2017 | Wilmen et al. |
| 10,053,515 | B2 | 8/2018 | Chen et al. |
| 10,221,247 | B2 | 3/2019 | Wilmen et al. |
| 2003/0083294 | A1 | 5/2003 | Sullenger et al. |
| 2004/0180855 | A1 | 9/2004 | Shumacher et al. |
| 2005/0059705 | A1 | 3/2005 | Mjalli et al. |
| 2005/0143317 | A1 | 6/2005 | Abdel-Megui et al. |
| 2006/0154915 | A1 | 7/2006 | Corte et al. |
| 2007/0105832 | A1 | 5/2007 | Bannister et al. |
| 2008/0051339 | A1 | 2/2008 | Sullenger et al. |
| 2008/0146811 | A1 | 6/2008 | Deng et al. |
| 2008/0161373 | A1 | 7/2008 | Pinto et al. |
| 2009/0062287 | A1 | 3/2009 | Corte et al. |
| 2009/0098119 | A1 | 4/2009 | Lu et al. |
| 2010/0022506 | A1 | 1/2010 | Pinto et al. |
| 2010/0125052 | A1 | 5/2010 | Lu et al. |
| 2010/0137414 | A1 | 6/2010 | Freier et al. |
| 2010/0249217 | A1 | 9/2010 | Sullenger et al. |
| 2010/0255000 | A1 | 10/2010 | Sinha et al. |
| 2010/0331392 | A1 | 12/2010 | Monia et al. |
| 2011/0015128 | A1 | 1/2011 | Sinha et al. |
| 2011/0020349 | A1 | 1/2011 | Gruber et al. |
| 2011/0021492 | A1 | 1/2011 | Corte et al. |
| 2011/0028446 | A1 | 2/2011 | Pinto et al. |
| 2011/0159006 | A1 | 6/2011 | Hack |
| 2012/0083522 | A1 | 4/2012 | Monia et al. |
| 2012/0214862 | A1 | 8/2012 | Freier et al. |
| 2012/0269788 | A1 | 10/2012 | Lu et al. |
| 2013/0129693 | A1 | 5/2013 | Sinha et al. |
| 2013/0190384 | A1 | 7/2013 | Freier et al. |
| 2013/0274308 | A1 | 10/2013 | Freier et al. |
| 2013/0296400 | A1 | 11/2013 | Monia et al. |
| 2014/0044773 | A1 | 2/2014 | Lu et al. |
| 2014/0079684 | A1 | 3/2014 | Lu et al. |
| 2014/0134151 | A1 | 5/2014 | Lu et al. |
| 2014/0194600 | A1 | 7/2014 | Hack |
| 2014/0275225 | A1 | 9/2014 | Sullenger et al. |
| 2014/0275226 | A1 | 9/2014 | Sullenger et al. |
| 2015/0025011 | A1 | 1/2015 | Sinha et al. |
| 2015/0057228 | A1 | 2/2015 | Lu et al. |
| 2015/0099298 | A1 | 4/2015 | Wilmen et al. |
| 2015/0343034 | A1 | 12/2015 | Pittman et al. |
| 2016/0002617 | A1 | 1/2016 | Sinha et al. |
| 2016/0354449 | A1 | 12/2016 | Lu et al. |
| 2017/0014492 | A1 | 1/2017 | Sinha et al. |
| 2017/0022292 | A1 | 1/2017 | Eder et al. |
| 2017/0035798 | A1 | 2/2017 | Freier et al. |
| 2017/0355780 | A1 | 12/2017 | Chen et al. |
| 2018/0022825 | A1 | 1/2018 | Ewert et al. |
| 2018/0112009 | A1 | 4/2018 | Wilmen et al. |
| 2018/0118850 | A1 | 5/2018 | Hack |
| 2018/0216093 | A1 | 8/2018 | Goletz et al. |
| 2018/0355056 | A1 | 12/2018 | Eder et al. |
| 2018/0355057 | A1 | 12/2018 | Gruber et al. |
| 2018/0362661 | A1 | 12/2018 | Chen et al. |

FOREIGN PATENT DOCUMENTS

| | | | | | |
|---|---|---|---|---|---|
| EP | 0 173 494 | A2 | 3/1986 | | |
| EP | 0 184 187 | A2 | 6/1986 | | |
| EP | 0 338 841 | A1 | 10/1989 | | |
| EP | 0 517 024 | A2 | 12/1992 | | |
| EP | 2070939 | | 6/2009 | | |
| EP | 2 297 207 | B1 | 3/2011 | | |
| EP | 2364990 | | 9/2011 | | |
| EP | 2915564 | | 9/2015 | | |
| EP | 2453910 | | 8/2016 | | |
| EP | 2414517 | | 9/2016 | | |
| EP | 3078743 | | 10/2016 | | |
| EP | 3121271 | | 1/2017 | | |
| EP | 3 404 045 | A1 | 11/2018 | | |
| JP | S6265693 | A | 3/1987 | | |
| WO | WO 86/01533 | | 3/1986 | | |
| WO | WO 87/02671 | | 5/1987 | | |
| WO | WO 87/04462 | | 7/1987 | | |
| WO | WO 89/01036 | | 2/1989 | | |
| WO | WO 94/29351 | | 12/1994 | | |
| WO | WO 95/017420 | A1 | 6/1995 | | |
| WO | WO 97/26010 | A1 | 7/1997 | | |
| WO | WO 00/042072 | | 7/2000 | | |
| WO | WO 02/064634 | A2 | 8/2002 | | |
| WO | 02096926 | | 12/2002 | | |
| WO | WO 02/100348 | A2 | 12/2002 | | |
| WO | WO 03/017935 | A2 | 3/2003 | | |
| WO | WO 03/040169 | A2 | 5/2003 | | |
| WO | WO 2004/035607 | A2 | 4/2004 | | |
| WO | WO 2004/043989 | A2 | 5/2004 | | |
| WO | WO 04/089297 | A1 | 10/2004 | | |
| WO | WO 04/103270 | A1 | 12/2004 | | |
| WO | WO 2004/108749 | A2 | 12/2004 | | |
| WO | WO 06/012504 | A1 | 2/2006 | | |
| WO | WO 2006/040153 | A2 | 4/2006 | | |
| WO | WO 06/076575 | A1 | 7/2006 | | |
| WO | WO 07/070826 | A1 | 6/2007 | | |
| WO | 09042962 | | 4/2009 | | |
| WO | 09061841 | | 5/2009 | | |
| WO | WO 2009/067660 | A2 | 5/2009 | | |
| WO | WO 2009/114677 | A1 | 9/2009 | | |
| WO | WO 2009/141458 | A1 | 11/2009 | | |
| WO | WO 2009/154461 | A1 | 12/2009 | | |
| WO | 10045509 | | 4/2010 | | |
| WO | 10056765 | | 5/2010 | | |
| WO | WO 2010/080623 | A2 | 7/2010 | | |
| WO | 10117729 | | 10/2010 | | |
| WO | 11008885 | | 1/2011 | | |
| WO | 11008995 | | 1/2011 | | |
| WO | 12151575 | | 11/2012 | | |
| WO | 2013167669 | | 11/2013 | | |
| WO | WO 2013/167669 | A1 | 11/2013 | | |
| WO | 14118677 | | 8/2014 | | |
| WO | 2016207858 | | 12/2016 | | |
| WO | WO-2016207858 | A1 * | 12/2016 | ............. | C07K 16/40 |
| WO | 17015558 | | 1/2017 | | |
| WO | 17015619 | | 1/2017 | | |
| WO | WO-2017015619 | A1 * | 1/2017 | ............. | C07K 16/36 |
| WO | WO 2017/021528 | A1 | 2/2017 | | |
| WO | WO 2017/127468 | A1 | 7/2017 | | |
| WO | WO 2017/162791 | A1 | 9/2017 | | |
| WO | 2017203450 | | 11/2017 | | |
| WO | WO 2017/218371 | A1 | 12/2017 | | |
| WO | WO 2018/053597 | A1 | 3/2018 | | |
| WO | WO 2018/054813 | A1 | 3/2018 | | |
| WO | WO 2018/116255 | A1 | 6/2018 | | |
| WO | WO 2018/116267 | A1 | 6/2018 | | |
| WO | WO 2018/134184 | A1 | 7/2018 | | |

OTHER PUBLICATIONS

Janeway et al., Immunobiology, 3rd edition, 1997 Garland Publishing Inc., pp. 3:1-3:11.*

Rudikoff et al., Proc Natl Acad Sci USA. Mar. 1982;79(6):1979-83.*

Kanyavuz et al., Nat Rev Immunol. Jun. 2019;19(6):355-368. doi: 10.1038/S41577-019-0126-7.*

(56) References Cited

OTHER PUBLICATIONS

Edwards et al.,J Mol Biol. Nov. 14, 2003;334(1): 103-18.*
Llyod et al., Protein Eng Des Sel. Mar. 2009;22(3):159-68. doi: 10.1093/protein/gzn058. Epub Oct. 29, 2008.*
Goel et al., J Immunol. Dec. 15, 2004; 173(12):7358-67.*
International Search Report/Written Opinion for International Application No. PCT/IB2017/053066 dated Sep. 1, 2017.
Eigenbrot, C. et al., "Structural Insight into How an Anti-idiotypic AntibodyAgainst D3H44 (anti-tissue Factor Antibody) Restores Normal Coagulation", Journal of Molecular Biology, 331(2):433-446. (Aug. 2003).
Greinacher, A., et al. "Reversal of anticoagulants: an overview of current developments", Thrombosis and Haemostatis, 113(5):931-942. (May 2015).
Akiyama, Hideki, et al., "Mechanism of Activation of Coagulation factor XI by by Factor XIIa Studied with monoclonal Antibodies", J. Clin. Invest, 78:1631-1637. 1986.
Al-Horani, Rami A. et al., "Designing Allosteric Inhibitors of Factor XIa. Lessons from the Interactions of Sulfated Pentagalloylglucopyranosides", *Journal of Medicinal Chemistry*, ACS Publications, 2014, 57, pp. 4805-4818.
Al-Horani & Umesh, "Factor XIa inhibitors: A review of the patent literature", Expert opinion on Therapeutic Patents, 26(3):323-345. 2016.
Argade, Malaika D., "Allosteric inhibition of Human Factor XIa: Discovery of Monosulfated Benzofurans as a Class of Promising Inhibitors", *Journal of Medicinal Chemistry*, ACS Publications, 2014, 57, pp. 3559-3569.
Baglia, F., et al. "A Binding Site for Thrombin in the Apple 1 Domain of Factor XI", *The Journal of Biological Chemistry*, 1996 271(7):3652-3658.
Berge, Stephen M. et al., "Pharmaceutical Salts", *Journal of Pharmaceutical Sciences*, 1977, 66(1):1-19.
Bern et al., Treatment of factor XI inhibitor using recombinant factor VIIa, Haemophilia, 11:20-25. 2005.
David et al., "Factor XIa-specific IgG and a reversal agent to probe factor XI function in thrombosis and hemostasis", Sci. Transl. Med., vol. 8 353ra112 (2016).
De La Cadena, et al., "Naturally Occurring human Antibodies Against Two Distinct Functional Domains in the Heavy Chain of FXI/FXIa", Blood, 72(5):1748-1754. 1988.
"Efficacy and Safety of MAA868 in Patients with Atrial Fibrillation", ClinicalTrials.gov, U.S. National Library of Medicine [online], https://www.clinicaltrials.gov/ct2/show/NCT03398434?term=maa868&rank=1.
Emsley, Jonas et al., "Structure and function of factor XI", *Blood*, vol. 115, No. 13, Apr. 1, 2010, pp. 2569-2577.
Fanger, Peter M. et al., "Bispecific Antibodies", *Critical Reviews in Immunology*, 1992, 12(3,4):101-124.
Fradera et al., "High-Resolution crystal structures of facrot XIa coagulation factor in complex with nobasic high-affinity synthetic inhibitors", Acta Cryst. F68, 404-408 (2012).
Fujikawa, et al., "Amino Acid Sequence of Human factor XI, a Blood Coagulation Factor with Four Tandem Repeats That Are Highly Homologous with Plasma Prekallikrein", Biochemistry, 25:2417-2424. 1986.
Gailani, David et al., "Model for a factor IX activation complex on blood platelets: dimeric conformation of factor XIa is essential", *Blood*, 2001, 97(10):3117-3122.
Gailani, D. et al., "A murine model of factor XI deficiency", *Blood Coagulation and Fibrinolysis*, 1997, vol. 8, pp. 134-144.
Gailani, D. et al., "The Intrinsic pathway of coagulation: a target for treating thromboembolic disease?" *Journal of Thrombosis and Haemostasis*, 2007, 5:1106-1112.
Goldsmith and Silverman, "Inhibitors of plasma thromboplastin antecedent (factor XI): Studies on mechanism of inhibition", J Lab. Clin Med. 106(3):279-285. 1985.
Gruber, Andras et al., "Antithrombotic factor XI antibody inhibition of the intrinsic pathway", *Blood*, 2001 98(11):42a.
Gruber and Hanon, "Factor XI-dependence of surface- and tissue factor-initiated thrombus propagation in primates", Blood, 102(3):953-955. 2003.
Hack, C.E. et al., "Disruption of the internal thioester bond in the third component of complement (C3) results in the exposure of neodeterminants also present on activation products of C3. An analysis with monoclonal antibodies", *Journal of Immunology*, 1988, 141:1602-1609.
Halvoet et al., "Measurement of Free, one-Chain Tissue-Type Plasminogen Activator in Human Plasma With an Enzyme-Linked Immunosorbent Assay Based on an Active Site-Specific Murine Monoclonal Antibody", Blood, 69(1):284-289. 1987.
Holliger, Philipp, et al., "Diabodies: Small bivalent and bispecific antibody fragments", *Proc Natl. Acad. Sci.*, 1993, 90:6444-6448.
Jin et al., "Crystal Structures of the FXIa Catalytic Domain in Complex with Ecotin Mutants Reveal Substrate-like Interactions", Journal of Biological Chemistry, 280(6):4704-4712 (2005).
Jin, Lei et al., "Mutation of surface residues to promote crystallization of activated factor XI as a complex with benzamidine: an essential sep for the iterative structure-based design of factor XI inhibitors", *Acta Cryst.* (2005) D61, pp. 1418-1425.
Kipriyanov, Sergey M. et al., "Generation and Production of Engineered Antibodies", *Molecular Biotechnology*, 2004, 26:39-60.
Koch, Alexander W., "MAA868, a novel FXI antibody with a unique binding mode, shows durable effects on markers of anticoagulation in humans", *Blood*, 2019, 133(13): 1507-1516.
Konings et al., "Ongoing Contact Activation in Patients with Hereditary Angioedema", PLOS ONE, 8(8):1-9. 2013.
Kravtsov et al., "Factor XI contributes to thrombin generation in the absence of factor XII", Blood, 114(2):452-458. 2009.
Matafonov, A. et al., "Evidence for factor IX-independent roles for factor XIa in blood coagulation", *Journal of Thrombosis and Haemostasis*, 2013, 11:2118-2127.
Mendez, Michael J. et al., "Functional transplant of megabase human immunoglobulin loci recapitulates human antibody response in mice", *Nature Genetics*, 1997, 15:146-156.
Minnema, et al., "Activation of Clotting Factors XI and IX in Patients With Acute Myocardial Infarction", Arterioscler Thromb Vasc Biol, 20:2489-2493. 2000.
Minnema M.C. et al., "Activation of Clotting Factor XI Without Detectable Contact Activation in Experimental Human Endotoxemia", *Blood*, 1998, 92(9):3294-3301.
Minnema et al., "Activation of the contact System of Coagulation Does Not Contribute to the Hemostatic Imbalance in Hypertriglyceridemia", Arterioscler Throm Vasc Biol. 19:2548-2553. 1999.
Minnema et al., "Enhancement of Rabbit Jugular Vein thrombolysis by neutralization of factor XI in Vivo Evidence for a Role of Factor XI as an Anti-fibrinolytic Factor", J. Clin. Invest., 101(1):10-14. 1998.
Mohammed, Bassem M. et al., "An Update on Factor XI Structure and Function", *Thromb Res.*, Jan. 2018; 161:94-105 (32 pages).
Morgan et al., "Acquired Factor XI Inhibitors in Two Patients with Hereditary Factor XI Deficiency", Thromb Haemostas, 51(3):371-375. 1984.
Naito and Fujikawa, "Activation of Human Blood Coagulation Factor XI Independent of Factor XII", The Journal of Biological Chemistry, 266(12):7353-7358. 1991.
Navaneetham et al., "Structural and Mutational Analyses of the Molecular Interactions between the Catalytic Domain of Factor XIa and the Kunitz Protease Inhibitor Domain of Protease Nexin 2", Journal of Biological Chemistry, 280(43):36165-36175 (2005).
Nishikado et al., "Murine Monoclonal Antibodies to Human Factor XI", Thrombosis Research, 42:225-234. 1986.
Ohkubo et al., "Characterization of a Panel of Monoclonal Antibodies to Human Coagulation Factor XI and Detection of Factor XI in Hep G2 Cell Conditioned Medium", Thrombosis and Haemostasis, 63(3):4170423. 1990.
Papagrigoriou, Evangelos et al., "Crystal Structure of the factor XI zymogen reveals a pathway for transactivation", *Nature Structural & Molecular Biology*, vol. 13, No. 6, Jun. 2006, pp. 557-558.

(56) References Cited

OTHER PUBLICATIONS

Peyvandi, Flora et al., "Factor XI deficiency in Iranians: its clinical manifestations in comparison with those of classic hemophilia", *Haemtologica*, 2002, 87(5):512-514.
"Prevention of Thromboembolic Events in Total Knee Replacement Positions", ClinicalTrials.gov, U.S. National Library of Medicine [online], https://www.clinicaltrials.gov/ct2/show/NCT03393481?term=maa868&rank=2.
Puy, Cristina et al., "Activated factor XI increases the procoagulant activity of the extrinsic pathway by inactivating tissue factor pathway inhibitor", *Blood*, 2015, 125(9):1488-1496.
Reagents, "Suplemmental Methods and Data", (Jan. 13, 2015), URL: http://www.bloodjournal.org/content/bloodjournal/suppl/2015/01/13/blood-2014-10-604587.DC1/blood-2014-10-604587-1.pdf.
Renne, T. et al., "Characterization of the H-kininogen-binding Site on Factor XI", *The Journal of Biological Chemistry*, 2002, 277(7):4892-4899.
Renne, Thomas et al., "Defective thrombus formation in mice lacking coagulation factor XII", *The Journal of Experimental Medicine*, 2005, 202(2):271-281.
Renne et al., "Factor XI deficiency in animal models", Journal of Thrombosis and Haemostasis, 7(Suppl. 1):79-83. 2009.
St. Groth, S. Fazekas et al., "Production of Monoclonal Antibodies: Strategy and Tactics", *Journal of Immunological Methods*, 1980, 35:1-21.
Salomon et al., "Prevalence, causes, and characterization of factor XI inhibitors in patients with inherited factor XI deficiency", Blood, 101(12):4783-4788. 2003.
Samuel et al., "Solution structure of the A4 domain of factor XI sheds light on the mechanism of zymogen activation", PNAS, 104(40):15693-15698. 2007.
Scott et al., "Amidolytic Assay of Human Factor Xi in Plasma: Comparison With a coagulant Assay and a new Rapid Radioimmunoassay", Blood, 63(1):42-50. 1984.
Shumacher et al., "Antithrombotic and hemostatic effects of a small molecule factor XIa inhibitor in rats", European Journal of Pharmacology, 570:167-174. 2007.
Sie et al., "An Acquired Antithrombin Autoantibody Directed toward the Catalytic Center of the Enzyme", J. Clin. Invest., 88:290-296. 1991.
Sinha et al., "Functional Characterization of Human Blood Coagulation factor XIa Using Hybridoma Antibodies", The journal of Biological Chemistry, 260(19):10714-10719. 1985.
Smeenk, Ruud J. et al., "Is Anticardiolipin Activity a Cross-Reaction of Anti-DNA or a Separate Entity?", *Arthritis and Rheumatism*, 1987, 30(6): 607-617.
Spronk et al., "Monitoring thrombin generation: Is addition of corn trypsin inhibitor needed", Throm Haemost, 101:1156-1162. 2009.
Stern et al., "Acquired Antibody to Factor XI in a Patient with Congenital factor XI Deficiency", J. Clin. Invest., 69:1270-1276. 1982.
Su, Ya-Chi et al., "The Role of Factor XIa (FXIa) Catalytic Domain Exosite Residues in Substrate Catalysis and Inhibition by the Kunitz Protease Inhibitor Domain of Protease Nexin 2", *The Journal of Biological Chemistry*, vol. 286, No. 36, Sep. 9, 2011, pp. 31904-31914.
Tait, Jonathan F. et al., "Primary Structure Requirements for the Binding of Human High Molecular Weight Kininogen to Plasma Prekallikrein and Factor XI", *Journal of Biological Chemistry*, 1987, 262(24): 11651-11656.
Tans, Guido et al., Studies on the effect of serine protease inhibitors on activated contact factors Application in amidolytic assays for factor $XII_a$, plasma kallikrein and factor $XI_a$, *Eur. J. Biochem*, 164, pp. 637-642 (1987).
Tucker et al., "Prevention of vascular graft occlusion and thrombus-associated thrombin generation by inhibition of factor XI", Blood, 113(4):936-944. 2009.
Ogawa, Taketoshi et al., "Exosite-mediated Substrate Recognition of Factor XI by Factor XIa", *Journal of Biological Chemistry*, 2005, 280(25):23523-23530.
Reagents, "Supplemental Methods and Data" (Jan. 13, 2015), URL:http://www.bloodjournal.org/content/bloodjournal/suppl/2015/01/13/blood-2014-10-604587.DC1/blood-2014-10-604587-1.pdf.
Sinha, Dipali et al., "Macromolecular Substrate-Binding Exosites on Both the Heavy and Light Chains of Factor XIa Mediate the Formation of the Michaelis Complex Required for Factor IX-Activation", *Biochemistry*, 2007, 46, 9830-9839.
Strejan, G.H. et al., "Suppression of Chronic-Relapsing Experimental Allergic Encephalomyelitis in Strain-13 Guinea Pigs by Administration of Liposome-Associated Myelin Basic Protein", *Journal of Neuroimmunology*, 1984, 7:27-41.
Sun, Yuehui et al., "Identification of a Factor IX Binding Site on the Third Apple Domain of Activated Factor XI", *The Journal of Biological Chemistry*, 1996, 271(46):29023-29028.
Takahashi, M. et al., Inhibition of factor XI reduced thrombus formation in rabbit jugular vein under endothelial denudation and/or blood stasis, *Thrombosis Research*, 2010, 125(5):464-470.
Tucker, Erik et al., "Inhibition of Factor XI decreases thrombin production and prevents vascular occlusion in experimental thrombosis in primates", *Blood*, 2007 110(11):1-5.
Van Der Graaf, Fedde et al., "Isolation and Functional Characterization of the Active Light Chain of Activated Human Blood Coagulation Factor XI", *The Journal of Biological Chemistry*, 1983, vol. 258, No. 16, pp. 9669-9675.
Van Montfoort and Meijers, "Anticoagulation beyond direct thrombin and factor Xa inhibitors: indications for targeting the intrinsic pathway", Thrombosis and Haemostasis, 110(2):223-232. 2013.
Van Montfoort, "Factor XI as target for antithrombotic therapy", Thesis. 2014.
Van Montfoort, Maurits L. et al., "Two novel inhibitory anti-human factor XI antibodies prevent cessation of blood flow in a murine venous thrombosis model", *Thrombosis and Haemostasis*, 2013, 110:1065-1073.
Wong, Szu et al., "A novel DFP tripeptide motif interacts with the coagulation factor XI apple 2 domain", *Blood*, vol. 127, No. 23, Jun. 9, 2016, pp. 2915-2923.
Wu, Yan et al., "Structural insight into distinct mechanisms of protease inhibition by antibodies", *PNAS*, Dec. 11, 2017, vol. 104, No. 50, pp. 19784-19789.
Wuillemin et al., "Activation of the Intrinsic Pathway of Coagulation in Children with Meningococcal Septic Shock", Thrombosis and Haemostasis, 74(6):1436-41. 1995.
Wuillemin, et al., "Thrombin-mediated activation of endogenous factor XI in plasma in the presence of physiological glycosaminoglycans occurs only with high concentrations of thrombin", British Journal of Haematology, 92:466-472. 1996.
Yamashita, A. et al., "Factor XI contributes to thrombus propagation on injured neointima of the rabbit iliac artery", *Journal of Thrombosis and Haemostasis*, 2006, 4:1496:1501.
Yang, Mark X. et al., "Crystalline monoclonal antibodies for subcutaneous delivery", *PNAS*, 2003 100(12):6934-6939.
Zucker et al., "Induction of an inhibitor antibody to factor XI in a patient with severe inherited factor XI deficiency by Rh immune globulin", Blood, 111(3):1306-1308. 2008.

* cited by examiner aPTT Assay: NOV1401 and anti-NOV1401 pre-incubated

SEQUENCE LISTING

```
<160> NUMBER OF SEQ ID NOS: 394

<210> SEQ ID NO 1
<211> LENGTH: 625
<212> TYPE: PRT
<213> ORGANISM: Homo sapiens

<400> SEQUENCE: 1

Met Ile Phe Leu Tyr Gln Val Val His Phe Ile Leu Phe Thr Ser Val
1               5                   10                  15

Ser Gly Glu Cys Val Thr Gln Leu Leu Lys Asp Thr Cys Phe Glu Gly
            20                  25                  30

Gly Asp Ile Thr Thr Val Phe Thr Pro Ser Ala Lys Tyr Cys Gln Val
        35                  40                  45

Val Cys Thr Tyr His Pro Arg Cys Leu Leu Phe Thr Phe Thr Ala Glu
    50                  55                  60

Ser Pro Ser Glu Asp Pro Thr Arg Trp Phe Thr Cys Val Leu Lys Asp
65                  70                  75                  80

Ser Val Thr Glu Thr Leu Pro Arg Val Asn Arg Thr Ala Ala Ile Ser
                85                  90                  95

Gly Tyr Ser Phe Lys Gln Cys Ser His Gln Ile Ser Ala Cys Asn Lys
            100                 105                 110

Asp Ile Tyr Val Asp Leu Asp Met Lys Gly Ile Asn Tyr Asn Ser Ser
        115                 120                 125

Val Ala Lys Ser Ala Gln Glu Cys Gln Glu Arg Cys Thr Asp Asp Val
    130                 135                 140

His Cys His Phe Phe Thr Tyr Ala Thr Arg Gln Phe Pro Ser Leu Glu
145                 150                 155                 160

His Arg Asn Ile Cys Leu Leu Lys His Thr Gln Thr Gly Thr Pro Thr
```

```
                165                 170                 175

Arg Ile Thr Lys Leu Asp Lys Val Val Ser Gly Phe Ser Leu Lys Ser
            180                 185                 190

Cys Ala Leu Ser Asn Leu Ala Cys Ile Arg Asp Ile Phe Pro Asn Thr
        195                 200                 205

Val Phe Ala Asp Ser Asn Ile Asp Ser Val Met Ala Pro Asp Ala Phe
    210                 215                 220

Val Ser Gly Arg Ile Cys Thr His His Pro Gly Cys Leu Phe Phe Thr
225                 230                 235                 240

Phe Phe Ser Gln Glu Trp Pro Lys Glu Ser Gln Arg Asn Leu Cys Leu
                245                 250                 255

Leu Lys Thr Ser Glu Ser Gly Leu Pro Ser Thr Arg Ile Lys Lys Ser
            260                 265                 270

Lys Ala Leu Ser Gly Phe Ser Leu Gln Ser Cys Arg His Ser Ile Pro
        275                 280                 285

Val Phe Cys His Ser Ser Phe Tyr His Asp Thr Asp Phe Leu Gly Glu
    290                 295                 300

Glu Leu Asp Ile Val Ala Ala Lys Ser His Glu Ala Cys Gln Lys Leu
305                 310                 315                 320

Cys Thr Asn Ala Val Arg Cys Gln Phe Phe Thr Tyr Thr Pro Ala Gln
                325                 330                 335

Ala Ser Cys Asn Glu Gly Lys Gly Lys Cys Tyr Leu Lys Leu Ser Ser
            340                 345                 350

Asn Gly Ser Pro Thr Lys Ile Leu His Gly Arg Gly Gly Ile Ser Gly
        355                 360                 365

Tyr Thr Leu Arg Leu Cys Lys Met Asp Asn Glu Cys Thr Thr Lys Ile
    370                 375                 380

Lys Pro Arg Ile Val Gly Gly Thr Ala Ser Val Arg Gly Glu Trp Pro
385                 390                 395                 400

Trp Gln Val Thr Leu His Thr Thr Ser Pro Thr Gln Arg His Leu Cys
                405                 410                 415

Gly Gly Ser Ile Ile Gly Asn Gln Trp Ile Leu Thr Ala Ala His Cys
            420                 425                 430

Phe Tyr Gly Val Glu Ser Pro Lys Ile Leu Arg Val Tyr Ser Gly Ile
        435                 440                 445

Leu Asn Gln Ser Glu Ile Lys Glu Asp Thr Ser Phe Phe Gly Val Gln
    450                 455                 460

Glu Ile Ile Ile His Asp Gln Tyr Lys Met Ala Glu Ser Gly Tyr Asp
465                 470                 475                 480

Ile Ala Leu Leu Lys Leu Glu Thr Thr Val Asn Tyr Thr Asp Ser Gln
                485                 490                 495

Arg Pro Ile Cys Leu Pro Ser Lys Gly Asp Arg Asn Val Ile Tyr Thr
            500                 505                 510

Asp Cys Trp Val Thr Gly Trp Gly Tyr Arg Lys Leu Arg Asp Lys Ile
        515                 520                 525

Gln Asn Thr Leu Gln Lys Ala Lys Ile Pro Leu Val Thr Asn Glu Glu
    530                 535                 540

Cys Gln Lys Arg Tyr Arg Gly His Lys Ile Thr His Lys Met Ile Cys
545                 550                 555                 560

Ala Gly Tyr Arg Glu Gly Gly Lys Asp Ala Cys Lys Gly Asp Ser Gly
                565                 570                 575

Gly Pro Leu Ser Cys Lys His Asn Glu Val Trp His Leu Val Gly Ile
            580                 585                 590
```

```
Thr Ser Trp Gly Glu Gly Cys Ala Gln Arg Glu Arg Pro Gly Val Tyr
        595                 600                 605

Thr Asn Val Val Glu Tyr Val Asp Trp Ile Leu Glu Lys Thr Gln Ala
    610                 615                 620

Val
625


<210> SEQ ID NO 2
<211> LENGTH: 3278
<212> TYPE: DNA
<213> ORGANISM: Homo sapiens

<400> SEQUENCE: 2

aggcacacag gcaaaatcaa gttctacatc tgtccctgtg tatgtcactt gtttgaatac      60

gaaataaaat taaaaaaata aattcagtgt attgagaaag caagcaattc tctcaaggta     120

tatttctgac atactaagat tttaacgact ttcacaaata tgctgtactg agagagaatg     180

ttacataaca ttgagaacta gtacaagtaa atattaaagt gaagtgacca tttcctacac     240

aagctcattc agaggaggat gaagaccatt ttggaggaag aaaagcaccc ttattaagaa     300

ttgcagcaag taagccaaca aggtcttttc aggatgattt tcttatatca agtggtacat     360

ttcattttat ttacttcagt ttctggtgaa tgtgtgactc agttgttgaa ggacacctgc     420

tttgaaggag ggacattac tacggtcttc acaccaagcg ccaagtactg ccaggtagtc     480

tgcacttacc acccaagatg tttactcttc actttcacgg cggaatcacc atctgaggat     540

cccacccgat ggtttacttg tgtcctgaaa gacagtgtta cagaaacact gccaagagtg     600

aataggacag cagcgatttc tggtattct ttcaagcaat gctcacacca aataagcgct     660

tgcaacaaag acatttatgt ggacctagac atgaagggca taaactataa cagctcagtt     720

gccaagagtg ctcaagaatg ccaagaaaga tgcacggatg acgtccactg ccactttttc     780

acgtacgcca caaggcagtt tcccagcctg gagcatcgta acatttgtct actgaagcac     840

acccaaacag ggacaccaac cagaataacg aagctcgata aagtggtgtc tggattttca     900

ctgaaatcct gtgcactttc taatctggct tgtattaggg acattttccc taatacggtg     960

tttgcagaca gcaacatcga cagtgtcatg gctcccgatg cttttgtctg tggccgaatc    1020

tgcactcatc atcccggttg cttgtttttt accttctttt cccaggaatg gcccaaagaa    1080

tctcaaagaa atctttgtct ccttaaaaca tctgagagtg gattgcccag tacacgcatt    1140

aaaaagagca aagctctttc tggtttcagt ctacaaagct gcaggcacag catcccagtg    1200

ttctgccatt cttcatttta ccatgacact gatttcttgg gagaagaact ggatattgtt    1260

gctgcaaaaa gtcacgaggc ctgccagaaa ctgtgcacca atgccgtccg ctgccagttt    1320

tttacctata ccccagccca agcatcctgc aacgaaggga agggcaagtg ttacttaaag    1380

ctttcttcaa acggatctcc aactaaaata cttcacggga gaggaggcat ctctggatac    1440

acattaaggt tgtgtaaaat ggataatgag tgtaccacca aaatcaagcc caggatcgtt    1500

ggaggaactg cgtctgttcg tggtgagtgg ccgtggcagg tgaccctgca cacaacctca    1560

cccactcaga gacacctgtg tggaggctcc atcattggaa accagtggat attaacagcc    1620

gctcactgtt tctatggggt agagtcacct aagattttgc gtgtctacag tggcatttta    1680

aatcaatctg aaataaaaga ggacacatct ttctttgggg ttcaagaaat aataatccat    1740

gatcagtata aaatggcaga aagcgggtat gatattgcct tgttgaaact ggaaaccaca    1800

gtgaattaca cagattctca acgacccata tgcctgcctt ccaaaggaga tagaaatgta    1860
```

```
atatacactg attgctgggt gactggatgg gggtacagaa aactaagaga caaaatacaa   1920

aatactctcc agaaagccaa gataccctta gtgaccaacg aagagtgcca gaagagatac   1980

agaggacata aaataaccca taagatgatc tgtgccggct acagggaagg agggaaggac   2040

gcttgcaagg gagattcggg aggccctctg tcctgcaaac acaatgaggt ctggcatctg   2100

gtaggcatca cgagctgggg cgaaggctgt gctcaaaggg agcggccagg tgtttacacc   2160

aacgtggtcg agtacgtgga ctggattctg gagaaaactc aagcagtgtg aatgggttcc   2220

caggggccat tggagtccct gaaggaccca ggatttgctg ggagagggtg ttgagttcac   2280

tgtgccagca tgcttcctcc acagtaacac gctgaagggg cttggtgttt gtaagaaaat   2340

gctagaagaa aacaaactgt cacaagttgt tatgtccaaa actcccgttc tatgatcgtt   2400

gtagtttgtt tgagcattca gtctctttgt ttttgatcac gcttctatgg agtccaagaa   2460

ttaccataag gcaatatttc tgaagattac tatataggca gatatagcag aaaataacca   2520

agtagtggca gtggggatca ggcagaagaa ctggtaaaag aagccaccat aaatagattt   2580

gttcgatgaa agatgaaaac tggaagaaag gagaacaaag acagtcttca ccattttgca   2640

ggaatctaca ctctgcctat gtgaacacat ttcttttgta aagaaagaaa ttgattgcat   2700

ttaatggcag attttcagaa tagtcaggaa ttcttgtcat ttccatttta aaatatatat   2760

taaaaaaaat cagttcgagt agacacgagc taagagtgaa tgtgaagata acagaatttc   2820

tgtgtggaag aggattacaa gcagcaattt acctggaagt gataccttag gggcaatctt   2880

gaagatacac tttcctgaaa aatgatttgt gatggattgt atatttattt aaaatatctt   2940

gggaggggag gctgatggag atagggagca tgctcaaacc tccctaagac aagctgctgc   3000

tgtgactatg ggctcccaaa gagctagatc gtatatttat ttgacaaaaa tcaccataga   3060

ctgcatccat actacagaga aaaaacaatt agggcgcaaa tggatagtta cagtaaagtc   3120

ttcagcaagc agctgcctgt attctaagca ctgggatttt ctgtttcgtg caaatattta   3180

tctcattatt gttgtgatct agttcaataa cctagaattt gaattgtcac cacatagctt   3240

tcaatctgtg ccaacaacta tacaattcat caagtgtg                           3278
```

<210> SEQ ID NO 3
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 3

```
Gly Phe Thr Phe Ser Thr Ala Ala Met Ser
1               5                   10
```

<210> SEQ ID NO 4
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 4

```
Gly Ile Ser Gly Ser Gly Ser Ser Thr Tyr Tyr Ala Asp Ser Val Lys
1               5                   10                  15
```

Gly

<210> SEQ ID NO 5
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 5

Glu Leu Ser Tyr Leu Tyr Ser Gly Tyr Tyr Phe Asp Tyr
1 5 10

<210> SEQ ID NO 6
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 6

Thr Ala Ala Met Ser
1 5

<210> SEQ ID NO 7
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 7

Gly Phe Thr Phe Ser Thr Ala
1 5

<210> SEQ ID NO 8
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 8

Ser Gly Ser Gly Ser Ser
1 5

<210> SEQ ID NO 9
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 9

Gly Phe Thr Phe Ser Thr Ala Ala
1 5

<210> SEQ ID NO 10

<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 10

Ile Ser Gly Ser Gly Ser Ser Thr
1 5

<210> SEQ ID NO 11
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 11

Ala Arg Glu Leu Ser Tyr Leu Tyr Ser Gly Tyr Tyr Phe Asp Tyr
1 5 10 15

<210> SEQ ID NO 12
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 12

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Thr Ala
20 25 30

Ala Met Ser Trp Val Arg Gln Ala Pro Gly Lys Gly Leu Glu Trp Val
35 40 45

Ser Gly Ile Ser Gly Ser Gly Ser Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Glu Leu Ser Tyr Leu Tyr Ser Gly Tyr Tyr Phe Asp Tyr Trp
100 105 110

Gly Gln Gly Thr Leu Val Thr Val Ser Ser
115 120

<210> SEQ ID NO 13
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13
caggtgcagc tgctggaatc aggcggcgga ctggtgcagc ctggcggtag cctgagactg 60
agctgcgctg ctagtggctt cacctttagc accgccgcta tgagctgggt tcgacaggcc 120

```
ccagggaaag gcctcgagtg ggtctcaggg attagcggta gcggctctag cacctactac    180

gccgatagcg tgaagggccg gttcactatc tctagggata actctaagaa caccctgtac    240

ctgcagatga atagcctgag agccgaggac accgccgtct actactgcgc tagagagctg    300

agctacctgt atagcggcta ctacttcgac tactggggtc aaggcaccct ggtcaccgtg    360

tctagc                                                               366
```

```
<210> SEQ ID NO 14
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Gly Ile Ser Gly Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Ala Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300
```

```
Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Ala Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450
```

<210> SEQ ID NO 15
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 15

```
caggtgcagc tgctggaatc aggcggcgga ctggtgcagc ctggcggtag cctgagactg     60

agctgcgctg ctagtggctt cacctttagc accgccgcta tgagctgggt tcgacaggcc    120

ccagggaaag gcctcgagtg ggtctcaggg attagcggta gcggctctag cacctactac    180

gccgatagcg tgaagggccg gttcactatc tctagggata actctaagaa caccctgtac    240

ctgcagatga atagcctgag agccgaggac accgccgtct actactgcgc tagagagctg    300

agctacctgt atagcggcta ctacttcgac tactggggtc aaggcaccct ggtcaccgtg    360

tctagcgcta gcactaaggg cccctccgtg ttccctctgg ccccttccag caagtctacc    420

tccggcggca cagctgctct gggctgcctg gtcaaggact acttccctga gcctgtgaca    480

gtgtcctgga actctggcgc cctgacctct ggcgtgcaca ccttccctgc cgtgctgcag    540

tcctccggcc tgtactccct gtcctccgtg gtcacagtgc cttcaagcag cctgggcacc    600

cagacctata tctgcaacgt gaaccacaag ccttccaaca ccaaggtgga caagcgggtg    660

gagcctaagt cctgcgacaa gacccacacc tgtcctccct gccctgctcc tgaactgctg    720

ggcggccctt ctgtgttcct gttccctcca aagcccaagg acaccctgat gatctcccgg    780

acccctgaag tgacctgcgt ggtggtggcc gtgtcccacg aggatcctga agtgaagttc    840

aattggtacg tggacggcgt ggaggtgcac aacgccaaga ccaagcctcg ggaggaacag    900

tacaactcca cctaccgggt ggtgtccgtg ctgaccgtgc tgcaccagga ctggctgaac    960

ggcaaagagt acaagtgcaa agtctccaac aaggccctgg ccgcccctat cgaaaagaca   1020

atctccaagg ccaagggcca gcctagggaa ccccaggtgt acaccctgcc acccagccgg   1080
```

gaggaaatga ccaagaacca ggtgtccctg acctgtctgg tcaagggctt ctacccttcc 1140
gatatcgccg tggagtggga gtctaacggc cagcctgaga acaactacaa gaccacccct 1200
cctgtgctgg actccgacgg ctccttcttc ctgtactcca aactgaccgt ggacaagtcc 1260
cggtggcagc agggcaacgt gttctcctgc tccgtgatgc acgaggccct gcacaaccac 1320
tacacccaga agtccctgtc cctgtctccc ggcaag 1356

<210> SEQ ID NO 16
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 16

Ser Gly Ser Ser Ser Asn Ile Gly Ser Asn Asp Val Ser
1 5 10

<210> SEQ ID NO 17
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 17

Lys Asn Tyr Asn Arg Pro Ser
1 5

<210> SEQ ID NO 18
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 18

Ser Ala Trp Asp Gln Arg Gln Phe Asp Val Val
1 5 10

<210> SEQ ID NO 19
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 19

Ser Ser Ser Asn Ile Gly Ser Asn Asp
1 5

<210> SEQ ID NO 20
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 20

Lys Asn Tyr
1

<210> SEQ ID NO 21
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 21

Trp Asp Gln Arg Gln Phe Asp Val
1 5

<210> SEQ ID NO 22
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 22

Ser Ser Asn Ile Gly Ser Asn Asp
1 5

<210> SEQ ID NO 23
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 23

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Asp Val Ser Trp Tyr Gln Gln Leu Pro Gly Thr Ala Pro Lys Leu Leu
35 40 45

Ile Tyr Lys Asn Tyr Asn Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ser Ala Trp Asp Gln Arg Gln
85 90 95

Phe Asp Val Val Phe Gly Gly Gly Thr Lys Leu Thr Val Leu
100 105 110

<210> SEQ ID NO 24
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 24
cagtcagtcc tgactcagcc ccctagcgct agtggcaccc ctggtcaaag agtgactatt 60
agctgtagcg gctctagctc taatatcggc tctaacgacg tcagctggta tcagcagctg 120
cccggcaccg cccctaagct gctgatctat aagaactata ataggcctag cggcgtgccc 180
gataggttta gcggatctaa atcagggact tctgctagtc tggctattag cggcctgcag 240
tcagaggacg aggccgacta ctactgtagc gcctgggatc agcgtcagtt cgacgtggtg 300
ttcggcggag gcactaagct gaccgtgctg 330

<210> SEQ ID NO 25
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 25

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Asp Val Ser Trp Tyr Gln Gln Leu Pro Gly Thr Ala Pro Lys Leu Leu
35 40 45

Ile Tyr Lys Asn Tyr Asn Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ser Ala Trp Asp Gln Arg Gln
85 90 95

Phe Asp Val Val Phe Gly Gly Gly Thr Lys Leu Thr Val Leu Gly Gln
100 105 110

Pro Lys Ala Ala Pro Ser Val Thr Leu Phe Pro Pro Ser Ser Glu Glu
115 120 125

Leu Gln Ala Asn Lys Ala Thr Leu Val Cys Leu Ile Ser Asp Phe Tyr
130 135 140

Pro Gly Ala Val Thr Val Ala Trp Lys Ala Asp Ser Ser Pro Val Lys
145 150 155 160

Ala Gly Val Glu Thr Thr Thr Pro Ser Lys Gln Ser Asn Asn Lys Tyr
165 170 175

Ala Ala Ser Ser Tyr Leu Ser Leu Thr Pro Glu Gln Trp Lys Ser His
180 185 190

Arg Ser Tyr Ser Cys Gln Val Thr His Glu Gly Ser Thr Val Glu Lys
195 200 205

Thr Val Ala Pro Thr Glu Cys Ser
210 215

<210> SEQ ID NO 26
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 26

```
cagtcagtcc tgactcagcc ccctagcgct agtggcaccc ctggtcaaag agtgactatt     60

agctgtagcg gctctagctc taatatcggc tctaacgacg tcagctggta tcagcagctg    120

cccggcaccg cccctaagct gctgatctat aagaactata ataggcctag cggcgtgccc    180

gataggttta gcggatctaa atcagggact tctgctagtc tggctattag cggcctgcag    240

tcagaggacg aggccgacta ctactgtagc gcctgggatc agcgtcagtt cgacgtggtg    300

ttcggcggag gcactaagct gaccgtgctg ggtcaaccta aggctgcccc cagcgtgacc    360

ctgttccccc ccagcagcga ggagctgcag gccaacaagg ccaccctggt gtgcctgatc    420

agcgacttct acccaggcgc cgtgaccgtg gcctggaagg ccgacagcag ccccgtgaag    480

gccggcgtgg agaccaccac ccccagcaag cagagcaaca acaagtacgc cgccagcagc    540

tacctgagcc tgacccccga gcagtggaag agccacaggt cctacagctg ccaggtgacc    600

cacgagggca gcaccgtgga aaagaccgtg gccccaaccg agtgcagc                 648
```

<210> SEQ ID NO 27
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 27

```
Gly Phe Thr Phe Ser Asp Tyr Ala Met Ser
1               5                   10
```

<210> SEQ ID NO 28
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 28

```
Val Ile Asp Tyr Ser Ser Ser Asn Thr Tyr Tyr Ala Asp Ser Val Lys
1               5                   10                  15

Gly
```

<210> SEQ ID NO 29
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 29

```
Glu Gly Tyr Ser Tyr Arg Ser Ile Arg Phe Asp Tyr
1               5                   10
```

<210> SEQ ID NO 30
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 30

Asp Tyr Ala Met Ser
1 5

<210> SEQ ID NO 31
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 31

Val Ile Asp Tyr Ser Ser Ser Asn Thr Tyr Tyr Ala Asp Ser Val Lys
1 5 10 15

Gly

<210> SEQ ID NO 32
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 32

Glu Gly Tyr Ser Tyr Arg Ser Ile Arg Phe Asp Tyr
1 5 10

<210> SEQ ID NO 33
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 33

Gly Phe Thr Phe Ser Asp Tyr
1 5

<210> SEQ ID NO 34
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 34

Asp Tyr Ser Ser Ser Asn
1 5

<210> SEQ ID NO 35
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 35

Glu Gly Tyr Ser Tyr Arg Ser Ile Arg Phe Asp Tyr
1 5 10

<210> SEQ ID NO 36
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 36

Gly Phe Thr Phe Ser Asp Tyr Ala
1 5

<210> SEQ ID NO 37
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 37

Ile Asp Tyr Ser Ser Ser Asn Thr
1 5

<210> SEQ ID NO 38
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 38

Ala Arg Glu Gly Tyr Ser Tyr Arg Ser Ile Arg Phe Asp Tyr
1 5 10

<210> SEQ ID NO 39
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 39

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Ala Met Ser Trp Val Arg Gln Ala Pro Gly Lys Gly Leu Glu Trp Val
35 40 45

Ser Val Ile Asp Tyr Ser Ser Ser Asn Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

```
Ala Arg Glu Gly Tyr Ser Tyr Arg Ser Ile Arg Phe Asp Tyr Trp Gly
            100                 105                 110

Gln Gly Thr Leu Val Thr Val Ser Ser
        115                 120


<210> SEQ ID NO 40
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 40

caagtgcagc tgctggaatc tggcggcgga ctggtgcagc ctggcggtag tctgagactg      60

tcttgcgccg cctccggctt caccttctcc gactacgcca tgtcctgggt ccgacaggcc     120

cctggcaagg gcctggagtg ggtgtccgtg atcgactact cctcctccaa cacctactac     180

gccgactccg tgaagggccg gttcaccatc tcccgggaca actccaagaa caccctgtac     240

ctgcagatga actccctgcg ggccgaggac accgccgtgt actactgcgc cagagagggc     300

tactcctacc ggtccatcag attcgactac tggggccagg gcaccctggt caccgtgtcc     360

tct                                                                   363


<210> SEQ ID NO 41
<211> LENGTH: 224
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Val Ile Asp Tyr Ser Ser Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Tyr Arg Ser Ile Arg Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

Pro Ser Ser Ser Leu Gly Thr Gln Thr Tyr Ile Cys Asn Val Asn His
195 200 205

Lys Pro Ser Asn Thr Lys Val Asp Lys Arg Val Glu Pro Lys Ser Cys
210 215 220

<210> SEQ ID NO 42
<211> LENGTH: 672
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 42
caagtgcagc tgctggaatc tggcggcgga ctggtgcagc ctggcggtag tctgagactg 60
tcttgcgccg cctccggctt caccttctcc gactacgcca tgtcctgggt ccgacaggcc 120
cctggcaagg gcctggagtg ggtgtccgtg atcgactact cctcctccaa cacctactac 180
gccgactccg tgaagggccg gttcaccatc tcccgggaca actccaagaa caccctgtac 240
ctgcagatga actccctgcg ggccgaggac accgccgtgt actactgcgc cagagagggc 300
tactcctacc ggtccatcag attcgactac tggggccagg gcaccctggt caccgtgtcc 360
tctgctagca ccaagggccc ctccgtgttc cctctggccc cttccagcaa gtctacctct 420
ggcggcaccg ctgctctggg ctgcctggtg aaggactact tccctgagcc tgtgacagtg 480
tcctggaact ctggcgccct gacctccggc gtgcacacct tccctgccgt gctgcagtcc 540
tccggcctgt actccctgtc ctccgtggtg acagtgcctt cctccagcct gggcacccag 600
acctatatct gcaacgtgaa ccacaagcct tccaacacca aggtggacaa gcgggtggag 660
cctaagtcat gc 672

<210> SEQ ID NO 43
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 43

Arg Ala Ser Gln Ser Ile Ser Ser Asn Leu Asn
1 5 10

<210> SEQ ID NO 44
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 44

Ala Ala Ser Asn Leu Gln Ser
1 5

<210> SEQ ID NO 45
<211> LENGTH: 9
<212> TYPE: PRT
<213> ORGANISM: Artificial Sequence
<220> FEATURE:

<221> NAME/KEY: source
<223> OTHER INFORMATION: /note="Description of Artificial Sequence: Synthetic peptide"

<400> SEQUENCE: 45

Leu Gln Phe Asp His Thr Pro Phe Thr
1 5

<210> SEQ ID NO 46
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 46

Arg Ala Ser Gln Ser Ile Ser Ser Asn Leu Asn
1 5 10

<210> SEQ ID NO 47
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 47

Ala Ala Ser Asn Leu Gln Ser
1 5

<210> SEQ ID NO 48
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 48

Leu Gln Phe Asp His Thr Pro Phe Thr
1 5

<210> SEQ ID NO 49
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 49

Ser Gln Ser Ile Ser Ser Asn
1 5

<210> SEQ ID NO 50
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 50

Ala Ala Ser
1

<210> SEQ ID NO 51
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 51

Phe Asp His Thr Pro Phe
1               5

<210> SEQ ID NO 52
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 52

Gln Ser Ile Ser Ser Asn
1               5

<210> SEQ ID NO 53
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 53

Ala Ala Ser
1

<210> SEQ ID NO 54
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 54

Leu Gln Phe Asp His Thr Pro Phe Thr
1               5

<210> SEQ ID NO 55
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 55

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Ser Ile Ser Ser Asn
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Phe Asp His Thr Pro Phe
                85                  90                  95

Thr Phe Gly Gln Gly Thr Lys Val Glu Ile Lys
            100                 105


<210> SEQ ID NO 56
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 56

gacatccaga tgacccagag cccctccagc ctgtccgcct ccgtgggcga cagagtgacc      60

atcacctgtc gggcctccca gtccatctcc tccaacctga actggtatca gcagaagccc     120

ggcaaggccc ctaagctgct gatctacgcc gccagcaacc tgcagtccgg cgtgccctcc     180

agattctccg gctctggctc cggcaccgac ttcaccctga ccatctccag cctgcagccc     240

gaggacttcg ccacctacta ctgcctgcag ttcgaccaca ccccttcac cttcggccag      300

ggcaccaaag tggaaatcaa g                                               321


<210> SEQ ID NO 57
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Asn
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Phe Asp His Thr Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 58
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 58
gacatccaga tgacccagag cccctccagc ctgtccgcct ccgtgggcga cagagtgacc 60
atcacctgtc gggcctccca gtccatctcc tccaacctga actggtatca gcagaagccc 120
ggcaaggccc ctaagctgct gatctacgcc gccagcaacc tgcagtccgg cgtgccctcc 180
agattctccg gctctggctc cggcaccgac ttcaccctga ccatctccag cctgcagccc 240
gaggacttcg ccacctacta ctgcctgcag ttcgaccaca ccccctttcac cttcggccag 300 ggcaccaaag tggaaatcaa gcgtacggtg gccgctccca gcgtgttcat cttccccccc 360
agcgacgagc agctgaagag cggcaccgcc agcgtggtgt gcctgctgaa caacttctac 420
ccccgggagg ccaaggtgca gtggaaggtg gacaacgccc tgcagagcgg caacagccag 480
gagagcgtca ccgagcagga cagcaaggac tccacctaca gcctgagcag caccctgacc 540
ctgagcaagg ccgactacga gaagcataag gtgtacgcct gcgaggtgac ccaccagggc 600
ctgtccagcc ccgtgaccaa gagcttcaac aggggcgagt gc 642

<210> SEQ ID NO 59
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 59

Gly Phe Thr Phe Ser Ser Ala Ala Val His
1               5                   10

<210> SEQ ID NO 60
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 60

Arg Ile Lys Ser Lys Ala Asp Gly Gly Thr Thr Asp Tyr Ala Ala Pro
1 5 10 15

Val Lys Gly

<210> SEQ ID NO 61
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 61

Asp Ser Pro Ser Ile Ser Ser Tyr Ser Ile Pro Tyr Phe Ser Gly Met
1 5 10 15

Asp Val

<210> SEQ ID NO 62
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 62

Ser Ala Ala Val His
1 5

<210> SEQ ID NO 63
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 63

Arg Ile Lys Ser Lys Ala Asp Gly Gly Thr Thr Asp Tyr Ala Ala Pro
1 5 10 15

Val Lys Gly

<210> SEQ ID NO 64
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 64

Asp Ser Pro Ser Ile Ser Ser Tyr Ser Ile Pro Tyr Phe Ser Gly Met
1 5 10 15

Asp Val

<210> SEQ ID NO 65
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 65

Gly Phe Thr Phe Ser Ser Ala
1               5

<210> SEQ ID NO 66
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 66

Lys Ser Lys Ala Asp Gly Gly Thr
1               5

<210> SEQ ID NO 67
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 67

Asp Ser Pro Ser Ile Ser Ser Tyr Ser Ile Pro Tyr Phe Ser Gly Met
1               5                   10                  15

Asp Val

<210> SEQ ID NO 68
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 68

Gly Phe Thr Phe Ser Ser Ala Ala
1               5

<210> SEQ ID NO 69
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 69

Ile Lys Ser Lys Ala Asp Gly Gly Thr Thr
1               5                   10

<210> SEQ ID NO 70
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 70

Ala Arg Asp Ser Pro Ser Ile Ser Ser Tyr Ser Ile Pro Tyr Phe Ser
1 5 10 15

Gly Met Asp Val
20

<210> SEQ ID NO 71
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 71

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Ala
20 25 30

Ala Val His Trp Val Arg Gln Ala Pro Gly Lys Gly Leu Glu Trp Val
35 40 45

Gly Arg Ile Lys Ser Lys Ala Asp Gly Gly Thr Thr Asp Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asn Ser Leu Lys Thr Glu Asp Thr Ala Val Tyr
85 90 95

Tyr Cys Ala Arg Asp Ser Pro Ser Ile Ser Ser Tyr Ser Ile Pro Tyr
100 105 110

Phe Ser Gly Met Asp Val Trp Gly Gln Gly Thr Leu Val Thr Val Ser
115 120 125

Ser

<210> SEQ ID NO 72
<211> LENGTH: 387
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 72
caagtgcagc tggtggaatc tggcggcgga ctggtcaagc ctggcggtag cctgagactg 60
tcttgcgccg cctccggctt caccttctcc tctgccgctg tgcactgggt ccgacaggcc 120
cctggcaagg gcctggagtg ggtcggacgg atcaagtcca aggccgacgg cggcaccacc 180
gactacgctg cccctgtgaa gggccggttc accatctccc gggacgactc caagaacacc 240
ctgtacctgc agatgaactc cctgaaaacc gaggacaccg ccgtgtacta ctgcgccaga 300
gactccccat ctatctccag ctactccatc ccctacttct ccggcatgga cgtgtggggc 360
cagggcaccc tggtcaccgt gtcctct 387

<210> SEQ ID NO 73
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 73

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Ala
            20                  25                  30

Ala Val His Trp Val Arg Gln Ala Pro Gly Lys Gly Leu Glu Trp Val
        35                  40                  45

Gly Arg Ile Lys Ser Lys Ala Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Ser Pro Ser Ile Ser Ser Tyr Ser Ile Pro Tyr
            100                 105                 110

Phe Ser Gly Met Asp Val Trp Gly Gln Gly Thr Leu Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Arg Val Glu Pro Lys Ser Cys
225                 230
```

<210> SEQ ID NO 74
<211> LENGTH: 696
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 74

```
caagtgcagc tggtggaatc tggcggcgga ctggtcaagc ctggcggtag cctgagactg     60

tcttgcgccg cctccggctt caccttctcc tctgccgctg tgcactgggt ccgacaggcc    120

cctggcaagg gcctggagtg ggtcggacgg atcaagtcca aggccgacgg cggcaccacc    180

gactacgctg cccctgtgaa gggccggttc accatctccc gggacgactc caagaacacc    240

ctgtacctgc agatgaactc cctgaaaacc gaggacaccg ccgtgtacta ctgcgccaga    300

gactccccat ctatctccag ctactccatc ccctacttct ccggcatgga cgtgtggggc    360

cagggcaccc tggtcaccgt gtcctctgct agcaccaagg gcccctccgt gttccctctg    420

gccccttcca gcaagtctac ctctggcggc accgctgctc tgggctgcct ggtgaaggac    480

tacttccctg agcctgtgac agtgtcctgg aactctggcg ccctgacctc cggcgtgcac    540
```

accttccctg ccgtgctgca gtcctccggc ctgtactccc tgtcctccgt ggtgacagtg 600
ccttcctcca gcctgggcac ccagacctat atctgcaacg tgaaccacaa gccttccaac 660
accaaggtgg acaagcgggt ggagcctaag tcatgc 696

<210> SEQ ID NO 75
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 75

Arg Ala Ser Gln Gly Ile Arg Ala Trp Leu Asn
1 5 10

<210> SEQ ID NO 76
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 76

Ala Ala Ser Ser Leu Gln Ser
1 5

<210> SEQ ID NO 77
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 77

His Gln Tyr Ile Thr His Pro Pro Thr
1 5

<210> SEQ ID NO 78
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 78

Arg Ala Ser Gln Gly Ile Arg Ala Trp Leu Asn
1 5 10

<210> SEQ ID NO 79
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 79

Ala Ala Ser Ser Leu Gln Ser
1 5

<210> SEQ ID NO 80
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 80

His Gln Tyr Ile Thr His Pro Pro Thr
1 5

<210> SEQ ID NO 81
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 81

Ser Gln Gly Ile Arg Ala Trp
1 5

<210> SEQ ID NO 82
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 82

Ala Ala Ser
1

<210> SEQ ID NO 83
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 83

Tyr Ile Thr His Pro Pro
1 5

<210> SEQ ID NO 84
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 84

Gln Gly Ile Arg Ala Trp
1 5

-continued

<210> SEQ ID NO 85
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 85

Ala Ala Ser
1

<210> SEQ ID NO 86
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 86

His Gln Tyr Ile Thr His Pro Pro Thr
1 5

<210> SEQ ID NO 87
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 87

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Ala Trp
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys His Gln Tyr Ile Thr His Pro Pro
85 90 95

Thr Phe Gly Gln Gly Thr Lys Val Glu Ile Lys
100 105

<210> SEQ ID NO 88
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 88
gacatccaga tgacccagag cccctccagc ctgtccgcct ccgtgggcga cagagtgacc 60
atcacctgtc gggcctctca gggcatccgg gcctggctga actggtatca gcagaagccc 120
ggcaaggccc ctaagctgct gatctacgcc gccagctccc tgcagtccgg cgtgccctcc 180
agattctccg gctctggctc cggcaccgac ttcaccctga ccatctccag cctgcagccc 240
gaggacttcg ccacctacta ctgccaccag tacatcaccc accctcccac cttcggccag 300
ggcaccaaag tggaaatcaa g 321

<210> SEQ ID NO 89
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 89

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Ala Trp
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys His Gln Tyr Ile Thr His Pro Pro
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 90
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 90
gacatccaga tgacccagag cccctccagc ctgtccgcct ccgtgggcga cagagtgacc 60
atcacctgtc gggcctctca gggcatccgg gcctggctga actggtatca gcagaagccc 120
ggcaaggccc ctaagctgct gatctacgcc gccagctccc tgcagtccgg cgtgccctcc 180

```
agattctccg gctctggctc cggcaccgac ttcaccctga ccatctccag cctgcagccc    240

gaggacttcg ccacctacta ctgccaccag tacatcaccc accctcccac cttcggccag    300

ggcaccaaag tggaaatcaa gcgtacggtg gccgctccca gcgtgttcat cttccccccc    360

agcgacgagc agctgaagag cggcaccgcc agcgtggtgt gcctgctgaa caacttctac    420

ccccgggagg ccaaggtgca gtggaaggtg gacaacgccc tgcagagcgg caacagccag    480

gagagcgtca ccgagcagga cagcaaggac tccacctaca gcctgagcag caccctgacc    540

ctgagcaagg ccgactacga gaagcataag gtgtacgcct gcgaggtgac ccaccagggc    600

ctgtccagcc ccgtgaccaa gagcttcaac aggggcgagt gc                       642
```

```
<210> SEQ ID NO 91
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Gly Phe Thr Phe Gln Ser Ala Ala Val His
1               5                   10


<210> SEQ ID NO 92
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Arg Ile Lys Ser Lys Ala Asp Gly Gly Thr Thr Asp Tyr Ala Ala Pro
1               5                   10                  15

Val Lys Gly


<210> SEQ ID NO 93
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Asp Ser Pro Ser Ile Ser Ser Tyr Ser Ile Pro Tyr Phe Ser Gly Met
1               5                   10                  15

Asp Val


<210> SEQ ID NO 94
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Ser Ala Ala Val His
1               5
```

<210> SEQ ID NO 95
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 95

Arg Ile Lys Ser Lys Ala Asp Gly Gly Thr Thr Asp Tyr Ala Ala Pro
1 5 10 15

Val Lys Gly

<210> SEQ ID NO 96
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 96

Asp Ser Pro Ser Ile Ser Ser Tyr Ser Ile Pro Tyr Phe Ser Gly Met
1 5 10 15

Asp Val

<210> SEQ ID NO 97
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 97

Gly Phe Thr Phe Gln Ser Ala
1 5

<210> SEQ ID NO 98
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 98

Lys Ser Lys Ala Asp Gly Gly Thr
1 5

<210> SEQ ID NO 99
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 99

Asp Ser Pro Ser Ile Ser Ser Tyr Ser Ile Pro Tyr Phe Ser Gly Met
1 5 10 15

Asp Val

<210> SEQ ID NO 100
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 100

Gly Phe Thr Phe Gln Ser Ala Ala
1 5

<210> SEQ ID NO 101
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 101

Ile Lys Ser Lys Ala Asp Gly Gly Thr Thr
1 5 10

<210> SEQ ID NO 102
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 102

Ala Arg Asp Ser Pro Ser Ile Ser Ser Tyr Ser Ile Pro Tyr Phe Ser
1 5 10 15

Gly Met Asp Val
20

<210> SEQ ID NO 103
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 103

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Gln Ser Ala
20 25 30

Ala Val His Trp Val Arg Gln Ala Pro Gly Lys Gly Leu Glu Trp Val
35 40 45

Gly Arg Ile Lys Ser Lys Ala Asp Gly Gly Thr Thr Asp Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asn Ser Leu Lys Thr Glu Asp Thr Ala Val Tyr

```
                85                  90                  95

Tyr Cys Ala Arg Asp Ser Pro Ser Ile Ser Ser Tyr Ser Ile Pro Tyr
            100                 105                 110

Phe Ser Gly Met Asp Val Trp Gly Gln Gly Thr Leu Val Thr Val Ser
        115                 120                 125

Ser


<210> SEQ ID NO 104
<211> LENGTH: 387
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 104

caagtgcagc tggtggaatc tggcggcgga ctggtcaagc ctggcggtag cctgagactg     60

tcttgcgccg cctccggctt caccttccag tctgccgctg tgcactgggt ccgacaggcc    120

cctggcaagg gcctggagtg ggtcggacgg atcaagtcca aggccgacgg cggcaccacc    180

gactacgctg cccctgtgaa gggccggttc accatctccc gggacgactc caagaacacc    240

ctgtacctgc agatgaactc cctgaaaacc gaggacaccg ccgtgtacta ctgcgccaga    300

gactccccat ctatctccag ctactccatc ccctacttct ccggcatgga cgtgtggggc    360

cagggcaccc tggtcaccgt gtcctct                                        387


<210> SEQ ID NO 105
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 105

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gln Ser Ala
            20                  25                  30

Ala Val His Trp Val Arg Gln Ala Pro Gly Lys Gly Leu Glu Trp Val
        35                  40                  45

Gly Arg Ile Lys Ser Lys Ala Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Ser Pro Ser Ile Ser Ser Tyr Ser Ile Pro Tyr
            100                 105                 110

Phe Ser Gly Met Asp Val Trp Gly Gln Gly Thr Leu Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
```

```
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Arg Val Glu Pro Lys Ser Cys
225                 230


<210> SEQ ID NO 106
<211> LENGTH: 696
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 106

caagtgcagc tggtggaatc tggcggcgga ctggtcaagc ctggcggtag cctgagactg     60

tcttgcgccg cctccggctt caccttccag tctgccgctg tgcactgggt ccgacaggcc    120

cctggcaagg gcctggagtg ggtcggacgg atcaagtcca aggccgacgg cggcaccacc    180

gactacgctg cccctgtgaa gggccggttc accatctccc gggacgactc caagaacacc    240

ctgtacctgc agatgaactc cctgaaaacc gaggacaccg ccgtgtacta ctgcgccaga    300

gactccccat ctatctccag ctactccatc ccctacttct ccggcatgga cgtgtggggc    360

cagggcaccc tggtcaccgt gtcctctgct agcaccaagg gcccctccgt gttccctctg    420

gccccttcca gcaagtctac ctctggcggc accgctgctc tgggctgcct ggtgaaggac    480

tacttccctg agcctgtgac agtgtcctgg aactctggcg ccctgacctc cggcgtgcac    540

accttccctg ccgtgctgca gtcctccggc ctgtactccc tgtcctccgt ggtgacagtg    600

ccttcctcca gcctgggcac ccagacctat atctgcaacg tgaaccacaa gccttccaac    660

accaaggtgg acaagcgggt ggagcctaag tcatgc                              696


<210> SEQ ID NO 107
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Arg Ala Ser Gln Gly Ile Arg Ala Trp Leu Asn
1               5                   10


<210> SEQ ID NO 108
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Ala Ala Ser Ser Leu Gln Ser
1               5
```

<210> SEQ ID NO 109
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 109

His Gln Tyr Ile Thr His Pro Pro Thr
1               5

<210> SEQ ID NO 110
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 110

Arg Ala Ser Gln Gly Ile Arg Ala Trp Leu Asn
1               5                   10

<210> SEQ ID NO 111
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 111

Ala Ala Ser Ser Leu Gln Ser
1               5

<210> SEQ ID NO 112
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 112

His Gln Tyr Ile Thr His Pro Pro Thr
1               5

<210> SEQ ID NO 113
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 113

Ser Gln Gly Ile Arg Ala Trp
1               5

<210> SEQ ID NO 114
<211> LENGTH: 3

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

Ala Ala Ser
1


<210> SEQ ID NO 115
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Tyr Ile Thr His Pro Pro
1               5


<210> SEQ ID NO 116
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Gln Gly Ile Arg Ala Trp
1               5


<210> SEQ ID NO 117
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Ala Ala Ser
1


<210> SEQ ID NO 118
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

His Gln Tyr Ile Thr His Pro Pro Thr
1               5


<210> SEQ ID NO 119
<211> LENGTH: 107
<212> TYPE: PRT
<213> ORGANISM: Artificial Sequence
<220> FEATURE:
<221> NAME/KEY: source
```

<223> OTHER INFORMATION: /note="Description of Artificial Sequence: Synthetic polypeptide"

<400> SEQUENCE: 119

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Ala Trp
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys His Gln Tyr Ile Thr His Pro Pro
85 90 95

Thr Phe Gly Gln Gly Thr Lys Val Glu Ile Lys
100 105

<210> SEQ ID NO 120
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 120
gacatccaga tgacccagag cccctccagc ctgtccgcct ccgtgggcga cagagtgacc 60
atcacctgtc gggcctctca gggcatccgg gcctggctga actggtatca gcagaagccc 120
ggcaaggccc ctaagctgct gatctacgcc gccagctccc tgcagtccgg cgtgccctcc 180
agattctccg gctctggctc cggcaccgac ttcaccctga ccatctccag cctgcagccc 240
gaggacttcg ccacctacta ctgccaccag tacatcaccc accctcccac cttcggccag 300
ggcaccaaag tggaaatcaa g 321

<210> SEQ ID NO 121
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 121

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Ala Trp
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys His Gln Tyr Ile Thr His Pro Pro
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 122
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 122
gacatccaga tgacccagag cccctccagc ctgtccgcct ccgtgggcga cagagtgacc 60
atcacctgtc gggcctctca gggcatccgg gcctggctga actggtatca gcagaagccc 120
ggcaaggccc ctaagctgct gatctacgcc gccagctccc tgcagtccgg cgtgccctcc 180
agattctccg gctctggctc cggcaccgac ttcaccctga ccatctccag cctgcagccc 240
gaggacttcg ccacctacta ctgccaccag tacatcaccc accctcccac cttcggccag 300
ggcaccaaag tggaaatcaa gcgtacggtg gccgctccca gcgtgttcat cttccccccc 360
agcgacgagc agctgaagag cggcaccgcc agcgtggtgt gcctgctgaa caacttctac 420
ccccgggagg ccaaggtgca gtggaaggtg gacaacgccc tgcagagcgg caacagccag 480
gagagcgtca ccgagcagga cagcaaggac tccacctaca gcctgagcag caccctgacc 540
ctgagcaagg ccgactacga gaagcataag gtgtacgcct gcgaggtgac ccaccagggc 600
ctgtccagcc ccgtgaccaa gagcttcaac aggggcgagt gc 642

<210> SEQ ID NO 123
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 123

Gly Phe Thr Phe Ser Ser Ala Ala Val His
1 5 10

<210> SEQ ID NO 124
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 124

Arg Ile Lys Ser Lys Ala Ser Gly Gly Thr Thr Asp Tyr Ala Ala Pro
1 5 10 15

Val Lys Gly

<210> SEQ ID NO 125
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 125

Asp Ser Pro Ser Ile Ser Ser Tyr Ser Ile Pro Tyr Phe Ser Gly Met
1 5 10 15

Asp Val

<210> SEQ ID NO 126
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 126

Ser Ala Ala Val His
1 5

<210> SEQ ID NO 127
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 127

Arg Ile Lys Ser Lys Ala Ser Gly Gly Thr Thr Asp Tyr Ala Ala Pro
1 5 10 15

Val Lys Gly

<210> SEQ ID NO 128
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 128

Asp Ser Pro Ser Ile Ser Ser Tyr Ser Ile Pro Tyr Phe Ser Gly Met
1 5 10 15

Asp Val

<210> SEQ ID NO 129
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 129

Gly Phe Thr Phe Ser Ser Ala
1 5

<210> SEQ ID NO 130
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 130

Lys Ser Lys Ala Ser Gly Gly Thr
1 5

<210> SEQ ID NO 131
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 131

Asp Ser Pro Ser Ile Ser Ser Tyr Ser Ile Pro Tyr Phe Ser Gly Met
1 5 10 15

Asp Val

<210> SEQ ID NO 132
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 132

Gly Phe Thr Phe Ser Ser Ala Ala
1 5

<210> SEQ ID NO 133
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 133

Ile Lys Ser Lys Ala Ser Gly Gly Thr Thr
1 5 10

<210> SEQ ID NO 134
<211> LENGTH: 20

<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 134

Ala Arg Asp Ser Pro Ser Ile Ser Ser Tyr Ser Ile Pro Tyr Phe Ser
1 5 10 15

Gly Met Asp Val
20

<210> SEQ ID NO 135
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 135

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Ala
20 25 30

Ala Val His Trp Val Arg Gln Ala Pro Gly Lys Gly Leu Glu Trp Val
35 40 45

Gly Arg Ile Lys Ser Lys Ala Ser Gly Gly Thr Thr Asp Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asn Ser Leu Lys Thr Glu Asp Thr Ala Val Tyr
85 90 95

Tyr Cys Ala Arg Asp Ser Pro Ser Ile Ser Ser Tyr Ser Ile Pro Tyr
100 105 110

Phe Ser Gly Met Asp Val Trp Gly Gln Gly Thr Leu Val Thr Val Ser
115 120 125

Ser

<210> SEQ ID NO 136
<211> LENGTH: 387
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 136
caagtgcagc tggtggaatc tggcggcgga ctggtcaagc ctggcggtag cctgagactg 60
tcttgcgccg cctccggctt caccttctcc tctgccgctg tgcactgggt ccgacaggcc 120
cctggcaagg gcctggagtg ggtcggacgg atcaagtcca aggcctccgg cggcaccacc 180
gactacgctg cccctgtgaa gggccggttc accatctccc gggacgactc caagaacacc 240
ctgtacctgc agatgaactc cctgaaaacc gaggacaccg ccgtgtacta ctgcgccaga 300
gactccccat ctatctccag ctactccatc ccctacttct ccggcatgga cgtgtggggc 360
cagggcaccc tggtcaccgt gtcctct 387

<210> SEQ ID NO 137
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 137

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Ala
            20                  25                  30

Ala Val His Trp Val Arg Gln Ala Pro Gly Lys Gly Leu Glu Trp Val
        35                  40                  45

Gly Arg Ile Lys Ser Lys Ala Ser Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Ser Pro Ser Ile Ser Ser Tyr Ser Ile Pro Tyr
            100                 105                 110

Phe Ser Gly Met Asp Val Trp Gly Gln Gly Thr Leu Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Arg Val Glu Pro Lys Ser Cys
225                 230
```

<210> SEQ ID NO 138
<211> LENGTH: 696
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 138

```
caagtgcagc tggtggaatc tggcggcgga ctggtcaagc ctggcggtag cctgagactg     60

tcttgcgccg cctccggctt caccttctcc tctgccgctg tgcactgggt ccgacaggcc    120

cctggcaagg gcctggagtg ggtcggacgg atcaagtcca aggcctccgg cggcaccacc    180

gactacgctg cccctgtgaa gggccggttc accatctccc gggacgactc caagaacacc    240

ctgtacctgc agatgaactc cctgaaaacc gaggacaccg ccgtgtacta ctgcgccaga    300
```

```
gactccccat ctatctccag ctactccatc ccctacttct ccggcatgga cgtgtggggc    360

cagggcaccc tggtcaccgt gtcctctgct agcaccaagg gcccctccgt gttccctctg    420

gccccttcca gcaagtctac ctctggcggc accgctgctc tgggctgcct ggtgaaggac    480

tacttccctg agcctgtgac agtgtcctgg aactctggcg ccctgacctc cggcgtgcac    540

accttccctg ccgtgctgca gtcctccggc ctgtactccc tgtcctccgt ggtgacagtg    600

ccttcctcca gcctgggcac ccagacctat atctgcaacg tgaaccacaa gccttccaac    660

accaaggtgg acaagcgggt ggagcctaag tcatgc                              696
```

<210> SEQ ID NO 139
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 139

```
Arg Ala Ser Gln Gly Ile Arg Ala Trp Leu Asn
1               5                   10
```

<210> SEQ ID NO 140
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 140

```
Ala Ala Ser Ser Leu Gln Ser
1               5
```

<210> SEQ ID NO 141
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 141

```
His Gln Tyr Ile Thr His Pro Pro Thr
1               5
```

<210> SEQ ID NO 142
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 142

```
Arg Ala Ser Gln Gly Ile Arg Ala Trp Leu Asn
1               5                   10
```

<210> SEQ ID NO 143
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 143

Ala Ala Ser Ser Leu Gln Ser
1 5

<210> SEQ ID NO 144
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 144

His Gln Tyr Ile Thr His Pro Pro Thr
1 5

<210> SEQ ID NO 145
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 145

Ser Gln Gly Ile Arg Ala Trp
1 5

<210> SEQ ID NO 146
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 146

Ala Ala Ser
1

<210> SEQ ID NO 147
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 147

Tyr Ile Thr His Pro Pro
1 5

<210> SEQ ID NO 148
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 148

Gln Gly Ile Arg Ala Trp
1               5

<210> SEQ ID NO 149
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 149

Ala Ala Ser
1

<210> SEQ ID NO 150
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 150

His Gln Tyr Ile Thr His Pro Pro Thr
1               5

<210> SEQ ID NO 151
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 151

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ala Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Ile Thr His Pro Pro
                85                  90                  95

Thr Phe Gly Gln Gly Thr Lys Val Glu Ile Lys
            100                 105

<210> SEQ ID NO 152
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 152
gacatccaga tgacccagag cccctccagc ctgtccgcct ccgtgggcga cagagtgacc 60
atcacctgtc gggcctctca gggcatccgg gcctggctga actggtatca gcagaagccc 120
ggcaaggccc ctaagctgct gatctacgcc gccagctccc tgcagtccgg cgtgccctcc 180
agattctccg gctctggctc cggcaccgac ttcaccctga ccatctccag cctgcagccc 240
gaggacttcg ccacctacta ctgccaccag tacatcaccc accctcccac cttcggccag 300
ggcaccaaag tggaaatcaa g 321

<210> SEQ ID NO 153
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 153

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Ala Trp
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys His Gln Tyr Ile Thr His Pro Pro
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 154
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 154

```
gacatccaga tgacccagag cccctccagc ctgtccgcct ccgtgggcga cagagtgacc     60

atcacctgtc gggcctctca gggcatccgg gcctggctga actggtatca gcagaagccc    120

ggcaaggccc ctaagctgct gatctacgcc gccagctccc tgcagtccgg cgtgccctcc    180

agattctccg gctctggctc cggcaccgac ttcaccctga ccatctccag cctgcagccc    240

gaggacttcg ccacctacta ctgccaccag tacatcaccc accctcccac cttcggccag    300

ggcaccaaag tggaaatcaa gcgtacggtg gccgctccca gcgtgttcat cttccccccc    360

agcgacgagc agctgaagag cggcaccgcc agcgtggtgt gcctgctgaa caacttctac    420

ccccgggagg ccaaggtgca gtggaaggtg gacaacgccc tgcagagcgg caacagccag    480

gagagcgtca ccgagcagga cagcaaggac tccacctaca gcctgagcag caccctgacc    540

ctgagcaagg ccgactacga gaagcataag gtgtacgcct gcgaggtgac ccaccagggc    600

ctgtccagcc ccgtgaccaa gagcttcaac aggggcgagt gc                       642
```

```
<210> SEQ ID NO 155
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Gly Phe Thr Phe Ser Ser Ala Ala Val His
1               5                   10


<210> SEQ ID NO 156
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 156

Arg Ile Lys Ser Lys Ala Asp Ala Gly Thr Thr Asp Tyr Ala Ala Pro
1               5                   10                  15

Val Lys Gly


<210> SEQ ID NO 157
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 157

Asp Ser Pro Ser Ile Ser Ser Tyr Ser Ile Pro Tyr Phe Ser Gly Met
1               5                   10                  15

Asp Val


<210> SEQ ID NO 158
<211> LENGTH: 5
<212> TYPE: PRT
<213> ORGANISM: Artificial Sequence
<220> FEATURE:
<221> NAME/KEY: source
```

<223> OTHER INFORMATION: /note="Description of Artificial Sequence: Synthetic peptide"

<400> SEQUENCE: 158

Ser Ala Ala Val His
1 5

<210> SEQ ID NO 159
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 159

Arg Ile Lys Ser Lys Ala Asp Ala Gly Thr Thr Asp Tyr Ala Ala Pro
1 5 10 15

Val Lys Gly

<210> SEQ ID NO 160
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 160

Asp Ser Pro Ser Ile Ser Ser Tyr Ser Ile Pro Tyr Phe Ser Gly Met
1 5 10 15

Asp Val

<210> SEQ ID NO 161
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 161

Gly Phe Thr Phe Ser Ser Ala
1 5

<210> SEQ ID NO 162
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 162

Lys Ser Lys Ala Asp Ala Gly Thr
1 5

<210> SEQ ID NO 163
<211> LENGTH: 18
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 163

Asp Ser Pro Ser Ile Ser Ser Tyr Ser Ile Pro Tyr Phe Ser Gly Met
1               5                   10                  15

Asp Val


<210> SEQ ID NO 164
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 164

Gly Phe Thr Phe Ser Ser Ala Ala
1               5


<210> SEQ ID NO 165
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 165

Ile Lys Ser Lys Ala Asp Ala Gly Thr Thr
1               5                   10


<210> SEQ ID NO 166
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Ala Arg Asp Ser Pro Ser Ile Ser Ser Tyr Ser Ile Pro Tyr Phe Ser
1               5                   10                  15

Gly Met Asp Val
            20


<210> SEQ ID NO 167
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 167

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Ala
            20                  25                  30

Ala Val His Trp Val Arg Gln Ala Pro Gly Lys Gly Leu Glu Trp Val
        35                  40                  45
```

Gly Arg Ile Lys Ser Lys Ala Asp Ala Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Ser Pro Ser Ile Ser Ser Tyr Ser Ile Pro Tyr
            100                 105                 110

Phe Ser Gly Met Asp Val Trp Gly Gln Gly Thr Leu Val Thr Val Ser
        115                 120                 125

Ser

<210> SEQ ID NO 168
<211> LENGTH: 387
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 168
caagtgcagc tggtggaatc tggcggcgga ctggtcaagc ctggcggtag cctgagactg 60
tcttgcgccg cctccggctt caccttctcc tctgccgctg tgcactgggt ccgacaggcc 120
cctggcaagg gcctggagtg ggtcggacgg atcaagtcca aggccgacgc cggcaccacc 180
gactacgctg cccctgtgaa gggccggttc accatctccc gggacgactc caagaacacc 240
ctgtacctgc agatgaactc cctgaaaacc gaggacaccg ccgtgtacta ctgcgccaga 300
gactccccat ctatctccag ctactccatc ccctacttct ccggcatgga cgtgtggggc 360
cagggcaccc tggtcaccgt gtcctct 387

<210> SEQ ID NO 169
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 169

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Ala
            20                  25                  30

Ala Val His Trp Val Arg Gln Ala Pro Gly Lys Gly Leu Glu Trp Val
        35                  40                  45

Gly Arg Ile Lys Ser Lys Ala Asp Ala Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Ser Pro Ser Ile Ser Ser Tyr Ser Ile Pro Tyr
            100                 105                 110

Phe Ser Gly Met Asp Val Trp Gly Gln Gly Thr Leu Val Thr Val Ser
        115                 120                 125

-continued

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Arg Val Glu Pro Lys Ser Cys
225                 230

<210> SEQ ID NO 170
<211> LENGTH: 696
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 170
caagtgcagc tggtggaatc tggcggcgga ctggtcaagc ctggcggtag cctgagactg 60
tcttgcgccg cctccggctt caccttctcc tctgccgctg tgcactgggt ccgacaggcc 120
cctggcaagg gcctggagtg ggtcggacgg atcaagtcca aggccgacgc cggcaccacc 180
gactacgctg cccctgtgaa gggccggttc accatctccc gggacgactc caagaacacc 240
ctgtacctgc agatgaactc cctgaaaacc gaggacaccg ccgtgtacta ctgcgccaga 300
gactccccat ctatctccag ctactccatc ccctacttct ccggcatgga cgtgtggggc 360
cagggcaccc tggtcaccgt gtcctctgct agcaccaagg gcccctccgt gttccctctg 420
gccccttcca gcaagtctac ctctggcggc accgctgctc tgggctgcct ggtgaaggac 480
tacttccctg agcctgtgac agtgtcctgg aactctggcg ccctgacctc cggcgtgcac 540
accttccctg ccgtgctgca gtcctccggc ctgtactccc tgtcctccgt ggtgacagtg 600
ccttcctcca gcctgggcac ccagacctat atctgcaacg tgaaccacaa gccttccaac 660
accaaggtgg acaagcgggt ggagcctaag tcatgc 696

<210> SEQ ID NO 171
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 171

Arg Ala Ser Gln Gly Ile Arg Ala Trp Leu Asn
1               5                   10

<210> SEQ ID NO 172
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 172

Ala Ala Ser Ser Leu Gln Ser
1 5

<210> SEQ ID NO 173
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 173

His Gln Tyr Ile Thr His Pro Pro Thr
1 5

<210> SEQ ID NO 174
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 174

Arg Ala Ser Gln Gly Ile Arg Ala Trp Leu Asn
1 5 10

<210> SEQ ID NO 175
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 175

Ala Ala Ser Ser Leu Gln Ser
1 5

<210> SEQ ID NO 176
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 176

His Gln Tyr Ile Thr His Pro Pro Thr
1 5

<210> SEQ ID NO 177
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 177

Ser Gln Gly Ile Arg Ala Trp
1 5

<210> SEQ ID NO 178
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 178

Ala Ala Ser
1

<210> SEQ ID NO 179
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 179

Tyr Ile Thr His Pro Pro
1 5

<210> SEQ ID NO 180
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 180

Gln Gly Ile Arg Ala Trp
1 5

<210> SEQ ID NO 181
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 181

Ala Ala Ser
1

<210> SEQ ID NO 182
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 182

His Gln Tyr Ile Thr His Pro Pro Thr
1 5

<210> SEQ ID NO 183
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 183

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ala Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Ile Thr His Pro Pro
                85                  90                  95

Thr Phe Gly Gln Gly Thr Lys Val Glu Ile Lys
            100                 105
```

<210> SEQ ID NO 184
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 184

```
gacatccaga tgacccagag cccctccagc ctgtccgcct ccgtgggcga cagagtgacc     60

atcacctgtc gggcctctca gggcatccgg gcctggctga actggtatca gcagaagccc    120

ggcaaggccc ctaagctgct gatctacgcc gccagctccc tgcagtccgg cgtgccctcc    180

agattctccg gctctggctc cggcaccgac ttcaccctga ccatctccag cctgcagccc    240

gaggacttcg ccacctacta ctgccaccag tacatcaccc accctcccac cttcggccag    300

ggcaccaaag tggaaatcaa g                                              321
```

<210> SEQ ID NO 185
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 185

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ala Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
```

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Ile Thr His Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 186
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 186

```
gacatccaga tgacccagag cccctccagc ctgtccgcct ccgtgggcga cagagtgacc     60

atcacctgtc gggcctctca gggcatccgg gcctggctga actggtatca gcagaagccc    120

ggcaaggccc ctaagctgct gatctacgcc gccagctccc tgcagtccgg cgtgccctcc    180

agattctccg gctctggctc cggcaccgac ttcaccctga ccatctccag cctgcagccc    240

gaggacttcg ccacctacta ctgccaccag tacatcaccc accctcccac cttcggccag    300

ggcaccaaag tggaaatcaa gcgtacggtg gccgctccca gcgtgttcat cttccccccc    360

agcgacgagc agctgaagag cggcaccgcc agcgtggtgt gcctgctgaa caacttctac    420

cccgggagg ccaaggtgca gtggaaggtg gacaacgccc tgcagagcgg caacagccag    480

gagagcgtca ccgagcagga cagcaaggac tccacctaca gcctgagcag caccctgacc    540

ctgagcaagg ccgactacga gaagcataag gtgtacgcct gcgaggtgac ccaccagggc    600

ctgtccagcc ccgtgaccaa gagcttcaac aggggcgagt gc                       642
```

<210> SEQ ID NO 187
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 187

```
Gly Tyr Ser Phe Thr Asn Tyr Trp Ile Gly
```

1 5 10

<210> SEQ ID NO 188
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 188

Ile Ile Phe Pro Gly Val Ser Tyr Thr Lys Tyr Ser Pro Ser Phe Gln
1 5 10 15

Gly

<210> SEQ ID NO 189
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 189

Gly Ser Asp Gln Thr Leu Arg Gly Ser Arg Ala Met Asp Tyr
1 5 10

<210> SEQ ID NO 190
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 190

Asn Tyr Trp Ile Gly
1 5

<210> SEQ ID NO 191
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 191

Ile Ile Phe Pro Gly Val Ser Tyr Thr Lys Tyr Ser Pro Ser Phe Gln
1 5 10 15

Gly

<210> SEQ ID NO 192
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 192

Gly Ser Asp Gln Thr Leu Arg Gly Ser Arg Ala Met Asp Tyr 1 5 10

<210> SEQ ID NO 193
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 193

Gly Tyr Ser Phe Thr Asn Tyr
1 5

<210> SEQ ID NO 194
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 194

Phe Pro Gly Val Ser Tyr
1 5

<210> SEQ ID NO 195
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 195

Gly Ser Asp Gln Thr Leu Arg Gly Ser Arg Ala Met Asp Tyr
1 5 10

<210> SEQ ID NO 196
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 196

Gly Tyr Ser Phe Thr Asn Tyr Trp
1 5

<210> SEQ ID NO 197
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 197

Ile Phe Pro Gly Val Ser Tyr Thr
1 5

<210> SEQ ID NO 198

-continued

<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 198

Ala Arg Gly Ser Asp Gln Thr Leu Arg Gly Ser Arg Ala Met Asp Tyr
1 5 10 15

<210> SEQ ID NO 199
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 199

Gln Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Asn Tyr
20 25 30

Trp Ile Gly Trp Val Arg Gln Met Pro Gly Lys Gly Leu Glu Trp Met
35 40 45

Gly Ile Ile Phe Pro Gly Val Ser Tyr Thr Lys Tyr Ser Pro Ser Phe
50 55 60

Gln Gly Gln Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Arg Gly Ser Asp Gln Thr Leu Arg Gly Ser Arg Ala Met Asp Tyr
100 105 110

Trp Gly Gln Gly Thr Leu Val Thr Val Ser Ser
115 120

<210> SEQ ID NO 200
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 200
caagtgcagc tggtgcagtc tggcgctgaa gtgaagaagc ccggcgagtc cctgaagatc 60
tcctgcaagg gctccggcta ctccttcacc aactactgga tcggctgggt ccgacagatg 120
cccggcaagg gcctggagtg gatgggcatc atcttccccg gcgtgtccta caccaagtac 180
agccccagct tccagggcca agtcacaatc tccgccgaca agtccatctc caccgcctac 240
ctgcagtggt cctccctgaa ggcctccgac accgccatgt actactgcgc cagaggctcc 300
gaccagaccc tgcggggctc cagagccatg gattactggg gccagggcac cctggtcacc 360
gtgtcctct 369

<210> SEQ ID NO 201
<211> LENGTH: 226
<212> TYPE: PRT

<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 201

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Phe Pro Gly Val Ser Tyr Thr Lys Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Ser Asp Gln Thr Leu Arg Gly Ser Arg Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys
225
```

<210> SEQ ID NO 202
<211> LENGTH: 678
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 202

```
caagtgcagc tggtgcagtc tggcgctgaa gtgaagaagc ccggcgagtc cctgaagatc     60

tcctgcaagg gctccggcta ctccttcacc aactactgga tcggctgggt ccgacagatg    120

cccggcaagg gcctggagtg gatgggcatc atcttccccg gcgtgtccta caccaagtac    180

agccccagct tccagggcca agtcacaatc tccgccgaca agtccatctc caccgcctac    240

ctgcagtggt cctccctgaa ggcctccgac accgccatgt actactgcgc cagaggctcc    300

gaccagaccc tgcggggctc cagagccatg gattactggg gccagggcac cctggtcacc    360

gtgtcctctg ctagcaccaa gggcccctcc gtgttccctc tggccccttc cagcaagtct    420
```

acctctggcg gcaccgctgc tctgggctgc ctggtgaagg actacttccc tgagcctgtg 480
acagtgtcct ggaactctgg cgccctgacc tccggcgtgc acaccttccc tgccgtgctg 540
cagtcctccg gcctgtactc cctgtcctcc gtggtgacag tgccttcctc cagcctgggc 600
acccagacct atatctgcaa cgtgaaccac aagccttcca acaccaaggt ggacaagcgg 660
gtggagccta agtcatgc 678

<210> SEQ ID NO 203
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 203

Thr Gly Thr Ser Ser Asp Val Gly Ile Ser Asn Tyr Val Ser
1 5 10

<210> SEQ ID NO 204
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 204

Glu Val Ser Asn Arg Pro Ser
1 5

<210> SEQ ID NO 205
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 205

Gln Ser Tyr Thr Ser Leu Asn Tyr Val
1 5

<210> SEQ ID NO 206
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 206

Thr Gly Thr Ser Ser Asp Val Gly Ile Ser Asn Tyr Val Ser
1 5 10

<210> SEQ ID NO 207
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 207

Glu Val Ser Asn Arg Pro Ser
1 5

<210> SEQ ID NO 208
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 208

Gln Ser Tyr Thr Ser Leu Asn Tyr Val
1 5

<210> SEQ ID NO 209
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 209

Thr Ser Ser Asp Val Gly Ile Ser Asn Tyr
1 5 10

<210> SEQ ID NO 210
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 210

Glu Val Ser
1

<210> SEQ ID NO 211
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 211

Tyr Thr Ser Leu Asn Tyr
1 5

<210> SEQ ID NO 212
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 212

Ser Ser Asp Val Gly Ile Ser Asn Tyr 1 5

<210> SEQ ID NO 213
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 213

Glu Val Ser
1

<210> SEQ ID NO 214
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 214

Gln Ser Tyr Thr Ser Leu Asn Tyr Val
1 5

<210> SEQ ID NO 215
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 215

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Ile Ser
20 25 30

Asn Tyr Val Ser Trp Tyr Gln Gln His Pro Gly Lys Ala Pro Lys Leu
35 40 45

Met Ile Tyr Glu Val Ser Asn Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Gln Ser Tyr Thr Ser Leu
85 90 95

Asn Tyr Val Phe Gly Gly Gly Thr Lys Leu Thr Val Leu
100 105

<210> SEQ ID NO 216
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 216
cagtccgccc tgacccagcc tgcctccgtg tctggctccc ctggccagtc catcaccatc 60

```
agctgcaccg gcacctccag cgacgtgggc atctccaact acgtgtcctg gtatcagcag    120

caccccggca aggcccctaa gctgatgatc tacgaagtgt ccaaccggcc ctccggcgtg    180

tccaacagat tctccggctc caagtccggc aacaccgcct ccctgaccat cagcggcctg    240

caggctgagg acgaggccga ctactactgc cagtcctaca cctccctgaa ctacgtgttc    300

ggcggaggca ccaagctgac cgtgctg                                        327


<210> SEQ ID NO 217
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 217

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ile Ser
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Thr Ser Leu
                85                  90                  95

Asn Tyr Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215


<210> SEQ ID NO 218
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 218

cagtccgccc tgacccagcc tgcctccgtg tctggctccc ctggccagtc catcaccatc     60

agctgcaccg gcacctccag cgacgtgggc atctccaact acgtgtcctg gtatcagcag    120
```

```
caccccggca aggcccctaa gctgatgatc tacgaagtgt ccaaccggcc ctccggcgtg    180

tccaacagat tctccggctc caagtccggc aacaccgcct ccctgaccat cagcggcctg    240

caggctgagg acgaggccga ctactactgc cagtcctaca cctccctgaa ctacgtgttc    300

ggcggaggca ccaagctgac cgtgctgggc cagcctaagg ctgcccccag cgtgaccctg    360

ttcccccccca gcagcgagga gctgcaggcc aacaaggcca ccctggtgtg cctgatcagc    420

gacttctacc caggcgccgt gaccgtggcc tggaaggccg acagcagccc cgtgaaggcc    480

ggcgtggaga ccaccacccc cagcaagcag agcaacaaca agtacgccgc cagcagctac    540

ctgagcctga cccccgagca gtggaagagc cacaggtcct acagctgcca ggtgacccac    600

gagggcagca ccgtggaaaa gaccgtggcc cccaaccgagt gcagc                 645
```

<210> SEQ ID NO 219
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 219

```
Gly Phe Thr Phe Ser Ser Asn Ala Met His
1               5                   10
```

<210> SEQ ID NO 220
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 220

```
Arg Ile Lys Ser Lys Thr Asp Gly Gly Thr Thr Asp Tyr Ala Ala Pro
1               5                   10                  15

Val Lys Gly
```

<210> SEQ ID NO 221
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 221

```
Asp His Tyr Tyr Tyr Pro Phe Ala Tyr
1               5
```

<210> SEQ ID NO 222
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 222

```
Ser Asn Ala Met His
```

1 5

<210> SEQ ID NO 223
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 223

Arg Ile Lys Ser Lys Thr Asp Gly Gly Thr Thr Asp Tyr Ala Ala Pro
1 5 10 15

Val Lys Gly

<210> SEQ ID NO 224
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 224

Asp His Tyr Tyr Tyr Pro Phe Ala Tyr
1 5

<210> SEQ ID NO 225
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 225

Gly Phe Thr Phe Ser Ser Asn
1 5

<210> SEQ ID NO 226
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 226

Lys Ser Lys Thr Asp Gly Gly Thr
1 5

<210> SEQ ID NO 227
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 227

Asp His Tyr Tyr Tyr Pro Phe Ala Tyr
1 5

<210> SEQ ID NO 228
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 228

Gly Phe Thr Phe Ser Ser Asn Ala
1               5

<210> SEQ ID NO 229
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 229

Ile Lys Ser Lys Thr Asp Gly Gly Thr Thr
1               5                   10

<210> SEQ ID NO 230
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 230

Ala Arg Asp His Tyr Tyr Tyr Pro Phe Ala Tyr
1               5                   10

<210> SEQ ID NO 231
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 231

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Asn
            20                  25                  30

Ala Met His Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp His Tyr Tyr Tyr Pro Phe Ala Tyr Trp Gly Gln
            100                 105                 110

Gly Thr Leu Val Thr Val Ser Ser 115 120

<210> SEQ ID NO 232
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 232
caagtgcagc tggtggaatc tggcggcgga ctggtcaagc ctggcggtag cctgagactg 60
tcttgcgccg cctccggctt caccttctcc tccaacgcca tgcactgggt ccgacaggcc 120
cctggcaagg gcctggagtg ggtcggacgg atcaagtcca agaccgacgg cggcaccacc 180
gactacgctg cccctgtgaa gggccggttc accatctccc gggacgactc caagaacacc 240
ctgtacctgc agatgaactc cctgaaaacc gaggacaccg ccgtgtacta ctgcgccagg 300
gaccactact actacccctt cgcctactgg ggccagggca ccctggtcac cgtgtcctct 360

<210> SEQ ID NO 233
<211> LENGTH: 223
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 233

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Asn
20 25 30

Ala Met His Trp Val Arg Gln Ala Pro Gly Lys Gly Leu Glu Trp Val
35 40 45

Gly Arg Ile Lys Ser Lys Thr Asp Gly Gly Thr Thr Asp Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asn Ser Leu Lys Thr Glu Asp Thr Ala Val Tyr
85 90 95

Tyr Cys Ala Arg Asp His Tyr Tyr Tyr Pro Phe Ala Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Arg Val Glu Pro Lys Ser Cys
210 215 220

<210> SEQ ID NO 234
<211> LENGTH: 669
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 234
caagtgcagc tggtggaatc tggcggcgga ctggtcaagc ctggcggtag cctgagactg 60
tcttgcgccg cctccggctt caccttctcc tccaacgcca tgcactgggt ccgacaggcc 120
cctggcaagg gcctggagtg ggtcggacgg atcaagtcca agaccgacgg cggcaccacc 180
gactacgctg cccctgtgaa gggccggttc accatctccc gggacgactc caagaacacc 240
ctgtacctgc agatgaactc cctgaaaacc gaggacaccg ccgtgtacta ctgcgccagg 300
gaccactact actacccctt cgcctactgg ggccagggca ccctggtcac cgtgtcctct 360
gctagcacca agggcccctc cgtgttccct ctggcccctt ccagcaagtc tacctctggc 420
ggcaccgctg ctctgggctg cctggtgaag gactacttcc ctgagcctgt gacagtgtcc 480
tggaactctg gcgccctgac ctccggcgtg cacaccttcc ctgccgtgct gcagtcctcc 540
ggcctgtact ccctgtcctc cgtggtgaca gtgccttcct ccagcctggg cacccagacc 600
tatatctgca acgtgaacca caagccttcc aacaccaagg tggacaagcg ggtggagcct 660
aagtcatgc 669

<210> SEQ ID NO 235
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 235

Arg Ala Ser Gln Ser Ile Arg Tyr Asn Leu Ala
1 5 10

<210> SEQ ID NO 236
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 236

Ala Ala Ser Ser Leu Gln Ser
1 5

<210> SEQ ID NO 237
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 237

His Gln Tyr Ile Ala Lys Pro Ile Thr
1 5

<210> SEQ ID NO 238
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 238

Arg Ala Ser Gln Ser Ile Arg Tyr Asn Leu Ala
1 5 10

<210> SEQ ID NO 239
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 239

Ala Ala Ser Ser Leu Gln Ser
1 5

<210> SEQ ID NO 240
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 240

His Gln Tyr Ile Ala Lys Pro Ile Thr
1 5

<210> SEQ ID NO 241
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 241

Ser Gln Ser Ile Arg Tyr Asn
1 5

<210> SEQ ID NO 242
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 242

Ala Ala Ser
1

<210> SEQ ID NO 243
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 243

Tyr Ile Ala Lys Pro Ile
1               5

<210> SEQ ID NO 244
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 244

Gln Ser Ile Arg Tyr Asn
1               5

<210> SEQ ID NO 245
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 245

Ala Ala Ser
1

<210> SEQ ID NO 246
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 246

His Gln Tyr Ile Ala Lys Pro Ile Thr
1               5

<210> SEQ ID NO 247
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 247

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Tyr Asn
            20                  25                  30

Leu Ala Trp Tyr Gln Gln Lys Pro Gly Lys Ala Pro Lys Leu Leu Ile
        35                  40                  45

```
Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Ile Ala Lys Pro Ile
                85                  90                  95

Thr Phe Gly Gln Gly Thr Lys Val Glu Ile Lys
            100                 105


<210> SEQ ID NO 248
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 248

gacatccaga tgacccagag cccctccagc ctgtccgcct ccgtgggcga cagagtgacc      60

atcacctgtc gggcctccca gtccatccgg tacaacctgg cctggtatca gcagaagccc     120

ggcaaggccc ctaagctgct gatctacgcc gccagctccc tgcagtccgg cgtgccctcc     180

agattctccg gctctggctc cggcaccgac ttcaccctga ccatctccag cctgcagccc     240

gaggacttcg ccacctacta ctgccaccag tatatcgcca agcccatcac cttcggccag     300

ggcaccaaag tggaaatcaa g                                               321


<210> SEQ ID NO 249
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 249

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Tyr Asn
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Ile Ala Lys Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 250
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 250

gacatccaga tgacccagag cccctccagc ctgtccgcct ccgtgggcga cagagtgacc      60

atcacctgtc gggcctccca gtccatccgg tacaacctgg cctggtatca gcagaagccc     120

ggcaaggccc ctaagctgct gatctacgcc gccagctccc tgcagtccgg cgtgccctcc     180

agattctccg gctctggctc cggcaccgac ttcaccctga ccatctccag cctgcagccc     240

gaggacttcg ccacctacta ctgccaccag tatatcgcca agcccatcac cttcggccag     300

ggcaccaaag tggaaatcaa gcgtacggtg gccgctccca gcgtgttcat cttccccccc     360

agcgacgagc agctgaagag cggcaccgcc agcgtggtgt gcctgctgaa caacttctac     420

ccccgggagg ccaaggtgca gtggaaggtg gacaacgccc tgcagagcgg caacagccag     480

gagagcgtca ccgagcagga cagcaaggac tccacctaca gcctgagcag caccctgacc     540

ctgagcaagg ccgactacga gaagcataag gtgtacgcct gcgaggtgac ccaccagggc     600

ctgtccagcc ccgtgaccaa gagcttcaac aggggcgagt gc                        642


<210> SEQ ID NO 251
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 251

Gly Phe Thr Phe Ser Ser Asn Ala Met His
1               5                   10


<210> SEQ ID NO 252
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 252

Arg Ile Lys Ser Lys Thr Ser Gly Gly Thr Thr Asp Tyr Ala Ala Pro
1               5                   10                  15

Val Lys Gly
```

<210> SEQ ID NO 253
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 253

Asp His Tyr Tyr Tyr Pro Phe Ala Tyr
1 5

<210> SEQ ID NO 254
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 254

Ser Asn Ala Met His
1 5

<210> SEQ ID NO 255
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 255

Arg Ile Lys Ser Lys Thr Ser Gly Gly Thr Thr Asp Tyr Ala Ala Pro
1 5 10 15

Val Lys Gly

<210> SEQ ID NO 256
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 256

Asp His Tyr Tyr Tyr Pro Phe Ala Tyr
1 5

<210> SEQ ID NO 257
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 257

Gly Phe Thr Phe Ser Ser Asn
1 5

<210> SEQ ID NO 258
<211> LENGTH: 8

<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 258

Lys Ser Lys Thr Ser Gly Gly Thr
1               5

<210> SEQ ID NO 259
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 259

Asp His Tyr Tyr Tyr Pro Phe Ala Tyr
1               5

<210> SEQ ID NO 260
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 260

Gly Phe Thr Phe Ser Ser Asn Ala
1               5

<210> SEQ ID NO 261
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 261

Ile Lys Ser Lys Thr Ser Gly Gly Thr Thr
1               5                   10

<210> SEQ ID NO 262
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 262

Ala Arg Asp His Tyr Tyr Tyr Pro Phe Ala Tyr
1               5                   10

<210> SEQ ID NO 263
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 263

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Asn
            20                  25                  30

Ala Met His Trp Val Arg Gln Ala Pro Gly Lys Gly Leu Glu Trp Val
        35                  40                  45

Gly Arg Ile Lys Ser Lys Thr Ser Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp His Tyr Tyr Tyr Pro Phe Ala Tyr Trp Gly Gln
            100                 105                 110

Gly Thr Leu Val Thr Val Ser Ser
        115                 120
```

<210> SEQ ID NO 264
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 264

```
caagtgcagc tggtggaatc tggcggcgga ctggtcaagc ctggcggtag cctgagactg      60

tcttgcgccg cctccggctt caccttctcc tccaacgcca tgcactgggt ccgacaggcc     120

cctggcaagg gcctggagtg ggtcggacgg atcaagtcca agacctccgg cggcaccacc     180

gactacgctg cccctgtgaa gggccggttc accatctccc gggacgactc caagaacacc     240

ctgtacctgc agatgaactc cctgaaaacc gaggacaccg ccgtgtacta ctgcgccagg     300

gaccactact actacccctt cgcctactgg ggccagggca ccctggtcac cgtgtcctct     360
```

<210> SEQ ID NO 265
<211> LENGTH: 223
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 265

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Asn
            20                  25                  30

Ala Met His Trp Val Arg Gln Ala Pro Gly Lys Gly Leu Glu Trp Val
        35                  40                  45

Gly Arg Ile Lys Ser Lys Thr Ser Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80
```

Leu Tyr Leu Gln Met Asn Ser Leu Lys Thr Glu Asp Thr Ala Val Tyr
85 90 95

Tyr Cys Ala Arg Asp His Tyr Tyr Tyr Pro Phe Ala Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Arg Val Glu Pro Lys Ser Cys
210 215 220

<210> SEQ ID NO 266
<211> LENGTH: 669
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 266
caagtgcagc tggtggaatc tggcggcgga ctggtcaagc ctggcggtag cctgagactg 60
tcttgcgccg cctccggctt caccttctcc tccaacgcca tgcactgggt ccgacaggcc 120
cctggcaagg gcctggagtg ggtcggacgg atcaagtcca agacctccgg cggcaccacc 180
gactacgctg cccctgtgaa gggccggttc accatctccc gggacgactc caagaacacc 240
ctgtacctgc agatgaactc cctgaaaacc gaggacaccg ccgtgtacta ctgcgccagg 300
gaccactact actacccctt cgcctactgg ggccagggca ccctggtcac cgtgtcctct 360
gctagcacca agggcccctc cgtgttccct ctggcccctt ccagcaagtc tacctctggc 420
ggcaccgctg ctctgggctg cctggtgaag gactacttcc ctgagcctgt gacagtgtcc 480
tggaactctg gcgccctgac ctccggcgtg cacaccttcc ctgccgtgct gcagtcctcc 540
ggcctgtact ccctgtcctc cgtggtgaca gtgccttcct ccagcctggg cacccagacc 600
tatatctgca acgtgaacca caagccttcc aacaccaagg tggacaagcg ggtggagcct 660
aagtcatgc 669

<210> SEQ ID NO 267
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 267

Arg Ala Ser Gln Ser Ile Arg Tyr Asn Leu Ala
1 5 10

<210> SEQ ID NO 268
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 268

Ala Ala Ser Ser Leu Gln Ser
1 5

<210> SEQ ID NO 269
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 269

His Gln Tyr Ile Ala Lys Pro Ile Thr
1 5

<210> SEQ ID NO 270
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 270

Arg Ala Ser Gln Ser Ile Arg Tyr Asn Leu Ala
1 5 10

<210> SEQ ID NO 271
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 271

Ala Ala Ser Ser Leu Gln Ser
1 5

<210> SEQ ID NO 272
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 272

His Gln Tyr Ile Ala Lys Pro Ile Thr
1 5

<210> SEQ ID NO 273
<211> LENGTH: 7
<212> TYPE: PRT

<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 273

Ser Gln Ser Ile Arg Tyr Asn
1 5

<210> SEQ ID NO 274
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 274

Ala Ala Ser
1

<210> SEQ ID NO 275
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 275

Tyr Ile Ala Lys Pro Ile
1 5

<210> SEQ ID NO 276
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 276

Gln Ser Ile Arg Tyr Asn
1 5

<210> SEQ ID NO 277
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 277

Ala Ala Ser
1

<210> SEQ ID NO 278
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 278

His Gln Tyr Ile Ala Lys Pro Ile Thr
1 5

<210> SEQ ID NO 279
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 279

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Arg Tyr Asn
20 25 30

Leu Ala Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys His Gln Tyr Ile Ala Lys Pro Ile
85 90 95

Thr Phe Gly Gln Gly Thr Lys Val Glu Ile Lys
100 105

<210> SEQ ID NO 280
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 280
gacatccaga tgacccagag cccctccagc ctgtccgcct ccgtgggcga cagagtgacc 60
atcacctgtc gggcctccca gtccatccgg tacaacctgg cctggtatca gcagaagccc 120
ggcaaggccc ctaagctgct gatctacgcc gccagctccc tgcagtccgg cgtgccctcc 180
agattctccg gctctggctc cggcaccgac ttcaccctga ccatctccag cctgcagccc 240
gaggacttcg ccacctacta ctgccaccag tatatcgcca agcccatcac cttcggccag 300
ggcaccaaag tggaaatcaa g 321

<210> SEQ ID NO 281
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 281

Asp Ile Gln Met Thr Gln Ser Pro Ser Ser Leu Ser Ala Ser Val Gly
1 5 10 15

```
Asp Arg Val Thr Ile Thr Cys Arg Ala Ser Gln Ser Ile Arg Tyr Asn
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Ile Ala Lys Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 282
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 282

```
gacatccaga tgacccagag cccctccagc ctgtccgcct ccgtgggcga cagagtgacc     60

atcacctgtc gggcctccca gtccatccgg tacaacctgg cctggtatca gcagaagccc    120

ggcaaggccc ctaagctgct gatctacgcc gccagctccc tgcagtccgg cgtgccctcc    180

agattctccg gctctggctc cggcaccgac ttcaccctga ccatctccag cctgcagccc    240

gaggacttcg ccacctacta ctgccaccag tatatcgcca agcccatcac cttcggccag    300

ggcaccaaag tggaaatcaa gcgtacggtg gccgctccca gcgtgttcat cttccccccc    360

agcgacgagc agctgaagag cggcaccgcc agcgtggtgt gcctgctgaa caacttctac    420

ccccgggagg ccaaggtgca gtggaaggtg gacaacgccc tgcagagcgg caacagccag    480

gagagcgtca ccgagcagga cagcaaggac tccacctaca gcctgagcag caccctgacc    540

ctgagcaagg ccgactacga gaagcataag gtgtacgcct gcgaggtgac ccaccagggc    600

ctgtccagcc ccgtgaccaa gagcttcaac aggggcgagt gc                       642
```

<210> SEQ ID NO 283
<211> LENGTH: 10
<212> TYPE: PRT
<213> ORGANISM: Artificial Sequence
<220> FEATURE:

<221> NAME/KEY: source
<223> OTHER INFORMATION: /note="Description of Artificial Sequence: Synthetic peptide"

<400> SEQUENCE: 283

Gly Tyr Thr Phe Thr Asn Tyr Tyr Val His
1 5 10

<210> SEQ ID NO 284
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 284

Trp Ile Asn Pro Tyr Asn Gly Asn Thr Asn Tyr Ala Gln Lys Phe Gln
1 5 10 15

Gly

<210> SEQ ID NO 285
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 285

Gly Ala Ser Ser Ile Arg Met Ser Tyr Tyr Leu Asp Val
1 5 10

<210> SEQ ID NO 286
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 286

Asn Tyr Tyr Val His
1 5

<210> SEQ ID NO 287
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 287

Trp Ile Asn Pro Tyr Asn Gly Asn Thr Asn Tyr Ala Gln Lys Phe Gln
1 5 10 15

Gly

<210> SEQ ID NO 288
<211> LENGTH: 13
<212> TYPE: PRT
<213> ORGANISM: Artificial Sequence
<220> FEATURE:

<221> NAME/KEY: source
<223> OTHER INFORMATION: /note="Description of Artificial Sequence:
Synthetic peptide"

<400> SEQUENCE: 288

Gly Ala Ser Ser Ile Arg Met Ser Tyr Tyr Leu Asp Val
1 5 10

<210> SEQ ID NO 289
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 289

Gly Tyr Thr Phe Thr Asn Tyr
1 5

<210> SEQ ID NO 290
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 290

Asn Pro Tyr Asn Gly Asn
1 5

<210> SEQ ID NO 291
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 291

Gly Ala Ser Ser Ile Arg Met Ser Tyr Tyr Leu Asp Val
1 5 10

<210> SEQ ID NO 292
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 292

Gly Tyr Thr Phe Thr Asn Tyr Tyr
1 5

<210> SEQ ID NO 293
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 293

Ile Asn Pro Tyr Asn Gly Asn Thr
1               5

<210> SEQ ID NO 294
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 294

Ala Arg Gly Ala Ser Ser Ile Arg Met Ser Tyr Tyr Leu Asp Val
1               5                   10                  15

<210> SEQ ID NO 295
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 295

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Val His Trp Val Arg Gln Ala Pro Gly Gln Gly Leu Glu Trp Met
        35                  40                  45

Gly Trp Ile Asn Pro Tyr Asn Gly Asn Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Gly Ala Ser Ser Ile Arg Met Ser Tyr Tyr Leu Asp Val Trp
            100                 105                 110

Gly Gln Gly Thr Leu Val Thr Val Ser Ser
        115                 120

<210> SEQ ID NO 296
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 296
caagtgcagc tggtgcagtc tggcgctgaa gtgaagaaac ctggcgcctc cgtgaaagtg 60
tcctgcaagg cctccggcta caccttcacc aactactacg tgcactgggt ccgacaggcc 120
ccaggccagg gcctggagtg gatgggctgg atcaacccct acaacggcaa caccaactac 180
gcccagaaat tccagggcag agtgaccatg acccgggaca cctccatctc caccgcctac 240
atggaactgt cccggctgcg gagcgaggac accgccgtgt actactgtgc cagaggcgcc 300
tcctccatcc ggatgtccta ctacctggac gtgtggggcc agggcaccct ggtcaccgtg 360
tcctct 366

<210> SEQ ID NO 297
<211> LENGTH: 225
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 297

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Val His Trp Val Arg Gln Ala Pro Gly Gln Gly Leu Glu Trp Met
        35                  40                  45

Gly Trp Ile Asn Pro Tyr Asn Gly Asn Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Gly Ala Ser Ser Ile Arg Met Ser Tyr Tyr Leu Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys
225
```

<210> SEQ ID NO 298
<211> LENGTH: 675
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 298

```
caagtgcagc tggtgcagtc tggcgctgaa gtgaagaaac ctggcgcctc cgtgaaagtg     60

tcctgcaagg cctccggcta caccttcacc aactactacg tgcactgggt ccgacaggcc    120

ccaggccagg gcctggagtg gatgggctgg atcaacccct acaacggcaa caccaactac    180

gcccagaaat tccagggcag agtgaccatg acccgggaca cctccatctc caccgcctac    240
```

```
atggaactgt cccggctgcg gagcgaggac accgccgtgt actactgtgc cagaggcgcc    300

tcctccatcc ggatgtccta ctacctggac gtgtggggcc agggcaccct ggtcaccgtg    360

tcctctgcta gcaccaaggg cccctccgtg ttccctctgg ccccttccag caagtctacc    420

tctggcggca ccgctgctct gggctgcctg gtgaaggact acttccctga gcctgtgaca    480

gtgtcctgga actctggcgc cctgacctcc ggcgtgcaca ccttccctgc cgtgctgcag    540

tcctccggcc tgtactccct gtcctccgtg gtgacagtgc cttcctccag cctgggcacc    600

cagacctata tctgcaacgt gaaccacaag ccttccaaca ccaaggtgga caagcgggtg    660

gagcctaagt catgc                                                     675
```

<210> SEQ ID NO 299
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 299

```
Arg Ala Ser Gln Ser Ile Ser Asn Tyr Leu Asn
1               5                   10
```

<210> SEQ ID NO 300
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 300

```
Ala Ala Ser Asn Leu Gln Ser
1               5
```

<210> SEQ ID NO 301
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 301

```
Phe Gln Tyr Thr His Ser Pro Ala Thr
1               5
```

<210> SEQ ID NO 302
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 302

```
Arg Ala Ser Gln Ser Ile Ser Asn Tyr Leu Asn
1               5                   10
```

<210> SEQ ID NO 303

<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 303

Ala Ala Ser Asn Leu Gln Ser
1 5

<210> SEQ ID NO 304
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 304

Phe Gln Tyr Thr His Ser Pro Ala Thr
1 5

<210> SEQ ID NO 305
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 305

Ser Gln Ser Ile Ser Asn Tyr
1 5

<210> SEQ ID NO 306
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 306

Ala Ala Ser
1

<210> SEQ ID NO 307
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 307

Tyr Thr His Ser Pro Ala
1 5

<210> SEQ ID NO 308
<211> LENGTH: 6
<212> TYPE: PRT
<213> ORGANISM: Artificial Sequence
<220> FEATURE:

<221> NAME/KEY: source
<223> OTHER INFORMATION: /note="Description of Artificial Sequence: Synthetic peptide"

<400> SEQUENCE: 308

Gln Ser Ile Ser Asn Tyr
1 5

<210> SEQ ID NO 309
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 309

Ala Ala Ser
1

<210> SEQ ID NO 310
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 310

Phe Gln Tyr Thr His Ser Pro Ala Thr
1 5

<210> SEQ ID NO 311
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 311

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Asn Tyr
20 25 30

Leu Asn Trp Tyr Gln Gln Lys Pro Gly Lys Ala Pro Lys Leu Leu Ile
35 40 45

Tyr Ala Ala Ser Asn Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Phe Gln Tyr Thr His Ser Pro Ala
85 90 95

Thr Phe Gly Gln Gly Thr Lys Val Glu Ile Lys
100 105

<210> SEQ ID NO 312
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 312
gacatccaga tgacccagag cccctccagc ctgtccgcct ccgtgggcga cagagtgacc 60
atcacctgtc gggcctccca gtccatctcc aactacctga actggtatca gcagaagccc 120
ggcaaggccc ctaagctgct gatctacgcc gcctccaacc tgcagtccgg cgtgccctcc 180
agattctccg gctctggctc cggcaccgac ttcaccctga ccatctccag cctgcagccc 240
gaggacttcg ccacctacta ctgcttccag tacacccaca gccccgccac cttcggccag 300
ggcaccaaag tggaaatcaa g 321

<210> SEQ ID NO 313
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 313

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Asn Tyr
20 25 30

Leu Asn Trp Tyr Gln Gln Lys Pro Gly Lys Ala Pro Lys Leu Leu Ile
35 40 45

Tyr Ala Ala Ser Asn Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Phe Gln Tyr Thr His Ser Pro Ala
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 314
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 314
gacatccaga tgacccagag cccctccagc ctgtccgcct ccgtgggcga cagagtgacc 60
atcacctgtc gggcctccca gtccatctcc aactacctga actggtatca gcagaagccc 120
ggcaaggccc ctaagctgct gatctacgcc gcctccaacc tgcagtccgg cgtgccctcc 180
agattctccg gctctggctc cggcaccgac ttcaccctga ccatctccag cctgcagccc 240
gaggacttcg ccacctacta ctgcttccag tacacccaca gccccgccac cttcggccag 300
ggcaccaaag tggaaatcaa gcgtacggtg gccgctccca gcgtgttcat cttccccccc 360
agcgacgagc agctgaagag cggcaccgcc agcgtggtgt gcctgctgaa caacttctac 420
ccccgggagg ccaaggtgca gtggaaggtg gacaacgccc tgcagagcgg caacagccag 480
gagagcgtca ccgagcagga cagcaaggac tccacctaca gcctgagcag caccctgacc 540
ctgagcaagg ccgactacga gaagcataag gtgtacgcct gcgaggtgac ccaccagggc 600
ctgtccagcc ccgtgaccaa gagcttcaac aggggcgagt gc 642

<210> SEQ ID NO 315
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 315

Gly Tyr Thr Phe Thr Asn Tyr Tyr Val His
1 5 10

<210> SEQ ID NO 316
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 316

Trp Ile Asn Pro Tyr Ser Gly Asn Thr Asn Tyr Ala Gln Lys Phe Gln
1 5 10 15

Gly

<210> SEQ ID NO 317
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 317

Gly Ala Ser Ser Ile Arg Met Ser Tyr Tyr Leu Asp Val
1 5 10

<210> SEQ ID NO 318
<211> LENGTH: 5
<212> TYPE: PRT
<213> ORGANISM: Artificial Sequence
<220> FEATURE:

<221> NAME/KEY: source
<223> OTHER INFORMATION: /note="Description of Artificial Sequence:
Synthetic peptide"

<400> SEQUENCE: 318

Asn Tyr Tyr Val His
1               5

<210> SEQ ID NO 319
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 319

Trp Ile Asn Pro Tyr Ser Gly Asn Thr Asn Tyr Ala Gln Lys Phe Gln
1               5                   10                  15

Gly

<210> SEQ ID NO 320
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 320

Gly Ala Ser Ser Ile Arg Met Ser Tyr Tyr Leu Asp Val
1               5                   10

<210> SEQ ID NO 321
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 321

Gly Tyr Thr Phe Thr Asn Tyr
1               5

<210> SEQ ID NO 322
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 322

Asn Pro Tyr Ser Gly Asn
1               5

<210> SEQ ID NO 323
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 323

Gly Ala Ser Ser Ile Arg Met Ser Tyr Tyr Leu Asp Val
1 5 10

<210> SEQ ID NO 324
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 324

Gly Tyr Thr Phe Thr Asn Tyr Tyr
1 5

<210> SEQ ID NO 325
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 325

Ile Asn Pro Tyr Ser Gly Asn Thr
1 5

<210> SEQ ID NO 326
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 326

Ala Arg Gly Ala Ser Ser Ile Arg Met Ser Tyr Tyr Leu Asp Val
1 5 10 15

<210> SEQ ID NO 327
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 327

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Tyr Val His Trp Val Arg Gln Ala Pro Gly Gln Gly Leu Glu Trp Met
35 40 45

Gly Trp Ile Asn Pro Tyr Ser Gly Asn Thr Asn Tyr Ala Gln Lys Phe
50 55 60

Gln Gly Arg Val Thr Met Thr Arg Asp Thr Ser Ile Ser Thr Ala Tyr
65 70 75 80

```
Met Glu Leu Ser Arg Leu Arg Ser Glu Asp Thr Ala Val Tyr Tyr Cys
                85                  90                  95

Ala Arg Gly Ala Ser Ser Ile Arg Met Ser Tyr Tyr Leu Asp Val Trp
            100                 105                 110

Gly Gln Gly Thr Leu Val Thr Val Ser Ser
        115                 120


<210> SEQ ID NO 328
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 328

caagtgcagc tggtgcagtc tggcgctgaa gtgaagaaac ctggcgcctc cgtgaaagtg     60

tcctgcaagg cctccggcta caccttcacc aactactacg tgcactgggt ccgacaggcc    120

ccaggccagg gcctggagtg gatgggctgg atcaacccct actccggcaa caccaactac    180

gcccagaaat tccagggcag agtgaccatg acccgggaca cctccatctc caccgcctac    240

atggaactgt cccggctgcg gagcgaggac accgccgtgt actactgtgc cagaggcgcc    300

tcctccatcc ggatgtccta ctacctggac gtgtggggcc agggcaccct ggtcaccgtg    360

tcctct                                                               366


<210> SEQ ID NO 329
<211> LENGTH: 225
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 329

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Val His Trp Val Arg Gln Ala Pro Gly Gln Gly Leu Glu Trp Met
        35                  40                  45

Gly Trp Ile Asn Pro Tyr Ser Gly Asn Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Gly Ala Ser Ser Ile Arg Met Ser Tyr Tyr Leu Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175
```

Ala Val Leu Gln Ser Ser Gly Leu Tyr Ser Leu Ser Ser Val Val Thr
180 185 190

Val Pro Ser Ser Ser Leu Gly Thr Gln Thr Tyr Ile Cys Asn Val Asn
195 200 205

His Lys Pro Ser Asn Thr Lys Val Asp Lys Arg Val Glu Pro Lys Ser
210 215 220

Cys
225

<210> SEQ ID NO 330
<211> LENGTH: 675
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 330
caagtgcagc tggtgcagtc tggcgctgaa gtgaagaaac ctggcgcctc cgtgaaagtg 60
tcctgcaagg cctccggcta caccttcacc aactactacg tgcactgggt ccgacaggcc 120
ccaggccagg gcctggagtg gatgggctgg atcaacccct actccggcaa caccaactac 180
gcccagaaat tccagggcag agtgaccatg acccgggaca cctccatctc caccgcctac 240
atggaactgt cccggctgcg gagcgaggac accgccgtgt actactgtgc cagaggcgcc 300
tcctccatcc ggatgtccta ctacctggac gtgtggggcc agggcaccct ggtcaccgtg 360
tcctctgcta gcaccaaggg cccctccgtg ttccctctgg ccccttccag caagtctacc 420
tctggcggca ccgctgctct gggctgcctg gtgaaggact acttccctga gcctgtgaca 480
gtgtcctgga actctggcgc cctgacctcc ggcgtgcaca ccttccctgc cgtgctgcag 540
tcctccggcc tgtactccct gtcctccgtg gtgacagtgc cttcctccag cctgggcacc 600
cagacctata tctgcaacgt gaaccacaag ccttccaaca ccaaggtgga caagcgggtg 660
gagcctaagt catgc 675

<210> SEQ ID NO 331
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 331

Arg Ala Ser Gln Ser Ile Ser Asn Tyr Leu Asn
1 5 10

<210> SEQ ID NO 332
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 332

Ala Ala Ser Asn Leu Gln Ser
1 5

<210> SEQ ID NO 333
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 333

Phe Gln Tyr Thr His Ser Pro Ala Thr
1 5

<210> SEQ ID NO 334
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 334

Arg Ala Ser Gln Ser Ile Ser Asn Tyr Leu Asn
1 5 10

<210> SEQ ID NO 335
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 335

Ala Ala Ser Asn Leu Gln Ser
1 5

<210> SEQ ID NO 336
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 336

Phe Gln Tyr Thr His Ser Pro Ala Thr
1 5

<210> SEQ ID NO 337
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 337

Ser Gln Ser Ile Ser Asn Tyr
1 5

<210> SEQ ID NO 338
<211> LENGTH: 3
<212> TYPE: PRT

<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 338

Ala Ala Ser
1

<210> SEQ ID NO 339
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 339

Tyr Thr His Ser Pro Ala
1 5

<210> SEQ ID NO 340
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 340

Gln Ser Ile Ser Asn Tyr
1 5

<210> SEQ ID NO 341
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 341

Ala Ala Ser
1

<210> SEQ ID NO 342
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 342

Phe Gln Tyr Thr His Ser Pro Ala Thr
1 5

<210> SEQ ID NO 343
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 343

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Asn Tyr
20 25 30

Leu Asn Trp Tyr Gln Gln Lys Pro Gly Lys Ala Pro Lys Leu Leu Ile
35 40 45

Tyr Ala Ala Ser Asn Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Phe Gln Tyr Thr His Ser Pro Ala
85 90 95

Thr Phe Gly Gln Gly Thr Lys Val Glu Ile Lys
100 105

<210> SEQ ID NO 344
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 344
gacatccaga tgacccagag cccctccagc ctgtccgcct ccgtgggcga cagagtgacc 60
atcacctgtc gggcctccca gtccatctcc aactacctga actggtatca gcagaagccc 120
ggcaaggccc ctaagctgct gatctacgcc gcctccaacc tgcagtccgg cgtgccctcc 180
agattctccg gctctggctc cggcaccgac ttcaccctga ccatctccag cctgcagccc 240
gaggacttcg ccacctacta ctgcttccag tacacccaca gccccgccac cttcggccag 300
ggcaccaaag tggaaatcaa g 321

<210> SEQ ID NO 345
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 345

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Asn Tyr
20 25 30

Leu Asn Trp Tyr Gln Gln Lys Pro Gly Lys Ala Pro Lys Leu Leu Ile
35 40 45

Tyr Ala Ala Ser Asn Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Phe Gln Tyr Thr His Ser Pro Ala
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 346
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 346
gacatccaga tgacccagag cccctccagc ctgtccgcct ccgtgggcga cagagtgacc 60
atcacctgtc gggcctccca gtccatctcc aactacctga actggtatca gcagaagccc 120
ggcaaggccc ctaagctgct gatctacgcc gcctccaacc tgcagtccgg cgtgccctcc 180
agattctccg gctctggctc cggcaccgac ttcaccctga ccatctccag cctgcagccc 240
gaggacttcg ccacctacta ctgcttccag tacacccaca gccccgccac cttcggccag 300
ggcaccaaag tggaaatcaa gcgtacggtg gccgctccca gcgtgttcat cttccccccc 360
agcgacgagc agctgaagag cggcaccgcc agcgtggtgt gcctgctgaa caacttctac 420
ccccgggagg ccaaggtgca gtggaaggtg gacaacgccc tgcagagcgg caacagccag 480
gagagcgtca ccgagcagga cagcaaggac tccacctaca gcctgagcag caccctgacc 540
ctgagcaagg ccgactacga gaagcataag gtgtacgcct gcgaggtgac ccaccagggc 600
ctgtccagcc ccgtgaccaa gagcttcaac aggggcgagt gc 642

<210> SEQ ID NO 347
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (5)..(5)
<223> OTHER INFORMATION: Any amino acid
<220> FEATURE:
<221> NAME/KEY: source
<223> OTHER INFORMATION: /note="See specification as filed for detailed description of substitutions and preferred embodiments"

<400> SEQUENCE: 347

Gly Phe Thr Phe Xaa Ser Ala Ala Val His 1 5 10

<210> SEQ ID NO 348
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (7)..(7)
<223> OTHER INFORMATION: Any amino acid
<220> FEATURE:
<221> NAME/KEY: source
<223> OTHER INFORMATION: /note="See specification as filed for detailed description of substitutions and preferred embodiments"

<400> SEQUENCE: 348

Arg Ile Lys Ser Lys Ala Xaa Gly Gly Thr Thr Asp Tyr Ala Ala Pro
1 5 10 15

Val Lys Gly

<210> SEQ ID NO 349
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (6)..(7)
<223> OTHER INFORMATION: Any amino acid
<220> FEATURE:
<221> NAME/KEY: source
<223> OTHER INFORMATION: /note="See specification as filed for detailed description of substitutions and preferred embodiments"

<400> SEQUENCE: 349

Arg Ile Lys Ser Lys Xaa Xaa Gly Gly Thr Thr Asp Tyr Ala Ala Pro
1 5 10 15

Val Lys Gly

<210> SEQ ID NO 350
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 350

Asp Ser Pro Ser Ile Ser Ser Tyr Ser Ile Pro Tyr Phe Ser Gly Met
1 5 10 15

Asp Val

<210> SEQ ID NO 351
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 351

Arg Ala Ser Gln Gly Ile Arg Ala Trp Leu Asn
1 5 10

<210> SEQ ID NO 352
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(9)
<223> OTHER INFORMATION: Any amino acid
<220> FEATURE:
<221> NAME/KEY: source
<223> OTHER INFORMATION: /note="See specification as filed for detailed description of substitutions and preferred embodiments"

<400> SEQUENCE: 352

Arg Ala Ser Gln Xaa Ile Xaa Xaa Xaa Leu Asn
1 5 10

<210> SEQ ID NO 353
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 353

Ala Ala Ser Ser Leu Gln Ser
1 5

<210> SEQ ID NO 354
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 354

His Gln Tyr Ile Thr His Pro Pro Thr
1 5

<210> SEQ ID NO 355
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: source
<223> OTHER INFORMATION: /note="See specification as filed for detailed description of substitutions and preferred embodiments"

<400> SEQUENCE: 355

His Gln Tyr Ile Xaa Xaa Pro Xaa Thr
1 5

<210> SEQ ID NO 356
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 356

Ser Ala Ala Val His
1 5

<210> SEQ ID NO 357
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (7)..(8)
<223> OTHER INFORMATION: Any amino acid
<220> FEATURE:
<221> NAME/KEY: source
<223> OTHER INFORMATION: /note="See specification as filed for detailed description of substitutions and preferred embodiments"

<400> SEQUENCE: 357

Arg Ile Lys Ser Lys Ala Xaa Xaa Gly Thr Thr Asp Tyr Ala Ala Pro
1 5 10 15

Val Lys Gly

<210> SEQ ID NO 358
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (6)..(8)
<223> OTHER INFORMATION: Any amino acid
<220> FEATURE:
<221> NAME/KEY: source
<223> OTHER INFORMATION: /note="See specification as filed for detailed description of substitutions and preferred embodiments"

<400> SEQUENCE: 358

Arg Ile Lys Ser Lys Xaa Xaa Xaa Gly Thr Thr Asp Tyr Ala Ala Pro
1 5 10 15

Val Lys Gly

<210> SEQ ID NO 359
<211> LENGTH: 7
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: Any amino acid

<400> SEQUENCE: 359

Ala Ala Ser Xaa Leu Gln Ser
1               5


<210> SEQ ID NO 360
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 360

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Gly Ile Ser Gly Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
```

-continued

```
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 361
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 361

caggtgcaat tgctggaaag cggcggtggc ctggtgcagc cgggtggcag cctgcgtctg      60

agctgcgcgg cgtccggatt caccttttct actgctgcta tgtcttgggt gcgccaggcc     120

ccgggcaaag gtctcgagtg ggtttccggt atctctggtt ctggttcttc tacctactat     180

gcggatagcg tgaaaggccg ctttaccatc agccgcgata attcgaaaaa caccctgtat     240

ctgcaaatga acagcctgcg tgcggaagat acggccgtgt attattgcgc gcgtgaactg     300

tcttacctgt actctggtta ctacttcgat tactggggcc aaggcaccct ggtgactgtt     360

agctcagcct ccaccaaggg tccatcggtc ttccccctgg caccctcctc caagagcacc     420

tctgggggca cagcggccct gggctgcctg gtcaaggact acttccccga accggtgacg     480

gtgtcgtgga actcaggcgc cctgaccagc ggcgtgcaca ccttcccggc tgtcctacag     540

tcctcaggac tctactccct cagcagcgtg gtgaccgtgc cctccagcag cttgggcacc     600

cagacctaca tctgcaacgt gaatcacaag cccagcaaca ccaaggtgga caagagagtt     660

gagcccaaat cttgtgacaa aactcacaca tgcccaccgt gcccagcacc tgaagcagcg     720

gggggaccgt cagtcttcct cttcccccca aaacccaagg acaccctcat gatctcccgg     780

acccctgagg tcacatgcgt ggtggtggac gtgagccacg aagaccctga ggtcaagttc     840

aactggtacg tggacggcgt ggaggtgcat aatgccaaga caaagccgcg ggaggagcag     900

tacaacagca cgtaccgggt ggtcagcgtc ctcaccgtcc tgcaccagga ctggctgaat     960
```

```
ggcaaggagt acaagtgcaa ggtctccaac aaagccctcc cagcccccat cgagaaaacc   1020

atctccaaag ccaaagggca gccccgagaa ccacaggtgt acaccctgcc cccatcccgg   1080

gaggagatga ccaagaacca ggtcagcctg acctgcctgg tcaaaggctt ctatcccagc   1140

gacatcgccg tggagtggga gagcaatggg cagccggaga acaactacaa gaccacgcct   1200

cccgtgctgg actccgacgg ctccttcttc ctctacagca agctcaccgt ggacaagagc   1260

aggtggcagc aggggaacgt cttctcatgc tccgtgatgc atgaggctct gcacaaccac   1320

tacacgcaga agagcctctc cctgtctccg ggtaaa                             1356
```

<210> SEQ ID NO 362
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 362

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Lys Asn Tyr Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu
            100                 105                 110
```

<210> SEQ ID NO 363
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 363

```
gatatcgtgc tgacccagcc gccgagcgtg agcggtgcac cgggccagcg cgtgaccatt     60

agctgtagcg gcagcagcag caacattggt tctaacgacg tgtcttggta ccagcagctg    120

ccgggcacgg cgccgaaact gctgatctac aaaaactaca accgcccgag cggcgtgccg    180

gatcgcttta gcggatccaa aagcggcacc agcgccagcc tggcgattac cggcctgcaa    240

gcagaagacg aagcggatta ttactgctct gcttgggacc agcgtcagtt cgacgttgtg    300

tttggcggcg gcacgaagtt aaccgtccta                                     330
```

<210> SEQ ID NO 364
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 364

Asp Ile Val Leu Thr Gln Pro Pro Ser Val Ser Gly Ala Pro Gly Gln
1 5 10 15

Arg Val Thr Ile Ser Cys Ser Gly Ser Ser Ser Asn Ile Gly Ser Asn
20 25 30

Asp Val Ser Trp Tyr Gln Gln Leu Pro Gly Thr Ala Pro Lys Leu Leu
35 40 45

Ile Tyr Lys Asn Tyr Asn Arg Pro Ser Gly Val Pro Asp Arg Phe Ser
50 55 60

Gly Ser Lys Ser Gly Thr Ser Ala Ser Leu Ala Ile Thr Gly Leu Gln
65 70 75 80

Ala Glu Asp Glu Ala Asp Tyr Tyr Cys Ser Ala Trp Asp Gln Arg Gln
85 90 95

Phe Asp Val Val Phe Gly Gly Gly Thr Lys Leu Thr Val Leu Gly Gln
100 105 110

Pro Lys Ala Ala Pro Ser Val Thr Leu Phe Pro Pro Ser Ser Glu Glu
115 120 125

Leu Gln Ala Asn Lys Ala Thr Leu Val Cys Leu Ile Ser Asp Phe Tyr
130 135 140

Pro Gly Ala Val Thr Val Ala Trp Lys Ala Asp Ser Ser Pro Val Lys
145 150 155 160

Ala Gly Val Glu Thr Thr Thr Pro Ser Lys Gln Ser Asn Asn Lys Tyr
165 170 175

Ala Ala Ser Ser Tyr Leu Ser Leu Thr Pro Glu Gln Trp Lys Ser His
180 185 190

Arg Ser Tyr Ser Cys Gln Val Thr His Glu Gly Ser Thr Val Glu Lys
195 200 205

Thr Val Ala Pro Thr Glu Cys Ser
210 215

<210> SEQ ID NO 365
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 365
gatatcgtgc tgacccagcc gccgagcgtg agcggtgcac cgggccagcg cgtgaccatt 60
agctgtagcg gcagcagcag caacattggt tctaacgacg tgtcttggta ccagcagctg 120
ccgggcacgg cgccgaaact gctgatctac aaaaactaca accgcccgag cggcgtgccg 180
gatcgcttta gcggatccaa aagcggcacc agcgccagcc tggcgattac cggcctgcaa 240
gcagaagacg aagcggatta ttactgctct gcttgggacc agcgtcagtt cgacgttgtg 300
tttggcggcg gcacgaagtt aaccgtccta ggtcagccca aggctgcccc ctcggtcact 360
ctgttcccgc cctcctctga ggagcttcaa gccaacaagg ccacactggt gtgtctcata 420
agtgacttct acccgggagc cgtgacagtg gcctggaagg cagatagcag ccccgtcaag 480
gcgggagtgg agaccaccac accctccaaa caaagcaaca acaagtacgc ggccagcagc 540
tatctgagcc tgacgcctga gcagtggaag tcccacagaa gctacagctg ccaggtcacg 600
catgaaggga gcaccgtgga gaagacagtg gcccctacag aatgttca 648

<210> SEQ ID NO 366
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 366

```
Thr Ile Asp Ser Trp Gly Asp Asp Thr Asp Tyr Ala Asp Ser Val Lys
1               5                   10                  15

Gly
```

<210> SEQ ID NO 367
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 367

```
Asp Ser Trp Gly Asp Asp
1               5
```

<210> SEQ ID NO 368
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 368

```
Ile Asp Ser Trp Gly Asp Asp Thr
1               5
```

<210> SEQ ID NO 369
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 369

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Thr Ile Asp Ser Trp Gly Asp Asp Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
```

```
            100                 105                 110

Gly Gln Gly Thr Leu Val Thr Val Ser Ser
        115                 120


<210> SEQ ID NO 370
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 370

caggtgcaat tgctggaaag cggcggtggc ctggtgcagc cgggtggcag cctgcgtctg      60

agctgcgcgg cgtccggatt caccttttct actgctgcta tgtcttgggt gcgccaggcc     120

ccgggcaaag gtctcgagtg ggtttccact atcgactctt ggggcgacga cactgactat     180

gcggatagcg tgaaaggccg ctttaccatc agccgcgata attcgaaaaa caccctgtat     240

ctgcaaatga acagcctgcg tgcggaagat acggccgtgt attattgcgc gcgtgaactg     300

tcttacctgt actctggtta ctacttcgat tactggggcc aaggcaccct ggtgactgtt     360

agctca                                                                366


<210> SEQ ID NO 371
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 371

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Thr Ile Asp Ser Trp Gly Asp Asp Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190
```

Val Pro Ser Ser Ser Leu Gly Thr Gln Thr Tyr Ile Cys Asn Val Asn
195 200 205

His Lys Pro Ser Asn Thr Lys Val Asp Lys Arg Val Glu Pro Lys Ser
210 215 220

Cys Asp Lys Thr His Thr Cys Pro Pro Cys Pro Ala Pro Glu Ala Ala
225 230 235 240

Gly Gly Pro Ser Val Phe Leu Phe Pro Pro Lys Pro Lys Asp Thr Leu
245 250 255

Met Ile Ser Arg Thr Pro Glu Val Thr Cys Val Val Val Asp Val Ser
260 265 270

His Glu Asp Pro Glu Val Lys Phe Asn Trp Tyr Val Asp Gly Val Glu
275 280 285

Val His Asn Ala Lys Thr Lys Pro Arg Glu Glu Gln Tyr Asn Ser Thr
290 295 300

Tyr Arg Val Val Ser Val Leu Thr Val Leu His Gln Asp Trp Leu Asn
305 310 315 320

Gly Lys Glu Tyr Lys Cys Lys Val Ser Asn Lys Ala Leu Pro Ala Pro
325 330 335

Ile Glu Lys Thr Ile Ser Lys Ala Lys Gly Gln Pro Arg Glu Pro Gln
340 345 350

Val Tyr Thr Leu Pro Pro Ser Arg Glu Glu Met Thr Lys Asn Gln Val
355 360 365

Ser Leu Thr Cys Leu Val Lys Gly Phe Tyr Pro Ser Asp Ile Ala Val
370 375 380

Glu Trp Glu Ser Asn Gly Gln Pro Glu Asn Asn Tyr Lys Thr Thr Pro
385 390 395 400

Pro Val Leu Asp Ser Asp Gly Ser Phe Phe Leu Tyr Ser Lys Leu Thr
405 410 415

Val Asp Lys Ser Arg Trp Gln Gln Gly Asn Val Phe Ser Cys Ser Val
420 425 430

Met His Glu Ala Leu His Asn His Tyr Thr Gln Lys Ser Leu Ser Leu
435 440 445

Ser Pro Gly Lys
450

<210> SEQ ID NO 372
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 372

Ser Ile Glu Tyr Tyr Asp Thr Asp Thr His Tyr Ala Asp Ser Val Lys
1 5 10 15

Gly

<210> SEQ ID NO 373
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 373

Glu Tyr Tyr Asp Thr Asp
1               5

<210> SEQ ID NO 374
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 374

Ile Glu Tyr Tyr Asp Thr Asp Thr
1               5

<210> SEQ ID NO 375
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 375

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Ser Ile Glu Tyr Tyr Asp Thr Asp Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser
        115                 120

<210> SEQ ID NO 376
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 376
caggtgcaat tgctggaaag cggcggtggc ctggtgcagc cgggtggcag cctgcgtctg 60
agctgcgcgg cgtccggatt caccttttct actgctgcta tgtcttgggt gcgccaggcc 120
ccgggcaaag gtctcgagtg ggtttcctct atcgaatact acgacactga cactcattat 180
gcggatagcg tgaaaggccg ctttaccatc agccgcgata attcgaaaaa caccctgtat 240
ctgcaaatga acagcctgcg tgcggaagat acggccgtgt attattgcgc gcgtgaactg 300
tcttacctgt actctggtta ctacttcgat tactggggcc aaggcaccct ggtgactgtt 360
agctca 366

<210> SEQ ID NO 377
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 377

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Thr Ala
20 25 30

Ala Met Ser Trp Val Arg Gln Ala Pro Gly Lys Gly Leu Glu Trp Val
35 40 45

Ser Ser Ile Glu Tyr Tyr Asp Thr Asp Thr His Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Glu Leu Ser Tyr Leu Tyr Ser Gly Tyr Tyr Phe Asp Tyr Trp
100 105 110

Gly Gln Gly Thr Leu Val Thr Val Ser Ser Ala Ser Thr Lys Gly Pro
115 120 125

Ser Val Phe Pro Leu Ala Pro Ser Ser Lys Ser Thr Ser Gly Gly Thr
130 135 140

Ala Ala Leu Gly Cys Leu Val Lys Asp Tyr Phe Pro Glu Pro Val Thr
145 150 155 160

Val Ser Trp Asn Ser Gly Ala Leu Thr Ser Gly Val His Thr Phe Pro
165 170 175

Ala Val Leu Gln Ser Ser Gly Leu Tyr Ser Leu Ser Ser Val Val Thr
180 185 190

Val Pro Ser Ser Ser Leu Gly Thr Gln Thr Tyr Ile Cys Asn Val Asn
195 200 205

His Lys Pro Ser Asn Thr Lys Val Asp Lys Arg Val Glu Pro Lys Ser
210 215 220

Cys Asp Lys Thr His Thr Cys Pro Pro Cys Pro Ala Pro Glu Ala Ala
225 230 235 240

Gly Gly Pro Ser Val Phe Leu Phe Pro Pro Lys Pro Lys Asp Thr Leu
245 250 255

Met Ile Ser Arg Thr Pro Glu Val Thr Cys Val Val Val Asp Val Ser
260 265 270

His Glu Asp Pro Glu Val Lys Phe Asn Trp Tyr Val Asp Gly Val Glu
275 280 285

Val His Asn Ala Lys Thr Lys Pro Arg Glu Glu Gln Tyr Asn Ser Thr
290 295 300

Tyr Arg Val Val Ser Val Leu Thr Val Leu His Gln Asp Trp Leu Asn
305 310 315 320

Gly Lys Glu Tyr Lys Cys Lys Val Ser Asn Lys Ala Leu Pro Ala Pro
325 330 335

Ile Glu Lys Thr Ile Ser Lys Ala Lys Gly Gln Pro Arg Glu Pro Gln
340 345 350

```
Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 378
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 378

caggtgcaat tgctggaaag cggcggtggc ctggtgcagc cgggtggcag cctgcgtctg     60

agctgcgcgg cgtccggatt caccttttct actgctgcta tgtcttgggt gcgccaggcc    120

ccgggcaaag gtctcgagtg ggtttcctct atcgaatact acgacactga cactcattat    180

gcggatagcg tgaaaggccg ctttaccatc agccgcgata attcgaaaaa caccctgtat    240

ctgcaaatga acagcctgcg tgcggaagat acggccgtgt attattgcgc gcgtgaactg    300

tcttacctgt actctggtta ctacttcgat tactggggcc aaggcaccct ggtgactgtt    360

agctcagcct ccaccaaggg tccatcggtc ttccccctgg caccctcctc caagagcacc    420

tctgggggca cagcggccct gggctgcctg gtcaaggact acttccccga accggtgacg    480

gtgtcgtgga actcaggcgc cctgaccagc ggcgtgcaca ccttcccggc tgtcctacag    540

tcctcaggac tctactccct cagcagcgtg gtgaccgtgc cctccagcag cttgggcacc    600

cagacctaca tctgcaacgt gaatcacaag cccagcaaca ccaaggtgga caagagagtt    660

gagcccaaat cttgtgacaa aactcacaca tgcccaccgt gcccagcacc tgaagcagcg    720

gggggaccgt cagtcttcct cttcccccca aaacccaagg acaccctcat gatctcccgg    780

acccctgagg tcacatgcgt ggtggtggac gtgagccacg aagaccctga ggtcaagttc    840

aactggtacg tggacggcgt ggaggtgcat aatgccaaga caaagccgcg ggaggagcag    900

tacaacagca cgtaccgggt ggtcagcgtc ctcaccgtcc tgcaccagga ctggctgaat    960

ggcaaggagt acaagtgcaa ggtctccaac aaagccctcc cagcccccat cgagaaaacc   1020

atctccaaag ccaaagggca gccccgagaa ccacaggtgt acaccctgcc cccatcccgg   1080

gaggagatga ccaagaacca ggtcagcctg acctgcctgg tcaaaggctt ctatcccagc   1140

gacatcgccg tggagtggga gagcaatggg cagccggaga acaactacaa gaccacgcct   1200

cccgtgctgg actccgacgg ctccttcttc ctctacagca agctcaccgt ggacaagagc   1260

aggtggcagc aggggaacgt cttctcatgc tccgtgatgc atgaggctct gcacaaccac   1320

tacacgcaga agagcctctc cctgtctccg ggtaaa                             1356
```

```
<210> SEQ ID NO 379
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 379

Thr Ile Glu Tyr Ser Ser Gln Glu Thr Tyr Tyr Ala Asp Ser Val Lys
1               5                   10                  15

Gly


<210> SEQ ID NO 380
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 380

Glu Tyr Ser Ser Gln Glu
1               5


<210> SEQ ID NO 381
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 381

Ile Glu Tyr Ser Ser Gln Glu Thr
1               5


<210> SEQ ID NO 382
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 382

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Thr Ile Glu Tyr Ser Ser Gln Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
```

```
            100                 105                 110

Gly Gln Gly Thr Leu Val Thr Val Ser Ser
        115                 120


<210> SEQ ID NO 383
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 383

caggtgcaat tgctggaaag cggcggtggc ctggtgcagc cgggtggcag cctgcgtctg     60

agctgcgcgg cgtccggatt caccttttct actgctgcta tgtcttgggt gcgccaggcc    120

ccgggcaaag gtctcgagtg ggtttccact atcgaatact ctagccagga aacttactat    180

gcggatagcg tgaaaggccg ctttaccatc agccgcgata attcgaaaaa caccctgtat    240

ctgcaaatga acagcctgcg tgcggaagat acggccgtgt attattgcgc gcgtgaactg    300

tcttacctgt actctggtta ctacttcgat tactggggcc aaggcaccct ggtgactgtt    360

agctca                                                               366


<210> SEQ ID NO 384
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 384

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Thr Ile Glu Tyr Ser Ser Gln Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190
```

```
Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 385
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 385

caggtgcaat tgctggaaag cggcggtggc ctggtgcagc cgggtggcag cctgcgtctg      60

agctgcgcgg cgtccggatt caccttttct actgctgcta tgtcttgggt gcgccaggcc     120

ccgggcaaag gtctcgagtg ggtttccact atcgaatact ctagccagga aacttactat     180

gcggatagcg tgaaaggccg ctttaccatc agccgcgata attcgaaaaa caccctgtat     240

ctgcaaatga acagcctgcg tgcggaagat acggccgtgt attattgcgc gcgtgaactg     300

tcttacctgt actctggtta ctacttcgat tactggggcc aaggcaccct ggtgactgtt     360

agctcagcct ccaccaaggg tccatcggtc ttccccctgg caccctcctc caagagcacc     420

tctgggggca cagcggccct gggctgcctg gtcaaggact acttccccga accggtgacg     480
```

```
gtgtcgtgga actcaggcgc cctgaccagc ggcgtgcaca ccttcccggc tgtcctacag    540

tcctcaggac tctactccct cagcagcgtg gtgaccgtgc cctccagcag cttgggcacc    600

cagacctaca tctgcaacgt gaatcacaag cccagcaaca ccaaggtgga caagagagtt    660

gagcccaaat cttgtgacaa aactcacaca tgcccaccgt gcccagcacc tgaagcagcg    720

gggggaccgt cagtcttcct cttcccccca aaacccaagg acaccctcat gatctcccgg    780

acccctgagg tcacatgcgt ggtggtggac gtgagccacg aagaccctga ggtcaagttc    840

aactggtacg tggacggcgt ggaggtgcat aatgccaaga caaagccgcg ggaggagcag    900

tacaacagca cgtaccgggt ggtcagcgtc ctcaccgtcc tgcaccagga ctggctgaat    960

ggcaaggagt acaagtgcaa ggtctccaac aaagccctcc cagcccccat cgagaaaacc   1020

atctccaaag ccaaagggca gccccgagaa ccacaggtgt acaccctgcc cccatcccgg   1080

gaggagatga ccaagaacca ggtcagcctg acctgcctgg tcaaaggctt ctatcccagc   1140

gacatcgccg tggagtggga gagcaatggg cagccggaga acaactacaa gaccacgcct   1200

cccgtgctgg actccgacgg ctccttcttc ctctacagca agctcaccgt ggacaagagc   1260

aggtggcagc aggggaacgt cttctcatgc tccgtgatgc atgaggctct gcacaaccac   1320

tacacgcaga agagcctctc cctgtctccg ggtaaa                              1356
```

<210> SEQ ID NO 386
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 386

```
Gln Ser Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Lys Asn Tyr Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu
            100                 105                 110
```

<210> SEQ ID NO 387
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 387

```
cagagcgtgc tgacacagcc tccctccgtg tctggcgccc ctggccagag agtgaccatc     60

tcctgctccg gctcctcctc caacatcggc tccaacgacg tgtcctggta tcagcagctg    120
```

cccggcaccg cccctaagct gctgatctac aagaactaca accggccctc cggcgtgccc 180
gaccggttct ctggctccaa gtctggcacc tccgcctccc tggctatcac cggcctgcag 240
gctgaggacg aggccgacta ctactgctcc gcctgggacc agcggcagtt cgacgtggtg 300
ttcggcggag gcaccaagct gaccgtgctg 330

<210> SEQ ID NO 388
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 388

Gln Ser Val Leu Thr Gln Pro Pro Ser Val Ser Gly Ala Pro Gly Gln
1 5 10 15

Arg Val Thr Ile Ser Cys Ser Gly Ser Ser Ser Asn Ile Gly Ser Asn
20 25 30

Asp Val Ser Trp Tyr Gln Gln Leu Pro Gly Thr Ala Pro Lys Leu Leu
35 40 45

Ile Tyr Lys Asn Tyr Asn Arg Pro Ser Gly Val Pro Asp Arg Phe Ser
50 55 60

Gly Ser Lys Ser Gly Thr Ser Ala Ser Leu Ala Ile Thr Gly Leu Gln
65 70 75 80

Ala Glu Asp Glu Ala Asp Tyr Tyr Cys Ser Ala Trp Asp Gln Arg Gln
85 90 95

Phe Asp Val Val Phe Gly Gly Gly Thr Lys Leu Thr Val Leu Gly Gln
100 105 110

Pro Lys Ala Ala Pro Ser Val Thr Leu Phe Pro Pro Ser Ser Glu Glu
115 120 125

Leu Gln Ala Asn Lys Ala Thr Leu Val Cys Leu Ile Ser Asp Phe Tyr
130 135 140

Pro Gly Ala Val Thr Val Ala Trp Lys Ala Asp Ser Ser Pro Val Lys
145 150 155 160

Ala Gly Val Glu Thr Thr Thr Pro Ser Lys Gln Ser Asn Asn Lys Tyr
165 170 175

Ala Ala Ser Ser Tyr Leu Ser Leu Thr Pro Glu Gln Trp Lys Ser His
180 185 190

Arg Ser Tyr Ser Cys Gln Val Thr His Glu Gly Ser Thr Val Glu Lys
195 200 205

Thr Val Ala Pro Thr Glu Cys Ser
210 215

<210> SEQ ID NO 389
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 389
cagagcgtgc tgacacagcc tccctccgtg tctggcgccc ctggccagag agtgaccatc 60
tcctgctccg gctcctcctc caacatcggc tccaacgacg tgtcctggta tcagcagctg 120
cccggcaccg cccctaagct gctgatctac aagaactaca accggccctc cggcgtgccc 180

```
gaccggttct ctggctccaa gtctggcacc tccgcctccc tggctatcac cggcctgcag    240

gctgaggacg aggccgacta ctactgctcc gcctgggacc agcggcagtt cgacgtggtg    300

ttcggcggag gcaccaagct gaccgtgctg ggccagccta aggctgcccc cagcgtgacc    360

ctgttccccc ccagcagcga ggagctgcag gccaacaagg ccaccctggt gtgcctgatc    420

agcgacttct acccaggcgc cgtgaccgtg gcctggaagg ccgacagcag ccccgtgaag    480

gccggcgtgg agaccaccac ccccagcaag cagagcaaca acaagtacgc cgccagcagc    540

tacctgagcc tgacccccga gcagtggaag agccacaggt cctacagctg ccaggtgacc    600

cacgagggca gcaccgtgga aaagaccgtg gccccaaccg agtgcagc                 648
```

```
<210> SEQ ID NO 390
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 390

caggtgcaat tgctggaaag cggcggtggc ctggtgcagc cgggtggcag cctgcgtctg     60

agctgcgcgg cgtccggatt caccttttct actgctgcta tgtcttgggt gcgccaggcc    120

ccgggcaaag gtctcgagtg ggtttccggt atctctggtt ctggttcttc tacctactat    180

gcggatagcg tgaaaggccg ctttaccatc agccgcgata attcgaaaaa caccctgtat    240

ctgcaaatga acagcctgcg tgcggaagat acggccgtgt attattgcgc gcgtgaactg    300

tcttacctgt actctggtta ctacttcgat tactggggcc aaggcaccct ggtgactgtt    360

agctca                                                               366
```

```
<210> SEQ ID NO 391
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 391

caggtgcaat tgctggaaag cggcggtggc ctggtgcagc cgggtggcag cctgcgtctg     60

agctgcgcgg cgtccggatt caccttttct actgctgcta tgtcttgggt gcgccaggcc    120

ccgggcaaag gtctcgagtg ggtttccact atcgactctt ggggcgacga cactgactat    180

gcggatagcg tgaaaggccg ctttaccatc agccgcgata attcgaaaaa caccctgtat    240

ctgcaaatga acagcctgcg tgcggaagat acggccgtgt attattgcgc gcgtgaactg    300

tcttacctgt actctggtta ctacttcgat tactggggcc aaggcaccct ggtgactgtt    360

agctcagcct ccaccaaggg tccatcggtc ttccccctgg caccctcctc caagagcacc    420

tctgggggca cagcggccct gggctgcctg gtcaaggact acttccccga accggtgacg    480

gtgtcgtgga actcaggcgc cctgaccagc ggcgtgcaca ccttcccggc tgtcctacag    540

tcctcaggac tctactccct cagcagcgtg gtgaccgtgc cctccagcag cttgggcacc    600

cagacctaca tctgcaacgt gaatcacaag cccagcaaca ccaaggtgga caagagagtt    660

gagcccaaat cttgtgacaa aactcacaca tgcccaccgt gcccagcacc tgaagcagcg    720
```

gggggaccgt cagtcttcct cttcccccca aaacccaagg acaccctcat gatctcccgg 780
acccctgagg tcacatgcgt ggtggtggac gtgagccacg aagaccctga ggtcaagttc 840
aactggtacg tggacggcgt ggaggtgcat aatgccaaga caaagccgcg ggaggagcag 900
tacaacagca cgtaccgggt ggtcagcgtc ctcaccgtcc tgcaccagga ctggctgaat 960
ggcaaggagt acaagtgcaa ggtctccaac aaagccctcc cagcccccat cgagaaaacc 1020
atctccaaag ccaaagggca gccccgagaa ccacaggtgt acaccctgcc cccatcccgg 1080
gaggagatga ccaagaacca ggtcagcctg acctgcctgg tcaaaggctt ctatcccagc 1140
gacatcgccg tggagtggga gagcaatggg cagccggaga acaactacaa gaccacgcct 1200
cccgtgctgg actccgacgg ctccttcttc ctctacagca agctcaccgt ggacaagagc 1260
aggtggcagc aggggaacgt cttctcatgc tccgtgatgc atgaggctct gcacaaccac 1320
tacacgcaga agagcctctc cctgtctccg ggtaaa 1356

<210> SEQ ID NO 392
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 392
caagtgcagc tgcttgaatc tggcggcgga ctggtgcagc ctggcggctc cctgagactg 60
tcttgcgccg cctccggctt caccttctcc accgccgcta tgtcctgggt ccgacaggct 120
cccggcaagg gcctggaatg ggtgtccacc attgagtact ccagccagga aacctactac 180
gccgactccg tgaagggccg gttcaccatc tcccgggaca actccaagaa caccctgtac 240
ctgcagatga actccctgcg ggccgaggac accgccgtgt actactgcgc cagagagctg 300
tcctacctgt actccggcta ctacttcgac tactggggcc agggcaccct ggtcaccgtg 360
tcctct 366

<210> SEQ ID NO 393
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 393
caagtgcagc tgcttgaatc tggcggcgga ctggtgcagc ctggcggctc cctgagactg 60
tcttgcgccg cctccggctt caccttctcc accgccgcta tgtcctgggt ccgacaggct 120
cccggcaagg gcctggaatg ggtgtccacc attgagtact ccagccagga aacctactac 180
gccgactccg tgaagggccg gttcaccatc tcccgggaca actccaagaa caccctgtac 240
ctgcagatga actccctgcg ggccgaggac accgccgtgt actactgcgc cagagagctg 300
tcctacctgt actccggcta ctacttcgac tactggggcc agggcaccct ggtcaccgtg 360
tcctctgcta gcaccaaggg cccctccgtg ttccctctgg ccccttccag caagtctacc 420
tccggcggca cagctgctct gggctgcctg gtcaaggact acttccctga gcctgtgaca 480
gtgtcctgga actctggcgc cctgacctct ggcgtgcaca ccttccctgc cgtgctgcag 540
tcctccggcc tgtactccct gtcctccgtg gtcacagtgc cttcaagcag cctgggcacc 600

-continued

```
cagacctata tctgcaacgt gaaccacaag ccttccaaca ccaaggtgga caagcgggtg    660

gagcctaagt cctgcgacaa gacccacacc tgtcctccct gccctgctcc tgaagctgct    720

ggcggccctt ctgtgttcct gttccctcca aagcccaagg acaccctgat gatctcccgg    780

acccctgaag tgacctgcgt ggtggtggac gtgtcccacg aggatcctga agtgaagttc    840

aattggtacg tggacggcgt ggaggtgcac aacgccaaga ccaagcctcg ggaggaacag    900

tacaactcca cctaccgggt ggtgtccgtg ctgaccgtgc tgcaccagga ctggctgaac    960

ggcaaagagt acaagtgcaa agtctccaac aaggccctgc ctgcccctat cgaaaagaca   1020

atctccaagg ccaagggcca gcctagggaa ccccaggtgt acaccctgcc acccagccgg   1080

gaggaaatga ccaagaacca ggtgtccctg acctgtctgg tcaagggctt ctacccttcc   1140

gatatcgccg tggagtggga gtctaacggc cagcctgaga acaactacaa gaccaccccc   1200

cctgtgctgg actccgacgg ctccttcttc ctgtactcca aactgaccgt ggacaagtcc   1260

cggtggcagc agggcaacgt gttctcctgc tccgtgatgc acgaggccct gcacaaccac   1320

tacacccaga agtccctgtc cctgtctccc ggcaag                             1356


<210> SEQ ID NO 394
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 394

His His His His His His
1               5
```

REVERSAL BINDING AGENTS FOR ANTI-FACTOR XI/XIA ANTIBODIES AND USES THEREOF

This application claims the benefit of U.S. Provisional Application No. 62/341,574 filed on May 25, 2016 and U.S. Provisional Application No. 62/438,754 filed on Dec. 23, 2016, each of which is hereby incorporated by reference in its entirety.

The instant application contains a Sequence Listing which has been submitted electronically in ASCII format and is hereby incorporated by reference in its entirety. Said ASCII copy, created on May 22, 2017, is named "PAT057330-WO-PCT_SL.txt" and is 238,587 bytes in size. Throughout the text of this application, should there be a discrepancy between the text of the specification (e.g., Tables 1 and 2) and the sequence listing, the text of the specification shall prevail.

TECHNICAL FIELD

The present disclosure relates to binding agents (e.g., anti-idiotype antibodies), which specifically binds to anti-Factor XI and/or anti-Factor XIa ("anti-FXI/FXIa") antibodies, and reverses one or more anticoagulant effects of the anti-Factor XI and/or anti-Factor XIa antibodies, as well as to methods of use thereof, such as methods for reversing anticoagulant effects of such anti-Factor XI and/or anti-Factor XIa antibodies.

BACKGROUND

Thrombosis refers to thrombus formation inside blood vessels, subsequent to a combination of hereditary and acquired risk factors, known as thrombophilia or hypercoagulable states. Vessel wall damage, stasis, increased platelets reactivity and activation of clotting factors are some of the fundamental features of thrombosis. Thrombosis can occur in both venous and arterial circulation and can result in the development of deep vein thrombosis (DVT), pulmonary embolism, and stroke. If a thrombus occurs in the arterial system, down-stream ischemia can occur, leading to acute coronary syndromes (ACS), ischemic stroke, and acute limb ischemia. Thrombus formation in the venous system typically leads to deep venous thrombosis, pulmonary embolism and chronic thromboembolic pulmonary hypertension. Clots may also form in the left atrial appendage in patients with atrial fibrillation (AF), and dislodged thrombi may result in potentially devastating complications, i.e. thromboembolic stroke and systemic embolism. The currently available antithrombotic medications, including low molecular weight heparin (LMWH), thrombin inhibitors, and Factor Xa (FXa) inhibitors, are all associated with a significant risk of bleeding (Weitz J. I. (2010) Thromb. Haemost. 103, 62). The development of an antithrombotic agent that does not affect hemostasis, and therefore does not result in bleeding complications, as well as specific reversal agents, would be highly desirable.

Current anticoagulants are either injected or taken orally. The injectable anticoagulant LMWH is widely used and offers an improved therapeutic profile over formerly applied unfractionated heparin. For the past few decades the most commonly used oral anticoagulant has been warfarin. Warfarin has a narrow therapeutic window that requires frequent monitoring of the coagulation status, and shows a variety of drug-drug interactions. More recently, orally available direct FXa and thrombin inhibitors entered the anticoagulant market and are increasingly applied.

LMWHs, FXa inhibitors, and thrombin inhibitors are all efficacious in the prevention of post-operative venous thromboembolic disease, in the treatment of spontaneous DVT and pulmonary embolism, and in the stroke prevention in atrial fibrillation. However, these anticoagulants are also associated with bleeding complications that were generally comparable to those observed with the older drugs warfarin and unfractionated heparin. In the ADVANCE-2 clinical trial, the FXa inhibitor apixaban (Eliquis) was compared to the LMWH enoxaparin in patients after total knee replacement. While acute apixaban therapy was more effective at preventing venous thromboembolic disease than enoxaparin, both agents were associated with a significant risk of bleeding. Clinically relevant bleeding occurred in 4% of patients receiving apixaban and in 5% of patients treated with enoxaparin (Lassen, M. R., et al. (2009) N. Engl. J. Med. 361, 594).

In the RE-LY trial, the direct thrombin inhibitor dabigatran (Pradaxa) was compared to warfarin in patients with atrial fibrillation and a risk of stroke (Connolly, S. J., et al. (2009) N. Engl. J. Med. 361, 1139). Chronic dabigatran therapy was associated with a significantly lower risk of stroke or systemic embolism. However, major bleeding complications occurred in 3.1% of patients receiving 150 mg per day of dabigatran and in 3.4% of patients receiving warfarin ($p=0.31$).

Atrial fibrillation (AF) remains the most common cardiac arrhythmia in clinical practice, accounting for approximately one third of hospitalizations for cardiac dysrhythmias. Currently, it is estimated to affect more than 6 million patients in Europe and approximately 2.3 million in the United States, and this number continues to grow rapidly because of the increasing proportion of the aging population. It is estimated that approximately 5% of the population over the age of 65 years, and 10% of people aged over 80 years, will develop AF, however, the prevalence of AF is increasing beyond what is explained by age alone. AF risk factors such as hypertension, congestive heart failure, left ventricular hypertrophy, coronary artery disease and diabetes mellitus, and obstructive sleep apnea are also on the rise. As such, the number of affected individuals with AF is expected to increase two to three times over the next three decades in western populations. (Kannel and Benjamin (2008) Med Clin North Am. 2008; 92:17-40; Bunch, et al. (2012) J Innovations of Card Rhythm Manag 2012; 3: 855-63).

The principal risk of AF is a four- to five fold increase in embolic stroke. The attributable risk for stroke associated with AF increases steeply with age to 23.5% at ages 80 to 89. AF is associated with a doubling of mortality in both genders (Kannel and Benjamin 2008). AF is also independently associated with cognitive decline and all forms of dementia (Marzona, et al. (2012) CMAJ 2012; 184: 329-36; Geita et al 2013; Bunch et al 2012).

Most patients with AF require life-long anticoagulation therapy to prevent cardioembolic stroke and systemic embolism. The CHA2DS2-VASc risk score is a validated and widely used stratification tool to predict thromboembolic risk in atrial fibrillation patients and to identify patients who should benefit from anticoagulation therapy (LIP 2011; Camm, et al. (2012) Eur Heart J 2012; 33: 2719-2747); the accumulated evidence shows that CHA2DS2-VASc is at least as accurate as or possibly better than, scores such as CHADS2 in identifying patients who develop stroke and thromboembolism and definitively better at identifying 'truly low-risk' patients with AF. It is estimated that 85 to 90% of AF patients will require anticoagulation therapy.

In a meta-analysis comprising 6 trials which evaluated the effect of vitamin K antagonists (VKA) in reducing stroke and systemic embolism, a highly significant risk reduction in stroke incidence (relative risk reduction of 67% for stoke) was observed. All-cause mortality was significantly reduced (26%) by adjusted-dose VKA vs. control (Hart, Pearce, and Aguilar (2007) Ann Intern Med 2007; 146:857-867). An international normalized ratio (INR) target between 2 and 3 was associated with best benefit-risk ratio (Hylek et al (2003) N Engl J Med; 349:1019-1026) and universally adopted by international and national guidelines.

In recent years, new oral anticoagulants (NOAC) also referred to as direct oral anticoagulants (DOAC) have been approved and introduced to clinical practice. These drugs are at least as effective or even better than warfarin for reducing thrombo-embolic disease (Connolly, et al. (2009) N Engl J Med; 361:1139-51; Connolly, et al. (2011) N Engl J Med; 364:806-17; Patel, et al. (2011) N Engl J Med 2011; 365: 883-91). NOAC were also associated with large reductions in the most devastating complications of warfarin namely hemorrhagic stroke and intracranial hemorrhage. Major bleeding events were similar or slightly lower than well conducted warfarin therapy. In addition NOAC are associated with a lower potential for drug-drug interaction than warfarin and could be used without routine monitoring; this is expected to ease their use in everyday medical practice.

Despite recent improvements, bleeding risk continues to be high with the use of anticoagulants. For instance, the annual incidence of major and clinically relevant non major bleeding was 14.9% and the annual incidence of major bleeding events was 3.6% in patients treated with rivaroxaban in the ROCKET study (Patel et al 2011). The annual incidence of major bleeding was >5% in patients at a high risk for bleeding defined as HAS Bled risk score ≥3 (Gallego, et al. (2012) Carc Arrhythm Electrophysiol.; 5:312-318). Major bleeding is a particularly relevant clinical outcome; for instance in the ROCKET study, once major bleeding has occurred, all-cause mortality rate was 20.4% in the rivaroxaban group and 26.1% in the warfarin group. Once major bleeding events have occurred stroke and systemic embolism occurred in 4.7% and 5.4% of patients in rivaroxaban and warfarin groups, respectively (Piccini, et al. (2014) Eur Heart J; 35:1873-80). Hospital stay, transfusion of blood products and resources utilization were also severely impacted by the occurrence of major bleeding. Bleeding risk is also a major reason for not receiving anticoagulants in eligible patients. In the Euro Heart Survey on Atrial Fibrillation comprising data from 182 hospitals in 35 countries and 5333 ambulant and hospitalized AF patients, only 67% of eligible patients received oral anticoagulant at discharge (Nieuwlaat, et al (2005) Eur Heart J; 26, 2422-2434). A high unmet medical need therefore exists for a safer therapy which can reduce AF thromboembolic complications such as stroke, systemic embolism, cognitive decline and mortality with comparable efficacy as existing therapy but with a lower bleeding liability.

Factor XI (FXI) holds important roles in both intrinsic and extrinsic coagulation pathways and in bridging the initiation and amplification phases of plasmatic hemostasis (Gailani and Renné (2007) Arterioscler Thromb Vasc Biol; 27(12): 2507-13). Both Factor XII and thrombin can activate FXI, resulting in a sustained thrombin generation and fibrinolysis inhibition. FXI plays a minor role in normal hemostasis in a high tissue factor environment "after vessel injury" whereas it appears to play a key role in thrombosis. Severe FXI deficiency is associated with a lower incidence of ischemic stroke and venous thromboembolic events (Salomon et al (2008) Blood; 111(8):4113-7; Salomon et al (2011) Thromb Haemost; 105(2):269-73). Furthermore, in a population-based study, a survival advantage of severe FXI deficiency was evoked as a result of a lower incidence of thromboembolic events (Duga and Salomon, (2013) Semin Thromb Hemost; 39(6):621-31). Bleeding manifestations in subjects with severe FXI deficiency are infrequent, usually mild, injury-related, and affect preferably tissues with increased fibrinolytic activity such as the oral mucosa, nasal mucosa and urinary tract (Bolton-Maggs, (2000) Haemophilia; 6 Suppl 1:100-9). Bleeding in vital organs is extremely rare or not existing.

Accordingly, as part of efforts to lower bleeding liability, there is also a high unmet medical need for specific, reversal agents for anticoagulant therapies, for example, in circumstances when reversal of the anticoagulant effects of a therapy is needed for emergency surgery/urgent procedures and in life-threatening or uncontrolled bleeding.

SUMMARY

Lower bleeding risk is associated with anticoagulant therapies involving anti-FXI/FXIa antibodies, compared to NOACs. For example, anti-Factor XI/FXIa antibody NOV1401 is a human antibody binding to the catalytic domain of FXI. NOV1401 inhibits both the zymogen (FXI) and the activated factor XI (FXIa) with high potency. Anti-FXI/FXIa antibody NOV1401 dose-dependently prolonged activated partial thromboplastin time (aPTT) in in vitro and in in vivo studies. After a single subcutaneous (s.c.) administration of NOV1401 at a 3 mg/kg dose, a sustained anticoagulant activity lasting more than one month was observed in cynomolgus monkeys. Moreover, Anti-FXI/FXIa antibody NOV1401 prevented experimental carotid artery thrombosis induced by $FeCl_3$ and induced prolongation in aPTT in FXI−/− mice reconstituted with human FXI. NOV1401 was well tolerated in the 13 week Good Laboratory Practice (GLP)-compliant toxicity study conducted in cynomolgus monkeys.

Despite the lower bleeding risk with anti-FXI/FXIa antibodies, such as antibody NOV1401, compared to NOACs, bleeding events may still happen due to trauma, surgery, procedures, co-medication and high prevalence of comorbidities that increase bleeding risk such as hypertension, heart failure, renal impairment, hepatic impairment, older age, prior bleeding events, risk of falls, use of antiplatelet agents or non-steroidal anti-inflammatory drugs, etc.

Accordingly, as part of efforts to lower bleeding liability, the present disclosure describes strategies to address the high unmet medical need for specific, reversal agents for anticoagulant therapies, such as anti-Factor XI/XIa antibodies (e.g., anti-FXI/FXIa antibodies which specifically bind to the catalytic domain of FXI/FXIa). In specific aspects, managing bleeding or bleeding risk is beneficial in circumstances when reversal of the anticoagulant effects of a therapy is needed, for example, for emergency surgery/urgent procedures and in cases of life-threatening or uncontrolled bleeding. In specific aspects, managing bleeding or bleeding risk is beneficial in patients identified as having high bleeding risk (e.g., previous history of bleeding).

The present disclosure relates to binding agents (e.g., anti-idiotype antibodies and fragments thereof such as Fabs) which specifically binds to antibodies that specifically bind coagulation Factor XI and XIa (activated Factor XI) (hereinafter, sometimes referred to as "FXI", "FXIa," and similar terms), and which are capable of reversing one or more anticoagulant effects of such anti-FXI/FXIa antibodies (e.g., capable of reducing aPTT or bleeding time) and/or inhibits binding of the antibodies to FXI/FXIa. The present disclosure also relates to pharmaceutical compositions comprising the binding agents, and methods of reversing one or more anticoagulant effects of an anti-FXI/FXIa antibody in a patient (e.g., human patient) being treated with the anti-FXI/FXIa antibody, comprising administering the binding agent. Such binding agents capable of reversing one or more anticoagulant effects of anti-FXI/FXIa antibodies achieve an unmet need in circumstances when reversal of the anticoagulant effects of a therapy, such as anti-FXI/XIa antibodies, is needed for emergency surgery/urgent procedures and in life-threatening or uncontrolled bleeding.

In specific aspects, such patients (e.g., human patients) are being treated with an anti-FXI/FXIa antibody for the prevention and/or treatment of thrombosis or thromboembolic disease/disorder (e.g., thrombic stroke, atrial fibrillation, stroke prevention in atrial fibrillation (SPAF), deep vein thrombosis, venous thromboembolism, pulmonary embolism, acute coronary syndromes (ACS), ischemic stroke, acute limb ischemia, chronic thromboembolic pulmonary hypertension, systemic embolism). In specific aspects, binding agents provided herein that reverses one or more anticoagulant effects of anti-FXI/FXIa antibodies are anti-idiotype antibodies, and in further specific aspects, such anti-idiotype antibodies are Fabs. In further specific aspects, such anti-idiotype antibodies are monoclonal antibodies, such as human monoclonal antibodies, e.g., recombinant human monoclonal antibodies.

In particular aspects, the present disclosure also relates to isolated polynucleotides and nucleic acids comprising a sequence encoding a binding agent provided herein, to vectors comprising one or more of the polynucleotides or nucleic acids provided herein, to host cells comprising such vectors or polynucleotides or nucleic acids. In specific aspects, the host cells are non-human mammalian cells, such as Chinese hamster ovary (CHO) cells.

Non-limiting embodiments of the present disclosure are described in the following aspects:

1. A binding agent (e.g., human anti-idiotype antibody such as a human anti-idiotype Fab) which specifically binds a target antibody that binds human Factor XI ("FXI") and/or Factor XIa ("FXIa") within the catalytic domain, wherein the binding agent inhibits an anticoagulant activity of the target antibody, wherein the binding agent binds to the target antibody with a dissociation constant ($K_D$) of 1 nM or less, and wherein the binding agent is capable of inhibiting the ability of the target antibody to delay activated partial thromboplastin time (aPTT) by at least 35%.

2. The binding agent of aspect 1, wherein the target antibody comprises (i) a heavy chain variable region (VH) comprising the amino acid sequence of SEQ ID NO: 12 and a light chain variable region (VL) comprising the amino acid sequence of SEQ ID NO: 23; or (ii) a heavy chain comprising the amino acid sequence of SEQ ID NO: 14 and a light chain comprising the amino acid sequence of SEQ ID NO: 25.

3. The binding agent of aspect 1, wherein the target antibody comprises (i) a VH comprising complementarity determining regions HCDR1, HCDR2 and HCDR3 of a VH comprising the amino acid sequence of SEQ ID NO: 12 and (ii) a VL comprising complementarity determining regions LCDR1, LCDR2, and LCDR3 of a VL comprising the amino acid sequence of SEQ ID NO: 23.

4. The binding agent of aspect 1, wherein the target antibody comprises:

(A)(i) a VH comprising complementarity determining regions HCDR1, HCDR2 and HCDR3 comprising the amino acid sequences of SEQ ID NO: 3, SEQ ID NO: 4, and SEQ ID NO: 5, respectively; and (ii) a VL comprising complementarity determining regions LCDR1, LCDR2, and LCDR3 comprising the amino acid sequence of SEQ ID NO: 16, SEQ ID NO: 17, and SEQ ID NO: 18, respectively;

(B)(i) a VH comprising complementarity determining regions HCDR1, HCDR2 and HCDR3 comprising the amino acid sequences of SEQ ID NO: 6, SEQ ID NO: 4, and SEQ ID NO: 5, respectively; and (ii) a VL comprising complementarity determining regions LCDR1, LCDR2, and LCDR3 comprising the amino acid sequence of SEQ ID NO: 16, SEQ ID NO: 17, and SEQ ID NO: 18, respectively;

(C)(i) a VH comprising complementarity determining regions HCDR1, HCDR2 and HCDR3 comprising the amino acid sequences of SEQ ID NO: 7, SEQ ID NO: 8, and SEQ ID NO: 5, respectively; and (ii) a VL comprising complementarity determining regions LCDR1, LCDR2, and LCDR3 comprising the amino acid sequence of SEQ ID NO: 19, SEQ ID NO: 20, and SEQ ID NO: 21, respectively; or (D)(i) a VH comprising complementarity determining regions HCDR1, HCDR2 and HCDR3 comprising the amino acid sequences of SEQ ID NO: 9, SEQ ID NO: 10, and SEQ ID NO: 11, respectively; and (ii) a VL comprising complementarity determining regions LCDR1, LCDR2, and LCDR3 comprising the amino acid sequence of SEQ ID NO: 22, SEQ ID NO: 20, and SEQ ID NO: 18, respectively.

5. The binding agent of aspect 1, wherein the target antibody competes with an anti-FXI/FXIa antibody comprising a heavy chain comprising the amino acid sequence of SEQ ID NO: 14 and a light chain comprising the amino acid sequence of SEQ ID NO: 25.

6. The binding agent of aspect 1, wherein the target antibody binds the same epitope as an anti-FXI/FXIa antibody comprising a heavy chain comprising the amino acid sequence of SEQ ID NO: 14 and a light chain comprising the amino acid sequence of SEQ ID NO: 25.

7. The binding agent of aspect 6, wherein the target antibody binds one or more epitopes of human FXI and/or FXIa comprising one, two, three, four, five, six, seven, eight, nine, ten, eleven, twelve, thirteen, fourteen, fifteen or more, or all of, amino acid residues selected from: Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604.

8. A binding agent which specifically binds a target antibody that binds human FXI and/or FXIa within the catalytic domain, wherein the binding agent inhibits an anticoagulant activity of the target antibody, wherein the target antibody comprises (i) a heavy chain variable region (VH) comprising the amino acid sequence of SEQ ID NO: 12 and a light chain variable region (VL) comprising the amino acid sequence of SEQ ID NO: 23, or (ii) a heavy chain comprising the amino acid sequence of SEQ ID NO: 14 and a light chain comprising the amino acid sequence of SEQ ID NO: 25; and wherein the binding agent is an antibody (e.g., human anti-idiotype antibody) or antigen-binding fragment thereof (e.g., Fab) comprising (1) a VH comprising complementarity determining regions HCDR1, HCDR2, and HCDR3 selected from those set forth in Table 2, and (2) a VL comprising complementarity determining regions LCDR1, LCDR2, and LCDR3 selected from those set forth in Table 2.

9. The binding agent of aspect 8, wherein the HCDR1 comprises the amino acid sequence GFTF-X1-SAAVH (SEQ ID NO: 347), wherein X1 is any amino acid or is S or Q;

the HCDR2 comprises the amino acid sequence RIK-SKA-X4-X5-GTTDYAAPVKG (SEQ ID NO: 357), RIKSK-X3-X4-X5-GTTDYAAPVKG (SEQ ID NO: 358), RIKSK-X3-X4-GGTTDYAAPVKG (SEQ ID NO: 349) or RIKSKA-X4-GGTTDYAAPVKG (SEQ ID NO: 348), wherein X3 is any amino acid or is T or A, X4 is any amino acid or is S or D, and X5 is any amino acid or is G or A;

the HCDR3 comprises the amino acid sequence DSPSIS-SYSIPYFSGMDV (SEQ ID NO: 350);

the LCDR1 comprises the amino acid sequence RASQ-GIRAWLN (SEQ ID NO: 351) or

RASQ-X6-I-X7-X8-X9-LN (SEQ ID NO: 352), wherein X6 is any amino acid or is S or G, X7 is any amino acid or is R or S, X8 is any amino acid or is A or N, and X9 is any amino acid or is W or Y;

the LCDR2 comprises the amino acid sequence AASS-LQS (SEQ ID NO: 353); and the LCDR3 comprises the amino acid sequence HQYITHPPT (SEQ ID NO: 354) or HQYI-X10-X11-P-X12-T (SEQ ID NO: 355), wherein X10 is any amino acid or is T or A, X11 is any amino acid or is H or K, and X12 is any amino acid or is P or I.

10. The binding agent of aspect 9, wherein the HCDR1 comprises the amino acid sequence GFTF-X1-SAAVH (SEQ ID NO: 347), wherein X1 is S or Q;

the HCDR2 comprises the amino acid sequence RIK-SKA-X4-X5-GTTDYAAPVKG (SEQ ID NO: 357), wherein X4 is S or D and X5 is G or A;

the HCDR3 comprises the amino acid sequence DSPSIS-SYSIPYFSGIVIDV (SEQ ID NO: 350);

the LCDR1 comprises the amino acid sequence RASQ-GIRAWLN (SEQ ID NO: 351);

the LCDR2 comprises the amino acid sequence AASS-LQS (SEQ ID NO: 353); and the LCDR3 comprises the amino acid sequence HQYITHPPT (SEQ ID NO: 354).

11. The binding agent of aspect 8, wherein the HCDR1 comprises the amino acid sequence SAAVH (SEQ ID NO: 356);

the HCDR2 comprises the amino acid sequence RIK-SKA-X4-X5-GTTDYAAPVKG (SEQ ID NO: 357), RIKSK-X3-X4-X5-GTTDYAAPVKG (SEQ ID NO: 358), RIKSK-X3-X4-GGTTDYAAPVKG (SEQ ID NO: 349) or RIKSKA-X4-GGTTDYAAPVKG (SEQ ID NO: 348), wherein X3 is any amino acid or is T or A, X4 is any amino acid or is S or D, and X5 is any amino acid or is G or A;

the LCDR1 comprises the amino acid sequence RASQ-GIRAWLN (SEQ ID NO: 351) or

RASQ-X6-I-X7-X8-X9-LN (SEQ ID NO: 352), wherein X6 is any amino acid or is S or G, X7 is any amino acid or is R or S, X8 is any amino acid or is A or N, and X9 is any amino acid or is W or Y;

the LCDR2 comprises the amino acid sequence AASS-LQS (SEQ ID NO: 353); and the LCDR3 comprises the amino acid sequence HQYITHPPT (SEQ ID NO: 354) or HQYI-X10-X11-P-X12-T (SEQ ID NO: 355), wherein X10 is any amino acid or is T or A, X11 is any amino acid or is H or K, and X12 is any amino acid or is P or I.

12. The binding agent of aspect 11, wherein the HCDR1 comprises the amino acid sequence SAAVH (SEQ ID NO: 356);

the HCDR2 comprises the amino acid sequence RIK-SKA-X4-X5-GTTDYAAPVKG (SEQ ID NO: 357), wherein X4 is S or D and X5 is G or A;

the HCDR3 comprises the amino acid sequence DSPSIS-SYSIPYFSGMDV (SEQ ID NO: 350);

the LCDR1 comprises the amino acid sequence RASQ-GIRAWLN (SEQ ID NO: 351);

the LCDR2 comprises the amino acid sequence AASS-LQS (SEQ ID NO: 353); and the LCDR3 comprises the amino acid sequence HQYITHPPT (SEQ ID NO: 354).

13. The binding agent of aspect 8, wherein (i) the HCDR1 comprises the amino acid sequence of SEQ ID NO: 91, the HCDR2 comprises the amino acid sequence of SEQ ID NO: 92, the HCDR3 comprises the amino acid sequence of SEQ ID NO: 93, the LCDR1 comprises the amino acid sequence of SEQ ID NO: 107, the LCDR2 comprises the amino acid sequence of SEQ ID NO: 108, and the LCDR3 comprises the amino acid sequence of SEQ ID NO: 109;

(ii) the HCDR1 comprises the amino acid sequence of SEQ ID NO: 94, the HCDR2 comprises the amino acid sequence of SEQ ID NO: 95, the HCDR3 comprises the amino acid sequence of SEQ ID NO: 96, the LCDR1 comprises the amino acid sequence of SEQ ID NO: 110, the LCDR2 comprises the amino acid sequence of SEQ ID NO: 111, and the LCDR3 comprises the amino acid sequence of SEQ ID NO: 112;

(iii) the HCDR1 comprises the amino acid sequence of SEQ ID NO: 97, the HCDR2 comprises the amino acid sequence of SEQ ID NO: 98, the HCDR3 comprises the amino acid sequence of SEQ ID NO: 99, the LCDR1 comprises the amino acid sequence of SEQ ID NO: 113, the LCDR2 comprises the amino acid sequence of SEQ ID NO: 114, and the LCDR3 comprises the amino acid sequence of SEQ ID NO: 115; or (iv) the HCDR1 comprises the amino acid sequence of SEQ ID NO: 100, the HCDR2 comprises the amino acid sequence of SEQ ID NO: 101, the HCDR3 comprises the amino acid sequence of SEQ ID NO: 102, the LCDR1 comprises the amino acid sequence of SEQ ID NO: 116, the LCDR2 comprises the amino acid sequence of SEQ ID NO: 117, and the LCDR3 comprises the amino acid sequence of SEQ ID NO: 118.

14. The binding agent of aspect 8, wherein (i) the HCDR1 comprises the amino acid sequence of SEQ ID NO: 27, the HCDR2 comprises the amino acid sequence of SEQ ID NO: 28, the HCDR3 comprises the amino acid sequence of SEQ ID NO: 29, the LCDR1 comprises the amino acid sequence of SEQ ID NO: 43, the LCDR2 comprises the amino acid sequence of SEQ ID NO: 44, and the LCDR3 comprises the amino acid sequence of SEQ ID NO: 45;

(ii) the HCDR1 comprises the amino acid sequence of SEQ ID NO: 30, the HCDR2 comprises the amino acid sequence of SEQ ID NO: 31, the HCDR3 comprises the amino acid sequence of SEQ ID NO: 32, the LCDR1 comprises the amino acid sequence of SEQ ID NO: 46, the LCDR2 comprises the amino acid sequence of SEQ ID NO: 47, and the LCDR3 comprises the amino acid sequence of SEQ ID NO: 48;

(iii) the HCDR1 comprises the amino acid sequence of SEQ ID NO: 33, the HCDR2 comprises the amino acid sequence of SEQ ID NO: 34, the HCDR3 comprises the amino acid sequence of SEQ ID NO: 35, the LCDR1 comprises the amino acid sequence of SEQ ID NO: 49, the LCDR2 comprises the amino acid sequence of SEQ ID NO: 50, and the LCDR3 comprises the amino acid sequence of SEQ ID NO: 51; or (iv) the HCDR1 comprises the amino acid sequence of SEQ ID NO: 36, the HCDR2 comprises the amino acid sequence of SEQ ID NO: 37, the HCDR3 comprises the amino acid sequence of SEQ ID NO: 38, the LCDR1 comprises the amino acid sequence of SEQ ID NO: 52, the LCDR2 comprises the amino acid sequence of SEQ ID NO: 53, and the LCDR3 comprises the amino acid sequence of SEQ ID NO: 54.

15. The binding agent of aspect 8, wherein (i) the HCDR1 comprises the amino acid sequence of SEQ ID NO: 59, the HCDR2 comprises the amino acid sequence of SEQ ID NO: 60, the HCDR3 comprises the amino acid sequence of SEQ ID NO: 61, the LCDR1 comprises the amino acid sequence of SEQ ID NO: 75, the LCDR2 comprises the amino acid sequence of SEQ ID NO: 76, and the LCDR3 comprises the amino acid sequence of SEQ ID NO: 77;

(ii) the HCDR1 comprises the amino acid sequence of SEQ ID NO: 62, the HCDR2 comprises the amino acid sequence of SEQ ID NO: 63, the HCDR3 comprises the amino acid sequence of SEQ ID NO: 64, the LCDR1 comprises the amino acid sequence of SEQ ID NO: 78, the LCDR2 comprises the amino acid sequence of SEQ ID NO: 79, and the LCDR3 comprises the amino acid sequence of SEQ ID NO: 80;

(iii) the HCDR1 comprises the amino acid sequence of SEQ ID NO: 65, the HCDR2 comprises the amino acid sequence of SEQ ID NO: 66, the HCDR3 comprises the amino acid sequence of SEQ ID NO: 67, the LCDR1 comprises the amino acid sequence of SEQ ID NO: 81, the LCDR2 comprises the amino acid sequence of SEQ ID NO: 82, and the LCDR3 comprises the amino acid sequence of SEQ ID NO: 83; or (iv) the HCDR1 comprises the amino acid sequence of SEQ ID NO: 68, the HCDR2 comprises the amino acid sequence of SEQ ID NO: 69, the HCDR3 comprises the amino acid sequence of SEQ ID NO: 70, the LCDR1 comprises the amino acid sequence of SEQ ID NO: 84, the LCDR2 comprises the amino acid sequence of SEQ ID NO: 85, and the LCDR3 comprises the amino acid sequence of SEQ ID NO: 86.

16. The binding agent of aspect 8, wherein (i) the HCDR1 comprises the amino acid sequence of SEQ ID NO: 123, the HCDR2 comprises the amino acid sequence of SEQ ID NO: 124, the HCDR3 comprises the amino acid sequence of SEQ ID NO: 125, the LCDR1 comprises the amino acid sequence of SEQ ID NO: 139, the LCDR2 comprises the amino acid sequence of SEQ ID NO: 140, and the LCDR3 comprises the amino acid sequence of SEQ ID NO: 141;

(ii) the HCDR1 comprises the amino acid sequence of SEQ ID NO: 126, the HCDR2 comprises the amino acid sequence of SEQ ID NO: 127, the HCDR3 comprises the amino acid sequence of SEQ ID NO: 128, the LCDR1 comprises the amino acid sequence of SEQ ID NO: 142, the LCDR2 comprises the amino acid sequence of SEQ ID NO: 143, and the LCDR3 comprises the amino acid sequence of SEQ ID NO: 144;

(iii) the HCDR1 comprises the amino acid sequence of SEQ ID NO: 129, the HCDR2 comprises the amino acid sequence of SEQ ID NO: 130, the HCDR3 comprises the amino acid sequence of SEQ ID NO: 131, the LCDR1 comprises the amino acid sequence of SEQ ID NO: 145, the LCDR2 comprises the amino acid sequence of SEQ ID NO: 146, and the LCDR3 comprises the amino acid sequence of SEQ ID NO: 147; or (iv) the HCDR1 comprises the amino acid sequence of SEQ ID NO: 132, the HCDR2 comprises the amino acid sequence of SEQ ID NO: 133, the HCDR3 comprises the amino acid sequence of SEQ ID NO: 134, the LCDR1 comprises the amino acid sequence of SEQ ID NO: 148, the LCDR2 comprises the amino acid sequence of SEQ ID NO: 149, and the LCDR3 comprises the amino acid sequence of SEQ ID NO: 150.

17. The binding agent of aspect 8, wherein (i) the HCDR1 comprises the amino acid sequence of SEQ ID NO: 155, the HCDR2 comprises the amino acid sequence of SEQ ID NO: 156, the HCDR3 comprises the amino acid sequence of SEQ ID NO: 157, the LCDR1 comprises the amino acid sequence of SEQ ID NO: 171, the LCDR2 comprises the amino acid sequence of SEQ ID NO: 172, and the LCDR3 comprises the amino acid sequence of SEQ ID NO: 173;

(ii) the HCDR1 comprises the amino acid sequence of SEQ ID NO: 158, the HCDR2 comprises the amino acid sequence of SEQ ID NO: 159, the HCDR3 comprises the amino acid sequence of SEQ ID NO: 160, the LCDR1 comprises the amino acid sequence of SEQ ID NO: 174, the LCDR2 comprises the amino acid sequence of SEQ ID NO: 175, and the LCDR3 comprises the amino acid sequence of SEQ ID NO: 176;

(iii) the HCDR1 comprises the amino acid sequence of SEQ ID NO: 161, the HCDR2 comprises the amino acid sequence of SEQ ID NO: 162, the HCDR3 comprises the amino acid sequence of SEQ ID NO: 163, the LCDR1 comprises the amino acid sequence of SEQ ID NO: 177, the LCDR2 comprises the amino acid sequence of SEQ ID NO: 178, and the LCDR3 comprises the amino acid sequence of SEQ ID NO: 179; or (iv) the HCDR1 comprises the amino acid sequence of SEQ ID NO: 164, the HCDR2 comprises the amino acid sequence of SEQ ID NO: 165, the HCDR3 comprises the amino acid sequence of SEQ ID NO: 166, the LCDR1 comprises the amino acid sequence of SEQ ID NO: 180, the LCDR2 comprises the amino acid sequence of SEQ ID NO: 181, and the LCDR3 comprises the amino acid sequence of SEQ ID NO: 182.

18. The binding agent of aspect 8, wherein (i) the HCDR1 comprises the amino acid sequence of SEQ ID NO: 187, the HCDR2 comprises the amino acid sequence of SEQ ID NO: 188, the HCDR3 comprises the amino acid sequence of SEQ ID NO: 189, the LCDR1 comprises the amino acid sequence of SEQ ID NO: 203, the LCDR2 comprises the amino acid sequence of SEQ ID NO: 204, and the LCDR3 comprises the amino acid sequence of SEQ ID NO: 205;

(ii) the HCDR1 comprises the amino acid sequence of SEQ ID NO: 190, the HCDR2 comprises the amino acid sequence of SEQ ID NO: 191, the HCDR3 comprises the amino acid sequence of SEQ ID NO: 192, the LCDR1 comprises the amino acid sequence of SEQ ID NO: 206, the LCDR2 comprises the amino acid sequence of SEQ ID NO: 207, and the LCDR3 comprises the amino acid sequence of SEQ ID NO: 208;

(iii) the HCDR1 comprises the amino acid sequence of SEQ ID NO: 193, the HCDR2 comprises the amino acid sequence of SEQ ID NO: 194, the HCDR3 comprises the amino acid sequence of SEQ ID NO: 195, the LCDR1 comprises the amino acid sequence of SEQ ID NO: 209, the LCDR2 comprises the amino acid sequence of SEQ ID NO: 210, and the LCDR3 comprises the amino acid sequence of SEQ ID NO: 211; or (iv) the HCDR1 comprises the amino acid sequence of SEQ ID NO: 196, the HCDR2 comprises the amino acid sequence of SEQ ID NO: 197, the HCDR3 comprises the amino acid sequence of SEQ ID NO: 198, the LCDR1 comprises the amino acid sequence of SEQ ID NO: 212, the LCDR2 comprises the amino acid sequence of SEQ ID NO: 213, and the LCDR3 comprises the amino acid sequence of SEQ ID NO: 214.

19. The binding agent of aspect 8, wherein (i) the HCDR1 comprises the amino acid sequence of SEQ ID NO: 219, the HCDR2 comprises the amino acid sequence of SEQ ID NO: 220, the HCDR3 comprises the amino acid sequence of SEQ ID NO: 221, the LCDR1 comprises the amino acid sequence of SEQ ID NO: 235, the LCDR2 comprises the amino acid sequence of SEQ ID NO: 236, and the LCDR3 comprises the amino acid sequence of SEQ ID NO: 237;

(ii) the HCDR1 comprises the amino acid sequence of SEQ ID NO: 222, the HCDR2 comprises the amino acid sequence of SEQ ID NO: 223, the HCDR3 comprises the amino acid sequence of SEQ ID NO: 224, the LCDR1 comprises the amino acid sequence of SEQ ID NO: 238, the LCDR2 comprises the amino acid sequence of SEQ ID NO: 239, and the LCDR3 comprises the amino acid sequence of SEQ ID NO: 240;

(iii) the HCDR1 comprises the amino acid sequence of SEQ ID NO: 225, the HCDR2 comprises the amino acid sequence of SEQ ID NO: 226, the HCDR3 comprises the amino acid sequence of SEQ ID NO: 227, the LCDR1 comprises the amino acid sequence of SEQ ID NO: 241, the LCDR2 comprises the amino acid sequence of SEQ ID NO: 242, and the LCDR3 comprises the amino acid sequence of SEQ ID NO: 243; or (iv) the HCDR1 comprises the amino acid sequence of SEQ ID NO: 228, the HCDR2 comprises the amino acid sequence of SEQ ID NO: 229, the HCDR3 comprises the amino acid sequence of SEQ ID NO: 230, the LCDR1 comprises the amino acid sequence of SEQ ID NO: 244, the LCDR2 comprises the amino acid sequence of SEQ ID NO: 245, and the LCDR3 comprises the amino acid sequence of SEQ ID NO: 246.

20. The binding agent of aspect 8, wherein (i) the HCDR1 comprises the amino acid sequence of SEQ ID NO: 251, the HCDR2 comprises the amino acid sequence of SEQ ID NO: 252, the HCDR3 comprises the amino acid sequence of SEQ ID NO: 253, the LCDR1 comprises the amino acid sequence of SEQ ID NO: 267, the LCDR2 comprises the amino acid sequence of SEQ ID NO: 268, and the LCDR3 comprises the amino acid sequence of SEQ ID NO: 269;

(ii) the HCDR1 comprises the amino acid sequence of SEQ ID NO: 254, the HCDR2 comprises the amino acid sequence of SEQ ID NO: 255, the HCDR3 comprises the amino acid sequence of SEQ ID NO: 256, the LCDR1 comprises the amino acid sequence of SEQ ID NO: 270, the LCDR2 comprises the amino acid sequence of SEQ ID NO: 271, and the LCDR3 comprises the amino acid sequence of SEQ ID NO: 272;

(iii) the HCDR1 comprises the amino acid sequence of SEQ ID NO: 257, the HCDR2 comprises the amino acid sequence of SEQ ID NO: 258, the HCDR3 comprises the amino acid sequence of SEQ ID NO: 259, the LCDR1 comprises the amino acid sequence of SEQ ID NO: 273, the LCDR2 comprises the amino acid sequence of SEQ ID NO: 274, and the LCDR3 comprises the amino acid sequence of SEQ ID NO: 275; or (iv) the HCDR1 comprises the amino acid sequence of SEQ ID NO: 260, the HCDR2 comprises the amino acid sequence of SEQ ID NO: 261, the HCDR3 comprises the amino acid sequence of SEQ ID NO: 262, the LCDR1 comprises the amino acid sequence of SEQ ID NO: 276, the LCDR2 comprises the amino acid sequence of SEQ ID NO: 277, and the LCDR3 comprises the amino acid sequence of SEQ ID NO: 278.

21. The binding agent of aspect 8, wherein a) the HCDR1 comprises the amino acid sequence of SEQ ID NO: 283, the HCDR2 comprises the amino acid sequence of SEQ ID NO: 284, the HCDR3 comprises the amino acid sequence of SEQ ID NO: 285, the LCDR1 comprises the amino acid sequence of SEQ ID NO: 299, the LCDR2 comprises the amino acid sequence of SEQ ID NO: 300, and the LCDR3 comprises the amino acid sequence of SEQ ID NO: 301;

b) the HCDR1 comprises the amino acid sequence of SEQ ID NO: 286, the HCDR2 comprises the amino acid sequence of SEQ ID NO: 287, the HCDR3 comprises the amino acid sequence of SEQ ID NO: 288, the LCDR1 comprises the amino acid sequence of SEQ ID NO: 302, the LCDR2 comprises the amino acid sequence of SEQ ID NO: 303, and the LCDR3 comprises the amino acid sequence of SEQ ID NO: 304;

c) the HCDR1 comprises the amino acid sequence of SEQ ID NO: 289, the HCDR2 comprises the amino acid sequence of SEQ ID NO: 290, the HCDR3 comprises the amino acid sequence of SEQ ID NO: 291, the LCDR1 comprises the amino acid sequence of SEQ ID NO: 305, the LCDR2 comprises the amino acid sequence of SEQ ID NO: 306, and the LCDR3 comprises the amino acid sequence of SEQ ID NO: 307; or d) the HCDR1 comprises the amino acid sequence of SEQ ID NO: 292, the HCDR2 comprises the amino acid sequence of SEQ ID NO: 293, the HCDR3 comprises the amino acid sequence of SEQ ID NO: 294, the LCDR1 comprises the amino acid sequence of SEQ ID NO: 308, the LCDR2 comprises the amino acid sequence of SEQ ID NO: 309, and the LCDR3 comprises the amino acid sequence of SEQ ID NO: 310.

22. The binding agent of aspect 8, wherein a) the HCDR1 comprises the amino acid sequence of SEQ ID NO: 315, the HCDR2 comprises the amino acid sequence of SEQ ID NO: 316, the HCDR3 comprises the amino acid sequence of SEQ ID NO: 317, the LCDR1 comprises the amino acid sequence of SEQ ID NO: 331, the LCDR2 comprises the amino acid sequence of SEQ ID NO: 332, and the LCDR3 comprises the amino acid sequence of SEQ ID NO: 333;

b) the HCDR1 comprises the amino acid sequence of SEQ ID NO: 318, the HCDR2 comprises the amino acid sequence of SEQ ID NO: 319, the HCDR3 comprises the amino acid sequence of SEQ ID NO: 320, the LCDR1 comprises the amino acid sequence of SEQ ID NO: 334, the LCDR2 comprises the amino acid sequence of SEQ ID NO: 335, and the LCDR3 comprises the amino acid sequence of SEQ ID NO: 336;

c) the HCDR1 comprises the amino acid sequence of SEQ ID NO: 321, the HCDR2 comprises the amino acid sequence of SEQ ID NO: 322, the HCDR3 comprises the amino acid sequence of SEQ ID NO: 323, the LCDR1 comprises the amino acid sequence of SEQ ID NO: 337, the LCDR2 comprises the amino acid sequence of SEQ ID NO: 338, and the LCDR3 comprises the amino acid sequence of SEQ ID NO: 339; or d) the HCDR1 comprises the amino acid sequence of SEQ ID NO: 324, the HCDR2 comprises the amino acid sequence of SEQ ID NO: 325, the HCDR3 comprises the amino acid sequence of SEQ ID NO: 326, the LCDR1 comprises the amino acid sequence of SEQ ID NO: 340, the LCDR2 comprises the amino acid sequence of SEQ ID NO: 341, and the LCDR3 comprises the amino acid sequence of SEQ ID NO: 342.

23. The binding agent of aspect 8, wherein a) the VH comprises the amino acid sequence of SEQ ID NO: 39 and the VL comprises the amino acid sequence of SEQ ID NO: 55;

b) the VH comprises the amino acid sequence of SEQ ID NO: 71 and the VL comprises the amino acid sequence of SEQ ID NO: 87;

c) the VH comprises the amino acid sequence of SEQ ID NO: 103 and the VL comprises the amino acid sequence of SEQ ID NO: 119;

d) the VH comprises the amino acid sequence of SEQ ID NO: 135 and the VL comprises the amino acid sequence of SEQ ID NO: 151;

e) the VH comprises the amino acid sequence of SEQ ID NO: 167 and the VL comprises the amino acid sequence of SEQ ID NO: 183;

f) the VH comprises the amino acid sequence of SEQ ID NO: 199 and the VL comprises the amino acid sequence of SEQ ID NO: 215;

g) the VH comprises the amino acid sequence of SEQ ID NO: 231 and the VL comprises the amino acid sequence of SEQ ID NO: 247;

h) the VH comprises the amino acid sequence of SEQ ID NO: 263 and the VL comprises the amino acid sequence of SEQ ID NO: 279;

i) the VH comprises the amino acid sequence of SEQ ID NO: 295 and the VL comprises the amino acid sequence of SEQ ID NO: 311; or j) the VH comprises the amino acid sequence of SEQ ID NO: 327 and the VL comprises the amino acid sequence of SEQ ID NO: 343.

24. The binding agent of aspect 8, which is an antibody comprising a heavy chain and a light chain, wherein a) the heavy chain comprises the amino acid sequence of SEQ ID NO: 41 and the light chain comprises the amino acid sequence of SEQ ID NO: 57;

b) the heavy chain comprises the amino acid sequence of SEQ ID NO: 73 and the light chain comprises the amino acid sequence of SEQ ID NO: 89;

c) the heavy chain comprises the amino acid sequence of SEQ ID NO: 105 and the light chain comprises the amino acid sequence of SEQ ID NO: 121;

d) the heavy chain comprises the amino acid sequence of SEQ ID NO: 137 and the light chain comprises the amino acid sequence of SEQ ID NO: 153;

e) the heavy chain comprises the amino acid sequence of SEQ ID NO: 169 and the light chain comprises the amino acid sequence of SEQ ID NO: 185;

f) the heavy chain comprises the amino acid sequence of SEQ ID NO: 201 and the light chain comprises the amino acid sequence of SEQ ID NO: 217;

g) the heavy chain comprises the amino acid sequence of SEQ ID NO: 233 and the light chain comprises the amino acid sequence of SEQ ID NO: 249;

h) the heavy chain comprises the amino acid sequence of SEQ ID NO: 265 and the light chain comprises the amino acid sequence of SEQ ID NO: 281;

i) the heavy chain comprises the amino acid sequence of SEQ ID NO: 297 and the light chain comprises the amino acid sequence of SEQ ID NO: 313; or j) the heavy chain comprises the amino acid sequence of SEQ ID NO: 329 and the light chain comprises the amino acid sequence of SEQ ID NO: 345.

25. The binding agent of aspect 5, wherein the binding agent is an antibody or an antigen-binding fragment thereof, wherein the antibody or antigen-binding fragment comprises a VH and a VL, and wherein a) the VH comprises an amino acid sequence that is at least 90% or at least 95% identical to the amino acid sequence of SEQ ID NO: 39 and the VL comprises an amino acid sequence that is at least 90% or at least 95% identical to the amino acid sequence of SEQ ID NO: 55;

b) the VH comprises an amino acid sequence that is at least 90% or at least 95% identical to the amino acid sequence of SEQ ID NO: 71 and the VL comprises the amino acid sequence of SEQ ID NO: 87;

c) the VH comprises an amino acid sequence that is at least 90% or at least 95% identical to the amino acid sequence of SEQ ID NO: 103 and the VL comprises the amino acid sequence of SEQ ID NO: 119;

d) the VH comprises an amino acid sequence that is at least 90% or at least 95% identical to the amino acid sequence of SEQ ID NO: 135 and the VL comprises an amino acid sequence that is at least 90% or at least 95% identical to the amino acid sequence of SEQ ID NO: 151;

e) the VH comprises an amino acid sequence that is at least 90% or at least 95% identical to the amino acid sequence of SEQ ID NO: 167 and the VL comprises an amino acid sequence that is at least 90% or at least 95% identical to the amino acid sequence of SEQ ID NO: 183;

f) the VH comprises an amino acid sequence that is at least 90% or at least 95% identical to the amino acid sequence of SEQ ID NO: 199 and the VL comprises an amino acid sequence that is at least 90% or at least 95% identical to the amino acid sequence of SEQ ID NO: 215;

g) the VH comprises an amino acid sequence that is at least 90% or at least 95% identical to the amino acid sequence of SEQ ID NO: 231 and the VL comprises an amino acid sequence that is at least 90% or at least 95% identical to the amino acid sequence of SEQ ID NO: 247;

h) the VH comprises an amino acid sequence that is at least 90% or at least 95% identical to the amino acid sequence of SEQ ID NO: 263 and the VL comprises an amino acid sequence that is at least 90% or at least 95% identical to the amino acid sequence of SEQ ID NO: 279;

i) the VH comprises an amino acid sequence that is at least 90% or at least 95% identical to the amino acid sequence of SEQ ID NO: 295 and the VL comprises an amino acid sequence that is at least 90% or at least 95% identical to the amino acid sequence of SEQ ID NO: 311; or j) the VH comprises an amino acid sequence that is at least 90% or at least 95% identical to the amino acid sequence of SEQ ID NO: 327 and the VL comprises an amino acid sequence that is at least 90% or at least 95% identical to the amino acid sequence of SEQ ID NO: 343.

26. The binding agent of aspect 25, wherein the differences in amino acid sequence is not within the complementarity determining regions.

27. The binding agent of aspect 8, wherein:

a. the HCDR1 comprises the amino acid sequence of SEQ ID NO: 27, 59, 91, 123, 155, 187, 219, 251, 283, or 315;

b. the HCDR2 comprises the amino acid sequence of SEQ ID NO: 28, 60, 92, 124, 156, 188, 220, 252, 284, or 316;

c. the HCDR3 comprises the amino acid sequence of SEQ ID NO: 29, 61, 93, 125, 157, 189, 221, 253, 285, or 317;

d. the LCDR1 comprises the amino acid sequence of SEQ ID NO: 43, 75, 107, 139, 171, 203, 235, 267, 299, or 331;

e. the LCDR2 comprises the amino acid sequence of SEQ ID NO: 44, 76, 108, 140, 172, 204, 236, 268, 300, or 332; and f. the LCDR3 comprises the amino acid sequence of SEQ ID NO: 45, 77, 109, 141, 173, 205, 237, 269, 301, or 333.

28. The binding agent of aspect 8, wherein:

a. the HCDR1 comprises the amino acid sequence of SEQ ID NO: 30, 62, 94, 126, 158, 190, 222, 254, 286, or 318;

b. the HCDR2 comprises the amino acid sequence of SEQ ID NO: 31, 63, 95, 127, 159, 191, 223, 255, 287, or 319;

c. the HCDR3 comprises the amino acid sequence of SEQ ID NO: 32, 64, 96, 128, 160, 192, 224, 256, 288, or 320;

d. the LCDR1 comprises the amino acid sequence of SEQ ID NO: 46, 78, 110, 142, 174, 206, 238, 270, 302, or 334;

e. the LCDR2 comprises the amino acid sequence of SEQ ID NO: 47, 79, 111, 143, 175, 207, 239, 271, 303, or 335; and f. the LCDR3 comprises the amino acid sequence of SEQ ID NO: 48, 80, 112, 144, 176, 208, 240, 272, 304, or 336.

29. The binding agent of any one of the preceding aspects, wherein the binding agent is an antibody Fab fragment.

30. The binding agent of any one of the preceding aspects, wherein the binding agent is a monoclonal human antibody.

31. A polynucleotide comprising nucleotide sequences encoding the binding agent of any one of the preceding aspects.

32. A vector comprising the polynucleotide of aspect 31.

33. A host cell comprising the polynucleotide of aspect 31.

34. A host cell comprising the vector of aspect 32.

35. A method of producing a binding agent, said method comprises culturing the host cell of aspect 33 or 34 under suitable conditions for expression of the binding agent or a portion thereof, wherein the method optionally comprises purifying the binding agent.

36. A pharmaceutical composition comprising the binding agent of any one of aspects 1-30.

37. A pharmaceutical composition for use as a medicament reversing the anticoagulant effect of an anti-FXI/FXIa antibody in a patient being treated with the anti-Factor XI/Factor XIa antibody, wherein the pharmaceutical composition comprises an effective amount of the binding agent of any one of aspects 1-30.

38. A method for reversing the anticoagulant effect of an anti-FXI/FXIa antibody in a patient being treated with the anti-FXI/FXIa antibody or antigen-binding fragment thereof, comprising administering an effective amount of the binding agent of any one of aspects 1-30 to a patient in need thereof.

39. The method of aspect 38, wherein the anti-FXI/FXIa antibody or antigen-binding fragment thereof comprises (i) a VH comprising the amino acid sequence of SEQ ID NO: 12 and a VL comprising the amino acid sequence of SEQ ID NO: 23; or (ii) a heavy chain comprising the amino acid sequence of SEQ ID NO: 14 and a light chain comprising the amino acid sequence of SEQ ID NO: 25.

40. The method of aspect 38, wherein the anti-FXI/FXIa antibody or antigen-binding fragment thereof comprises (i) a VH comprising complementarity determining regions HCDR1, HCDR2 and HCDR3 of a VH comprising the amino acid sequence of SEQ ID NO: 12 and (ii) a VL comprising complementarity determining regions LCDR1, LCDR2, and LCDR3 of a VL comprising the amino acid sequence of SEQ ID NO: 23.

41. The method of aspect 38, wherein the anti-FXI/FXIa antibody or antigen-binding fragment thereof comprises:

(A)(i) a VH comprising complementarity determining regions HCDR1, HCDR2 and HCDR3 comprising the amino acid sequences of SEQ ID NO: 3, SEQ ID NO: 4, and SEQ ID NO: 5, respectively; and (ii) a VL comprising complementarity determining regions LCDR1, LCDR2, and LCDR3 comprising the amino acid sequence of SEQ ID NO: 16, SEQ ID NO: 17, and SEQ ID NO: 18, respectively;

(B)(i) a VH comprising complementarity determining regions HCDR1, HCDR2 and HCDR3 comprising the amino acid sequences of SEQ ID NO: 6, SEQ ID NO: 4, and SEQ ID NO: 5, respectively; and (ii) a VL comprising complementarity determining regions LCDR1, LCDR2, and LCDR3 comprising the amino acid sequence of SEQ ID NO: 16, SEQ ID NO: 17, and SEQ ID NO: 18, respectively;

(C)(i) a VH comprising complementarity determining regions HCDR1, HCDR2 and HCDR3 comprising the amino acid sequences of SEQ ID NO: 7, SEQ ID NO: 8, and SEQ ID NO: 5, respectively; and (ii) a VL comprising complementarity determining regions LCDR1, LCDR2, and LCDR3 comprising the amino acid sequence of SEQ ID NO: 19, SEQ ID NO: 20, and SEQ ID NO: 21, respectively; or (D)(i) a VH comprising complementarity determining regions HCDR1, HCDR2 and HCDR3 comprising the amino acid sequences of SEQ ID NO: 9, SEQ ID NO: 10, and SEQ ID NO: 11, respectively; and (ii) a VL comprising complementarity determining regions LCDR1, LCDR2, and LCDR3 comprising the amino acid sequence of SEQ ID NO: 22, SEQ ID NO: 20, and SEQ ID NO: 18, respectively.

42. The method of aspect 38, wherein the anti-FXI/FXIa antibody competes with, or binds to the same epitope as, a reference anti-FXI/FXIa antibody comprising a heavy chain comprising the amino acid sequence of SEQ ID NO: 14 and a light chain comprising the amino acid sequence of SEQ ID NO: 25.

43. The method of aspect 38, wherein the anti-FXI/FXIa antibody binds an epitope of human FXI and/or FXIa comprising one, two, three, four, five, six, seven, eight, nine, ten, eleven, twelve, thirteen, fourteen, fifteen or more, or all of, amino acid residues selected from: Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604.

44. The method of any one of aspects 38-43, wherein the method further comprises applying one of the following to the patient: (i) fluid replacement using colloids, crystalloids, human plasma or plasma proteins such as albumin; (ii) transfusion with packed red blood or whole blood; or (iii) administration of fresh frozen plasma (FFP), prothrombin complex concentrates (PCC), activated PCC (APCC), such as, factor VIII inhibitor, and/or recombinant, activated factor VII.

45. The method of any one of aspects 38-44, wherein the patient has or is at risk of developing thrombosis.

46. The method of any one of aspects 38-45, wherein the patient has a. atrial fibrillation;

b. suspected or confirmed cardiac arrhythmia such as paroxysmal, persistent or permanent atrial fibrillation or atrial flutter;

c. Chronic Thromboembolic Pulmonary Hypertension (CTEPH);

d. valvular heart disease with or without atrial fibrillation;

e. pulmonary hypertension;

f. congenital or acquired thrombophilia including but not exclusively factor V Leiden, prothrombin mutation, antithrombin III, protein C and protein S deficiencies, factor XIII mutation, familial dysfibrinogenemia, congenital deficiency of plasminogen, increased levels of factor XI, sickle cell disease, antiphospholipid syndrome, autoimmune disease, chronic bowel disease, nephrotic syndrome, hemolytic uremia, myeloproliferative disease, disseminated intra vascular coagulation, paroxysmal nocturnal hemoglobinuria and heparin induced thrombopenia; or g. chronic kidney disease.

47. The method of any one of aspects 38-45, wherein the patient has non-valvular atrial fibrillation.

48. The method of any one of aspects 38-47, wherein the patient has a demonstrated high risk of bleeding.

49. The method of any one of aspects 38-48, wherein the patient has chronic kidney disease.

50. The method of aspect 49, wherein patient has end stage renal disease (ESRD).

51. The method of aspect 50, wherein the patient has ESRD and is undergoing dialysis.

52. The method of aspect 51, wherein the patient has non-valvular atrial fibrillation.

53. The method of any one of aspects 38-52, wherein the patient is being administered the anti-FXI/FXIa antibody or antigen-binding fragment thereof to reduce the risk of stroke and/or systemic embolism.

54. The method of any one of aspects 38-53, wherein reversal of the anticoagulant effect of the anti-FXI/FXIa antibody or antigen-binding fragment thereof is needed for emergency surgery/urgent procedures and in life-threatening or uncontrolled bleeding.

55. An anti-idiotype antibody that specifically binds to an anti-FXI/FXIa antibody that binds within the catalytic domain of FXI/FXIa.

56. The anti-idiotype antibody of aspect 55, wherein the anti-FXI/FXIa antibody binds to one or more epitopes of anti-FXI and/or FXIa, wherein the epitope comprises two or more amino acid residues of Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604.

57. The anti-idiotype antibody of aspect 56, wherein the epitope comprises four or more amino acid residues of Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604.

58. The anti-idiotype antibody of aspect 56, wherein the epitope comprises six or more amino acid residues of Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604.

59. The anti-idiotype antibody of aspect 56, wherein the epitope comprises eight or more amino acid residues of Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604.

60. The anti-idiotype antibody of aspect 56, wherein the epitope comprises the residues of Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604.

61. The anti-idiotype antibody of aspect 56, wherein the epitope comprises amino acid residues of Pro410, Arg413, Lys527 and one or more amino acid residues of Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Arg548, His552, Ser575, Ser594, Trp595, Gly596, Glu597, Arg602, Glu603, and Arg604.

62. The anti-idiotype antibody of aspect 56, wherein the epitope comprises amino acid residues of Pro410, Arg413, Lys527 and four or more amino acid residues of Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Arg548, His552, Ser575, Ser594, Trp595, Gly596, Glu597, Arg602, Glu603, and Arg604.

63. The anti-idiotype antibody of aspect 56, wherein the epitope comprises amino acid residues of Pro410, Arg413, Lys527 and six or more amino acid residues of Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Arg548, His552, Ser575, Ser594, Trp595, Gly596, Glu597, Arg602, Glu603, and Arg604.

64. The anti-idiotype antibody of aspect 55, wherein the anti-FXI/FXIa antibody is NOV1401 or comprises the heavy chain variable region CDRs and light chain variable region CDRs of NOV1401.

65. The anti-idiotype antibody of aspect 55, wherein the anti-FXI/FXIa antibody binds to the same epitope of FXI/FXIa as NOV1401, or competes for binding to FXI/FXIa with NOV1401.

66. The anti-idiotype antibody of any one of aspects 55-65, which blocks the anti-FXI/FXIa antibody from binding to FXI/FXIa.

67. The anti-idiotype antibody of any one of aspects 55-66, wherein the anti-idiotype antibody reverses or inhibits the anti-FXI/FXIa antibody's anti-coagulant effects.

68. A method of managing bleeding or bleeding risk in a patient treated or administered an anti-FXI/FXIa antibody, comprising the step of administering to the patient in need thereof, an anti-idiotype antibody of the anti-FXI/FXIa antibody, wherein the anti-idiotype antibody specifically binds to the anti-FXI/FXIa antibody and blocks the anti-FXI/FXIa antibody from binding to FXI/FXIa.

69. The method of aspect 68, wherein the anti-FXI/FXIa antibody is NOV1401 or comprises the heavy chain variable region CDRs and light chain variable region CDRs of NOV1401.

70. The method of aspect 68, wherein the anti-FXI/FXIa antibody binds to the same epitope of FXI/FXIa as NOV1401, or competes for binding to FXI/FXIa with NOV1401.

71. The method of aspect 68, wherein the anti-FXI/FXIa antibody binds within the catalytic domain of FXI/FXIa.

72. The method of aspect 71, wherein the anti-FXI/FXIa antibody binds to one or more epitopes of FXI and/or FXIa, wherein the epitope comprises two or more amino acid residues of Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604.

73. The method of aspect 72, wherein the epitope comprises four or more amino acid residues of Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604.

74. The method of aspect 72, wherein the epitope comprises six or more amino acid residues of Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604.

75. The method of aspect 72, wherein the epitope comprises eight or more amino acid residues of Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604.

76. The method of aspect 72, wherein the epitope comprises the residues of Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604.

77. The method of aspect 72, wherein the epitope comprises amino acid residues of Pro410, Arg413, Lys527 and one or more amino acid residues of Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Arg548, His552, Ser575, Ser594, Trp595, Gly596, Glu597, Arg602, Glu603 and Arg604.

78. The method of aspect 72, wherein the epitope comprises amino acid residues of Pro410, Arg413, Lys527 and four or more amino acid residues of Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Arg548, His552, Ser575, Ser594, Trp595, Gly596, Glu597, Arg602, Glu603, and Arg604.

79. The method of aspect 72, wherein the epitope comprises amino acid residues of Pro410, Arg413, Lys527 and six or more amino acid residues of Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Arg548, His552, Ser575, Ser594, Trp595, Gly596, Glu597, Arg602, Glu603, and Arg604.

80. The method of any one of aspect 68-79, wherein the anti-idiotype antibody or antigen binding fragment thereof reverses the effects of the anti-FXI/FXIa antibody.

81. The method of any one of aspect 68-80, wherein the anti-idiotype antibody or antigen binding fragment thereof reverses or inhibits anti-coagulant effects of the anti-FXI/FXIa antibody.

82. A method of managing bleeding or bleeding risk in a patient treated or administered an anti-FXI/FXIa antibody, comprising the step of administering to the patient in need thereof, an anti-idiotype antibody of the anti-FXI/FXIa antibody, wherein the anti-idiotype antibody or antigen binding fragment thereof specifically binds to the antigen-binding region of the anti-FXI/FXIa antibody and blocks the anti-FXI/FXIa antibody from binding to FXI and/or FXIa, and wherein the anti-FXI/FXIa antibody is NOV1401.

83. The method of aspect 82, wherein the anti-idiotype antibody or antigen binding fragment thereof is a Fab.

84. The method of aspect 82 or 83, wherein the patient is diagnosed with atrial fibrillation and is being administered the anti-FXI/FXIa antibody for treating or preventing stroke associated with atrial fibrillation.

85. Use of the binding agent of any one of aspects 1-30 in the preparation of a medicament for reversing the anti-coagulant effect of an anti-FXI/FXIa antibody or for managing bleeding or bleeding risk, in a patient being treated with the anti-Factor XI/Factor XIa antibody, wherein the patient is being treated with the anti-Factor XI/Factor XIa for a thromboembolic disease or disorder.

86. The use of aspect 85, wherein the patient is diagnosed with atrial fibrillation, optionally with a high bleeding risk, and is being administered the anti-FXI/FXIa antibody to reduce the risk of stroke and/or systemic embolism.

DETAILED DESCRIPTION

Terminology

Figure 1:
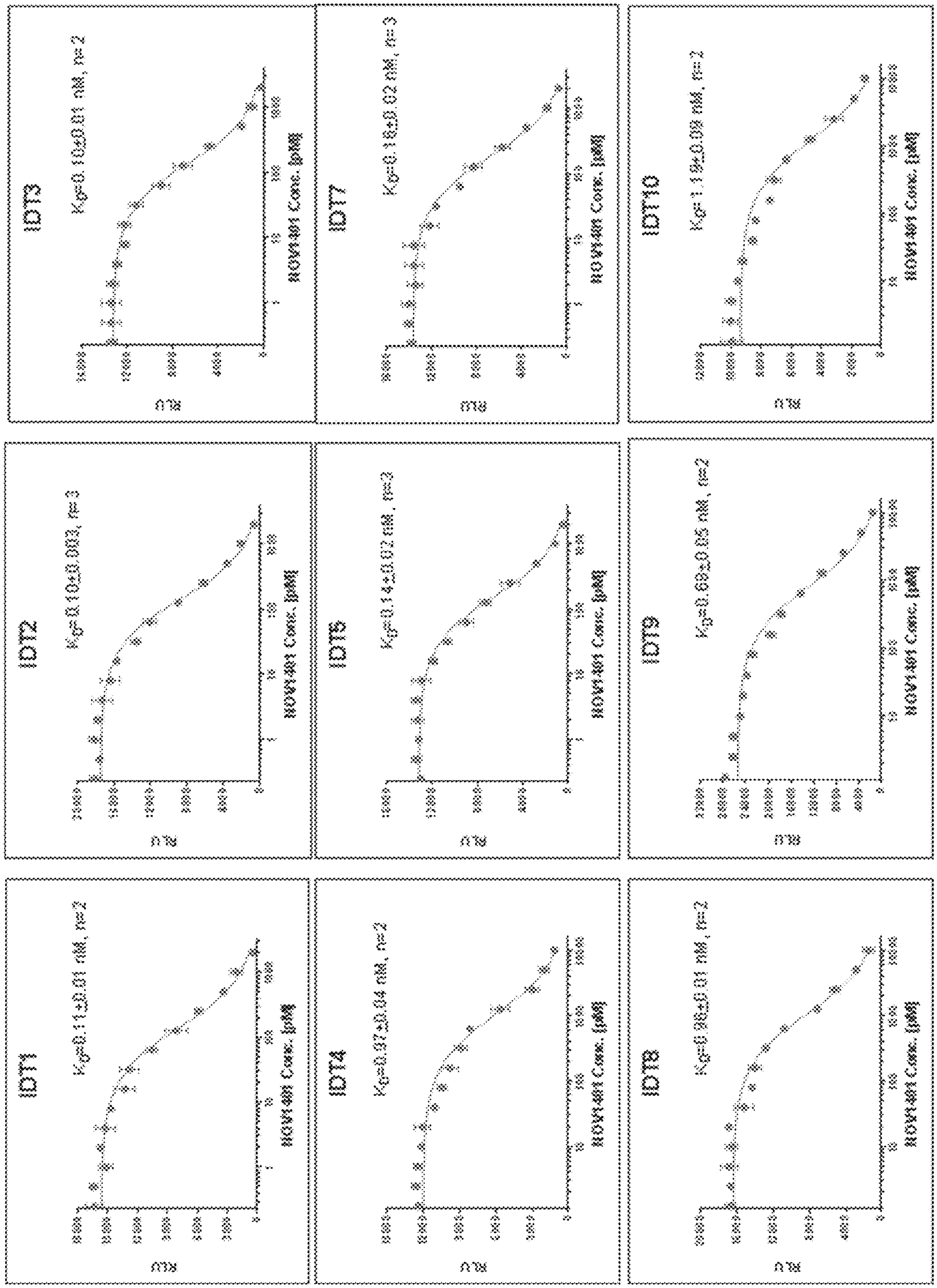
FIG. 1 shows representative binding curves from SET experiments for each of the 10 anti-NOV1401 antibodies as described in Examples. $K_D$ values were determined from fitting the experimental data to a 1:1 binding model for Fabs as described in Examples. Average $K_D$ values from two to three individual experiments are shown.

Unless defined otherwise, all technical and scientific terms used herein have the same meaning as commonly understood by those of ordinary skill in the art to which this present disclosure pertains.

As used in the specification and claims, the singular form "a", "an" and "the" include plural references unless the context clearly dictates otherwise. For example, the term "a cell" includes a plurality of cells, including mixtures thereof.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about." It also is to be understood, although not always explicitly stated, that the reagents described herein are merely examples and that equivalents of such are known in the art.

The terms "binding agent," "reversal agent," and "antidote" are used interchangeably, and, in the context of an antibody which specifically binds to Factor XI and/or Factor XIa ("anti-FXI/FXIa antibody"), refer to a protein, polypeptide, or a complex thereof, such as an anti-idiotype antibody or a fragment thereof such as a Fab fragment, or an inactive FXI/FXIa-derived polypeptide or protein fragment that specifically binds to an anti-FXI/FXIa antibody, such as, the antigen-binding region(s) or variable region(s) of the anti-FXI/FXIa antibody. In specific aspects provided herein, the binding agent is capable of reversing (e.g., partially reversing by at least 10%, at least 20%, at least 30%, at least 40%, at least 50%, at least 60%, at least 70%) one or more anticoagulant effects of the anti-FXI/FXIa antibody (e.g., antibody NOV1401). In further specific aspects provided herein, the binding agent is capable of blocking binding of an anti-FXI/FXIa antibody to its antigen, e.g., FXI/FXIa. In a specific aspect, as used herein, the terms "anti-NOV1401," "anti-NOV1401 antibody," "anti-NOV1401 Fab," "NOV1401 binding agent," "NOV1401 antidote," and the likes, are used interchangeably and refer to a binding agent or reversal agent, such as an anti-idiotype antibody or a fragment thereof, which specifically binds to anti-Factor XI antibody NOV1401 (see Table 1). Non-limiting examples of NOV1401 binding/reversal agents are described herein, for example, Table 2.

The terms "anti-idiotype antibody," "anti-Id antibody," and "anti-idiotypic antibody" are used interchangeably, and refer to an antibody and fragments thereof (e.g., Fab fragment) that specifically binds to the antigen-binding region(s) of another antibody. Anti-idiotype antibodies are typically raised against the antigen-binding region(s) or complementarity determining regions (CDRs) (idiotype) of a target antibody. Anti-Idiotype antibodies can be produced by various methods described previously, see, e.g., Pan et al., 1995, FASEB J. 9:43-49.

The terms "FXI protein," "FXI antigen," and "FXI" are used interchangeably, and refer to the Factor XI protein in different species. Factor XI is the mammalian plasma coagulation factor XI, a glycoprotein present in human plasma at a concentration of 25-30 nM as a zymogen that when converted by limited proteolysis to an active serine protease, participates in the intrinsic pathway of blood coagulation.

The terms "FXIa protein," "FXIa antigen," and "FXIa", are used interchangeably, and refers to the activated FXI protein in different species. The zymogen Factor XI is converted into its active form, the coagulation factor XIa (FXIa), either via the contact phase of blood coagulation or through thrombin-mediated activation on the platelet surface. During this activation of factor XI, an internal peptide bond is cleaved in each of the two chains, resulting in the activated factor XIa, a serine protease composed of two heavy and two light chains held together by disulfide bonds. This serine protease FXIa converts the coagulation Factor IX into IXa, which subsequently activates coagulation Factor X (Xa). Xa then can mediate coagulation Factor 11/Thrombin activation. For example, human FXI has the sequence as set out in Table 1 (SEQ ID NO:1), and has been described in previous reports and literature (Mandle R J Jr, et al. (1979) Blood; 54(4): 850; NCBI Reference Sequence: AAA51985).

In the context of this disclosure, the terms "FXI" and "FXIa" (and the like) include mutants and variants of the natural FXI and FXIa protein, respectively, which have substantially the same amino acid sequence as that of the native primary structure (amino acid sequence) described in the above-mentioned reports.

The term "catalytic domain," "serine protease catalytic domain," and similar terms as used herein in the context of FXI, means amino acids Ile370 to Val607, as counted from the Glu1 at the N-terminus of the mature protein that is in circulation. It can also be described as residues 388-625 at the C-terminus of FXI. As used herein, the term "active site" means the catalytic triad comprised of the amino acids His413, Asp462 and Se557. (Bane and Gailani (2014) Drug Disc. 19(9), which is incorporated by reference herein in its entirety).

The term "antibody" as used herein means a whole antibody and any antigen binding fragment (i.e., "antigen-binding portion") or single chain thereof and is derived from an immunoglobulin molecule that specifically binds to an antigen. A whole antibody is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. In some specific aspects, an antibody can be a monoclonal antibody, human antibody, humanized antibody, camelised antibody, or chimeric antibody. Antibodies can be of any isotype (e.g., IgG, IgE, IgM, IgD, IgA and IgY), class (e.g., IgG1, IgG2, IgG3, IgG4, IgA1 and IgA2) or subclass.

The term "antigen binding portion" or "antigen binding fragment" of an antibody, as used herein, refers to one or more fragments of an intact antibody that retain the ability to specifically bind to a given antigen (e.g., anti-FXI/FXIa antibody, such as NOV1401). Antigen binding functions of an antibody can be performed by fragments of an intact antibody. Examples of binding fragments encompassed within the term antigen binding portion or antigen binding fragment of an antibody include a Fab fragment, a monovalent fragment consisting of the VL, VH, CL and CH1 domains; a F(ab)2 fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989 Nature 341: 544-546), which consists of a VH domain or a VL domain; and an isolated complementarity determining region (CDR).

Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies include one or more antigen binding portions or fragments of an antibody. These antibody fragments are obtained using conventional techniques known to those of skill in the art, and the fragments are screened for utility in the same manner as are intact antibodies.

Antigen binding fragments can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136). Antigen binding portions of antibodies can be grafted into scaffolds based on polypeptides such as Fibronectin type III (Fn3) (see U.S. Pat. No. 6,703, 199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., 1995 Protein Eng. 8(10):1057-1062; and U.S. Pat. No. 5,641,870).

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. As used herein, the term "high affinity" for an antibody or antigen binding fragments thereof (e.g., a Fab fragment) generally refers to an antibody, or antigen binding fragment, having a $K_D$ of 10-9 M or less (e.g., a $K_D$ of 10-10 M or less, a $K_D$ of 10-11 M or less, a $K_D$ of 10-12 M or less, a $K_D$ of 10-13 M or less, a $K_D$ of 10-14 M or less, etc.).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "binding specificity" as used herein refers to the ability of an individual antibody combining site to react with only one antigenic determinant.

As used herein, the terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen may bind to other peptides or polypeptides, generally with lower affinity as determined by, e.g., immunoassays, Biacore™, KinExA 3000 instrument (Sapidyne Instruments, Boise, Id.), or other assays known in the art. In a specific embodiment, molecules that immunospecifically bind to an antigen bind to the antigen with a Ka that is at least 2 logs, 2.5 logs, 3 logs, 4 logs or greater than the Ka when the molecules bind to another antigen. In another specific embodiment, molecules that immunospecifically bind to an antigen do not cross react with other proteins.

The term "FXI and/or FXIa mediated" refers to the fact that FXI and/or FXIa mediates the intrinsic and/or common coagulation pathways by directly or indirectly activating Factor IX (also known as FIX), Factor X (FX), and/or thrombin, and/or by binding to platelet receptors.

The term "hemostasis" represents the principal mechanisms for arresting the flow of blood at sites of injury and restoring vascular patency during wound healing, respectively. During normal hemostasis and pathological thrombosis, three mechanisms become activated simultaneously: primary hemostasis meaning the interactions of activated platelets with the vessel wall, the formation of fibrin, and a process termed as fibrinolysis.

The terms "coagulation and coagulation cascade," "cascade model of coagulation," and the like, refer to the protein based system which serves to stabilize a clot that has formed to seal up a wound. The coagulation pathway is a proteolytic cascade. Each enzyme of the pathway is present in the plasma as a Zymogen (in an inactive form), which on activation undergoes proteolytic cleavage to release the active factor from the precursor molecule. The coagulation cascade functions as a series of positive and negative feedback loops which control the activation process. The ultimate goal of the pathway is to produce thrombin, which can then convert soluble fibrinogen into fibrin that forms a clot.

The process of generation of thrombin can be divided into three phases: the intrinsic and extrinsic pathways, which provide alternative routes for the generation of an active clotting factor: FXa (Activated Factor-X), and the final common pathway, which results in thrombin formation (Hoffman M. M. and Monroe D. M. (2005) Curr Hematol Rep. 4:391-396; Johne J, et al. (2006) Biol Chem. 387:173-178).

As used herein, the terms “manage,” “managing,” and “management” refer to the beneficial effects that a subject derives from a therapy (e.g., a prophylactic or therapeutic agent), which does not result in a cure of a disease, disorder, or condition (e.g., thrombosis or thromboembolic disorder). In certain embodiments, a subject is administered one or more therapies (e.g., binding agent or antibody described herein) to “manage” thrombosis or thromboembolic disorder, one or more symptoms thereof, so as to prevent the progression or worsening of the condition or disorder.

“Platelet aggregation” refers to the process whereby when a break in a blood vessel occurs, substances are exposed that normally are not in direct contact with the blood flow. These substances (primarily collagen and von Willebrand factor) allow the platelets to adhere to the broken surface. Once a platelet adheres to the surface, it releases chemicals that attract additional platelets to the damaged area, referred to as platelet aggregation. These two processes are the first responses to stop bleeding.

A “thromboembolic disorder,” or similar terms as used herein, refer to any number of conditions or diseases in which the intrinsic and/or common coagulation pathways are aberrantly activated or are not naturally deactivated (e.g., without therapeutic means). These conditions include but are not limited to thrombic stroke, atrial fibrillation, stroke prevention in atrial fibrillation (SPAF), deep vein thrombosis, venous thromboembolism, and pulmonary embolism. These can also include catheter-related conditions (e.g., Hickman catheter in oncology patients) in which catheters become thrombosed, and extracorporeal membrane oxygenation (ECMO), in which the tubing develops clots.

A “thromboembolic,” or similar terms as used herein, can also refer to any number of the following, which the anti-FXI and/or FXIa Abs or antigen binding fragments thereof of the present disclosure can be used to prevent or treat or to reduce the risk of:

- thromboembolism in subjects with suspected or confirmed cardiac arrhythmia such as paroxysmal, persistent or permanent atrial fibrillation or atrial flutter;
- stroke prevention in atrial fibrillation (SPAF), a subpopulation of which is AF patients undergoing percutaneous coronary interventions (PCI);
- acute venous thromboembolic events (VTE) treatment and extended secondary VTE prevention in patients at high risk for bleeding;
- cerebral and cardiovascular events in secondary prevention after transient ischemic attack (TIA) or non-disabling stroke and prevention of thromboembolic events in heart failure with sinus rhythm;
- clot formation in left atrium and thromboembolism in subjects undergoing cardioversion for cardiac arrhythmia;
- thrombosis before, during and after ablation procedure for cardiac arrhythmia;
- venous thrombosis, this includes but not exclusively, treatment and secondary prevention of deep or superficial veins thrombosis in the lower members or upper member, thrombosis in the abdominal and thoracic veins, sinus thrombosis and thrombosis of jugular veins;
- thrombosis on any artificial surface in the veins like catheter or pacemaker wires;
- pulmonary embolism in patients with or without venous thrombosis;
- Chronic Thromboembolic Pulmonary Hypertension (CTEPH);
- arterial thrombosis on ruptured atherosclerotic plaque, thrombosis on intra-arterial prosthesis or catheter and thrombosis in apparently normal arteries, this includes but not limited to acute coronary syndromes, ST elevation myocardial infarction, non ST elevation myocardial infarction, unstable angina, stent thrombosis, thrombosis of any artificial surface in the arterial system and thrombosis of pulmonary arteries in subjects with or without pulmonary hypertension;
- thrombosis and thromboembolism in patients undergoing percutaneous coronary interventions (PCI);
- cardioembolic and cryptogenic strokes;
- thrombosis in patients with invasive and non-invasive cancer malignancies;
- thrombosis over an indwelling catheter;
- thrombosis and thromboembolism in severely ill patients;
- cardiac thrombosis and thromboembolism, this includes but not exclusively cardiac thrombosis after myocardial infarction, cardiac thrombosis related to condition such as cardiac aneurysm, myocardial fibrosis, cardiac enlargement and insufficiency, myocarditis and artificial surface in the heart;
- thromboembolism in patients with valvular heart disease with or without atrial fibrillation;
- thromboembolism over valvular mechanic or biologic prostheses;
- thromboembolism in patients who had native or artificial cardiac patches, arterial or venous conduit tubes after heart repair of simple or complex cardiac malformations;
- venous thrombosis and thromboembolism after knee replacement surgery, hip replacement surgery, and orthopedic surgery, thoracic or abdominal surgery;
- arterial or venous thrombosis after neurosurgery including intracranial and spinal cord interventions;
- congenital or acquired thrombophilia including but not exclusively factor V Leiden, prothrombin mutation, antithrombin III, protein C and protein S deficiencies, factor XIII mutation, familial dysfibrinogenemia, congenital deficiency of plasminogen, increased levels of factor XI, sickle cell disease, antiphospholipid syndrome, autoimmune disease, chronic bowel disease, nephrotic syndrome, hemolytic uremia, myeloproliferative disease, disseminated intra vascular coagulation, paroxysmal nocturnal hemoglobinuria and heparin induced thrombopenia;
- thrombosis and thromboembolism in chronic kidney disease; and
- thrombosis and thromboembolism in patients undergoing hemodialysis and in patients undergoing extra-corporal membrane oxygenation.

The term “chimeric antibody” is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the present disclosure. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. Two antibodies are said to "compete" if one antibody is shown to bind the same epitope as the second antibody in a competitive binding assay, by any of the methods well known to those of skill in the art.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the present disclosure may include amino acid residues not encoded by human sequences (e.g., mutations introduced by random or site-specific mutagenesis in vitro or by somatic mutation in vivo).

The term "human monoclonal antibody" refers to antibodies displaying a single binding specificity which have variable regions in which both the framework and CDR regions are derived from human sequences. In one embodiment, the human monoclonal antibodies are prepared using phage display methods for screening libraries of human immunoglobulin genes.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239:1534-1536, 1988; Padlan, Molec. Immun., 28:489-498, 1991; and Padlan, Molec. Immun., 31:169-217, 1994. Other examples of human engineering technology include, but are not limited to Xoma technology disclosed in U.S. Pat. No. 5,766,886.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, John Wiley & Sons, Inc. (Ringbou ed., 2003)).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available on the world wide web at gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "isolated antibody" refers to an antibody that is substantially free of other antibodies having different antigenic specificities (e.g., an isolated antibody that specifically binds FXI and/or FXIa is substantially free of antibodies that specifically bind antigens other than FXI and/or FXIa, or an isolated anti-idiotype antibody that specifically binds an anti-FXI/FXIa antibody is substantially free of antibodies that specifically bind antigens other than the anti-FXI/FXIa antibody). An isolated antibody that specifically binds FXI and/or FXIa may, however, have cross-reactivity to other antigens. Moreover, an isolated antibody may be substantially free of other cellular material and/or chemicals.

The term "isotype" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors.

The term "kassoc" or "ka", as used herein, is intended to refer to the association rate of a particular antibody-antigen interaction, whereas the term "kdis" or "kd," as used herein, is intended to refer to the dissociation rate of a particular antibody-antigen interaction. The term "KD", as used herein, is intended to refer to the dissociation constant, which is obtained from the ratio of kd to ka (i.e. kd/ka) and is expressed as a molar concentration (M). KD values for antibodies can be determined using methods well established in the art. Methods for determining the KD of an antibody include measuring surface plasmon resonance using a biosensor system such as a Biacore™ system, or measuring affinity in solution by solution equilibrium titration (SET).

The terms "monoclonal antibody" or "monoclonal antibody composition" as used herein refer to a preparation of antibody molecules of single molecular composition. A monoclonal antibody composition displays a single binding specificity and affinity for a particular epitope.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

The term "operably linked" refers to a functional relationship between two or more polynucleotide (e.g., DNA) segments. Typically, the term refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, the term, "optimized" means that a nucleotide sequence has been altered to encode an amino acid sequence using codons that are preferred in the production cell or organism, generally a eukaryotic cell, for example, a cell of *Pichia*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells. However, optimized expression of these sequences in other eukaryotic cells or prokaryotic cells is also envisioned herein. The amino acid sequences encoded by optimized nucleotide sequences are also referred to as optimized.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "subject" includes human and non-human animals. Non-human animals include all vertebrates (e.g.: mammals and non-mammals) such as, non-human primates (e.g.: cynomolgus monkey), sheep, rabbit, dog, cow, chickens, amphibians, and reptiles. Except when noted, the terms "patient" or "subject" are used herein interchangeably. As used herein, the terms "cyno" or "cynomolgus" refer to the cynomolgus monkey (*Macaca fascicularis*). In some specific aspects provided herein, a patient or a subject is a human.

As used herein, the term "treating" or "treatment" of any disease or disorder (e.g., a thromboembolic disorder) refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

"Prevention" as it relates to indications described herein, including, e.g., a thromboembolic disorder, means any action that prevents or slows a worsening in e.g., a thromboembolic disease parameters, as described below, in a patient at risk for being afflicted with a thromboembolic disorder or at risk for said worsening.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, such as an adeno-associated viral vector (AAV, or AAV2), wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the present disclosure is intended to include such other forms of expression vectors, such as viral vectors (e.g., replication defective retroviruses, adenoviruses and adeno-associated viruses), which serve equivalent functions.

Factor XI/XIa and Anti-Factor XI/FXIa Antibodies

This section describes exemplary anti-FXI/FXIa antibodies (e.g., antibodies described in Table 1) to which reversal binding agents provided herein (e.g., anti-idiotype antibodies and fragments thereof) specifically bind, wherein reversal binding agents are capable of reversing one or more anticoagulant effects of such anti-FXI/FXIa antibodies and/or inhibits binding of such anti-FXI/FXIa antibodies to FXI and/or FXIa.

FXI holds important roles in both intrinsic and extrinsic coagulation pathways and in bridging the initiation and amplification phases of plasmatic hemostasis. Both Factor XIIa and thrombin can activate FXI, resulting in a sustained thrombin generation and fibrinolysis inhibition. FXI plays a minor role in normal hemostasis in a high tissue factor environment "after vessel injury" whereas it appears to play a key role in thrombosis. Severe Factor XI deficiency is associated with a lower incidence of ischemic stroke and venous thromboembolic events (Salomon et al 2008; Salomon, et al. (2011) Thromb Haemost.; 105:269-73). Bleeding manifestations in subjects with severe factor XI deficiency are infrequent, often mild, injury-induced and affect preferably tissues with increased fibrinolytic activity such as the oral mucosa, nasal mucosa and urinary tract (Salomon et al 2011). Bleeding in critical organs is extremely rare or not existing.

Plasma coagulation is a sequential process by which coagulation factors in the blood interact and are activated, ultimately resulting in fibrin generation and clot formation. In the classical cascade model of coagulation, the process of fibrin generation can be initiated by two distinct pathways, i.e., the intrinsic and the extrinsic pathway, respectively (Mackman, 2008).

In the extrinsic pathway, vessel injury allows extravascular tissue factor (TF) to interact with and activate factor VII (FVII), which sequentially leads to the activation of factor X and prothrombin. The active thrombin ultimately converts soluble fibrinogen into fibrin. The extrinsic pathway is central for hemostasis, interfering with coagulation factors in this pathway results in a risk of bleeding.

In the intrinsic pathway, factor XII may in some cases be activated by a process referred to as contact activation. Generation of activated factor XIIa leads to the sequential activations of factor XI and factor IX. As factor IXa activates factor X, the extrinsic and intrinsic pathways converge at this stage (at the common pathway). Thrombin activity is boosted by amplifying its own generation through a feed-forward loop in which thrombin activates factor XI independently of factor XII. This feed-forward loop contributes to sustained thrombus growth but is only minimally involved in hemostasis, as the strong activation by extravascular tissue factor is sufficient to clot formation. The intrinsic pathway therefore is not substantially involved in hemostasis (Gailani and Renné (2007) Arterioscler Thromb Vasc Biol. 2007, 27(12):2507-13, Müller Gailani, and Renné 2011).

Preclinical studies using a variety of approaches to inhibit FXI or FXIa across a variety of species have contributed to the validation of this target. FXI−/− mice are resistant to experimental venous (Wang, et al. (2006) J Thromb Haemost; 4:1982-8) and arterial (Wang, et al. (2005) J Thromb Haemost; 3:695-702) thrombosis. Treatment of mice with an antibody (Ab, 14E11) that blocks the activation of FXI by FXIIa resulted in inhibition of experimental thrombosis (Cheng, et al. (2010) Blood, 116:3981-9) and reduced cerebral infarct size in a mouse model of ischemic stroke (Leung, et al. (2012) Transl Stroke Res 2012; 3:381-9). In baboons administered an anti-FXI antibody that blocks binding and activation of FIX by FXIa, reduced growth of platelet-rich thrombi was observed on collagen-coated vascular grafts (Tucker, et al. (2009) Blood 2009; 113:936-44), and similar results were found with 14E11 in this model (Cheng 2010). Excessive bleeding was not noted in any of these studies.

Blocking FXI synthesis with antisense oligonucleotides in mice (Zhang, et al. (2010) Blood 2010; 116:4684-92), cynomolgus monkeys (Younis, et al. (2012) Blood 2012; 119:2401-8), and baboons (Crosby, et al. (2013) Arterioscler Thromb Vasc Biol 2013; 33:1670-8) resulted in antithrombotic and anticoagulant effects without excessive bleeding. Moreover, similar effects have been produced by blocking FXIa with low molecular weight inhibitors in venous and arterial models of thrombosis in rats (Schumacher, et al. (2007) Eur J Pharmacol 2007; 570:167-74) and rabbits (Wong, et al. (2011) J Thromb Thrombolysis 2011; 32:129-37).

Patients with severe FXI deficiency rarely bleed spontaneously and they show only mild trauma-induced bleeding, except in tissues with high fibrinolytic activity. The rarity of severe FXI deficiency necessitates the use of population studies for revealing the thrombotic profile of these patients relative to the general population. Notably, such studies report the incidence of ischemic stroke (Salomon 2008) and deep vein thrombosis (DVT) (Salomon, et al. (2011) Blood 2008; 111: 4113-17) to be reduced in these patients. Thus, the number of ischemic strokes (N=1) observed in 115 patients with severe FXI deficiency was less ($p<0.003$) than the expected incidence (N=8.6) in the general population of Israel, while the incidence of DVT (N=0) was lower ($p<0.019$) in patients with severe FXI deficiency than expected in the control population (N=4.7). Conversely, individuals with FXI levels above the 90th percentile had a two-fold risk of developing DVT (Meijers, et al. (2000) N Engl J Med. 2000; 342:696-701).

Recently, patients undergoing total knee replacement, a procedure that predisposes to DVT, were treated with FXI antisense therapy or standard of care (enoxaparin). The antisense group (300 mg) showed a 7-fold decreased incidence in venous thrombosis and fewer (not significant) bleeding events compared to standard of care (Büller et al, (2014) N Engl J Med. 372(3):232-40. doi: 10.1056/NEJMoa1405760. Epub 2014 Dec. 7).

Antibodies that specifically bind to FXI and/or FXIa have been described. See for example, PCT International Publication Nos. WO2017/015619, WO2016/207858, WO 2013/167669, WO2009/067660, WO 2009/154461, and WO 2010/080623, each of which is incorporated by reference herein in its entirety. Non-limiting examples of anti-FXI/FXIa antibodies include: 076D-M007-H04, 076D-M007-H04-CDRL3-N110D, and 076D-M028-H17 as described in WO 2013/167669; 1A6 as described in WO2009/067660; and 14E11 as described in WO 2010/080623. In specific aspects, provided herein are binding agents, such as anti-idiotype antibodies, that specifically bind to anti-FXI/FXIa antibody 076D-M007-H04, 076D-M007-H04-CDRL3-N110D, or 076D-M028-H17, and is capable of inhibiting binding of the anti-FXI/FXIa antibody to FXI/FXIa and/or is capable of reversing an anticoagulant effect of the anti-FXI/FXIa antibody. In specific aspects, provided herein are binding agents, such as anti-idiotype antibodies that specifically bind to an anti-FXI/FXIa antibody which competes (e.g., in a dose-dependent manner) with 076D-M007-H04, 076D-M007-H04-CDRL3-N110D, or 076D-M028-H17 for binding to FXI/FXIa, and is capable of inhibiting binding of the anti-FXI/FXIa antibody to FXI/FXIa and/or is capable of reversing an anticoagulant effect of the anti-FXI/FXIa antibody.

Table 1 provides exemplary amino acid sequences and corresponding encoding nucleotide sequences for human FXI and anti-FXI/FXIa antibodies, for example, antibody NOV1401 and NOV1090. In particular, Table 1 provides the following amino acid sequences for antibodies NOV1401, NOV1090, AM1, AM2, AM3, and AM4, as well as corresponding encoding nucleotide sequences: heavy chain variable region (VH), light chain variable region (VL), heavy chain, light chain, VH complementarity determining regions HCDR1, HCDR2, and HCDR3, VL complementarity determining regions LCDR1, LCDR2, and LCDR3. In specific aspects, reversal binding agents provided herein specifically bind to an anti-FXI/FXIa antibody described in Table 1 and is capable of inhibiting (e.g., in a dose dependent manner) binding of the anti-FXI/FXIa antibody to human FXI/FXIa, and/or of reversing one or more anticoagulant activities of the anti-FXI/FXIa antibody. In specific aspects, reversal binding agents provided herein (e.g., anti-idiotype antibody or antigen-binding fragment thereof such a Fab) specifically bind to anti-FXI/FXIa antibody NOV1401, NOV1090, AM1, AM2, AM3, and/or AM4, and is capable of inhibiting binding of the anti-FXI/FXIa antibody to human FXI/FXIa and/or is capable of reversing an anticoagulant effect of the anti-FXI/FXIa antibody.

Antibody NOV1401 is a human antibody which specifically binds the catalytic domain of human FXI, and has been previously described, see, for example, PCT International Patent Application No. PCT/IB2016/053790 filed on Jun. 24, 2016 (PCT International Publication No. WO2016/207858) and U.S. patent application Ser. No. 15/192,020 filed on Jun. 24, 2016, each of which is hereby incorporated by reference in its entirety. Antibody NOV1401 is capable of binding both human FXI zymogen as well as FXIa. NOV1401 has been described to contact human FXI/FXIa epitopes formed of the following residues: Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604 (see PCT International Publication No. WO2016/207858). In specific aspects, antibody NOV1401 contacts one, two, three, four, five, six, seven, eight, nine, ten, eleven, twelve, thirteen, fourteen, fifteen or more, or all of, amino acid residues of human FXI selected from: Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604.

In addition, the paratope of NOV1401 has been described (see PCT International Publication No. WO2016/207858). In particular, the following residues of the light chain of NOV1401 contact human FXI/FXIa: Ser27, Gly30, Ser31, Asn32, Asp33, Tyr50, Lys51, Tyr53, Asn54, Lys67, Trp92, Gln94, Arg95, Phe97, Asp98, and Val99 (residues are numbered with reference to SEQ ID NO: 25); and the following residues of the heavy chain of NOV1401 contact human FXI/FXIa: Phe27, Thr28, Ser30, Thr31, Ala33, Trp47, Ser52, Tyr59, Tyr60, Glu99, Ser101, Tyr102, Leu103, Tyr104, and Ser105 (residues are numbered with reference to SEQ ID NO: 14). Accordingly, in specific aspects, provided herein are reversal binding agents (e.g., anti-idiotype antibodies and fragment thereof such as Fabs) that bind to the antigen-binding region of NOV1401, and contacts one or more of the residues in light chain and heavy chain of NOV1401 forming the paratope. In specific aspects, a reversal binding agent (e.g., anti-idiotype antibody and fragment thereof such as a Fab) provided herein binds to NOV1401 within the antigen-binding region, and contacts one, two, three, four, five six, seven, eight, nine, or more, or all, of the following residues in the light chain of NOV1401: Ser27, Gly30, Ser31, Asn32, Asp33, Tyr50, Lys51, Tyr53, Asn54, Lys67, Trp92, Gln94, Arg95, Phe97, Asp98, and Val99 (residues are numbered with reference to SEQ ID NO: 25). In specific aspects, a reversal binding agent (e.g., anti-idiotype antibody and fragment thereof such as a Fab) provided herein binds to NOV1401 within the antigen-binding region, and contacts one, two, three, four, five six, seven, eight, nine, or more, or all, of the following residues in the heavy chain of NOV1401 contact human FXI/FXIa: Phe27, Thr28, Ser30, Thr31, Ala33, Trp47, Ser52, Tyr59, Tyr60, Glu99, Ser101, Tyr102, Leu103, Tyr104, and Ser105 (residues are numbered with reference to SEQ ID NO: 14). In specific aspects, a reversal binding agent (e.g., anti-idiotype antibody and fragment thereof such as a Fab) provided herein binds to NOV1401 within the antigen-binding region, and contacts one, two, three, four, five six, seven, eight, nine, ten or more amino acid residues selected from the following in light chain and/or the heavy chain of NOV1401 forming the paratope: (i) Ser27, Gly30, Ser31, Asn32, Asp33, Tyr50, Lys51, Tyr53, Asn54, Lys67, Trp92, Gln94, Arg95, Phe97, Asp98, and Val99 in the light chain of NOV1401 (residues are numbered with reference to SEQ ID NO: 25); and (ii) Phe27, Thr28, Ser30, Thr31, Ala33, Trp47, Ser52, Tyr59, Tyr60, Glu99, Ser101, Tyr102, Leu103, Tyr104, and Ser105 in the heavy chain of NOV1401 (residues are numbered with reference to SEQ ID NO: 14).

Other anti-FXI/FXIa antibodies described in Table 1 herein include NOV1090, AM1, AM2, AM3, and AM4. Antibodies NOV1401 and NOV1090 share the same CDRs. Antibodies AM1, AM2, AM3, and AM4 are exemplary affinity matured variants of antibody NOV1090.

In specific aspects, reversal binding agents provided herein (e.g., anti-idiotype antibodies) bind to an anti-FXI/FXIa antibody which competes (e.g., in a dose dependent manner) with NOV1401 for binding to human FXI/FXIa. In other aspects, reversal binding agents provided herein (e.g., human anti-idiotype antibodies) bind to an anti-FXI/FXIa antibody which binds to the same epitope of FXI/FXIa as NOV1401. In particular aspects, reversal binding agents provided herein (e.g., human anti-idiotype antibodies) bind to an anti-FXI/FXIa antibody which contacts one, two, three, four, five, six, seven, eight, nine, ten, eleven, twelve, thirteen, fourteen, fifteen or more, or all of, amino acid residues of human FXI selected from: Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604. In specific aspects, reversal binding agents provided herein (e.g., human anti-idiotype antibodies) bind to an anti-FXI/FXIa antibody which is NOV1401 or competes for binding with NOV1401 to human FXI/FXIa and which anti-FXI/FXIa antibody does not contact amino acid residue Asp480 of human FXI/FXIa. In specific aspects, reversal binding agents provided herein (e.g., human anti-idiotype antibodies) bind to an anti-FXI/FXIa antibody which is NOV1401 or competes for binding with NOV1401 to human FXI/FXIa and which anti-FXI/FXIa antibody does not contact one or more amino acid residues selected from: His414, Ser477, Asp480, Lys572, Asp569, and Gly598 of human FXI/FXIa. In specific aspects, reversal binding agents provided herein (e.g., human anti-idiotype antibodies) bind to an anti-FXI/FXIa antibody which is NOV1401 or competes for binding with NOV1401 to human FXI/FXIa and which anti-FXI/FXIa antibody contacts one, two, three, four, five, six, seven, eight, or more, or all, of amino acid residues Leu415, Cys416, His431, Cys432, Gly435, Glu437, Tyr472, Lys473, Glu476, Arg548, His552, Ser575, Trp595, Gly596, Glu597, Arg602, Glu603, and Arg604 of human FXI/FXIa. In specific aspects, reversal binding agents provided herein (e.g., human anti-idiotype antibodies) bind to an anti-FXI/FXIa antibody which contacts amino acid residues His431 and Ser575 of human FXI/FXIa.

In particular aspects, an anti-FXI/FXIa antibody has one or more of the following anticoagulant activities, which can be reversed (e.g., partially reversed) by a reversal binding agent (e.g., anti-idiotype antibody or fragment thereof such as Fab) provided herein: (i) aPTT prolongation as determined by aPTT assay, (ii) reduction in the amount of thrombin in a thrombin generation assay (TGA) in human plasma, and (iii) inhibition of Factor XI activity. These activities can be readily measured with assays described in the art and provided herein. For example, TGA and aPTT assays are described in the art and herein (e.g., Examples Section). In further aspects, other biomarkers of the extrinsic coagulation pathway can be measured to determine anticoagulant activity, for example, prothrombin time (PT) assay and thrombin time (TT) assay. Other, non-limiting examples of assays for anticoagulation/coagulation activity include chromogenic assays such as ecarin chromogenic assay (ECA), ecarin clotting time (ECT) assay, and anti-Factor Xa activity assay. In specific aspects, reversal binding agents provided herein (e.g., anti-idiotype antibodies) is capable of reversing (e.g., partially reversing) one or more of these anticoagulant activities. In particular aspects, reversal binding agents provided herein is capable of reducing the bleeding time in patients administered an anti-FXI/FXIa antibody.

TABLE 1

Examples of FXI/FXIa Antibodies, Fabs and FXI/FXIa Proteins

| Sequence Description | Sequence Identifier (SEQ ID NO:) | Amino acid or polynucleotide sequence |
|---|---|---|
| Human FXI full-length protein sequence (NCBI Reference Sequence: AAA51985) | 1 | MIFLYQVVHF ILFTSVSGEC VTQLLKDTCF EGGDITTVFT PSAKYCQVVC TYHPRCLLFT FTAESPSEDP TRWFTCVLKD SVTETLPRVN RTAAISGYSF KQCSHQISAC NKDIYVDLDM KGINYNSSVA KSAQECQERC TDDVHCHFFT YATRQFPSLE HRNICLLKHT QTGTPTRITK LDKVVSGFSL KSCALSNLAC IRDIFPNTVF ADSNIDSVMA PDAFVSGRIC THHPGCLFFT FFSQEWPKES QRNLCLLKTS ESGLPSTRIK KSKALSGFSL QSCRHSIPVF CHSSFYHDTD FLGEELDIVA AKSHEACQKL CTNAVRCQFF TYTPAQASCN EGKGKCYLKL SSNGSPTKIL HGRGGISGYT LRLCKMDNEC TTKIKPRIVG GTASVRGEWP WQVTLHTTSP TQRHLCGGSI IGNQWILTAA HCFYGVESPK ILRVYSGILN QSEIKEDTSF FGVQEIIIHD QYKMAESGYD IALLKLETTV NYTDSQRPIC LPSKGDRNVI YTDCWVTGWG YRKLRDKIQN TLQKAKIPLV TNEECQKRYR GHKITHKMIC AGYREGGKDA CKGDSGGPLS CKHNEVWHLV GITSWGEGCA QRERPGVYTN VVEYVDWILE KTQAV |
| Human FXI full-length nucleotide sequence (NCBI Reference Sequence: NM_000128.3) | 2 | AGGCACACAG GCAAAATCAA GTTCTACATC TGTCCCTGTG TATGTCACTT GTTTGAATAC GAAATAAAAT TAAAAAAATA AATTCAGTGT ATTGAGAAAG CAAGCAATTC TCTCAAGGTA TATTTCTGAC ATACTAAGAT TTTAACGACT TTCACAAATA TGCTGTACTG AGAGAGAATG TTACATAACA TTGAGAACTA GTACAAGTAA ATATTAAAGT GAAGTGACCA TTTCCTACAC AAGCTCATTC AGAGGAGGAT GAAGACCATT TTGGAGGAAG AAAAGCACCC TTATTAAGAA TTGCAGCAAG TAAGCCAACA AGGTCTTTTC AGGATGATTT TCTTATATCA AGTGGTACAT TTCATTTTAT TTACTTCAGT TTCTGGTGAA TGTGTGACTC AGTTGTTGAA GGACACCTGC TTTGAAGGAG GGGACATTAC TACGGTCTTC ACACCAAGCG CCAAGTACTG CCAGGTAGTC TGCACTTACC ACCCAAGATG TTTACTCTTC ACTTTCACGG CGGAATCACC ATCTGAGGAT CCCACCCGAT GGTTTACTTG TGTCCTGAAA GACAGTGTTA CAGAAACACT GCCAAGAGTG AATAGGACAG CAGCGATTTC TGGGTATTCT TTCAAGCAAT GCTCACACCA AATAAGCGCT TGCAACAAAG ACATTTATGT |

TABLE 1-continued

Examples of FXI/FXIa Antibodies, Fabs and FXI/FXIa Proteins

| Sequence Description | Sequence Identifier (SEQ ID NO:) | Amino acid or polynucleotide sequence |
|---|---|---|
| | | GGACCTAGAC ATGAAGGGCA TAAACTATAA CAGCTCAGTT |
| | | GCCAAGAGTG CTCAAGAATG CCAAGAAAGA TGCACGGATG |
| | | ACGTCCACTG CCACTTTTTC ACGTACGCCA CAAGGCAGTT |
| | | TCCCAGCCTG GAGCATCGTA ACATTTGTCT ACTGAAGCAC |
| | | ACCCAAACAG GGACACCAAC CAGAATAACG AAGCTCGATA |
| | | AAGTGGTGTC TGGATTTTCA CTGAAATCCT GTGCACTTTC |
| | | TAATCTGGCT TGTATTAGGG ACATTTTCCC TAATACGGTG |
| | | TTTGCAGACA GCAACATCGA CAGTGTCATG GCTCCCGATG |
| | | CTTTTGTCTG TGGCCGAATC TGCACTCATC ATCCCGGTTG |
| | | CTTGTTTTTT ACCTTCTTTT CCCAGGAATG GCCCAAAGAA |
| | | TCTCAAAGAA ATCTTTGTCT CCTTAAAACA TCTGAGAGTG |
| | | GATTGCCCAG TACACGCATT AAAAAGAGCA AAGCTCTTTC |
| | | TGGTTTCAGT CTACAAAGCT GCAGGCACAG CATCCCAGTG |
| | | TTCTGCCATT CTTCATTTTA CCATGACACT GATTTCTTGG |
| | | GAGAAGAACT GGATATTGTT GCTGCAAAAA GTCACGAGGC |
| | | CTGCCAGAAA CTGTGCACCA ATGCCGTCCG CTGCCAGTTT |
| | | TTTACCTATA CCCCAGCCCA AGCATCCTGC AACGAAGGGA |
| | | AGGGCAAGTG TTACTTAAAG CTTTCTTCAA ACGGATCTCC |
| | | AACTAAAATA CTTCACGGGA GAGGAGGCAT CTCTGGATAC |
| | | ACATTAAGGT TGTGTAAAAT GGATAATGAG TGTACCACCA |
| | | AAATCAAGCC CAGGATCGTT GGAGGAACTG CGTCTGTTCG |
| | | TGGTGAGTGG CCGTGGCAGG TGACCCTGCA CACAACCTCA |
| | | CCCACTCAGA GACACCTGTG TGGAGGCTCC ATCATTGGAA |
| | | ACCAGTGGAT ATTAACAGCC GCTCACTGTT TCTATGGGGT |
| | | AGAGTCACCT AAGATTTTGC GTGTCTACAG TGGCATTTTA |
| | | AATCAATCTG AAATAAAAGA GGACACATCT TTCTTTGGGG |
| | | TTCAAGAAAT AATAATCCAT GATCAGTATA AAATGGCAGA |
| | | AAGCGGGTAT GATATTGCCT TGTTGAAACT GGAAACCACA |
| | | GTGAATTACA CAGATTCTCA ACGACCCATA TGCCTGCCTT |
| | | CCAAAGGAGA TAGAAATGTA ATATACACTG ATTGCTGGGT |
| | | GACTGGATGG GGGTACAGAA AACTAAGAGA CAAAATACAA |
| | | AATACTCTCC AGAAAGCCAA GATACCCTTA GTGACCAACG |
| | | AAGAGTGCCA GAAGAGATAC AGAGGACATA AAATAACCCA |
| | | TAAGATGATC TGTGCCGGCT ACAGGGAAGG AGGGAAGGAC |
| | | GCTTGCAAGG GAGATTCGGG AGGCCCTCTG TCCTGCAAAC |
| | | ACAATGAGGT CTGGCATCTG GTAGGCATCA CGAGCTGGGG |
| | | CGAAGGCTGT GCTCAAAGGG AGCGGCCAGG TGTTTACACC |
| | | AACGTGGTCG AGTACGTGGA CTGGATTCTG GAGAAAACTC |
| | | AAGCAGTGTG AATGGGTTCC CAGGGGCCAT TGGAGTCCCT |
| | | GAAGGACCCA GGATTTGCTG GGAGAGGGTG TTGAGTTCAC |
| | | TGTGCCAGCA TGCTTCCTCC ACAGTAACAC GCTGAAGGGG |
| | | CTTGGTGTTT GTAAGAAAAT GCTAGAAGAA AACAAACTGT |
| | | CACAAGTTGT TATGTCCAAA ACTCCCGTTC TATGATCGTT |
| | | GTAGTTTGTT TGAGCATTCA GTCTCTTTGT TTTTGATCAC |
| | | GCTTCTATGG AGTCCAAGAA TTACCATAAG GCAATATTTC |
| | | TGAAGATTAC TATATAGGCA GATATAGCAG AAAATAACCA |
| | | AGTAGTGGCA GTGGGGATCA GGCAGAAGAA CTGGTAAAAG |
| | | AAGCCACCAT AAATAGATTT GTTCGATGAA AGATGAAAAC |
| | | TGGAAGAAAG GAGAACAAAG ACAGTCTTCA CCATTTTGCA |
| | | GGAATCTACA CTCTGCCTAT GTGAACACAT TTCTTTTGTA |
| | | AAGAAAGAAA TTGATTGCAT TTAATGGCAG ATTTTCAGAA |
| | | TAGTCAGGAA TTCTTGTCAT TTCCATTTTA AAATATATAT |
| | | TAAAAAAAAT CAGTTCGAGT AGACACGAGC TAAGAGTGAA |
| | | TGTGAAGATA ACAGAATTTC TGTGTGGAAG AGGATTACAA |
| | | GCAGCAATTT ACCTGGAAGT GATACCTTAG GGGCAATCTT |
| | | GAAGATACAC TTTCCTGAAA AATGATTTGT GATGGATTGT |
| | | ATATTTATTT AAAATATCTT GGGAGGGGAG GCTGATGGAG |
| | | ATAGGGAGCA TGCTCAAACC TCCCTAAGAC AAGCTGCTGC |
| | | TGTGACTATG GGCTCCCAAA GAGCTAGATC GTATATTTAT |
| | | TTGACAAAAA TCACCATAGA CTGCATCCAT ACTACAGAGA |
| | | AAAAACAATT AGGGCGCAAA TGGATAGTTA CAGTAAAGTC |
| | | TTCAGCAAGC AGCTGCCTGT ATTCTAAGCA CTGGGATTTT |
| | | CTGTTTCGTG CAAATATTTA TCTCATTATT GTTGTGATCT |
| | | AGTTCAATAA CCTAGAATTT GAATTGTCAC CACATAGCTT |
| | | TCAATCTGTG CCAACAACTA TACAATTCAT CAAGTGTG |
| | | NOV1401 |
| HCDR1 (Combined) | 3 | GFTFSTAAMS |
| HCDR2 (Combined) | 4 | GISGSGSSTYYADSVKG |

TABLE 1-continued

Examples of FXI/FXIa Antibodies, Fabs and FXI/FXIa Proteins

| Sequence Description | Sequence Identifier (SEQ ID NO:) | Amino acid or polynucleotide sequence |
|---|---|---|
| HCDR3 (Combined) | 5 | ELSYLYSGYYFDY |
| HCDR1 (Kabat) | 6 | TAAMS |
| HCDR2 (Kabat) | 4 | GISGSGSSTYYADSVKG |
| HCDR3 (Kabat) | 5 | ELSYLYSGYYFDY |
| HCDR1 (Chothia) | 7 | GFTFSTA |
| HCDR2 (Chothia) | 8 | SGSGSS |
| HCDR3 (Chothia) | 5 | ELSYLYSGYYFDY |
| HCDR1 (IMGT) | 9 | GFTFSTAA |
| HCDR2 (IMGT) | 10 | ISGSGSST |
| HCDR3 (IMGT) | 11 | ARELSYLYSGYYFDY |
| VH | 12 | QVQLLESGGGLVQPGGSLRLSCAASGFTFSTAAMSWVRQAPGK GLEWVSGISGSGSSTYYADSVKGRFTISRDNSKNTLYLQMNSL RAEDTAVYYCARELSYLYSGYYFDYWGQGTLVTVSS |
| DNA encoding VH | 13 | CAGGTGCAGCTGCTGGAATCAGGCGGCGGACTGGTGCAGCCTG GCGGTAGCCTGAGACTGAGCTGCGCTGCTAGTGGCTTCACCTT TAGCACCGCCGCTATGAGCTGGGTTCGACAGGCCCCAGGGAAA GGCCTCGAGTGGGTCTCAGGGATTAGCGGTAGCGGCTCTAGCA CCTACTACGCCGATAGCGTGAAGGGCCGGTTCACTATCTCTAG GGATAACTCTAAGAACACCCTGTACCTGCAGATGAATAGCCTG AGAGCCGAGGACACCGCCGTCTACTACTGCGCTAGAGAGCTGA GCTACCTGTATAGCGGCTACTACTTCGACTACTGGGGTCAAGG CACCCTGGTCACCGTGTCTAGC |
| Heavy Chain | 14 | QVQLLESGGGLVQPGGSLRLSCAASGFTFSTAAMSWVRQAPGK GLEWVSGISGSGSSTYYADSVKGRFTISRDNSKNTLYLQMNSL RAEDTAVYYCARELSYLYSGYYFDYWGQGTLVTVSSASTKGPS VFPLAPSSKSTSGGTAALGCLVKDYFPEPVTVSWNSGALTSGV HTFPAVLQSSGLYSLSSVVTVPSSSLGTQTYICNVNHKPSNTK VDKRVEPKSCDKTHTCPPCPAPELLGGPSVFLFPPKPKDTLMI SRTPEVTCVVVAVSHEDPEVKFNWYVDGVEVHNAKTKPREEQY NSTYRVVSVLTVLHQDWLNGKEYKCKVSNKALAAPIEKTISKA KGQPREPQVYTLPPSREEMTKNQVSLTCLVKGFYPSDIAVEWE SNGQPENNYKTTPPVLDSDGSFFLYSKLTVDKSRWQQGNVFSC SVMHEALHNHYTQKSLSLSPGK |
| DNA encoding Heavy Chain | 15 | CAGGTGCAGCTGCTGGAATCAGGCGGCGGACTGGTGCAGCCTG GCGGTAGCCTGAGACTGAGCTGCGCTGCTAGTGGCTTCACCTT TAGCACCGCCGCTATGAGCTGGGTTCGACAGGCCCCAGGGAAA GGCCTCGAGTGGGTCTCAGGGATTAGCGGTAGCGGCTCTAGCA CCTACTACGCCGATAGCGTGAAGGGCCGGTTCACTATCTCTAG GGATAACTCTAAGAACACCCTGTACCTGCAGATGAATAGCCTG AGAGCCGAGGACACCGCCGTCTACTACTGCGCTAGAGAGCTGA GCTACCTGTATAGCGGCTACTACTTCGACTACTGGGGTCAAGG CACCCTGGTCACCGTGTCTAGCGCTAGCACTAAGGGCCCCTCC GTGTTCCCTCTGGCCCCTTCCAGCAAGTCTACCTCCGGCGGCA CAGCTGCTCTGGGCTGCCTGGTCAAGGACTACTTCCCTGAGCC TGTGACAGTGTCCTGGAACTCTGGCGCCCTGACCTCTGGCGTG CACACCTTCCCTGCCGTGCTGCAGTCCTCCGGCCTGTACTCCC TGTCCTCCGTGGTCACAGTGCCTTCAAGCAGCCTGGGCACCCA GACCTATATCTGCAACGTGAACCACAAGCCTTCCAACACCAAG GTGGACAAGCGGGTGGAGCCTAAGTCCTGCGACAAGACCCACA CCTGTCCTCCCTGCCCTGCTCCTGAACTGCTGGGCGGCCCTTC TGTGTTCCTGTTCCCTCCAAAGCCCAAGGACACCCTGATGATC TCCCGGACCCCTGAAGTGACCTGCGTGGTGGTGGCCGTGTCCC ACGAGGATCCTGAAGTGAAGTTCAATTGGTACGTGGACGGCGT GGAGGTGCACAACGCCAAGACCAAGCCTCGGGAGGAACAGTAC AACTCCACCTACCGGGTGGTGTCCGTGCTGACCGTGCTGCACC AGGACTGGCTGAACGGCAAAGAGTACAAGTGCAAAGTCTCCAA CAAGGCCCTGGCCGCCCCTATCGAAAAGACAATCTCCAAGGCC AAGGGCCAGCCTAGGGAACCCCAGGTGTACACCCTGCCACCCA GCCGGGAGGAAATGACCAAGAACCAGGTGTCCCTGACCTGTCT GGTCAAGGGCTTCTACCCTTCCGATATCGCCGTGGAGTGGGAG TCTAACGGCCAGCCTGAGAACAACTACAAGACCACCCCTCCTG TGCTGGACTCCGACGGCTCCTTCTTCCTGTACTCCAAACTGAC CGTGGACAAGTCCCGGTGGCAGCAGGGCAACGTGTTCTCCTGC TCCGTGATGCACGAGGCCCTGCACAACCACTACACCCAGAAGT CCCTGTCCCTGTCTCCCGGCAAG |
| LCDR1 (Combined) | 16 | SGSSSNIGSNDVS |
| LCDR2 (Combined) | 17 | KNYNRPS |

TABLE 1-continued

Examples of FXI/FXIa Antibodies, Fabs and FXI/FXIa Proteins

| Sequence Description | Sequence Identifier (SEQ ID NO:) | Amino acid or polynucleotide sequence |
|---|---|---|
| LCDR3 (Combined) | 18 | SAWDQRQFDVV |
| LCDR1 (Kabat) | 16 | SGSSSNIGSNDVS |
| LCDR2 (Kabat) | 17 | KNYNRPS |
| LCDR3 (Kabat) | 18 | SAWDQRQFDVV |
| LCDR1 (Chothia) | 19 | SSSNIGSND |
| LCDR2 (Chothia) | 20 | KNY |
| LCDR3 (Chothia) | 21 | WDQRQFDV |
| LCDR1 (IMGT) | 22 | SSNIGSND |
| LCDR2 (IMGT) | 20 | KNY |
| LCDR3 (IMGT) | 18 | SAWDQRQFDVV |
| VL | 23 | QSVLTQPPSASGTPGQRVTISCSGSSSNIGSNDVSWYQQLPGT APKLLIYKNYNRPSGVPDRFSGSKSGTSASLAISGLQSEDEAD YYCSAWDQRQFDVVFGGGTKLTVL |
| DNA encoding VL | 24 | CAGTCAGTCCTGACTCAGCCCCCTAGCGCTAGTGGCACCCCTG GTCAAAGAGTGACTATTAGCTGTAGCGGCTCTAGCTCTAATAT CGGCTCTAACGACGTCAGCTGGTATCAGCAGCTGCCCGGCACC GCCCCTAAGCTGCTGATCTATAAGAACTATAATAGGCCTAGCG GCGTGCCCGATAGGTTTAGCGGATCTAAATCAGGGACTTCTGC TAGTCTGGCTATTAGCGGCCTGCAGTCAGAGGACGAGGCCGAC TACTACTGTAGCGCCTGGGATCAGCGTCAGTTCGACGTGGTGT TCGGCGGAGGCACTAAGCTGACCGTGCTG |
| Light Chain | 25 | QSVLTQPPSASGTPGQRVTISCSGSSSNIGSNDVSWYQQLPGT APKLLIYKNYNRPSGVPDRFSGSKSGTSASLAISGLQSEDEAD YYCSAWDQRQFDVVFGGGTKLTVLGQPKAAPSVTLFPPSSEEL QANKATLVCLISDFYPGAVTVAWKADSSPVKAGVETTTPSKQS NNKYAASSYLSLTPEQWKSHRSYSCQVTHEGSTVEKTVAPTEC S |
| DNA encoding Light Chain | 26 | CAGTCAGTCCTGACTCAGCCCCCTAGCGCTAGTGGCACCCCTG GTCAAAGAGTGACTATTAGCTGTAGCGGCTCTAGCTCTAATAT CGGCTCTAACGACGTCAGCTGGTATCAGCAGCTGCCCGGCACC GCCCCTAAGCTGCTGATCTATAAGAACTATAATAGGCCTAGCG GCGTGCCCGATAGGTTTAGCGGATCTAAATCAGGGACTTCTGC TAGTCTGGCTATTAGCGGCCTGCAGTCAGAGGACGAGGCCGAC TACTACTGTAGCGCCTGGGATCAGCGTCAGTTCGACGTGGTGT TCGGCGGAGGCACTAAGCTGACCGTGCTGGGTCAACCTAAGGC TGCCCCCAGCGTGACCCTGTTCCCCCCCAGCAGCGAGGAGCTG CAGGCCAACAAGGCCACCCTGGTGTGCCTGATCAGCGACTTCT ACCCAGGCGCCGTGACCGTGGCCTGGAAGGCCGACAGCAGCCC CGTGAAGGCCGGCGTGGAGACCACCACCCCCAGCAAGCAGAGC AACAACAAGTACGCCGCCAGCAGCTACCTGAGCCTGACCCCCG AGCAGTGGAAGAGCCACAGGTCCTACAGCTGCCAGGTGACCCA CGAGGGCAGCACCGTGGAAAAGACCGTGGCCCCAACCGAGTGC AGC |
| | | NOV1090 |
| HCDR1 (Combined) | 3 | GFTFSTAAMS |
| HCDR2 (Combined) | 4 | GISGSGSSTYYADSVKG |
| HCDR3 (Combined) | 5 | ELSYLYSGYYFDY |
| HCDR1 (Kabat) | 6 | TAAMS |
| HCDR2 (Kabat) | 4 | GISGSGSSTYYADSVKG |
| HCDR3 (Kabat) | 5 | ELSYLYSGYYFDY |
| HCDR1 (Chothia) | 7 | GFTFSTA |
| HCDR2 (Chothia) | 8 | SGSGSS |
| HCDR3 (Chothia) | 5 | ELSYLYSGYYFDY |
| HCDR1 (IMGT) | 9 | GFTFSTAA |
| HCDR2 (IMGT) | 10 | ISGSGSST |
| HCDR3 (IMGT) | 11 | ARELSYLYSGYYFDY |
| VH | 12 | QVQLLESGGGLVQPGGSLRLSCAASGFTFSTAAMSWVRQAPGK GLEWVSGISGSGSSTYYADSVKGRFTISRDNSKNTLYLQMNSL RAEDTAVYYCARELSYLYSGYYFDYWGQGTLVTVSS |
| DNA encoding VH | 390 | CAGGTGCAATTGCTGGAAAGCGGCGGTGGCCTGGTGCAGCCGG GTGGCAGCCTGCGTCTGAGCTGCGCGGCGTCCGGATTCACCTT |

TABLE 1-continued

Examples of FXI/FXIa Antibodies, Fabs and FXI/FXIa Proteins

| Sequence Description | Sequence Identifier (SEQ ID NO:) | Amino acid or polynucleotide sequence |
|---|---|---|
| | | TTCTACTGCTGCTATGTCTTGGGTGCGCCAGGCCCCGGGCAAA GGTCTCGAGTGGGTTTCCGGTATCTCTGGTTCTGGTTCTTCTA CCTACTATGCGGATAGCGTGAAAGGCCGCTTTACCATCAGCCG CGATAATTCGAAAAACACCCTGTATCTGCAAATGAACAGCCTG CGTGCGGAAGATACGGCCGTGTATTATTGCGCGCGTGAACTGT CTTACCTGTACTCTGGTTACTACTTCGATTACTGGGGCCAAGG CACCCTGGTGACTGTTAGCTCA |
| Heavy Chain | 360 | QVQLLESGGGLVQPGGSLRLSCAASGFTFSTAAMSWVRQAPGK GLEWVSGISGSGSSTYYADSVKGRFTISRDNSKNTLYLQMNSL RAEDTAVYYCARELSYLYSGYYFDYWGQGTLVTVSSASTKGPS VFPLAPSSKSTSGGTAALGCLVKDYFPEPVTVSWNSGALTSGV HTFPAVLQSSGLYSLSSVVTVPSSSLGTQTYICNVNHKPSNTK VDKRVEPKSCDKTHTCPPCPAPEAAGGPSVFLFPPKPKDTLMI SRTPEVTCVVVDVSHEDPEVKFNWYVDGVEVHNAKTKPREEQY NSTYRVVSVLTVLHQDWLNGKEYKCKVSNKALPAPIEKTISKA KGQPREPQVYTLPPSREEMTKNQVSLTCLVKGFYPSDIAVEWE SNGQPENNYKTTPPVLDSDGSFFLYSKLTVDKSRWQQGNVFSC SVMHEALHNHYTQKSLSLSPGK |
| DNA encoding Heavy Chain | 361 | CAGGTGCAATTGCTGGAAAGCGGCGGTGGCCTGGTGCAGCCGG GTGGCAGCCTGCGTCTGAGCTGCGCGGCGTCCGGATTCACCTT TTCTACTGCTGCTATGTCTTGGGTGCGCCAGGCCCCGGGCAAA GGTCTCGAGTGGGTTTCCGGTATCTCTGGTTCTGGTTCTTCTA CCTACTATGCGGATAGCGTGAAAGGCCGCTTTACCATCAGCCG CGATAATTCGAAAAACACCCTGTATCTGCAAATGAACAGCCTG CGTGCGGAAGATACGGCCGTGTATTATTGCGCGCGTGAACTGT CTTACCTGTACTCTGGTTACTACTTCGATTACTGGGGCCAAGG CACCCTGGTGACTGTTAGCTCAGCCTCCACCAAGGGTCCATCG GTCTTCCCCCTGGCACCCTCCTCCAAGAGCACCTCTGGGGGCA CAGCGGCCCTGGGCTGCCTGGTCAAGGACTACTTCCCCGAACC GGTGACGGTGTCGTGGAACTCAGGCGCCCTGACCAGCGGCGTG CACACCTTCCCGGCTGTCCTACAGTCCTCAGGACTCTACTCCC TCAGCAGCGTGGTGACCGTGCCCTCCAGCAGCTTGGGCACCCA GACCTACATCTGCAACGTGAATCACAAGCCCAGCAACACCAAG GTGGACAAGAGAGTTGAGCCCAAATCTTGTGACAAAACTCACA CATGCCCACCGTGCCCAGCACCTGAAGCAGCGGGGGGACCGTC AGTCTTCCTCTTCCCCCCAAAACCCAAGGACACCCTCATGATC TCCCGGACCCCTGAGGTCACATGCGTGGTGGTGGACGTGAGCC ACGAAGACCCTGAGGTCAAGTTCAACTGGTACGTGGACGGCGT GGAGGTGCATAATGCCAAGACAAAGCCGCGGGAGGAGCAGTAC AACAGCACGTACCGGGTGGTCAGCGTCCTCACCGTCCTGCACC AGGACTGGCTGAATGGCAAGGAGTACAAGTGCAAGGTCTCCAA CAAAGCCCTCCCAGCCCCCATCGAGAAAACCATCTCCAAAGCC AAAGGGCAGCCCCGAGAACCACAGGTGTACACCCTGCCCCCAT CCCGGGAGGAGATGACCAAGAACCAGGTCAGCCTGACCTGCCT GGTCAAAGGCTTCTATCCCAGCGACATCGCCGTGGAGTGGGAG AGCAATGGGCAGCCGGAGAACAACTACAAGACCACGCCTCCCG TGCTGGACTCCGACGGCTCCTTCTTCCTCTACAGCAAGCTCAC CGTGGACAAGAGCAGGTGGCAGCAGGGGAACGTCTTCTCATGC TCCGTGATGCATGAGGCTCTGCACAACCACTACACGCAGAAGA GCCTCTCCCTGTCTCCGGGTAAA |
| LCDR1 (Combined) | 16 | SGSSSNIGSNDVS |
| LCDR2 (Combined) | 17 | KNYNRPS |
| LCDR3 (Combined) | 18 | SAWDQRQFDVV |
| LCDR1 (Kabat) | 16 | SGSSSNIGSNDVS |
| LCDR2 (Kabat) | 17 | KNYNRPS |
| LCDR3 (Kabat) | 18 | SAWDQRQFDVV |
| LCDR1 (Chothia) | 19 | SSSNIGSND |
| LCDR2 (Chothia) | 20 | KNY |
| LCDR3 (Chothia) | 21 | WDQRQFDV |
| LCDR1 (IMGT) | 22 | SSNIGSND |
| LCDR2 (IMGT) | 20 | KNY |
| LCDR3 (IMGT) | 18 | SAWDQRQFDVV |
| VL | 362 | DIVLTQPPSVSGAPGQRVTISCSGSSSNIGSNDVSWYQQLPGT APKLLIYKNYNRPSGVPDRFSGSKSGTSASLAITGLQAEDEAD YYCSAWDQRQFDVVFGGGTKLTVL |
| DNA encoding VL | 363 | GATATCGTGCTGACCCAGCCGCCGAGCGTGAGCGGTGCACCGG GCCAGCGCGTGACCATTAGCTGTAGCGGCAGCAGCAGCAACAT |

TABLE 1-continued

Examples of FXI/FXIa Antibodies, Fabs and FXI/FXIa Proteins

| Sequence Description | Sequence Identifier (SEQ ID NO:) | Amino acid or polynucleotide sequence |
|---|---|---|
| | | TGGTTCTAACGACGTGTCTTGGTACCAGCAGCTGCCGGGCACG GCGCCGAAACTGCTGATCTACAAAAACTACAACCGCCCGAGCG GCGTGCCGGATCGCTTTAGCGGATCCAAAAGCGGCACCAGCGC CAGCCTGGCGATTACCGGCCTGCAAGCAGAAGACGAAGCGGAT TATTACTGCTCTGCTTGGGACCAGCGTCAGTTCGACGTTGTGT TTGGCGGCGGCACGAAGTTAACCGTCCTA |
| Light Chain | 364 | DIVLTQPPSVSGAPGQRVTISCSGSSSNIGSNDVSWYQQLPGT APKLLIYKNYNRPSGVPDRFSGSKSGTSASLAITGLQAEDEAD YYCSAWDQRQFDVVFGGGTKLTVLGQPKAAPSVTLFPPSSEEL QANKATLVCLISDFYPGAVTVAWKADSSPVKAGVETTTPSKQS NNKYAASSYLSLTPEQWKSHRSYSCQVTHEGSTVEKTVAPTEC S |
| DNA encoding Light Chain | 365 | GATATCGTGCTGACCCAGCCGCCGAGCGTGAGCGGTGCACCGG GCCAGCGCGTGACCATTAGCTGTAGCGGCAGCAGCAGCAACAT TGGTTCTAACGACGTGTCTTGGTACCAGCAGCTGCCGGGCACG GCGCCGAAACTGCTGATCTACAAAAACTACAACCGCCCGAGCG GCGTGCCGGATCGCTTTAGCGGATCCAAAAGCGGCACCAGCGC CAGCCTGGCGATTACCGGCCTGCAAGCAGAAGACGAAGCGGAT TATTACTGCTCTGCTTGGGACCAGCGTCAGTTCGACGTTGTGT TTGGCGGCGGCACGAAGTTAACCGTCCTAGGTCAGCCCAAGGC TGCCCCCTCGGTCACTCTGTTCCCGCCCTCCTCTGAGGAGCTT CAAGCCAACAAGGCCACACTGGTGTGTCTCATAAGTGACTTCT ACCCGGGAGCCGTGACAGTGGCCTGGAAGGCAGATAGCAGCCC CGTCAAGGCGGGAGTGGAGACCACCACACCCTCCAAACAAAGC AACAACAAGTACGCGGCCAGCAGCTATCTGAGCCTGACGCCTG AGCAGTGGAAGTCCCACAGAAGCTACAGCTGCCAGGTCACGCA TGAAGGGAGCACCGTGGAGAAGACAGTGGCCCCTACAGAATGT TCA |
| | | AM1 |
| HCDR1 (Combined) | 3 | GFTFSTAAMS |
| HCDR2 (Combined) | 366 | TIDSWGDDTDYADSVKG |
| HCDR3 (Combined) | 5 | ELSYLYSGYYFDY |
| HCDR1 (Kabat) | 6 | TAAMS |
| HCDR2 (Kabat) | 366 | TIDSWGDDTDYADSVKG |
| HCDR3 (Kabat) | 5 | ELSYLYSGYYFDY |
| HCDR1 (Chothia) | 7 | GFTFSTA |
| HCDR2 (Chothia) | 367 | DSWGDD |
| HCDR3 (Chothia) | 5 | ELSYLYSGYYFDY |
| HCDR1 (IMGT) | 9 | GFTFSTAA |
| HCDR2 (IMGT) | 368 | IDSWGDDT |
| HCDR3 (IMGT) | 11 | ARELSYLYSGYYFDY |
| VH | 369 | QVQLLESGGGLVQPGGSLRLSCAASGFTFSTAAMSWVRQ APGKGLEwVSTIDSWGDDIDYADSVKGRFTISRDNSKNT LYLQMNSLRAEDTAVYYCARELSYLYSGYYFDYWGQGTL VTVSS |
| DNA VH | 370 | CAGGTGCAATTGCTGGAAAGCGGCGGTGGCCTGGTGCAG CCGGGTGGCAGCCTGCGTCTGAGCTGCGCGGCGTCCGGA TTCACCTTTTCTACTGCTGCTATGTCTTGGGTGCGCCAG GCCCCGGGCAAAGGTCTCGAGTGGGTTTCCACTATCGAC TCTTGGGGCGACGACACTGACTATGCGGATAGCGTGAAA GGCCGCTTTACCATCAGCCGCGATAATTCGAAAAACACC CTGTATCTGCAAATGAACAGCCTGCGTGCGGAAGATACG GCCGTGTATTATTGCGCGCGTGAACTGTCTTACCTGTAC TCTGGTTACTACTTCGATTACTGGGGCCAAGGCACCCTG GTGACTGTTAGCTCA |
| Heavy Chain | 371 | QVQLLESGGGLVQPGGSLRLSCAASGFTFSTAAMSWVRQ APGKGLEMVSTIDSWGDDIDYADSVKGRFTISRDNSKNT LYLQMNSLRAEDTAVYYCARELSYLYSGYYFDYWGQGTL VTVSSASTKGPSVFPLAPSSKSTSGGTAALGCLVKDYFP EPVTVSWNSGALTSGVHTFPAVLQSSGLYSLSSVVTVPS SSLGTQTYICNVNHKPSNTKVDKRVEPKSCDKTHTCPPC PAPEAAGGPSVFLFPPKPKDTLMISRTPEVTCVVVDVSH EDPEVKFNWYVDGVEVHNAKTKPREEQYNSTYRVVSVLT VLHQDWLNGKEYKCKVSNKALPAPIEKTISKAKGQPREP QVYTLPPSREEMTKNQVSLTCLVKGFYPSDIAVEWESNG |

TABLE 1-continued

Examples of FXI/FXIa Antibodies, Fabs and FXI/FXIa Proteins

| Sequence Description | Sequence Identifier (SEQ ID NO:) | Amino acid or polynucleotide sequence |
|---|---|---|
| | | QPENNYKTTPPVLDSDGSFFLYSKLTVDKSRWQQGNVFS CSVMHEALHNHYTQKSLSLSPGK |
| DNA Heavy Chain | 391 | CAGGTGCAATTGCTGGAAAGCGGCGGTGGCCTGGTGCAG CCGGGTGGCAGCCTGCGTCTGAGCTGCGCGGCGTCCGGA TTCACCTTTTCTACTGCTGCTATGTCTTGGGTGCGCCAG GCCCCGGGCAAAGGTCTCGAGTGGGTTTCCACTATCGAC TCTTGGGGCGACGACACTGACTATGCGGATAGCGTGAAA GGCCGCTTTACCATCAGCCGCGATAATTCGAAAAACACC CTGTATCTGCAAATGAACAGCCTGCGTGCGGAAGATACG GCCGTGTATTATTGCGCGCGTGAACTGTCTTACCTGTAC TCTGGTTACTACTTCGATTACTGGGGCCAAGGCACCCTG GTGACTGTTAGCTCAGCCTCCACCAAGGGTCCATCGGTC TTCCCCCTGGCACCCTCCTCCAAGAGCACCTCTGGGGGC ACAGCGGCCCTGGGCTGCCTGGTCAAGGACTACTTCCCC GAACCGGTGACGGTGTCGTGGAACTCAGGCGCCCTGACC AGCGGCGTGCACACCTTCCCGGCTGTCCTACAGTCCTCA GGACTCTACTCCCTCAGCAGCGTGGTGACCGTGCCCTCC AGCAGCTTGGGCACCCAGACCTACATCTGCAACGTGAAT CACAAGCCCAGCAACACCAAGGTGGACAAGAGAGTTGAG CCCAAATCTTGTGACAAAACTCACACATGCCCACCGTGC CCAGCACCTGAAGCAGCGGGGGGACCGTCAGTCTTCCTC TTCCCCCCAAAACCCAAGGACACCCTCATGATCTCCCGG ACCCCTGAGGTCACATGCGTGGTGGTGGACGTGAGCCAC GAAGACCCTGAGGTCAAGTTCAACTGGTACGTGGACGGC GTGGAGGTGCATAATGCCAAGACAAAGCCGCGGGAGGAG CAGTACAACAGCACGTACCGGGTGGTCAGCGTCCTCACC GTCCTGCACCAGGACTGGCTGAATGGCAAGGAGTACAAG TGCAAGGTCTCCAACAAAGCCCTCCCAGCCCCCATCGAG AAAACCATCTCCAAAGCCAAAGGGCAGCCCCGAGAACCA CAGGTGTACACCCTGCCCCCATCCCGGGAGGAGATGACC AAGAACCAGGTCAGCCTGACCTGCCTGGTCAAAGGCTTC TATCCCAGCGACATCGCCGTGGAGTGGGAGAGCAATGGG CAGCCGGAGAACAACTACAAGACCACGCCTCCCGTGCTG GACTCCGACGGCTCCTTCTTCCTCTACAGCAAGCTCACC GTGGACAAGAGCAGGTGGCAGCAGGGGAACGTCTTCTCA TGCTCCGTGATGCATGAGGCTCTGCACAACCACTACACG CAGAAGAGCCTCTCCCTGTCTCCGGGTAAA |
| LCDR1 (Combined) | 16 | SGSSSNIGSNDVS |
| LCDR2 (Combined) | 17 | KNYNRPS |
| LCDR3 (Combined) | 18 | SAWDQRQFDVV |
| LCDR1 (Kabat) | 16 | SGSSSNIGSNDVS |
| LCDR2 (Kabat) | 17 | KNYNRPS |
| LCDR3 (Kabat) | 18 | SAWDQRQFDVV |
| LCDR1 (Chothia) | 19 | SSSNIGSND |
| LCDR2 (Chothia) | 20 | KNY |
| LCDR3 (Chothia) | 21 | WDQRQFDV |
| LCDR1 (IMGT) | 22 | SSNIGSND |
| LCDR2 (IMGT) | 20 | KNY |
| LCDR3 (IMGT) | 18 | SAWDQRQFDVV |
| VL | 362 | DIVLTQPPSVSGAPGQRVTISCSGSSSNIGSNDVSWYQQ LPGTAPKLLIYKNYNRPSGVPDRFSGSKSGTSASLAITG LQAEDEADYYCSAWDQRQFDVVFGGGTKLTVL |
| DNA VL | 363 | GATATCGTGCTGACCCAGCCGCCGAGCGTGAGCGGTGCA CCGGGCCAGCGCGTGACCATTAGCTGTAGCGGCAGCAGC AGCAACATTGGTTCTAACGACGTGTCTTGGTACCAGCAG CTGCCGGGCACGGCGCCGAAACTGCTGATCTACAAAAAC TACAACCGCCCGAGCGGCGTGCCGGATCGCTTTAGCGGA TCCAAAAGCGGCACCAGCGCCAGCCTGGCGATTACCGGC CTGCAAGCAGAAGACGAAGCGGATTATTACTGCTCTGCT TGGGACCAGCGTCAGTTCGACGTTGTGTTTGGCGGCGGC ACGAAGTTAACCGTCCTA |
| Light Chain | 364 | DIVLTQPPSVSGAPGQRVTISCSGSSSNIGSNDVSWYQQ LPGTAPKLLIYKNYNRPSGVPDRFSGSKSGTSASLAITG LQAEDEADYYCSAWDQRQFDVVFGGGTKLTVLGQPKAAP SVTLFPPSSEELQANKATLVCLISDFYPGAVTVAWKADS SPVKAGVETTTPSKQSNNKYAASSYLSLTPEQWKSHRSY SCQVTHEGSTVEKTVAPTECS |

TABLE 1-continued

Examples of FXI/FXIa Antibodies, Fabs and FXI/FXIa Proteins

| Sequence Description | Sequence Identifier (SEQ ID NO:) | Amino acid or polynucleotide sequence |
|---|---|---|
| DNA Light Chain | 365 | GATATCGTGCTGACCCAGCCGCCGAGCGTGAGCGGTGCA CCGGGCCAGCGCGTGACCATTAGCTGTAGCGGCAGCAGC AGCAACATTGGTTCTAACGACGTGTCTTGGTACCAGCAG CTGCCGGGCACGGCGCCGAAACTGCTGATCTACAAAAAC TACAACCGCCCGAGCGGCGTGCCGGATCGCTTTAGCGGA TCCAAAAGCGGCACCAGCGCCAGCCTGGCGATTACCGGC CTGCAAGCAGAAGACGAAGCGGATTATTACTGCTCTGCT TGGGACCAGCGTCAGTTCGACGTTGTGTTTGGCGGCGGC ACGAAGTTAACCGTCCTAGGTCAGCCCAAGGCTGCCCCC TCGGTCACTCTGTTCCCGCCCTCCTCTGAGGAGCTTCAA GCCAACAAGGCCACACTGGTGTGTCTCATAAGTGACTTC TACCCGGGAGCCGTGACAGTGGCCTGGAAGGCAGATAGC AGCCCCGTCAAGGCGGGAGTGGAGACCACCACACCCTCC AAACAAAGCAACAACAAGTACGCGGCCAGCAGCTATCTG AGCCTGACGCCTGAGCAGTGGAAGTCCCACAGAAGCTAC AGCTGCCAGGTCACGCATGAAGGGAGCACCGTGGAGAAG ACAGTGGCCCCTACAGAATGTTCA |
| | | AN2 |
| HCDR1 (Combined) | 3 | GFTFSTAAMS |
| HCDR2 (Combined) | 372 | SIEYYDTDTHYADSVKG |
| HCDR3 (Combined) | 5 | ELSYLYSGYYFDY |
| HCDR1 (Kabat) | 6 | TAAMS |
| HCDR2 (Kabat) | 372 | SIEYYDTDTHYADSVKG |
| HCDR3 (Kabat) | 5 | ELSYLYSGYYFDY |
| HCDR1 (Chothia) | 7 | GFTFSTA |
| HCDR2 (Chothia) | 373 | EYYDTD |
| HCDR3 (Chothia) | 5 | ELSYLYSGYYFDY |
| HCDR1 (IMGT) | 9 | GFTFSTAA |
| HCDR2 (IMGT) | 374 | IEYYDTDT |
| HCDR3 (IMGT) | 11 | ARELSYLYSGYYFDY |
| VH | 375 | QVQLLESGGGLVQPGGSLRLSCAASGFTFSTAAMSWVRQ APGKGLEWVSSIEYYDTDTHYADSVKGRFTISRDNSKNT LYLQMNSLRAEDTAVYYCARELSYLYSGYYFDYWGQGTL VTVSS |
| DNA VH | 376 | CAGGTGCAATTGCTGGAAAGCGGCGGTGGCCTGGTGCAG CCGGGTGGCAGCCTGCGTCTGAGCTGCGCGGCGTCCGGA TTCACCTTTTCTACTGCTGCTATGTCTTGGGTGCGCCAG GCCCCGGGCAAAGGTCTCGAGTGGGTTTCCTCTATCGAA TACTACGACACTGACACTCATTATGCGGATAGCGTGAAA GGCCGCTTTACCATCAGCCGCGATAATTCGAAAAACACC CTGTATCTGCAAATGAACAGCCTGCGTGCGGAAGATACG GCCGTGTATTATTGCGCGCGTGAACTGTCTTACCTGTAC TCTGGTTACTACTTCGATTACTGGGGCCAAGGCACCCTG GTGACTGTTAGCTCA |
| Heavy Chain | 377 | QVQLLESGGGLVQPGGSLRLSCAASGFTFSTAAMSWVRQ APGKGLEWVSSIEYYDTDTHYADSVKGRFTISRDNSKNT LYLQMNSLRAEDTAVYYCARELSYLYSGYYFDYWGQGTL VTVSSASTKGPSVFPLAPSSKSTSGGTAALGCLVKDYFP EPVTVSWNSGALTSGVHTFPAVLQSSGLYSLSSVVTVPS SSLGTQTYICNVNHKPSNTKVDKRVEPKSCDKTHTCPPC PAPEAAGGPSVFLFPPKPKDTLMISRTPEVTCVVVDVSH EDPEVKFNWYVDGVEVHNAKTKPREEQYNSTYRVVSVLT VLHQDWLNGKEYKCKVSNKALPAPIEKTISKAKGQPREP QVYTLPPSREEMTKNQVSLTCLVKGFYPSDIAVEWESNG QPENNYKTTPPVLDSDGSFFLYSKLTVDKSRWQQGNVFS CSVMHEALHNHYTQKSLSLSPGK |
| DNA Heavy Chain | 378 | CAGGTGCAATTGCTGGAAAGCGGCGGTGGCCTGGTGCAG CCGGGTGGCAGCCTGCGTCTGAGCTGCGCGGCGTCCGGA TTCACCTTTTCTACTGCTGCTATGTCTTGGGTGCGCCAG GCCCCGGGCAAAGGTCTCGAGTGGGTTTCCTCTATCGAA TACTACGACACTGACACTCATTATGCGGATAGCGTGAAA GGCCGCTTTACCATCAGCCGCGATAATTCGAAAAACACC CTGTATCTGCAAATGAACAGCCTGCGTGCGGAAGATACG GCCGTGTATTATTGCGCGCGTGAACTGTCTTACCTGTAC TCTGGTTACTACTTCGATTACTGGGGCCAAGGCACCCTG |

TABLE 1-continued

Examples of FXI/FXIa Antibodies, Fabs and FXI/FXIa Proteins

| Sequence Description | Sequence Identifier (SEQ ID NO:) | Amino acid or polynucleotide sequence |
|---|---|---|
| | | GTGACTGTTAGCTCAGCCTCCACCAAGGGTCCATCGGTC<br>TTCCCCCTGGCACCCTCCTCCAAGAGCACCTCTGGGGGC<br>ACAGCGGCCCTGGGCTGCCTGGTCAAGGACTACTTCCCC<br>GAACCGGTGACGGTGTCGTGGAACTCAGGCGCCCTGACC<br>AGCGGCGTGCACACCTTCCCGGCTGTCCTACAGTCCTCA<br>GGACTCTACTCCCTCAGCAGCGTGGTGACCGTGCCCTCC<br>AGCAGCTTGGGCACCCAGACCTACATCTGCAACGTGAAT<br>CACAAGCCCAGCAACACCAAGGTGGACAAGAGAGTTGAG<br>CCCAAATCTTGTGACAAAACTCACACATGCCCACCGTGC<br>CCAGCACCTGAAGCAGCGGGGGGACCGTCAGTCTTCCTC<br>TTCCCCCCAAAACCCAAGGACACCCTCATGATCTCCCGG<br>ACCCCTGAGGTCACATGCGTGGTGGTGGACGTGAGCCAC<br>GAAGACCCTGAGGTCAAGTTCAACTGGTACGTGGACGGC<br>GTGGAGGTGCATAATGCCAAGACAAAGCCGCGGGAGGAG<br>CAGTACAACAGCACGTACCGGGTGGTCAGCGTCCTCACC<br>GTCCTGCACCAGGACTGGCTGAATGGCAAGGAGTACAAG<br>TGCAAGGTCTCCAACAAAGCCCTCCCAGCCCCCATCGAG<br>AAAACCATCTCCAAAGCCAAAGGGCAGCCCCGAGAACCA<br>CAGGTGTACACCCTGCCCCCATCCCGGGAGGAGATGACC<br>AAGAACCAGGTCAGCCTGACCTGCCTGGTCAAAGGCTTC<br>TATCCCAGCGACATCGCCGTGGAGTGGGAGAGCAATGGG<br>CAGCCGGAGAACAACTACAAGACCACGCCTCCCGTGCTG<br>GACTCCGACGGCTCCTTCTTCCTCTACAGCAAGCTCACC<br>GTGGACAAGAGCAGGTGGCAGCAGGGGAACGTCTTCTCA<br>TGCTCCGTGATGCATGAGGCTCTGCACAACCACTACACG<br>CAGAAGAGCCTCTCCCTGTCTCCGGGTAAA |
| LCDR1 (Combined) | 16 | SGSSSNIGSNDVS |
| LCDR2 (Combined) | 17 | KNYNRPS |
| LCDR3 (Combined) | 18 | SAWDQRQFDVV |
| LCDR1 (Kabat) | 16 | SGSSSNIGSNDVS |
| LCDR2 (Kabat) | 17 | KNYNRPS |
| LCDR3 (Kabat) | 18 | SAWDQRQFDVV |
| LCDR1 (Chothia) | 19 | SSSNIGSND |
| LCDR2 (Chothia) | 20 | KNY |
| LCDR3 (Chothia) | 21 | WDQRQFDV |
| LCDR1 (IMGT) | 22 | SSNIGSND |
| LCDR2 (IMGT) | 20 | KNY |
| LCDR3 (IMGT) | 18 | SAWDQRQFDVV |
| VL | 362 | DIVLTQPPSVSGAPGQRVTISCSGSSSNIGSNDVSWYQQ<br>LPGTAPKLLIYKNYNRPSGVPDRFSGSKSGTSASLAITG<br>LQAEDEADYYCSAWDQRQFDVVFGGGTKLTVL |
| DNA VL | 363 | GATATCGTGCTGACCCAGCCGCCGAGCGTGAGCGGTGCA<br>CCGGGCCAGCGCGTGACCATTAGCTGTAGCGGCAGCAGC<br>AGCAACATTGGTTCTAACGACGTGTCTTGGTACCAGCAG<br>CTGCCGGGCACGGCGCCGAAACTGCTGATCTACAAAAAC<br>TACAACCGCCCGAGCGGCGTGCCGGATCGCTTTAGCGGA<br>TCCAAAAGCGGCACCAGCGCCAGCCTGGCGATTACCGGC<br>CTGCAAGCAGAAGACGAAGCGGATTATTACTGCTCTGCT<br>TGGGACCAGCGTCAGTTCGACGTTGTGTTTGGCGGCGGC<br>ACGAAGTTAACCGTCCTA |
| Light Chain | 364 | DIVLTQPPSVSGAPGQRVTISCSGSSSNIGSNDVSWYQQ<br>LPGTAPKLLIYKNYNRPSGVPDRFSGSKSGTSASLAITG<br>LQAEDEADYYCSAWDQRQFDVVFGGGTKLTVLGQPKAAP<br>SVTLFPPSSEELQANKATLVCLISDFYPGAVTVAWKADS<br>SPVKAGVETTTPSKQSNNKYAASSYLSLTPEQWKSHRSY<br>SCQVTHEGSTVEKTVAPTECS |
| DNA Light Chain | 365 | GATATCGTGCTGACCCAGCCGCCGAGCGTGAGCGGTGCA<br>CCGGGCCAGCGCGTGACCATTAGCTGTAGCGGCAGCAGC<br>AGCAACATTGGTTCTAACGACGTGTCTTGGTACCAGCAG<br>CTGCCGGGCACGGCGCCGAAACTGCTGATCTACAAAAAC<br>TACAACCGCCCGAGCGGCGTGCCGGATCGCTTTAGCGGA<br>TCCAAAAGCGGCACCAGCGCCAGCCTGGCGATTACCGGC<br>CTGCAAGCAGAAGACGAAGCGGATTATTACTGCTCTGCT<br>TGGGACCAGCGTCAGTTCGACGTTGTGTTTGGCGGCGGC<br>ACGAAGTTAACCGTCCTAGGTCAGCCCAAGGCTGCCCCC<br>TCGGTCACTCTGTTCCCGCCCTCCTCTGAGGAGCTTCAA<br>GCCAACAAGGCCACACTGGTGTGTCTCATAAGTGACTTC |

TABLE 1-continued

Examples of FXI/FXIa Antibodies, Fabs and FXI/FXIa Proteins

| Sequence Description | Sequence Identifier (SEQ ID NO:) | Amino acid or polynucleotide sequence |
|---|---|---|
| | | TACCCGGGAGCCGTGACAGTGGCCTGGAAGGCAGATAGC AGCCCCGTCAAGGCGGGAGTGGAGACCACCACACCCTCC AAACAAAGCAACAACAAGTACGCGGCCAGCAGCTATCTG AGCCTGACGCCTGAGCAGTGGAAGTCCCACAGAAGCTAC AGCTGCCAGGTCACGCATGAAGGGAGCACCGTGGAGAAG ACAGTGGCCCCTACAGAATGTTCA |
| | | AM3 |
| HCDR1 (Combined) | 3 | GFTFSTAAMS |
| HCDR2 (Combined) | 379 | TIEYSSQETYYADSVKG |
| HCDR3 (Combined) | 5 | ELSYLYSGYYFDY |
| HCDR1 (Kabat) | 6 | TAAMS |
| HCDR2 (Kabat) | 379 | TIEYSSQETYYADSVKG |
| HCDR3 (Kabat) | 5 | ELSYLYSGYYFDY |
| HCDR1 (Chothia) | 7 | GFTFSTA |
| HCDR2 (Chothia) | 380 | EYSSQE |
| HCDR3 (Chothia) | 5 | ELSYLYSGYYFDY |
| HCDR1 (IMGT) | 9 | GFTFSTAA |
| HCDR2 (IMGT) | 381 | IEYSSQET |
| HCDR3 (IMGT) | 11 | ARELSYLYSGYYFDY |
| VH | 382 | QVQLLESGGGLVQPGGSLRLSCAASGFTFSTAAMSWVRQ APGKGLEWVSTIEYSSQETYYADSVKGRFTISRDNSKNT LYLQMNSLRAEDTAVYYCARELSYLYSGYYFDYWGQGTL VTVSS |
| DNA VH | 383 | CAGGTGCAATTGCTGGAAAGCGGCGGTGGCCTGGTGCAG CCGGGTGGCAGCCTGCGTCTGAGCTGCGCGGCGTCCGGA TTCACCTTTTCTACTGCTGCTATGTCTTGGGTGCGCCAG GCCCCGGGCAAAGGTCTCGAGTGGGTTTCCACTATCGAA TACTCTAGCCAGGAAACTTACTATGCGGATAGCGTGAAA GGCCGCTTTACCATCAGCCGCGATAATTCGAAAAACACC CTGTATCTGCAAATGAACAGCCTGCGTGCGGAAGATACG GCCGTGTATTATTGCGCGCGTGAACTGTCTTACCTGTAC TCTGGTTACTACTTCGATTACTGGGGCCAAGGCACCCTG GTGACTGTTAGCTCA |
| Heavy Chain | 384 | QVQLLESGGGLVQPGGSLRLSCAASGFTFSTAAMSWVRQ APGKGLEWVSTIEYSSQETYYADSVKGRFTISRDNSKNT LYLQMNSLRAEDTAVYYCARELSYLYSGYYFDYWGQGTL VTVSSASTKGPSVFPLAPSSKSTSGGTAALGCLVKDYFP EPVTVSWNSGALTSGVHTFPAVLQSSGLYSLSSVVTVPS SSLGTQTYICNVNHKPSNTKVDKRVEPKSCDKTHTCPPC PAPEAAGGPSVFLFPPKPKDTLMISRTPEVTCVVVDVSH EDPEVKFNWYVDGVEVHNAKTKPREEQYNSTYRVVSVLT VLHQDWLNGKEYKCKVSNKALPAPIEKTISKAKGQPREP QVYTLPPSREEMTKNQVSLTCLVKGFYPSDIAVEWESNG QPENNYKTTPPVLDSDGSFFLYSKLTVDKSRWQQGNVFS CSVMHEALHNHYTQKSLSLSPGK |
| DNA Heavy Chain | 385 | CAGGTGCAATTGCTGGAAAGCGGCGGTGGCCTGGTGCAG CCGGGTGGCAGCCTGCGTCTGAGCTGCGCGGCGTCCGGA TTCACCTTTTCTACTGCTGCTATGTCTTGGGTGCGCCAG GCCCCGGGCAAAGGTCTCGAGTGGGTTTCCACTATCGAA TACTCTAGCCAGGAAACTTACTATGCGGATAGCGTGAAA GGCCGCTTTACCATCAGCCGCGATAATTCGAAAAACACC CTGTATCTGCAAATGAACAGCCTGCGTGCGGAAGATACG GCCGTGTATTATTGCGCGCGTGAACTGTCTTACCTGTAC TCTGGTTACTACTTCGATTACTGGGGCCAAGGCACCCTG GTGACTGTTAGCTCAGCCTCCACCAAGGGTCCATCGGTC TTCCCCCTGGCACCCTCCTCCAAGAGCACCTCTGGGGGC ACAGCGGCCCTGGGCTGCCTGGTCAAGGACTACTTCCCC GAACCGGTGACGGTGTCGTGGAACTCAGGCGCCCTGACC AGCGGCGTGCACACCTTCCCGGCTGTCCTACAGTCCTCA GGACTCTACTCCCTCAGCAGCGTGGTGACCGTGCCCTCC AGCAGCTTGGGCACCCAGACCTACATCTGCAACGTGAAT CACAAGCCCAGCAACACCAAGGTGGACAAGAGAGTTGAG CCCAAATCTTGTGACAAAACTCACACATGCCCACCGTGC CCAGCACCTGAAGCAGCGGGGGGACCGTCAGTCTTCCTC TTCCCCCCAAAACCCAAGGACACCCTCATGATCTCCCGG ACCCCTGAGGTCACATGCGTGGTGGTGGACGTGAGCCAC |

TABLE 1-continued

| Examples of FXI/FXIa Antibodies, Fabs and FXI/FXIa Proteins | | |
|---|---|---|
| Sequence Description | Sequence Identifier (SEQ ID NO:) | Amino acid or polynucleotide sequence |
| | | GAAGACCCTGAGGTCAAGTTCAACTGGTACGTGGACGGC GTGGAGGTGCATAATGCCAAGACAAAGCCGCGGGAGGAG CAGTACAACAGCACGTACCGGGTGGTCAGCGTCCTCACC GTCCTGCACCAGGACTGGCTGAATGGCAAGGAGTACAAG TGCAAGGTCTCCAACAAAGCCCTCCCAGCCCCCATCGAG AAAACCATCTCCAAAGCCAAAGGGCAGCCCCGAGAACCA CAGGTGTACACCCTGCCCCCATCCCGGGAGGAGATGACC AAGAACCAGGTCAGCCTGACCTGCCTGGTCAAAGGCTTC TATCCCAGCGACATCGCCGTGGAGTGGGAGAGCAATGGG CAGCCGGAGAACAACTACAAGACCACGCCTCCCGTGCTG GACTCCGACGGCTCCTTCTTCCTCTACAGCAAGCTCACC GTGGACAAGAGCAGGTGGCAGCAGGGGAACGTCTTCTCA TGCTCCGTGATGCATGAGGCTCTGCACAACCACTACACG CAGAAGAGCCTCTCCCTGTCTCCGGGTAAA |
| LCDR1 (Combined) | 16 | SGSSSNIGSNDVS |
| LCDR2 (Combined) | 17 | KNYNRPS |
| LCDR3 (Combined) | 18 | SAWDQRQFDVV |
| LCDR1 (Kabat) | 16 | SGSSSNIGSNDVS |
| LCDR2 (Kabat) | 17 | KNYNRPS |
| LCDR3 (Kabat) | 18 | SAWDQRQFDVV |
| LCDR1 (Chothia) | 19 | SSSNIGSND |
| LCDR2 (Chothia) | 20 | KNY |
| LCDR3 (Chothia) | 21 | WDQRQFDV |
| LCDR1 (IMGT) | 22 | SSNIGSND |
| LCDR2 (IMGT) | 20 | KNY |
| LCDR3 (IMGT) | 18 | SAWDQRQFDVV |
| VL | 362 | DIVLTQPPSVSGAPGQRVTISCSGSSSNIGSNDVSWYQQ LPGTAPKLLIYKNYNRPSGVPDRFSGSKSGTSASLAITG LQAEDEADYYCSAWDQRQFDVVFGGGTKLTVL |
| DNA VL | 363 | GATATCGTGCTGACCCAGCCGCCGAGCGTGAGCGGTGCA CCGGGCCAGCGCGTGACCATTAGCTGTAGCGGCAGCAGC AGCAACATTGGTTCTAACGACGTGTCTTGGTACCAGCAG CTGCCGGGCACGGCGCCGAAACTGCTGATCTACAAAAAC TACAACCGCCCGAGCGGCGTGCCGGATCGCTTTAGCGGA TCCAAAAGCGGCACCAGCGCCAGCCTGGCGATTACCGGC CTGCAAGCAGAAGACGAAGCGGATTATTACTGCTCTGCT TGGGACCAGCGTCAGTTCGACGTTGTGTTTGGCGGCGGC ACGAAGTTAACCGTCCTA |
| Light Chain | 364 | DIVLTQPPSVSGAPGQRVTISCSGSSSNIGSNDVSWYQQ LPGTAPKLLIYKNYNRPSGVPDRFSGSKSGTSASLAITG LQAEDEADYYCSAWDQRQFDVVFGGGTKLTVLGQPKAAP SVTLFPPSSEELQANKATLVCLISDFYPGAVTVAWKADS SPVKAGVETTTPSKQSNNKYAASSYLSLTPEQWKSHRSY SCQVTHEGSTVEKTVAPTECS |
| DNA Light Chain | 365 | GATATCGTGCTGACCCAGCCGCCGAGCGTGAGCGGTGCA CCGGGCCAGCGCGTGACCATTAGCTGTAGCGGCAGCAGC AGCAACATTGGTTCTAACGACGTGTCTTGGTACCAGCAG CTGCCGGGCACGGCGCCGAAACTGCTGATCTACAAAAAC TACAACCGCCCGAGCGGCGTGCCGGATCGCTTTAGCGGA TCCAAAAGCGGCACCAGCGCCAGCCTGGCGATTACCGGC CTGCAAGCAGAAGACGAAGCGGATTATTACTGCTCTGCT TGGGACCAGCGTCAGTTCGACGTTGTGTTTGGCGGCGGC ACGAAGTTAACCGTCCTAGGTCAGCCCAAGGCTGCCCCC TCGGTCACTCTGTTCCCGCCCTCCTCTGAGGAGCTTCAA GCCAACAAGGCCACACTGGTGTGTCTCATAAGTGACTTC TACCCGGGAGCCGTGACAGTGGCCTGGAAGGCAGATAGC AGCCCCGTCAAGGCGGGAGTGGAGACCACCACACCCTCC AAACAAAGCAACAACAAGTACGCGGCCAGCAGCTATCTG AGCCTGACGCCTGAGCAGTGGAAGTCCCACAGAAGCTAC AGCTGCCAGGTCACGCATGAAGGGAGCACCGTGGAGAAG ACAGTGGCCCCTACAGAATGTTCA |

TABLE 1-continued

Examples of FXI/FXIa Antibodies, Fabs and FXI/FXIa Proteins

| Sequence Description | Sequence Identifier (SEQ ID NO:) | Amino acid or polynucleotide sequence |
|---|---|---|
| | | AM4 |
| HCDR1 (Combined) | 3 | GFTFSTAAMS |
| HCDR2 (Combined) | 379 | TIEYSSQETYYADSVKG |
| HCDR3 (Combined) | 5 | ELSYLYSGYYFDY |
| HCDR1 (Kabat) | 6 | TAAMS |
| HCDR2 (Kabat) | 379 | TIEYSSQETYYADSVKG |
| HCDR3 (Kabat) | 5 | ELSYLYSGYYFDY |
| HCDR1 (Chothia) | 7 | GFTFSTA |
| HCDR2 (Chothia) | 380 | EYSSQE |
| HCDR3 (Chothia) | 5 | ELSYLYSGYYFDY |
| HCDR1 (IMGT) | 9 | GFTFSTAA |
| HCDR2 (IMGT) | 381 | IEYSSQET |
| HCDR3 (IMGT) | 11 | ARELSYLYSGYYFDY |
| VH | 382 | QVQLLESGGGLVQPGGSLRLSCAASGFTFSTAAMSWVRQ<br>APGKGLEWVSTIEYSSQETYYADSVKGRFTISRDNSKNT<br>LYLQMNSLRAEDTAVYYCARELSYLYSGYYFDYWGQGTL<br>VTVSS |
| DNA VH | 392 | CAAGTGCAGCTGCTTGAATCTGGCGGCGGACTGGTGCAG<br>CCTGGCGGCTCCCTGAGACTGTCTTGCGCCGCCTCCGGC<br>TTCACCTTCTCCACCGCCGCTATGTCCTGGGTCCGACAG<br>GCTCCCGGCAAGGGCCTGGAATGGGTGTCCACCATTGAG<br>TACTCCAGCCAGGAAACCTACTACGCCGACTCCGTGAAG<br>GGCCGGTTCACCATCTCCCGGGACAACTCCAAGAACACC<br>CTGTACCTGCAGATGAACTCCCTGCGGGCCGAGGACACC<br>GCCGTGTACTACTGCGCCAGAGAGCTGTCCTACCTGTAC<br>TCCGGCTACTACTTCGACTACTGGGGCCAGGGCACCCTG<br>GTCACCGTGTCCTCT |
| Heavy Chain | 384 | QVQLLESGGGLVQPGGSLRLSCAASGFTFSTAAMSWVRQ<br>APGKGLEWVSTIEYSSQETYYADSVKGRFTISRDNSKNT<br>LYLQMNSLRAEDTAVYYCARELSYLYSGYYFDYWGQGTL<br>VTVSSASTKGPSVFPLAPSSKSTSGGTAALGCLVKDYFP<br>EPVTVSWNSGALTSGVHTFPAVLQSSGLYSLSSVVTVPS<br>SSLGTQTYICNVNHKPSNTKVDKRVEPKSCDKTHTCPPC<br>PAPEAAGGPSVFLFPPKPKDTLMISRTPEVTCVVVDVSH<br>EDPEVKFNWYVDGVEVHNAKTKPREEQYNSTYRVVSVLT<br>VLHQDWLNGKEYKCKVSNKALPAPIEKTISKAKGQPREP<br>QVYTLPPSREEMTKNQVSLTCLVKGFYPSDIAVEWESNG<br>QPENNYKTTPPVLDSDGSFFLYSKLTVDKSRWQQGNVFS<br>CSVMHEALHNHYTQKSLSLSPGK |
| DNA Heavy Chain | 393 | CAAGTGCAGCTGCTTGAATCTGGCGGCGGACTGGTGCAG<br>CCTGGCGGCTCCCTGAGACTGTCTTGCGCCGCCTCCGGC<br>TTCACCTTCTCCACCGCCGCTATGTCCTGGGTCCGACAG<br>GCTCCCGGCAAGGGCCTGGAATGGGTGTCCACCATTGAG<br>TACTCCAGCCAGGAAACCTACTACGCCGACTCCGTGAAG<br>GGCCGGTTCACCATCTCCCGGGACAACTCCAAGAACACC<br>CTGTACCTGCAGATGAACTCCCTGCGGGCCGAGGACACC<br>GCCGTGTACTACTGCGCCAGAGAGCTGTCCTACCTGTAC<br>TCCGGCTACTACTTCGACTACTGGGGCCAGGGCACCCTG<br>GTCACCGTGTCCTCTGCTAGCACCAAGGGCCCCTCCGTG<br>TTCCCTCTGGCCCCTTCCAGCAAGTCTACCTCCGGCGGC<br>ACAGCTGCTCTGGGCTGCCTGGTCAAGGACTACTTCCCT<br>GAGCCTGTGACAGTGTCCTGGAACTCTGGCGCCCTGACC<br>TCTGGCGTGCACACCTTCCCTGCCGTGCTGCAGTCCTCC<br>GGCCTGTACTCCCTGTCCTCCGTGGTCACAGTGCCTTCA<br>AGCAGCCTGGGCACCCAGACCTATATCTGCAACGTGAAC<br>CACAAGCCTTCCAACACCAAGGTGGACAAGCGGGTGGAG<br>CCTAAGTCCTGCGACAAGACCCACACCTGTCCTCCCTGC<br>CCTGCTCCTGAAGCTGCTGGCGGCCCTTCTGTGTTCCTG<br>TTCCCTCCAAAGCCCAAGGACACCCTGATGATCTCCCGG<br>ACCCCTGAAGTGACCTGCGTGGTGGTGGACGTGTCCCAC<br>GAGGATCCTGAAGTGAAGTTCAATTGGTACGTGGACGGC<br>GTGGAGGTGCACAACGCCAAGACCAAGCCTCGGGAGGAA<br>CAGTACAACTCCACCTACCGGGTGGTGTCCGTGCTGACC<br>GTGCTGCACCAGGACTGGCTGAACGGCAAAGAGTACAAG<br>TGCAAAGTCTCCAACAAGGCCCTGCCTGCCCCTATCGAA |

TABLE 1-continued

Examples of FXI/FXIa Antibodies, Fabs and FXI/FXIa Proteins

| Sequence Description | Sequence Identifier (SEQ ID NO:) | Amino acid or polynucleotide sequence |
|---|---|---|
| | | AAGACAATCTCCAAGGCCAAGGGCCAGCCTAGGGAACCC CAGGTGTACACCCTGCCACCCAGCCGGGAGGAAATGACC AAGAACCAGGTGTCCCTGACCTGTCTGGTCAAGGGCTTC TACCCTTCCGATATCGCCGTGGAGTGGGAGTCTAACGGC CAGCCTGAGAACAACTACAAGACCACCCCTCCTGTGCTG GACTCCGACGGCTCCTTCTTCCTGTACTCCAAACTGACC GTGGACAAGTCCCGGTGGCAGCAGGGCAACGTGTTCTCC TGCTCCGTGATGCACGAGGCCCTGCACAACCACTACACC CAGAAGTCCCTGTCCCTGTCTCCCGGCAAG |
| LCDR1 (Combined) | 16 | SGSSSNIGSNDVS |
| LCDR2 (Combined) | 17 | KNYNRPS |
| LCDR3 (Combined) | 18 | SAWDQRQFDVV |
| LCDR1 (Kabat) | 16 | SGSSSNIGSNDVS |
| LCDR2 (Kabat) | 17 | KNYNRPS |
| LCDR3 (Kabat) | 18 | SAWDQRQFDVV |
| LCDR1 (Chothia) | 19 | SSSNIGSND |
| LCDR2 (Chothia) | 20 | KNY |
| LCDR3 (Chothia) | 21 | WDQRQFDV |
| LCDR1 (IMGT) | 22 | SSNIGSND |
| LCDR2 (IMGT) | 20 | KNY |
| LCDR3 (IMGT) | 18 | SAWDQRQFDVV |
| VL | 386 | QSVLTQPPSVSGAPGQRVTISCSGSSSNIGSNDVSWYQQ LPGTAPKLLIYKNYNRPSGVPDRFSGSKSGTSASLAITG LQAEDEADYYCSAWDQRQFDVVFGGGTKLTVL |
| DNA VL | 387 | CAGAGCGTGCTGACACAGCCTCCCTCCGTGTCTGGCGCC CCTGGCCAGAGAGTGACCATCTCCTGCTCCGGCTCCTCC TCCAACATCGGCTCCAACGACGTGTCCTGGTATCAGCAG CTGCCCGGCACCGCCCCTAAGCTGCTGATCTACAAGAAC TACAACCGGCCCTCCGGCGTGCCCGACCGGTTCTCTGGC TCCAAGTCTGGCACCTCCGCCTCCCTGGCTATCACCGGC CTGCAGGCTGAGGACGAGGCCGACTACTACTGCTCCGCC TGGGACCAGCGGCAGTTCGACGTGGTGTTCGGCGGAGGC ACCAAGCTGACCGTGCTG |
| Light Chain | 388 | QSVLTQPPSVSGAPGQRVTISCSGSSSNIGSNDVSWYQQ LPGTAPKLLIYKNYNRPSGVPDRFSGSKSGTSASLAITG LQAEDEADYYCSAWDQRQFDVVFGGGTKLTVLGQPKAAP SVTLFPPSSEELQANKATLVCLISDFYPGAVTVAWKADS SPVKAGVETTTPSKQSNNKYAASSYLSLTPEQWKSHRSY SCQVTHEGSTVEKTVAPTECS |
| DNA Light Chain | 389 | CAGAGCGTGCTGACACAGCCTCCCTCCGTGTCTGGCGCC CCTGGCCAGAGAGTGACCATCTCCTGCTCCGGCTCCTCC TCCAACATCGGCTCCAACGACGTGTCCTGGTATCAGCAG CTGCCCGGCACCGCCCCTAAGCTGCTGATCTACAAGAAC TACAACCGGCCCTCCGGCGTGCCCGACCGGTTCTCTGGC TCCAAGTCTGGCACCTCCGCCTCCCTGGCTATCACCGGC CTGCAGGCTGAGGACGAGGCCGACTACTACTGCTCCGCC TGGGACCAGCGGCAGTTCGACGTGGTGTTCGGCGGAGGC ACCAAGCTGACCGTGCTGGGCCAGCCTAAGGCTGCCCCC AGCGTGACCCTGTTCCCCCCCAGCAGCGAGGAGCTGCAG GCCAACAAGGCCACCCTGGTGTGCCTGATCAGCGACTTC TACCCAGGCGCCGTGACCGTGGCCTGGAAGGCCGACAGC AGCCCCGTGAAGGCCGGCGTGGAGACCACCACCCCCAGC AAGCAGAGCAACAACAAGTACGCCGCCAGCAGCTACCTG AGCCTGACCCCCGAGCAGTGGAAGAGCCACAGGTCCTAC AGCTGCCAGGTGACCCACGAGGGCAGCACCGTGGAAAAG ACCGTGGCCCCAACCGAGTGCAGC |

Binding/Reversal Agents

In specific aspects, provided herein are reversal or binding agents, such as inactive FXI/FXIa-derived polypeptide or protein fragments and anti-idiotype antibodies and fragments thereof, which specifically bind a target antibody that binds human Factor XI ("FXI") and/or Factor XIa ("FXIa") ("anti-FXI/FXIa antibody"). In particular aspects, such reversal or binding agents inhibit an anticoagulant activity of the target antibody. In a specific aspect, such reversal or binding agents block the target antibody from binding to human FXI and/or FXIa. In a specific aspect, such reversal or binding agents (e.g., anti-idiotype antibodies and fragments thereof) bind to the antigen-binding region of the target anti-FXI/FXIa antibody and block the target antibody from binding to human FXI and/or FXIa.

In a specific aspect, provided herein is a reversal or binding agent which is an inactive FXI/FXIa-derived polypeptide or protein fragment that specifically binds to a target anti-FXI/FXIa antibody (e.g., an antibody described in Table 1), and is capable of inhibiting an anticoagulant activity of the target antibody and/or is capable of blocking the target antibody from binding to human FXI and/or FXIa. The activity of a human FXI/FXIa-derived polypeptide or protein fragment can be determined using methods described in the art, for example, biochemical assays detecting the cleavage of a fluorescently labelled peptide, which can be cleaved by FXIa (e.g., fluorescently labelled peptide with the sequence D-Leu-Pro-Arg*Rh110-D-Pro (product number BS-2494; Biosyntan GmbH, Berlin, Germany), where "*" indicates the scissile bond, D-Leu: D-leucine, Pro: proline, Arg: arginine, Rh110: rhodamine 110, D-Pro: D-proline). In a particular aspect, a reversal or binding agent which is an inactive FXI/FXIa-derived polypeptide or protein fragment comprises or consists essentially of an incomplete fragment of the catalytic domain of human FXI, and comprises one or more of the following amino acid residues of human FXI: Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604. In a particular aspect, a reversal or binding agent which is an inactive FXI/FXIa-derived polypeptide or protein fragment comprises or consists essentially of a fragment from amino acid residue 400, 401, 402, 403, 404, or 405 up to amino acid residue 600, 601, 602, 603, 604, or 605, of human FXI (e.g., SEQ ID NO: 1), or fragments thereof with approximately 100-150 amino acid residues thereof. In a specific aspect, In a particular aspect, a reversal or binding agent which is an inactive FXI/FXIa-derived polypeptide or protein fragment described herein comprises one or more mutations rendering the fragment inactive, for example, as measured by biochemical assays detecting the cleavage of a fluorescently labelled peptide. Other non-limiting examples of variants of FXIa which can be used as a reversal agent are described in PCT International Publication No. WO2017/015558.

In one aspect, the present disclosure relates to a reversal or binding agent (e.g., anti-idiotype antibody and fragments thereof, for example a Fab fragment) which specifically binds a target antibody that binds human Factor XI ("FXI") and/or Factor XIa ("FXIa") ("anti-FXI/FXIa antibody"), for example an anti-FXI/FXIa antibody described in Table 1, such as antibody NOV1401, or affinity matured variants thereof, such as antibody AM1, AM2, AM3, or AM4. In a particular aspect, provided herein is a binding agent which specifically binds a target antibody that binds human Factor XI ("FXI") and/or Factor XIa ("FXIa") ("anti-FXI/FXIa antibody", such as antibody NOV1401) within the catalytic domain, wherein the binding agent inhibits an anticoagulant activity of the target antibody, wherein the binding agent binds to the target antibody with a dissociation constant ($K_D$) of 1 nM or less, and wherein the binding agent is capable of inhibiting the ability of the target antibody to delay activated partial thromboplastin time (aPTT) by at least 35%. In further specific aspects, the binding agent is capable of inhibiting the ability of the target antibody to delay activated partial thromboplastin time (aPTT) by at least 40%. In further specific aspects, the binding agent is capable of inhibiting the ability of the target antibody to delay activated partial thromboplastin time (aPTT) by at least 50%. In further specific aspects, the binding agent is capable of inhibiting the ability of the target antibody to delay activated partial thromboplastin time (aPTT) by at least 60%. In further specific aspects, the binding agent is capable of inhibiting the ability of the target antibody to delay activated partial thromboplastin time (aPTT) by at least 70%. Methods for determining aPTT and delay to aPTT have been described in the art, and are also described herein, e.g., Examples Section.

In specific aspects, provided herein are binding agents which inhibit or reverses an anticoagulant activity of a target anti-FXI/FXIa antibody (e.g., NOV1401), wherein the binding agents are antigen-binding human antibody fragments such as human Fabs. In particular aspects, provided herein are binding agents which inhibit or reverses an anticoagulant activity of a target anti-FXI/FXIa antibody (e.g., NOV1401), wherein the binding agents are human anti-idiotype Fabs. In particular aspects, provided herein are binding agents which inhibit or reverses an anticoagulant activity of a target anti-FXI/FXIa antibody (e.g., NOV1401), wherein the binding agents are human IgG1, IgG2, or IgG4 antibodies, or variants thereof.

In further specific aspects, provided herein is a binding agent (e.g., anti-idiotype antibody) which specifically binds a target anti-FXI/FXIa antibody, wherein the binding agent inhibits an anticoagulant activity of the target anti-FXI/FXIa antibody, and wherein the target anti-FXI/FXIa antibody comprises (i) a heavy chain variable region (VH) comprising the amino acid sequence of SEQ ID NO: 12 and a light chain variable region (VL) comprising the amino acid sequence of SEQ ID NO: 23; or (ii) a heavy chain comprising the amino acid sequence of SEQ ID NO: 14 and a light chain comprising the amino acid sequence of SEQ ID NO: 25.

In further specific aspects, provided herein is a binding agent (e.g., anti-idiotype antibody) which specifically binds a target anti-FXI/FXIa antibody, wherein the binding agent inhibits an anticoagulant activity of the target anti-FXI/FXIa antibody, and wherein the target anti-FXI/FXIa antibody comprises (i) a heavy chain variable region (VH) comprising an amino acid sequence that is at least 90% or 95% identical to the amino acid sequence of SEQ ID NO: 12 and a light chain variable region (VL) comprising an amino acid sequence that is at least 90% or 95% identical to the amino acid sequence of SEQ ID NO: 23; or (ii) a heavy chain comprising an amino acid sequence that is at least 90% or 95% identical to the amino acid sequence of SEQ ID NO: 14 and a light chain comprising an amino acid sequence that is at least 90% or 95% identical to the amino acid sequence of SEQ ID NO: 25.

In further specific aspects, provided herein is a binding agent (e.g., anti-idiotype antibody) which specifically binds a target anti-FXI/FXIa antibody, wherein the binding agent inhibits an anticoagulant activity of the target anti-FXI/FXIa antibody, and wherein the target anti-FXI/FXIa antibody comprises (i) a VH comprising complementarity determining regions HCDR1, HCDR2 and HCDR3 of a VH comprising the amino acid sequence of SEQ ID NO: 12 and (ii) a VL comprising complementarity determining regions LCDR1, LCDR2, and LCDR3 of a VL comprising the amino acid sequence of SEQ ID NO: 23.

In further specific aspects, provided herein is a binding agent (e.g., anti-idiotype antibody) which specifically binds a target anti-FXI/FXIa antibody, wherein the binding agent inhibits an anticoagulant activity of the target anti-FXI/FXIa antibody, and wherein the target anti-FXI/FXIa antibody comprises:

(A)(i) a VH comprising complementarity determining regions HCDR1, HCDR2 and HCDR3 comprising the amino acid sequences of SEQ ID NO: 3, SEQ ID NO: 4, and SEQ ID NO: 5, respectively; and (ii) a VL comprising complementarity determining regions LCDR1, LCDR2, and LCDR3 comprising the amino acid sequence of SEQ ID NO: 16, SEQ ID NO: 17, and SEQ ID NO: 18, respectively;

(B)(i) a VH comprising complementarity determining regions HCDR1, HCDR2 and HCDR3 comprising the amino acid sequences of SEQ ID NO: 6, SEQ ID NO: 4, and SEQ ID NO: 5, respectively; and (ii) a VL comprising complementarity determining regions LCDR1, LCDR2, and LCDR3 comprising the amino acid sequence of SEQ ID NO: 16, SEQ ID NO: 17, and SEQ ID NO: 18, respectively;

(C)(i) a VH comprising complementarity determining regions HCDR1, HCDR2 and HCDR3 comprising the amino acid sequences of SEQ ID NO: 7, SEQ ID NO: 8, and SEQ ID NO: 5, respectively; and (ii) a VL comprising complementarity determining regions LCDR1, LCDR2, and LCDR3 comprising the amino acid sequence of SEQ ID NO: 19, SEQ ID NO: 20, and SEQ ID NO: 21, respectively; or (D)(i) a VH comprising complementarity determining regions HCDR1, HCDR2 and HCDR3 comprising the amino acid sequences of SEQ ID NO: 9, SEQ ID NO: 10, and SEQ ID NO: 11, respectively; and (ii) a VL comprising complementarity determining regions LCDR1, LCDR2, and LCDR3 comprising the amino acid sequence of SEQ ID NO: 22, SEQ ID NO: 20, and SEQ ID NO: 18, respectively;

In further specific aspects, provided herein is a binding agent (e.g., anti-idiotype antibody) which specifically binds a target anti-FXI/FXIa antibody, wherein the binding agent inhibits an anticoagulant activity of the target anti-FXI/FXIa antibody, and wherein the target anti-FXI/FXIa antibody competes, for binding to FXI/FXIa, with another anti-FXI/FXIa antibody (e.g., antibody NOV1401) comprising a heavy chain comprising the amino acid sequence of SEQ ID NO: 14 and a light chain comprising the amino acid sequence of SEQ ID NO: 25.

In further specific aspects, provided herein is a binding agent (e.g., anti-idiotype antibody) which specifically binds a target anti-FXI/FXIa antibody, wherein the binding agent inhibits an anticoagulant activity of the target anti-FXI/FXIa antibody, and wherein the target anti-FXI/FXIa antibody binds the same epitope as another anti-FXI/FXIa antibody (e.g., antibody NOV1401) comprising a heavy chain comprising the amino acid sequence of SEQ ID NO: 14 and a light chain comprising the amino acid sequence of SEQ ID NO: 25.

In further specific aspects, provided herein is a binding agent (e.g., anti-idiotype antibody) which specifically binds a target anti-FXI/FXIa antibody, wherein the binding agent inhibits an anticoagulant activity of the target anti-FXI/FXIa antibody, and wherein the target anti-FXI/FXIa antibody binds an epitope of human FXI and/or FXIa comprising one, two, three, four, five, six, seven, eight, nine, ten, eleven, twelve, thirteen, fourteen, fifteen or more, or all of, amino acid residues selected from: Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604. In particular aspects, provided herein is a binding agent (e.g., anti-idiotype antibody) which specifically binds a target anti-FXI/FXIa antibody, wherein the binding agent inhibits an anticoagulant activity of the target anti-FXI/FXIa antibody, and wherein the target anti-FXI/FXIa antibody contacts one, two, three, four, five, six, seven, eight, nine, ten, eleven, twelve, thirteen, fourteen, fifteen or more, or all of, amino acid residues of human FXI selected from: Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604. In specific aspects, reversal binding agents provided herein (e.g., human anti-idiotype antibodies) bind to an anti-FXI/FXIa antibody which is NOV1401 or competes for binding with NOV1401 to human FXI/FXIa and which anti-FXI/FXIa antibody does not contact amino acid residue Asp480 of human FXI/FXIa. In specific aspects, reversal binding agents provided herein (e.g., human anti-idiotype antibodies) bind to an anti-FXI/FXIa antibody which is NOV1401 or competes for binding with NOV1401 to human FXI/FXIa and which anti-FXI/FXIa antibody does not contact one or more amino acid residues selected from: His414, Ser477, Asp480, Lys572, Asp569, and Gly598 of human FXI/FXIa. In specific aspects, reversal binding agents provided herein (e.g., human anti-idiotype antibodies) bind to an anti-FXI/FXIa antibody which is NOV1401 or competes for binding with NOV1401 to human FXI/FXIa and which anti-FXI/FXIa antibody contacts one, two, three, four, five, six, seven, eight, or more, or all, of amino acid residues Leu415, Cys416, His431, Cys432, Gly435, Glu437, Tyr472, Lys473, Glu476, Arg548, His552, Ser575, Trp595, Gly596, Glu597, Arg602, Glu603, and Arg604 of human FXI/FXIa. In specific aspects, reversal binding agents provided herein (e.g., human anti-idiotype antibodies) bind to an anti-FXI/FXIa antibody which contacts amino acid residues His431 and Ser575 of human FXI/FXIa. In specific aspects, a reversal binding agent provided herein, which binds to an anti-FXI/FXIa antibody (e.g., NOV1401), is not antibody C4 (anti-idiotype antibody targeting anti-FXI/FXIa antibody DEF as described in PCT International Publication No. WO2017/015619).

In specific aspects, provided herein are reversal binding agents (e.g., anti-idiotype antibodies and fragment thereof such as Fabs) that bind to the antigen-binding region of NOV1401, and contacts one or more of the residues in light chain and heavy chain of NOV1401 forming the paratope. In specific aspects, a reversal binding agent (e.g., anti-idiotype antibody and fragment thereof such as a Fab) provided herein binds to NOV1401 within the antigen-binding region, and contacts one, two, three, four, five six, seven, eight, nine, or more, or all, of the following residues in the light chain of NOV1401: Ser27, Gly30, Ser31, Asn32, Asp33, Tyr50, Lys51, Tyr53, Asn54, Lys67, Trp92, Gln94, Arg95, Phe97, Asp98, and Val99 (residues are numbered with reference to SEQ ID NO: 25). In specific aspects, a reversal binding agent (e.g., anti-idiotype antibody and fragment thereof such as a Fab) provided herein binds to NOV1401 within the antigen-binding region, and contacts one, two, three, four, five six, seven, eight, nine, or more, or all, of the following residues in the heavy chain of NOV1401 contact human FXI/FXIa: Phe27, Thr28, Ser30, Thr31, Ala33, Trp47, Ser52, Tyr59, Tyr60, Glu99, Ser101, Tyr102, Leu103, Tyr104, and Ser105 (residues are numbered with reference to SEQ ID NO: 14). In specific aspects, a reversal binding agent (e.g., anti-idiotype antibody and fragment thereof such as a Fab) provided herein binds to NOV1401 within the antigen-binding region, and contacts one, two, three, four, five six, seven, eight, nine, ten or more amino acid residues selected from the following in light chain and/or the heavy chain of NOV1401 forming the paratope: (i) Ser27, Gly30, Ser31, Asn32, Asp33, Tyr50, Lys51, Tyr53, Asn54, Lys67, Trp92, Gln94, Arg95, Phe97, Asp98, and Val99 in the light chain of NOV1401 (residues are numbered with reference to SEQ ID NO: 25); and (ii) Phe27, Thr28, Ser30, Thr31, Ala33, Trp47, Ser52, Tyr59, Tyr60, Glu99, Ser101, Tyr102, Leu103, Tyr104, and Ser105 in the heavy chain of NOV1401 (residues are numbered with reference to SEQ ID NO: 14).

In particular aspects, anti-FXI/FXIa antibody binding agents provided herein is capable of reducing, inhibiting, or reversing (e.g., partially reversing) one or more of the following anticoagulant effects mediated by an anti-FXI/FXIa antibody: (i) aPTT prolongation in aPTT assays and (ii) reduction in the amount of thrombin in a thrombin generation assay (TGA) in human plasma. Protocols and assays to measure these anticoagulant activities have been described, and exemplary assays are described herein, e.g., in the Examples Section.

In a specific aspect, an anti-FXI/FXIa antibody binding agent provided herein is capable reversing anticoagulant effects of a target FXI/FXIa antibody as characterized by reducing, inhibiting, or reversing aPTT prolongation by an anti-FXI/FXIa antibody (e.g., NOV1401) by at least 10%, at least 20%, at least 30%, at least 40%, at least 50%, at least 60%, at least 70%, at least 80%, or at least 90%, as determined by an aPTT assay, described in the art or herein.

In a specific aspect, an anti-FXI/FXIa antibody binding agent provided herein is capable reversing anticoagulant effects of a target FXI/FXIa antibody as characterized by reducing, inhibiting, or reversing reduction in the amount of thrombin in a thrombin generation assay (TGA) in human plasma by an anti-FXI/FXIa antibody (e.g., NOV1401) by at least 10%, at least 20%, at least 30%, at least 40%, at least 50%, at least 60%, at least 70%, at least 80%, or at least 90%.

In further specific aspects, provided herein is a binding agent (e.g., anti-idiotype antibody) which specifically binds a target anti-FXI/FXIa antibody, wherein the binding agent inhibits an anticoagulant activity of the target anti-FXI/FXIa antibody, wherein the target anti-FXI/FXIa antibody comprises (i) a heavy chain variable region (VH) comprising the amino acid sequence of SEQ ID NO: 12 and a light chain variable region (VL) comprising the amino acid sequence of SEQ ID NO: 23; or (ii) a heavy chain comprising the amino acid sequence of SEQ ID NO: 14 and a light chain comprising the amino acid sequence of SEQ ID NO: 25, and wherein the binding agent is an antibody or antigen-binding fragment thereof comprising (1) a VH comprising complementarity determining regions HCDR1, HCDR2, and HCDR3 selected from those set forth in Table 2, and (2) a VL comprising complementarity determining regions LCDR1, LCDR2, and LCDR3 selected from those set forth in Table 2. In a particular aspect, the binding agent (e.g., anti-idiotype antibody) comprises Combined HCDR1, HCDR2, and HCDR3 selected from those set forth in Table 2 and Combined LCDR1, LCDR2, and LCDR3 selected from those set forth in Table 2. In a particular aspect, the binding agent (e.g., anti-idiotype antibody) comprises Kabat HCDR1, HCDR2, and HCDR3 selected from those set forth in Table 2 and Kabat LCDR1, LCDR2, and LCDR3 selected from those set forth in Table 2. In a particular aspect, the binding agent (e.g., anti-idiotype antibody) comprises Chothia HCDR1, HCDR2, and HCDR3 selected from those set forth in Table 2 and Chothia LCDR1, LCDR2, and LCDR3 selected from those set forth in Table 2. In a particular aspect, the binding agent (e.g., anti-idiotype antibody) comprises IMGT HCDR1, HCDR2, and HCDR3 selected from those set forth in Table 2 and IMGT LCDR1, LCDR2, and LCDR3 selected from those set forth in Table 2.

TABLE 2

Examples of anti-FXI/FXIa Antibody Binding Agents (e.g., anti-idiotype antibody and Fab fragments

| | description | DNA or amino acid sequence |
|---|---|---|
| | | IDT1 |
| SEQ ID NO: 27 (Combined) | HCDR1 | GFTFSDYAMS |
| SEQ ID NO: 28 (Combined) | HCDR2 | VIDYSSSNTYYADSVKG |
| SEQ ID NO: 29 (Combined) | HCDR3 | EGYSYRSIRFDY |
| SEQ ID NO: 30 (Kabat) | HCDR1 | DYAMS |
| SEQ ID NO: 31 (Kabat) | HCDR2 | VIDYSSSNTYYADSVKG |
| SEQ ID NO: 32 (Kabat) | HCDR3 | EGYSYRSIRFDY |
| SEQ ID NO: 33 (Chothia) | HCDR1 | GFTFSDY |
| SEQ ID NO: 34 (Chothia) | HCDR2 | DYSSSN |
| SEQ ID NO: 35 (Chothia) | HCDR3 | EGYSYRSIRFDY |
| SEQ ID NO: 36 (IMGT) | HCDR1 | GFTFSDYA |
| SEQ ID NO: 37 (IMGT) | HCDR2 | IDYSSSNT |
| SEQ ID NO: 38 (IMGT) | HCDR3 | AREGYSYRSIRFDY |

TABLE 2-continued

Examples of anti-FXI/FXIa Antibody Binding Agents (e.g., anti-idiotype antibody and Fab fragments

| | description | DNA or amino acid sequence |
|---|---|---|
| SEQ ID NO: 39 | VH | QVQLLESGGGLVQPGGSLRLSCAASGFTFSDYAMSWVRQAPGKG LEWVSVIDYSSSNTYYADSVKGRFTISRDNSKNTLYLQMNSLRA EDTAVYYCAREGYSYRSIRFDYWGQGTLVTVSS |
| SEQ ID NO: 40 | DNA VH | CAAGTGCAGCTGCTGGAATCTGGCGGCGGACTGGTGCAGCCTGG CGGTAGTCTGAGACTGTCTTGCGCCGCCTCCGGCTTCACCTTCT CCGACTACGCCATGTCCTGGGTCCGACAGGCCCCTGGCAAGGGC CTGGAGTGGGTGTCCGTGATCGACTACTCCTCCTCCAACACCTA CTACGCCGACTCCGTGAAGGGCCGGTTCACCATCTCCCGGGACA ACTCCAAGAACACCCTGTACCTGCAGATGAACTCCCTGCGGGCC GAGGACACCGCCGTGTACTACTGCGCCAGAGAGGGCTACTCCTA CCGGTCCATCAGATTCGACTACTGGGGCCAGGGCACCCTGGTCA CCGTGTCCTCT |
| SEQ ID NO: 41 | Heavy Chain | QVQLLESGGGLVQPGGSLRLSCAASGFTFSDYAMSWVRQAPGKG LEWVSVIDYSSSNTYYADSVKGRFTISRDNSKNTLYLQMNSLRA EDTAVYYCAREGYSYRSIRFDYWGQGTLVTVSSASTKGPSVFPL APSSKSTSGGTAALGCLVKDYFPEPVTVSWNSGALTSGVHTFPA VLQSSGLYSLSSVVTVPSSSLGTQTYICNVNHKPSNTKVDKRVE PKSC |
| SEQ ID NO: 42 | DNA Heavy Chain | CAAGTGCAGCTGCTGGAATCTGGCGGCGGACTGGTGCAGCCTGG CGGTAGTCTGAGACTGTCTTGCGCCGCCTCCGGCTTCACCTTCT CCGACTACGCCATGTCCTGGGTCCGACAGGCCCCTGGCAAGGGC CTGGAGTGGGTGTCCGTGATCGACTACTCCTCCTCCAACACCTA CTACGCCGACTCCGTGAAGGGCCGGTTCACCATCTCCCGGGACA ACTCCAAGAACACCCTGTACCTGCAGATGAACTCCCTGCGGGCC GAGGACACCGCCGTGTACTACTGCGCCAGAGAGGGCTACTCCTA CCGGTCCATCAGATTCGACTACTGGGGCCAGGGCACCCTGGTCA CCGTGTCCTCTGCTAGCACCAAGGGCCCCTCCGTGTTCCCTCTG GCCCCTTCCAGCAAGTCTACCTCTGGCGGCACCGCTGCTCTGGG CTGCCTGGTGAAGGACTACTTCCCTGAGCCTGTGACAGTGTCCT GGAACTCTGGCGCCCTGACCTCCGGCGTGCACACCTTCCCTGCC GTGCTGCAGTCCTCCGGCCTGTACTCCCTGTCCTCCGTGGTGAC AGTGCCTTCCTCCAGCCTGGGCACCCAGACCTATATCTGCAACG TGAACCACAAGCCTTCCAACACCAAGGTGGACAAGCGGGTGGAG CCTAAGTCATGC |
| SEQ ID NO: 43 (Combined) | LCDR1 | RASQSISSNLN |
| SEQ ID NO: 44 (Combined) | LCDR2 | AASNLQS |
| SEQ ID NO: 45 (Combined) | LCDR3 | LQFDHTPFT |
| SEQ ID NO: 46 (Kabat) | LCDR1 | RASQSISSNLN |
| SEQ ID NO: 47 (Kabat) | LCDR2 | AASNLQS |
| SEQ ID NO: 48 (Kabat) | LCDR3 | LQFDHTPFT |
| SEQ ID NO: 49 (Chothia) | LCDR1 | SQSISSN |
| SEQ ID NO: 50 (Chothia) | LCDR2 | AAS |
| SEQ ID NO: 51 (Chothia) | LCDR3 | FDHTPF |
| SEQ ID NO: 52 (IMGT) | LCDR1 | QSISSN |
| SEQ ID NO: 53 (IMGT) | LCDR2 | AAS |
| SEQ ID NO: 54 (IMGT) | LCDR3 | LQFDHTPFT |
| SEQ ID NO: 55 | VL | DIQMTQSPSSLSASVGDRVTITCRASQSISSNLNWYQQKPGKAP KLLIYAASNLQSGVPSRFSGSGSGTDFTLTISSLQPEDFATYYC LQFDHTPFTFGQGTKVEIK |
| SEQ ID NO: 56 | DNA VL | GACATCCAGATGACCCAGAGCCCCTCCAGCCTGTCCGCCTCCGT GGGCGACAGAGTGACCATCACCTGTCGGGCCTCCCAGTCCATCT CCTCCAACCTGAACTGGTATCAGCAGAAGCCCGGCAAGGCCCCT AAGCTGCTGATCTACGCCGCCAGCAACCTGCAGTCCGGCGTGCC CTCCAGATTCTCCGGCTCTGGCTCCGGCACCGACTTCACCCTGA CCATCTCCAGCCTGCAGCCCGAGGACTTCGCCACCTACTACTGC CTGCAGTTCGACCACACCCCTTTCACCTTCGGCCAGGGCACCAA AGTGGAAATCAAG |
| SEQ ID NO: 57 | Light Chain | DIQMTQSPSSLSASVGDRVTITCRASQSISSNLNWYQQKPGKAP KLLIYAASNLQSGVPSRFSGSGSGTDFTLTISSLQPEDFATYYC LQFDHTPFTFGQGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |

TABLE 2-continued

Examples of anti-FXI/FXIa Antibody Binding Agents (e.g., anti-idiotype antibody and Fab fragments

| | description | DNA or amino acid sequence |
|---|---|---|
| SEQ ID NO: 58 | DNA Light Chain | GACATCCAGATGACCCAGAGCCCCTCCAGCCTGTCCGCCTCCGT GGGCGACAGAGTGACCATCACCTGTCGGGCCTCCCAGTCCATCT CCTCCAACCTGAACTGGTATCAGCAGAAGCCCGGCAAGGCCCCT AAGCTGCTGATCTACGCCGCCAGCAACCTGCAGTCCGGCGTGCC CTCCAGATTCTCCGGCTCTGGCTCCGGCACCGACTTCACCCTGA CCATCTCCAGCCTGCAGCCCGAGGACTTCGCCACCTACTACTGC CTGCAGTTCGACCACACCCCTTTCACCTTCGGCCAGGGCACCAA AGTGGAAATCAAGCGTACGGTGGCCGCTCCCAGCGTGTTCATCT TCCCCCCCAGCGACGAGCAGCTGAAGAGCGGCACCGCCAGCGTG GTGTGCCTGCTGAACAACTTCTACCCCCGGGAGGCCAAGGTGCA GTGGAAGGTGGACAACGCCCTGCAGAGCGGCAACAGCCAGGAGA GCGTCACCGAGCAGGACAGCAAGGACTCCACCTACAGCCTGAGC AGCACCCTGACCCTGAGCAAGGCCGACTACGAGAAGCATAAGGT GTACGCCTGCGAGGTGACCCACCAGGGCCTGTCCAGCCCCGTGA CCAAGAGCTTCAACAGGGGCGAGTGC |
| | | IDT2 |
| SEQ ID NO: 59 (Combined) | HCDR1 | GFTFSSAAVH |
| SEQ ID NO: 60 (Combined) | HCDR2 | RIKSKADGGTTDYAAPVKG |
| SEQ ID NO: 61 (Combined) | HCDR3 | DSPSISSYSIPYFSGMDV |
| SEQ ID NO: 62 (Kabat) | HCDR1 | SAAVH |
| SEQ ID NO: 63 (Kabat) | HCDR2 | RIKSKADGGTTDYAAPVKG |
| SEQ ID NO: 64 (Kabat) | HCDR3 | DSPSISSYSIPYFSGMDV |
| SEQ ID NO: 65 (Chothia) | HCDR1 | GFTFSSA |
| SEQ ID NO: 66 (Chothia) | HCDR2 | KSKADGGT |
| SEQ ID NO: 67 (Chothia) | HCDR3 | DSPSISSYSIPYFSGMDV |
| SEQ ID NO: 68 (IMGT) | HCDR1 | GFTFSSAA |
| SEQ ID NO: 69 (IMGT) | HCDR2 | IKSKADGGTT |
| SEQ ID NO: 70 (IMGT) | HCDR3 | ARDSPSISSYSIPYFSGMDV |
| SEQ ID NO: 71 | VH | QVQLVESGGGLVKPGGSLRLSCAASGFTFSSAAVHWVRQAPGKG LEWVGRIKSKADGGTTDYAAPVKGRFTISRDDSKNTLYLQMNSL KTEDTAVYYCARDSPSISSYSIPYFSGMDVWGQGTLVTVSS |
| SEQ ID NO: 72 | DNA VH | CAAGTGCAGCTGGTGGAATCTGGCGGCGGACTGGTCAAGCCTGG CGGTAGCCTGAGACTGTCTTGCGCCGCCTCCGGCTTCACCTTCT CCTCTGCCGCTGTGCACTGGGTCCGACAGGCCCCTGGCAAGGGC CTGGAGTGGGTCGGACGGATCAAGTCCAAGGCCGACGGCGGCAC CACCGACTACGCTGCCCCTGTGAAGGGCCGGTTCACCATCTCCC GGGACGACTCCAAGAACACCCTGTACCTGCAGATGAACTCCCTG AAAACCGAGGACACCGCCGTGTACTACTGCGCCAGAGACTCCCC ATCTATCTCCAGCTACTCCATCCCCTACTTCTCCGGCATGGACG TGTGGGGCCAGGGCACCCTGGTCACCGTGTCCTCT |
| SEQ ID NO: 73 | Heavy Chain | QVQLVESGGGLVKPGGSLRLSCAASGFTFSSAAVHWVRQAPGKG LEWVGRIKSKADGGTTDYAAPVKGRFTISRDDSKNTLYLQMNSL KTEDTAVYYCARDSPSISSYSIPYFSGMDVWGQGTLVTVSSAST KGPSVFPLAPSSKSTSGGTAALGCLVKDYFPEPVTVSWNSGALT SGVHTFPAVLQSSGLYSLSSVVTVPSSSLGTQTYICNVNHKPSN TKVDKRVEPKSC |
| SEQ ID NO: 74 | DNA Heavy Chain | CAAGTGCAGCTGGTGGAATCTGGCGGCGGACTGGTCAAGCCTGG CGGTAGCCTGAGACTGTCTTGCGCCGCCTCCGGCTTCACCTTCT CCTCTGCCGCTGTGCACTGGGTCCGACAGGCCCCTGGCAAGGGC CTGGAGTGGGTCGGACGGATCAAGTCCAAGGCCGACGGCGGCAC CACCGACTACGCTGCCCCTGTGAAGGGCCGGTTCACCATCTCCC GGGACGACTCCAAGAACACCCTGTACCTGCAGATGAACTCCCTG AAAACCGAGGACACCGCCGTGTACTACTGCGCCAGAGACTCCCC ATCTATCTCCAGCTACTCCATCCCCTACTTCTCCGGCATGGACG TGTGGGGCCAGGGCACCCTGGTCACCGTGTCCTCTGCTAGCACC AAGGGCCCCTCCGTGTTCCCTCTGGCCCCTTCCAGCAAGTCTAC CTCTGGCGGCACCGCTGCTCTGGGCTGCCTGGTGAAGGACTACT TCCCTGAGCCTGTGACAGTGTCCTGGAACTCTGGCGCCCTGACC TCCGGCGTGCACACCTTCCCTGCCGTGCTGCAGTCCTCCGGCCT GTACTCCCTGTCCTCCGTGGTGACAGTGCCTTCCTCCAGCCTGG |

TABLE 2-continued

Examples of anti-FXI/FXIa Antibody Binding Agents (e.g., anti-idiotype antibody and Fab fragments

| | description | DNA or amino acid sequence |
|---|---|---|
| | | GCACCCAGACCTATATCTGCAACGTGAACCACAAGCCTTCCAAC<br>ACCAAGGTGGACAAGCGGGTGGAGCCTAAGTCATGC |
| SEQ ID NO: 75 (Combined) | LCDR1 | RASQGIRAWLN |
| SEQ ID NO: 76 (Combined) | LCDR2 | AASSLQS |
| SEQ ID NO: 77 (Combined) | LCDR3 | HQYITHPPT |
| SEQ ID NO: 78 (Kabat) | LCDR1 | RASQGIRAWLN |
| SEQ ID NO: 79 (Kabat) | LCDR2 | AASSLQS |
| SEQ ID NO: 80 (Kabat) | LCDR3 | HQYITHPPT |
| SEQ ID NO: 81 (Chothia) | LCDR1 | SQGIRAW |
| SEQ ID NO: 82 (Chothia) | LCDR2 | AAS |
| SEQ ID NO: 83 (Chothia) | LCDR3 | YITHPP |
| SEQ ID NO: 84 (IMGT) | LCDR1 | QGIRAW |
| SEQ ID NO: 85 (IMGT) | LCDR2 | AAS |
| SEQ ID NO: 86 (IMGT) | LCDR3 | HQYITHPPT |
| SEQ ID NO: 87 | VL | DIQMTQSPSSLSASVGDRVTITCRASQGIRAWLNWYQQKPGKAP<br>KLLIYAASSLQSGVPSRFSGSGSGTDFTLTISSLQPEDFATYYC<br>HQYITHPPTFGQGTKVEIK |
| SEQ ID NO: 88 | DNA VL | GACATCCAGATGACCCAGAGCCCCTCCAGCCTGTCCGCCTCCGT<br>GGGCGACAGAGTGACCATCACCTGTCGGGCCTCTCAGGGCATCC<br>GGGCCTGGCTGAACTGGTATCAGCAGAAGCCCGGCAAGGCCCCT<br>AAGCTGCTGATCTACGCCGCCAGCTCCCTGCAGTCCGGCGTGCC<br>CTCCAGATTCTCCGGCTCTGGCTCCGGCACCGACTTCACCCTGA<br>CCATCTCCAGCCTGCAGCCCGAGGACTTCGCCACCTACTACTGC<br>CACCAGTACATCACCCACCCTCCCACCTTCGGCCAGGGCACCAA<br>AGTGGAAATCAAG |
| SEQ ID NO: 89 | Light Chain | DIQMTQSPSSLSASVGDRVTITCRASQGIRAWLNWYQQKPGKAP<br>KLLIYAASSLQSGVPSRFSGSGSGTDFTLTISSLQPEDFATYYC<br>HQYITHPPTFGQGTKVEIKRTVAAPSVFIFPPSDEQLKSGTASV<br>VCLLNNFYPREAKVQWKVDNALQSGNSQESVTEQDSKDSTYSLS<br>STLTLSKADYEKHKVYACEVTHQGLSSPVTKSFNRGEC |
| SEQ ID NO: 90 | DNA Light Chain | GACATCCAGATGACCCAGAGCCCCTCCAGCCTGTCCGCCTCCGT<br>GGGCGACAGAGTGACCATCACCTGTCGGGCCTCTCAGGGCATCC<br>GGGCCTGGCTGAACTGGTATCAGCAGAAGCCCGGCAAGGCCCCT<br>AAGCTGCTGATCTACGCCGCCAGCTCCCTGCAGTCCGGCGTGCC<br>CTCCAGATTCTCCGGCTCTGGCTCCGGCACCGACTTCACCCTGA<br>CCATCTCCAGCCTGCAGCCCGAGGACTTCGCCACCTACTACTGC<br>CACCAGTACATCACCCACCCTCCCACCTTCGGCCAGGGCACCAA<br>AGTGGAAATCAAGCGTACGGTGGCCGCTCCCAGCGTGTTCATCT<br>TCCCCCCCAGCGACGAGCAGCTGAAGAGCGGCACCGCCAGCGTG<br>GTGTGCCTGCTGAACAACTTCTACCCCCGGGAGGCCAAGGTGCA<br>GTGGAAGGTGGACAACGCCCTGCAGAGCGGCAACAGCCAGGAGA<br>GCGTCACCGAGCAGGACAGCAAGGACTCCACCTACAGCCTGAGC<br>AGCACCCTGACCCTGAGCAAGGCCGACTACGAGAAGCATAAGGT<br>GTACGCCTGCGAGGTGACCCACCAGGGCCTGTCCAGCCCCGTGA<br>CCAAGAGCTTCAACAGGGGCGAGTGC |
| | IDT3 | |
| SEQ ID NO: 91 (Combined) | HCDR1 | GFTFQSAAVH |
| SEQ ID NO: 92 (Combined) | HCDR2 | RIKSKADGGTTDYAAPVKG |
| SEQ ID NO: 93 (Combined) | HCDR3 | DSPSISSYSIPYFSGMDV |
| SEQ ID NO: 94 (Kabat) | HCDR1 | SAAVH |
| SEQ ID NO: 95 (Kabat) | HCDR2 | RIKSKADGGTTDYAAPVKG |
| SEQ ID NO: 96 (Kabat) | HCDR3 | DSPSISSYSIPYFSGMDV |
| SEQ ID NO: 97 (Chothia) | HCDR1 | GFTFQSA |

TABLE 2-continued

Examples of anti-FXI/FXIa Antibody Binding Agents (e.g., anti-idiotype antibody and Fab fragments

| | description | DNA or amino acid sequence |
|---|---|---|
| SEQ ID NO: 98 (Chothia) | HCDR2 | KSKADGGT |
| SEQ ID NO: 99 (Chothia) | HCDR3 | DSPSISSYSIPYFSGMDV |
| SEQ ID NO: 100 (IMGT) | HCDR1 | GFTFQSAA |
| SEQ ID NO: 101 (IMGT) | HCDR2 | IKSKADGGTT |
| SEQ ID NO: 102 (IMGT) | HCDR3 | ARDSPSISSYSIPYFSGMDV |
| SEQ ID NO: 103 | VH | QVQLVESGGGLVKPGGSLRLSCAASGFTFQSAAVHWVRQAPGKG LEWVGRIKSKADGGTTDYAAPVKGRFTISRDDSKNTLYLQMNSL KTEDTAVYYCARDSPSISSYSIPYFSGMDVWGQGTLVTVSS |
| SEQ ID NO: 104 | DNA VH | CAAGTGCAGCTGGTGGAATCTGGCGGCGGACTGGTCAAGCCTGG CGGTAGCCTGAGACTGTCTTGCGCCGCCTCCGGCTTCACCTTCC AGTCTGCCGCTGTGCACTGGGTCCGACAGGCCCCTGGCAAGGGC CTGGAGTGGGTCGGACGGATCAAGTCCAAGGCCGACGGCGGCAC CACCGACTACGCTGCCCCTGTGAAGGGCCGGTTCACCATCTCCC GGGACGACTCCAAGAACACCCTGTACCTGCAGATGAACTCCCTG AAAACCGAGGACACCGCCGTGTACTACTGCGCCAGAGACTCCCC ATCTATCTCCAGCTACTCCATCCCCTACTTCTCCGGCATGGACG TGTGGGGCCAGGGCACCCTGGTCACCGTGTCCTCT |
| SEQ ID NO: 105 | Heavy Chain | QVQLVESGGGLVKPGGSLRLSCAASGFTFQSAAVHWVRQAPGKG LEWVGRIKSKADGGTTDYAAPVKGRFTISRDDSKNTLYLQMNSL KTEDTAVYYCARDSPSISSYSIPYFSGMDVWGQGTLVTVSSAST KGPSVFPLAPSSKSTSGGTAALGCLVKDYFPEPVTVSWNSGALT SGVHTFPAVLQSSGLYSLSSVVTVPSSSLGTQTYICNVNHKPSN TKVDKRVEPKSC |
| SEQ ID NO: 106 | DNA Heavy Chain | CAAGTGCAGCTGGTGGAATCTGGCGGCGGACTGGTCAAGCCTGG CGGTAGCCTGAGACTGTCTTGCGCCGCCTCCGGCTTCACCTTCC AGTCTGCCGCTGTGCACTGGGTCCGACAGGCCCCTGGCAAGGGC CTGGAGTGGGTCGGACGGATCAAGTCCAAGGCCGACGGCGGCAC CACCGACTACGCTGCCCCTGTGAAGGGCCGGTTCACCATCTCCC GGGACGACTCCAAGAACACCCTGTACCTGCAGATGAACTCCCTG AAAACCGAGGACACCGCCGTGTACTACTGCGCCAGAGACTCCCC ATCTATCTCCAGCTACTCCATCCCCTACTTCTCCGGCATGGACG TGTGGGGCCAGGGCACCCTGGTCACCGTGTCCTCTGCTAGCACC AAGGGCCCCTCCGTGTTCCCTCTGGCCCCTTCCAGCAAGTCTAC CTCTGGCGGCACCGCTGCTCTGGGCTGCCTGGTGAAGGACTACT TCCCTGAGCCTGTGACAGTGTCCTGGAACTCTGGCGCCCTGACC TCCGGCGTGCACACCTTCCCTGCCGTGCTGCAGTCCTCCGGCCT GTACTCCCTGTCCTCCGTGGTGACAGTGCCTTCCTCCAGCCTGG GCACCCAGACCTATATCTGCAACGTGAACCACAAGCCTTCCAAC ACCAAGGTGGACAAGCGGGTGGAGCCTAAGTCATGC |
| SEQ ID NO: 107 (Combined) | LCDR1 | RASQGIRAWLN |
| SEQ ID NO: 108 (Combined) | LCDR2 | AASSLQS |
| SEQ ID NO: 109 (Combined) | LCDR3 | HQYITHPPT |
| SEQ ID NO: 110 (Kabat) | LCDR1 | RASQGIRAWLN |
| SEQ ID NO: 111 (Kabat) | LCDR2 | AASSLQS |
| SEQ ID NO: 112 (Kabat) | LCDR3 | HQYITHPPT |
| SEQ ID NO: 113 (Chothia) | LCDR1 | SQGIRAW |
| SEQ ID NO: 114 (Chothia) | LCDR2 | AAS |
| SEQ ID NO: 115 (Chothia) | LCDR3 | YITHPP |
| SEQ ID NO: 116 (IMGT) | LCDR1 | QGIRAW |
| SEQ ID NO: 117 (IMGT) | LCDR2 | AAS |
| SEQ ID NO: 118 (IMGT) | LCDR3 | HQYITHPPT |
| SEQ ID NO: 119 | VL | DIQMTQSPSSLSASVGDRVTITCRASQGIRAWLNWYQQKPGKAP KLLIYAASSLQSGVPSRFSGSGSGTDFTLTISSLQPEDFATYYC HQYITHPPTFGQGTKVEIK |
| SEQ ID NO: 120 | DNA VL | GACATCCAGATGACCCAGAGCCCCTCCAGCCTGTCCGCCTCCGT GGGCGACAGAGTGACCATCACCTGTCGGGCCTCTCAGGGCATCC GGGCCTGGCTGAACTGGTATCAGCAGAAGCCCGGCAAGGCCCCT AAGCTGCTGATCTACGCCGCCAGCTCCCTGCAGTCCGGCGTGCC |

TABLE 2-continued

Examples of anti-FXI/FXIa Antibody Binding Agents (e.g., anti-idiotype antibody and Fab fragments

| | description | DNA or amino acid sequence |
|---|---|---|
| | | CTCCAGATTCTCCGGCTCTGGCTCCGGCACCGACTTCACCCTGA<br>CCATCTCCAGCCTGCAGCCCGAGGACTTCGCCACCTACTACTGC<br>CACCAGTACATCACCCACCCTCCCACCTTCGGCCAGGGCACCAA<br>AGTGGAAATCAAG |
| SEQ ID NO: 121 | Light Chain | DIQMTQSPSSLSASVGDRVTITCRASQGIRAWLNWYQQKPGKAP<br>KLLIYAASSLQSGVPSRFSGSGSGTDFTLTISSLQPEDFATYYC<br>HQYITHPPTFGQGTKVEIKRTVAAPSVFIFPPSDEQLKSGTASV<br>VCLLNNFYPREAKVQWKVDNALQSGNSQESVTEQDSKDSTYSLS<br>STLTLSKADYEKHKVYACEVTHQGLSSPVTKSFNRGEC |
| SEQ ID NO: 122 | DNA Light Chain | GACATCCAGATGACCCAGAGCCCCTCCAGCCTGTCCGCCTCCGT<br>GGGCGACAGAGTGACCATCACCTGTCGGGCCTCTCAGGGCATCC<br>GGGCCTGGCTGAACTGGTATCAGCAGAAGCCCGGCAAGGCCCCT<br>AAGCTGCTGATCTACGCCGCCAGCTCCCTGCAGTCCGGCGTGCC<br>CTCCAGATTCTCCGGCTCTGGCTCCGGCACCGACTTCACCCTGA<br>CCATCTCCAGCCTGCAGCCCGAGGACTTCGCCACCTACTACTGC<br>CACCAGTACATCACCCACCCTCCCACCTTCGGCCAGGGCACCAA<br>AGTGGAAATCAAGCGTACGGTGGCCGCTCCCAGCGTGTTCATCT<br>TCCCCCCCAGCGACGAGCAGCTGAAGAGCGGCACCGCCAGCGTG<br>GTGTGCCTGCTGAACAACTTCTACCCCCGGGAGGCCAAGGTGCA<br>GTGGAAGGTGGACAACGCCCTGCAGAGCGGCAACAGCCAGGAGA<br>GCGTCACCGAGCAGGACAGCAAGGACTCCACCTACAGCCTGAGC<br>AGCACCCTGACCCTGAGCAAGGCCGACTACGAGAAGCATAAGGT<br>GTACGCCTGCGAGGTGACCCACCAGGGCCTGTCCAGCCCCGTGA<br>CCAAGAGCTTCAACAGGGGCGAGTGC |
| | IDT4 | |
| SEQ ID NO: 123 (Combined) | HCDR1 | GFTFSSAAVH |
| SEQ ID NO: 124 (Combined) | HCDR2 | RIKSKASGGTTDYAAPVKG |
| SEQ ID NO: 125 (Combined) | HCDR3 | DSPSISSYSIPYFSGMDV |
| SEQ ID NO: 126 (Kabat) | HCDR1 | SAAVH |
| SEQ ID NO: 127 (Kabat) | HCDR2 | RIKSKASGGTTDYAAPVKG |
| SEQ ID NO: 128 (Kabat) | HCDR3 | DSPSISSYSIPYFSGMDV |
| SEQ ID NO: 129 (Chothia) | HCDR1 | GFTFSSA |
| SEQ ID NO: 130 (Chothia) | HCDR2 | KSKASGGT |
| SEQ ID NO: 131 (Chothia) | HCDR3 | DSPSISSYSIPYFSGMDV |
| SEQ ID NO: 132 (IMGT) | HCDR1 | GFTFSSAA |
| SEQ ID NO: 133 (IMGT) | HCDR2 | IKSKASGGTT |
| SEQ ID NO: 134 (IMGT) | HCDR3 | ARDSPSISSYSIPYFSGMDV |
| SEQ ID NO: 135 | VH | QVQLVESGGGLVKPGGSLRLSCAASGFTFSSAAVHWVRQAPGKG<br>LEWVGRIKSKASGGTTDYAAPVKGRFTISRDDSKNTLYLQMNSL<br>KTEDTAVYYCARDSPSISSYSIPYFSGMDVWGQGTLVTVSS |
| SEQ ID NO: 136 | DNA VH | CAAGTGCAGCTGGTGGAATCTGGCGGCGGACTGGTCAAGCCTGG<br>CGGTAGCCTGAGACTGTCTTGCGCCGCCTCCGGCTTCACCTTCT<br>CCTCTGCCGCTGTGCACTGGGTCCGACAGGCCCCTGGCAAGGGC<br>CTGGAGTGGGTCGGACGGATCAAGTCCAAGGCCTCCGGCGGCAC<br>CACCGACTACGCTGCCCCTGTGAAGGGCCGGTTCACCATCTCCC<br>GGGACGACTCCAAGAACACCCTGTACCTGCAGATGAACTCCCTG<br>AAAACCGAGGACACCGCCGTGTACTACTGCGCCAGAGACTCCCC<br>ATCTATCTCCAGCTACTCCATCCCCTACTTCTCCGGCATGGACG<br>TGTGGGGCCAGGGCACCCTGGTCACCGTGTCCTCT |
| SEQ ID NO: 137 | Heavy Chain | QVQLVESGGGLVKPGGSLRLSCAASGFTFSSAAVHWVRQAPGKG<br>LEWVGRIKSKASGGTTDYAAPVKGRFTISRDDSKNTLYLQMNSL<br>KTEDTAVYYCARDSPSISSYSIPYFSGMDVWGQGTLVTVSSAST<br>KGPSVFPLAPSSKSTSGGTAALGCLVKDYFPEPVTVSWNSGALT<br>SGVHTFPAVLQSSGLYSLSSVVTVPSSSLGTQTYICNVNHKPSN<br>TKVDKRVEPKSC |
| SEQ ID NO: 138 | DNA Heavy Chain | CAAGTGCAGCTGGTGGAATCTGGCGGCGGACTGGTCAAGCCTGG<br>CGGTAGCCTGAGACTGTCTTGCGCCGCCTCCGGCTTCACCTTCT<br>CCTCTGCCGCTGTGCACTGGGTCCGACAGGCCCCTGGCAAGGGC<br>CTGGAGTGGGTCGGACGGATCAAGTCCAAGGCCTCCGGCGGCAC<br>CACCGACTACGCTGCCCCTGTGAAGGGCCGGTTCACCATCTCCC<br>GGGACGACTCCAAGAACACCCTGTACCTGCAGATGAACTCCCTG |

TABLE 2-continued

Examples of anti-FXI/FXIa Antibody Binding Agents (e.g., anti-idiotype antibody and Fab fragments

| | description | DNA or amino acid sequence |
|---|---|---|
| | | AAAACCGAGGACACCGCCGTGTACTACTGCGCCAGAGACTCCCC ATCTATCTCCAGCTACTCCATCCCCTACTTCTCCGGCATGGACG TGTGGGGCCAGGGCACCCTGGTCACCGTGTCCTCTGCTAGCACC AAGGGCCCCTCCGTGTTCCCTCTGGCCCCTTCCAGCAAGTCTAC CTCTGGCGGCACCGCTGCTCTGGGCTGCCTGGTGAAGGACTACT TCCCTGAGCCTGTGACAGTGTCCTGGAACTCTGGCGCCCTGACC TCCGGCGTGCACACCTTCCCTGCCGTGCTGCAGTCCTCCGGCCT GTACTCCCTGTCCTCCGTGGTGACAGTGCCTTCCTCCAGCCTGG GCACCCAGACCTATATCTGCAACGTGAACCACAAGCCTTCCAAC ACCAAGGTGGACAAGCGGGTGGAGCCTAAGTCATGC |
| SEQ ID NO: 139 (Combined) | LCDR1 | RASQGIRAWLN |
| SEQ ID NO: 140 (Combined) | LCDR2 | AASSLQS |
| SEQ ID NO: 141 (Combined) | LCDR3 | HQYITHPPT |
| SEQ ID NO: 142 (Kabat) | LCDR1 | RASQGIRAWLN |
| SEQ ID NO: 143 (Kabat) | LCDR2 | AASSLQS |
| SEQ ID NO: 144 (Kabat) | LCDR3 | HQYITHPPT |
| SEQ ID NO: 145 (Chothia) | LCDR1 | SQGIRAW |
| SEQ ID NO: 146 (Chothia) | LCDR2 | AAS |
| SEQ ID NO: 147 (Chothia) | LCDR3 | YITHPP |
| SEQ ID NO: 148 (IMGT) | LCDR1 | QGIRAW |
| SEQ ID NO: 149 (IMGT) | LCDR2 | AAS |
| SEQ ID NO: 150 (IMGT) | LCDR3 | HQYITHPPT |
| SEQ ID NO: 151 | VL | DIQMTQSPSSLSASVGDRVTITCRASQGIRAWLNWYQQKPGKAP KLLIYAASSLQSGVPSRFSGSGSGTDFTLTISSLQPEDFATYYC HQYITHPPTFGQGTKVEIK |
| SEQ ID NO: 152 | DNA VL | GACATCCAGATGACCCAGAGCCCCTCCAGCCTGTCCGCCTCCGT GGGCGACAGAGTGACCATCACCTGTCGGGCCTCTCAGGGCATCC GGGCCTGGCTGAACTGGTATCAGCAGAAGCCCGGCAAGGCCCCT AAGCTGCTGATCTACGCCGCCAGCTCCCTGCAGTCCGGCGTGCC CTCCAGATTCTCCGGCTCTGGCTCCGGCACCGACTTCACCCTGA CCATCTCCAGCCTGCAGCCCGAGGACTTCGCCACCTACTACTGC CACCAGTACATCACCCACCCTCCCACCTTCGGCCAGGGCACCAA AGTGGAAATCAAG |
| SEQ ID NO: 153 | Light Chain | DIQMTQSPSSLSASVGDRVTITCRASQGIRAWLNWYQQKPGKAP KLLIYAASSLQSGVPSRFSGSGSGTDFTLTISSLQPEDFATYYC HQYITHPPTFGQGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| SEQ ID NO: 154 | DNA Light Chain | GACATCCAGATGACCCAGAGCCCCTCCAGCCTGTCCGCCTCCGT GGGCGACAGAGTGACCATCACCTGTCGGGCCTCTCAGGGCATCC GGGCCTGGCTGAACTGGTATCAGCAGAAGCCCGGCAAGGCCCCT AAGCTGCTGATCTACGCCGCCAGCTCCCTGCAGTCCGGCGTGCC CTCCAGATTCTCCGGCTCTGGCTCCGGCACCGACTTCACCCTGA CCATCTCCAGCCTGCAGCCCGAGGACTTCGCCACCTACTACTGC CACCAGTACATCACCCACCCTCCCACCTTCGGCCAGGGCACCAA AGTGGAAATCAAGCGTACGGTGGCCGCTCCCAGCGTGTTCATCT TCCCCCCCAGCGACGAGCAGCTGAAGAGCGGCACCGCCAGCGTG GTGTGCCTGCTGAACAACTTCTACCCCCGGGAGGCCAAGGTGCA GTGGAAGGTGGACAACGCCCTGCAGAGCGGCAACAGCCAGGAGA GCGTCACCGAGCAGGACAGCAAGGACTCCACCTACAGCCTGAGC AGCACCCTGACCCTGAGCAAGGCCGACTACGAGAAGCATAAGGT GTACGCCTGCGAGGTGACCCACCAGGGCCTGTCCAGCCCCGTGA CCAAGAGCTTCAACAGGGGCGAGTGC |
| | IDT5 | |
| SEQ ID NO: 155 (Combined) | HCDR1 | GFTFSSAAVH |
| SEQ ID NO: 156 (Combined) | HCDR2 | RIKSKADAGTTDYAAPVKG |
| SEQ ID NO: 157 (Combined) | HCDR3 | DSPSISSYSIPYFSGMDV |

TABLE 2-continued

Examples of anti-FXI/FXIa Antibody Binding Agents (e.g., anti-idiotype antibody and Fab fragments

| | description | DNA or amino acid sequence |
|---|---|---|
| SEQ ID NO: 158 (Kabat) | HCDR1 | SAAVH |
| SEQ ID NO: 159 (Kabat) | HCDR2 | RIKSKADAGTTDYAAPVKG |
| SEQ ID NO: 160 (Kabat) | HCDR3 | DSPSISSYSIPYFSGMDV |
| SEQ ID NO: 161 (Chothia) | HCDR1 | GFTFSSA |
| SEQ ID NO: 162 (Chothia) | HCDR2 | KSKADAGT |
| SEQ ID NO: 163 (Chothia) | HCDR3 | DSPSISSYSIPYFSGMDV |
| SEQ ID NO: 164 (IMGT) | HCDR1 | GFTFSSAA |
| SEQ ID NO: 165 (IMGT) | HCDR2 | IKSKADAGTT |
| SEQ ID NO: 166 (IMGT) | HCDR3 | ARDSPSISSYSIPYFSGMDV |
| SEQ ID NO: 167 | VH | QVQLVESGGGLVKPGGSLRLSCAASGFTFSSAAVHWVRQAPGKG LEWVGRIKSKADAGTIDYAAPVKGRFTISRDDSKNTLYLQMNSL KTEDTAVYYCARDSPSISSYSIPYFSGMDVWGQGTLVTVSS |
| SEQ ID NO: 168 | DNA VH | CAAGTGCAGCTGGTGGAATCTGGCGGCGGACTGGTCAAGCCTGG CGGTAGCCTGAGACTGTCTTGCGCCGCCTCCGGCTTCACCTTCT CCTCTGCCGCTGTGCACTGGGTCCGACAGGCCCCTGGCAAGGGC CTGGAGTGGGTCGGACGGATCAAGTCCAAGGCCGACGCCGGCAC CACCGACTACGCTGCCCCTGTGAAGGGCCGGTTCACCATCTCCC GGGACGACTCCAAGAACACCCTGTACCTGCAGATGAACTCCCTG AAAACCGAGGACACCGCCGTGTACTACTGCGCCAGAGACTCCCC ATCTATCTCCAGCTACTCCATCCCCTACTTCTCCGGCATGGACG TGTGGGGCCAGGGCACCCTGGTCACCGTGTCCTCT |
| SEQ ID NO: 169 | Heavy Chain | QVQLVESGGGLVKPGGSLRLSCAASGFTFSSAAVHWVRQAPGKG LEWVGRIKSKADAGTTDYAAPVKGRFTISRDDSKNTLYLQMNSL KTEDTAVYYCARDSPSISSYSIPYFSGMDVWGQGTLVTVSSAST KGPSVFPLAPSSKSTSGGTAALGCLVKDYFPEPVTVSWNSGALT SGVHTFPAVLQSSGLYSLSSVVTVPSSSLGTQTYICNVNHKPSN TKVDKRVEPKSC |
| SEQ ID NO: 170 | DNA Heavy Chain | CAAGTGCAGCTGGTGGAATCTGGCGGCGGACTGGTCAAGCCTGG CGGTAGCCTGAGACTGTCTTGCGCCGCCTCCGGCTTCACCTTCT CCTCTGCCGCTGTGCACTGGGTCCGACAGGCCCCTGGCAAGGGC CTGGAGTGGGTCGGACGGATCAAGTCCAAGGCCGACGCCGGCAC CACCGACTACGCTGCCCCTGTGAAGGGCCGGTTCACCATCTCCC GGGACGACTCCAAGAACACCCTGTACCTGCAGATGAACTCCCTG AAAACCGAGGACACCGCCGTGTACTACTGCGCCAGAGACTCCCC ATCTATCTCCAGCTACTCCATCCCCTACTTCTCCGGCATGGACG TGTGGGGCCAGGGCACCCTGGTCACCGTGTCCTCTGCTAGCACC AAGGGCCCCTCCGTGTTCCCTCTGGCCCCTTCCAGCAAGTCTAC CTCTGGCGGCACCGCTGCTCTGGGCTGCCTGGTGAAGGACTACT TCCCTGAGCCTGTGACAGTGTCCTGGAACTCTGGCGCCCTGACC TCCGGCGTGCACACCTTCCCTGCCGTGCTGCAGTCCTCCGGCCT GTACTCCCTGTCCTCCGTGGTGACAGTGCCTTCCTCCAGCCTGG GCACCCAGACCTATATCTGCAACGTGAACCACAAGCCTTCCAAC ACCAAGGTGGACAAGCGGGTGGAGCCTAAGTCATGC |
| SEQ ID NO: 171 (Combined) | LCDR1 | RASQGIRAWLN |
| SEQ ID NO: 172 (Combined) | LCDR2 | AASSLQS |
| SEQ ID NO: 173 (Combined) | LCDR3 | HQYITHPPT |
| SEQ ID NO: 174 (Kabat) | LCDR1 | RASQGIRAWLN |
| SEQ ID NO: 175 (Kabat) | LCDR2 | AASSLQS |
| SEQ ID NO: 176 (Kabat) | LCDR3 | HQYITHPPT |
| SEQ ID NO: 177 (Chothia) | LCDR1 | SQGIRAW |
| SEQ ID NO: 178 (Chothia) | LCDR2 | AAS |
| SEQ ID NO: 179 (Chothia) | LCDR3 | YITHPP |
| SEQ ID NO: 180 (IMGT) | LCDR1 | QGIRAW |
| SEQ ID NO: 181 (IMGT) | LCDR2 | AAS |

TABLE 2-continued

Examples of anti-FXI/FXIa Antibody Binding Agents (e.g., anti-idiotype antibody and Fab fragments

| | description | DNA or amino acid sequence |
|---|---|---|
| SEQ ID NO: 182 (IMGT) | LCDR3 | HQYITHPPT |
| SEQ ID NO: 183 | VL | DIQMTQSPSSLSASVGDRVTITCRASQGIRAWLNWYQQKPGKAP KLLIYAASSLQSGVPSRFSGSGSGTDFTLTISSLQPEDFATYYC HQYITHPPTFGQGTKVEIK |
| SEQ ID NO: 184 | DNA VL | GACATCCAGATGACCCAGAGCCCCTCCAGCCTGTCCGCCTCCGT GGGCGACAGAGTGACCATCACCTGTCGGGCCTCTCAGGGCATCC GGGCCTGGCTGAACTGGTATCAGCAGAAGCCCGGCAAGGCCCCT AAGCTGCTGATCTACGCCGCCAGCTCCCTGCAGTCCGGCGTGCC CTCCAGATTCTCCGGCTCTGGCTCCGGCACCGACTTCACCCTGA CCATCTCCAGCCTGCAGCCCGAGGACTTCGCCACCTACTACTGC CACCAGTACATCACCCACCCTCCCACCTTCGGCCAGGGCACCAA AGTGGAAATCAAG |
| SEQ ID NO: 185 | Light Chain | DIQMTQSPSSLSASVGDRVTITCRASQGIRAWLNWYQQKPGKAP KLLIYAASSLQSGVPSRFSGSGSGTDFTLTISSLQPEDFATYYC HQYITHPPTFGQGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| SEQ ID NO: 186 | DNA Light Chain | GACATCCAGATGACCCAGAGCCCCTCCAGCCTGTCCGCCTCCGT GGGCGACAGAGTGACCATCACCTGTCGGGCCTCTCAGGGCATCC GGGCCTGGCTGAACTGGTATCAGCAGAAGCCCGGCAAGGCCCCT AAGCTGCTGATCTACGCCGCCAGCTCCCTGCAGTCCGGCGTGCC CTCCAGATTCTCCGGCTCTGGCTCCGGCACCGACTTCACCCTGA CCATCTCCAGCCTGCAGCCCGAGGACTTCGCCACCTACTACTGC CACCAGTACATCACCCACCCTCCCACCTTCGGCCAGGGCACCAA AGTGGAAATCAAGCGTACGGTGGCCGCTCCCAGCGTGTTCATCT TCCCCCCCAGCGACGAGCAGCTGAAGAGCGGCACCGCCAGCGTG GTGTGCCTGCTGAACAACTTCTACCCCCGGGAGGCCAAGGTGCA GTGGAAGGTGGACAACGCCCTGCAGAGCGGCAACAGCCAGGAGA GCGTCACCGAGCAGGACAGCAAGGACTCCACCTACAGCCTGAGC AGCACCCTGACCCTGAGCAAGGCCGACTACGAGAAGCATAAGGT GTACGCCTGCGAGGTGACCCACCAGGGCCTGTCCAGCCCCGTGA CCAAGAGCTTCAACAGGGGCGAGTGC |
| | IDT6 | |
| SEQ ID NO: 187 (Combined) | HCDR1 | GYSFTNYWIG |
| SEQ ID NO: 188 (Combined) | HCDR2 | IIFPGVSYTKYSPSFQG |
| SEQ ID NO: 189 (Combined) | HCDR3 | GSDQTLRGSRAMDY |
| SEQ ID NO: 190 (Kabat) | HCDR1 | NYWIG |
| SEQ ID NO: 191 (Kabat) | HCDR2 | IIFPGVSYTKYSPSFQG |
| SEQ ID NO: 192 (Kabat) | HCDR3 | GSDQTLRGSRAMDY |
| SEQ ID NO: 193 (Chothia) | HCDR1 | GYSFTNY |
| SEQ ID NO: 194 (Chothia) | HCDR2 | FPGVSY |
| SEQ ID NO: 195 (Chothia) | HCDR3 | GSDQTLRGSRAMDY |
| SEQ ID NO: 196 (IMGT) | HCDR1 | GYSFTNYW |
| SEQ ID NO: 197 (IMGT) | HCDR2 | IFPGVSYT |
| SEQ ID NO: 198 (IMGT) | HCDR3 | ARGSDQTLRGSRAMDY |
| SEQ ID NO: 199 | VH | QVQLVQSGAEVKKPGESLKISCKGSGYSFTNYWIGWVRQMPGKG LEWMGIIFPGVSYTKYSPSFQGQVTISADKSISTAYLQWSSLKA SDTAMYYCARGSDQTLRGSRAMDYWGQGTLVTVSS |
| SEQ ID NO: 200 | DNA VH | CAAGTGCAGCTGGTGCAGTCTGGCGCTGAAGTGAAGAAGCCCGG CGAGTCCCTGAAGATCTCCTGCAAGGGCTCCGGCTACTCCTTCA CCAACTACTGGATCGGCTGGGTCCGACAGATGCCCGGCAAGGGC CTGGAGTGGATGGGCATCATCTTCCCCGGCGTGTCCTACACCAA GTACAGCCCCAGCTTCCAGGGCCAAGTCACAATCTCCGCCGACA AGTCCATCTCCACCGCCTACCTGCAGTGGTCCTCCCTGAAGGCC TCCGACACCGCCATGTACTACTGCGCCAGAGGCTCCGACCAGAC CCTGCGGGGCTCCAGAGCCATGGATTACTGGGGCCAGGGCACCC TGGTCACCGTGTCCTCT |
| SEQ ID NO: 201 | Heavy Chain | QVQLVQSGAEVKKPGESLKISCKGSGYSFTNYWIGWVRQMPGKG LEWMGIIFPGVSYTKYSPSFQGQVTISADKSISTAYLQWSSLKA SDTAMYYCARGSDQTLRGSRAMDYWGQGTLVTVSSASTKGPSVF |

TABLE 2-continued

Examples of anti-FXI/FXIa Antibody Binding Agents (e.g., anti-idiotype antibody and Fab fragments

| | description | DNA or amino acid sequence |
|---|---|---|
| | | PLAPSSKSTSGGTAALGCLVKDYFPEPVTVSWNSGALTSGVHTF PAVLQSSGLYSLSSVVTVPSSSLGTQTYICNVNHKPSNTKVDKR VEPKSC |
| SEQ ID NO: 202 | DNA Heavy Chain | CAAGTGCAGCTGGTGCAGTCTGGCGCTGAAGTGAAGAAGCCCGG CGAGTCCCTGAAGATCTCCTGCAAGGGCTCCGGCTACTCCTTCA CCAACTACTGGATCGGCTGGGTCCGACAGATGCCCGGCAAGGGC CTGGAGTGGATGGGCATCATCTTCCCCGGCGTGTCCTACACCAA GTACAGCCCCAGCTTCCAGGGCCAAGTCACAATCTCCGCCGACA AGTCCATCTCCACCGCCTACCTGCAGTGGTCCTCCCTGAAGGCC TCCGACACCGCCATGTACTACTGCGCCAGAGGCTCCGACCAGAC CCTGCGGGGCTCCAGAGCCATGGATTACTGGGGCCAGGGCACCC TGGTCACCGTGTCCTCTGCTAGCACCAAGGGCCCCTCCGTGTTC CCTCTGGCCCCTTCCAGCAAGTCTACCTCTGGCGGCACCGCTGC TCTGGGCTGCCTGGTGAAGGACTACTTCCCTGAGCCTGTGACAG TGTCCTGGAACTCTGGCGCCCTGACCTCCGGCGTGCACACCTTC CCTGCCGTGCTGCAGTCCTCCGGCCTGTACTCCCTGTCCTCCGT GGTGACAGTGCCTTCCTCCAGCCTGGGCACCCAGACCTATATCT GCAACGTGAACCACAAGCCTTCCAACACCAAGGTGGACAAGCGG GTGGAGCCTAAGTCATGC |
| SEQ ID NO: 203 (Combined) | LCDR1 | TGTSSDVGISNYVS |
| SEQ ID NO: 204 (Combined) | LCDR2 | EVSNRPS |
| SEQ ID NO: 205 (Combined) | LCDR3 | QSYTSLNYV |
| SEQ ID NO: 206 (Kabat) | LCDR1 | TGTSSDVGISNYVS |
| SEQ ID NO: 207 (Kabat) | LCDR2 | EVSNRPS |
| SEQ ID NO: 208 (Kabat) | LCDR3 | QSYTSLNYV |
| SEQ ID NO: 209 (Chothia) | LCDR1 | TSSDVGISNY |
| SEQ ID NO: 210 (Chothia) | LCDR2 | EVS |
| SEQ ID NO: 211 (Chothia) | LCDR3 | YTSLNY |
| SEQ ID NO: 212 (IMGT) | LCDR1 | SSDVGISNY |
| SEQ ID NO: 213 (IMGT) | LCDR2 | EVS |
| SEQ ID NO: 214 (IMGT) | LCDR3 | QSYTSLNYV |
| SEQ ID NO: 215 | VL | QSALTQPASVSGSPGQSITISCTGTSSDVGISNYVSWYQQHPGK APKLMIYEVSNRPSGVSNRFSGSKSGNTASLTISGLQAEDEADY YCQSYTSLNYVFGGGTKLTVL |
| SEQ ID NO: 216 | DNA VL | CAGTCCGCCCTGACCCAGCCTGCCTCCGTGTCTGGCTCCCCTGG CCAGTCCATCACCATCAGCTGCACCGGCACCTCCAGCGACGTGG GCATCTCCAACTACGTGTCCTGGTATCAGCAGCACCCCGGCAAG GCCCCTAAGCTGATGATCTACGAAGTGTCCAACCGGCCCTCCGG CGTGTCCAACAGATTCTCCGGCTCCAAGTCCGGCAACACCGCCT CCCTGACCATCAGCGGCCTGCAGGCTGAGGACGAGGCCGACTAC TACTGCCAGTCCTACACCTCCCTGAACTACGTGTTCGGCGGAGG CACCAAGCTGACCGTGCTG |
| SEQ ID NO: 217 | Light Chain | QSALTQPASVSGSPGQSITISCTGTSSDVGISNYVSWYQQHPGK APKLMIYEVSNRPSGVSNRFSGSKSGNTASLTISGLQAEDEADY YCQSYTSLNYVFGGGTKLTVLGQPKAAPSVTLFPPSSEELQANK ATLVCLISDFYPGAVTVAWKADSSPVKAGVETTTPSKQSNNKYA ASSYLSLTPEQWKSHRSYSCQVTHEGSTVEKTVAPTECS |
| SEQ ID NO: 218 | DNA Light Chain | CAGTCCGCCCTGACCCAGCCTGCCTCCGTGTCTGGCTCCCCTGG CCAGTCCATCACCATCAGCTGCACCGGCACCTCCAGCGACGTGG GCATCTCCAACTACGTGTCCTGGTATCAGCAGCACCCCGGCAAG GCCCCTAAGCTGATGATCTACGAAGTGTCCAACCGGCCCTCCGG CGTGTCCAACAGATTCTCCGGCTCCAAGTCCGGCAACACCGCCT CCCTGACCATCAGCGGCCTGCAGGCTGAGGACGAGGCCGACTAC TACTGCCAGTCCTACACCTCCCTGAACTACGTGTTCGGCGGAGG CACCAAGCTGACCGTGCTGGGCCAGCCTAAGGCTGCCCCCAGCG TGACCCTGTTCCCCCCCAGCAGCGAGGAGCTGCAGGCCAACAAG GCCACCCTGGTGTGCCTGATCAGCGACTTCTACCCAGGCGCCGT GACCGTGGCCTGGAAGGCCGACAGCAGCCCCGTGAAGGCCGGCG TGGAGACCACCACCCCCAGCAAGCAGAGCAACAACAAGTACGCC GCCAGCAGCTACCTGAGCCTGACCCCCGAGCAGTGGAAGAGCCA CAGGTCCTACAGCTGCCAGGTGACCCACGAGGGCAGCACCGTGG AAAAGACCGTGGCCCCAACCGAGTGCAGC |

TABLE 2-continued

Examples of anti-FXI/FXIa Antibody Binding Agents (e.g., anti-idiotype antibody and Fab fragments

| | description | DNA or amino acid sequence |
|---|---|---|
| | | IDT7 |
| SEQ ID NO: 219 (Combined) | HCDR1 | GFTFSSNAMH |
| SEQ ID NO: 220 (Combined) | HCDR2 | RIKSKTDGGTTDYAAPVKG |
| SEQ ID NO: 221 (Combined) | HCDR3 | DHYYYPFAY |
| SEQ ID NO: 222 (Kabat) | HCDR1 | SNAMH |
| SEQ ID NO: 223 (Kabat) | HCDR2 | RIKSKTDGGTTDYAAPVKG |
| SEQ ID NO: 224 (Kabat) | HCDR3 | DHYYYPFAY |
| SEQ ID NO: 225 (Chothia) | HCDR1 | GFTFSSN |
| SEQ ID NO: 226 (Chothia) | HCDR2 | KSKTDGGT |
| SEQ ID NO: 227 (Chothia) | HCDR3 | DHYYYPFAY |
| SEQ ID NO: 228 (IMGT) | HCDR1 | GFTFSSNA |
| SEQ ID NO: 229 (IMGT) | HCDR2 | IKSKTDGGTT |
| SEQ ID NO: 230 (IMGT) | HCDR3 | ARDHYYYPFAY |
| SEQ ID NO: 231 | VH | QVQLVESGGGLVKPGGSLRLSCAASGFTFSSNAMHWVRQAPGKG<br>LEWVGRIKSKTDGGTTDYAAPVKGRFTISRDDSKNTLYLQMNSL<br>KTEDTAVYYCARDHYYYPFAYWGQGTLVTVSS |
| SEQ ID NO: 232 | DNA VH | CAAGTGCAGCTGGTGGAATCTGGCGGCGGACTGGTCAAGCCTGG<br>CGGTAGCCTGAGACTGTCTTGCGCCGCCTCCGGCTTCACCTTCT<br>CCTCCAACGCCATGCACTGGGTCCGACAGGCCCCTGGCAAGGGC<br>CTGGAGTGGGTCGGACGGATCAAGTCCAAGACCGACGGCGGCAC<br>CACCGACTACGCTGCCCCTGTGAAGGGCCGGTTCACCATCTCCC<br>GGGACGACTCCAAGAACACCCTGTACCTGCAGATGAACTCCCTG<br>AAAACCGAGGACACCGCCGTGTACTACTGCGCCAGGGACCACTA<br>CTACTACCCCTTCGCCTACTGGGGCCAGGGCACCCTGGTCACCG<br>TGTCCTCT |
| SEQ ID NO: 233 | Heavy Chain | QVQLVESGGGLVKPGGSLRLSCAASGFTFSSNAMHWVRQAPGKG<br>LEWVGRIKSKTDGGTTDYAAPVKGRFTISRDDSKNTLYLQMNSL<br>KTEDTAVYYCARDHYYYPFAYWGQGTLVTVSSASTKGPSVFPLA<br>PSSKSTSGGTAALGCLVKDYFPEPVTVSWNSGALTSGVHTFPAV<br>LQSSGLYSLSSVVTVPSSSLGTQTYICNVNHKPSNTKVDKRVEP<br>KSC |
| SEQ ID NO: 234 | DNA Heavy Chain | CAAGTGCAGCTGGTGGAATCTGGCGGCGGACTGGTCAAGCCTGG<br>CGGTAGCCTGAGACTGTCTTGCGCCGCCTCCGGCTTCACCTTCT<br>CCTCCAACGCCATGCACTGGGTCCGACAGGCCCCTGGCAAGGGC<br>CTGGAGTGGGTCGGACGGATCAAGTCCAAGACCGACGGCGGCAC<br>CACCGACTACGCTGCCCCTGTGAAGGGCCGGTTCACCATCTCCC<br>GGGACGACTCCAAGAACACCCTGTACCTGCAGATGAACTCCCTG<br>AAAACCGAGGACACCGCCGTGTACTACTGCGCCAGGGACCACTA<br>CTACTACCCCTTCGCCTACTGGGGCCAGGGCACCCTGGTCACCG<br>TGTCCTCTGCTAGCACCAAGGGCCCCTCCGTGTTCCCTCTGGCC<br>CCTTCCAGCAAGTCTACCTCTGGCGGCACCGCTGCTCTGGGCTG<br>CCTGGTGAAGGACTACTTCCCTGAGCCTGTGACAGTGTCCTGGA<br>ACTCTGGCGCCCTGACCTCCGGCGTGCACACCTTCCCTGCCGTG<br>CTGCAGTCCTCCGGCCTGTACTCCCTGTCCTCCGTGGTGACAGT<br>GCCTTCCTCCAGCCTGGGCACCCAGACCTATATCTGCAACGTGA<br>ACCACAAGCCTTCCAACACCAAGGTGGACAAGCGGGTGGAGCCT<br>AAGTCATGC |
| SEQ ID NO: 235 (Combined) | LCDR1 | RASQSIRYNLA |
| SEQ ID NO: 236 (Combined) | LCDR2 | AASSLQS |
| SEQ ID NO: 237 (Combined) | LCDR3 | HQYIAKPIT |
| SEQ ID NO: 238 (Kabat) | LCDR1 | RASQSIRYNLA |
| SEQ ID NO: 239 (Kabat) | LCDR2 | AASSLQS |
| SEQ ID NO: 240 (Kabat) | LCDR3 | HQYIAKPIT |
| SEQ ID NO: 241 (Chothia) | LCDR1 | SQSIRYN |

TABLE 2-continued

Examples of anti-FXI/FXIa Antibody Binding Agents (e.g., anti-idiotype antibody and Fab fragments

| | description | DNA or amino acid sequence |
|---|---|---|
| SEQ ID NO: 242 (Chothia) | LCDR2 | AAS |
| SEQ ID NO: 243 (Chothia) | LCDR3 | YIAKPI |
| SEQ ID NO: 244 (IMGT) | LCDR1 | QSIRYN |
| SEQ ID NO: 245 (IMGT) | LCDR2 | AAS |
| SEQ ID NO: 246 (IMGT) | LCDR3 | HQYIAKPIT |
| SEQ ID NO: 247 | VL | DIQMTQSPSSLSASVGDRVTITCRASQSIRYNLAWYQQKPGKAP KLLIYAASSLQSGVPSRFSGSGSGTDFTLTISSLQPEDFATYYC HQYIAKPITFGQGTKVEIK |
| SEQ ID NO: 248 | DNA VL | GACATCCAGATGACCCAGAGCCCCTCCAGCCTGTCCGCCTCCGT GGGCGACAGAGTGACCATCACCTGTCGGGCCTCCCAGTCCATCC GGTACAACCTGGCCTGGTATCAGCAGAAGCCCGGCAAGGCCCCT AAGCTGCTGATCTACGCCGCCAGCTCCCTGCAGTCCGGCGTGCC CTCCAGATTCTCCGGCTCTGGCTCCGGCACCGACTTCACCCTGA CCATCTCCAGCCTGCAGCCCGAGGACTTCGCCACCTACTACTGC CACCAGTATATCGCCAAGCCCATCACCTTCGGCCAGGGCACCAA AGTGGAAATCAAG |
| SEQ ID NO: 249 | Light Chain | DIQMTQSPSSLSASVGDRVTITCRASQSIRYNLAWYQQKPGKAP KLLIYAASSLQSGVPSRFSGSGSGTDFTLTISSLQPEDFATYYC HQYIAKPITFGQGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| SEQ ID NO: 250 | DNA Light Chain | GACATCCAGATGACCCAGAGCCCCTCCAGCCTGTCCGCCTCCGT GGGCGACAGAGTGACCATCACCTGTCGGGCCTCCCAGTCCATCC GGTACAACCTGGCCTGGTATCAGCAGAAGCCCGGCAAGGCCCCT AAGCTGCTGATCTACGCCGCCAGCTCCCTGCAGTCCGGCGTGCC CTCCAGATTCTCCGGCTCTGGCTCCGGCACCGACTTCACCCTGA CCATCTCCAGCCTGCAGCCCGAGGACTTCGCCACCTACTACTGC CACCAGTATATCGCCAAGCCCATCACCTTCGGCCAGGGCACCAA AGTGGAAATCAAGCGTACGGTGGCCGCTCCCAGCGTGTTCATCT TCCCCCCCAGCGACGAGCAGCTGAAGAGCGGCACCGCCAGCGTG GTGTGCCTGCTGAACAACTTCTACCCCCGGGAGGCCAAGGTGCA GTGGAAGGTGGACAACGCCCTGCAGAGCGGCAACAGCCAGGAGA GCGTCACCGAGCAGGACAGCAAGGACTCCACCTACAGCCTGAGC AGCACCCTGACCCTGAGCAAGGCCGACTACGAGAAGCATAAGGT GTACGCCTGCGAGGTGACCCACCAGGGCCTGTCCAGCCCCGTGA CCAAGAGCTTCAACAGGGGCGAGTGC |
| | IDT8 | |
| SEQ ID NO: 251 (Combined) | HCDR1 | GFTFSSNAMH |
| SEQ ID NO: 252 (Combined) | HCDR2 | RIKSKTSGGTTDYAAPVKG |
| SEQ ID NO: 253 (Combined) | HCDR3 | DHYYYPFAY |
| SEQ ID NO: 254 (Kabat) | HCDR1 | SNAMH |
| SEQ ID NO: 255 (Kabat) | HCDR2 | RIKSKTSGGTTDYAAPVKG |
| SEQ ID NO: 256 (Kabat) | HCDR3 | DHYYYPFAY |
| SEQ ID NO: 257 (Chothia) | HCDR1 | GFTFSSN |
| SEQ ID NO: 258 (Chothia) | HCDR2 | KSKTSGGT |
| SEQ ID NO: 259 (Chothia) | HCDR3 | DHYYYPFAY |
| SEQ ID NO: 260 (IMGT) | HCDR1 | GFTFSSNA |
| SEQ ID NO: 261 (IMGT) | HCDR2 | IKSKTSGGTT |
| SEQ ID NO: 262 (IMGT) | HCDR3 | ARDHYYYPFAY |
| SEQ ID NO: 263 | VH | QVQLVESGGGLVKPGGSLRLSCAASGFTFSSNAMHWVRQAPGKG LEWVGRIKSKTSGGTTDYAAPVKGRFTISRDDSKNTLYLQMNSL KTEDTAVYYCARDHYYYPFAYWGQGTLVTVSS |
| SEQ ID NO: 264 | DNA VH | CAAGTGCAGCTGGTGGAATCTGGCGGCGGACTGGTCAAGCCTGG CGGTAGCCTGAGACTGTCTTGCGCCGCCTCCGGCTTCACCTTCT CCTCCAACGCCATGCACTGGGTCCGACAGGCCCCTGGCAAGGGC CTGGAGTGGGTCGGACGGATCAAGTCCAAGACCTCCGGCGGCAC |

TABLE 2-continued

Examples of anti-FXI/FXIa Antibody Binding Agents (e.g., anti-idiotype antibody and Fab fragments

| | description | DNA or amino acid sequence |
|---|---|---|
| | | CACCGACTACGCTGCCCCTGTGAAGGGCCGGTTCACCATCTCCC GGGACGACTCCAAGAACACCCTGTACCTGCAGATGAACTCCCTG AAAACCGAGGACACCGCCGTGTACTACTGCGCCAGGGACCACTA CTACTACCCCTTCGCCTACTGGGGCCAGGGCACCCTGGTCACCG TGTCCTCT |
| SEQ ID NO: 265 | Heavy Chain | QVQLVESGGGLVKPGGSLRLSCAASGFTFSSNAMHWVRQAPGKG LEWVGRIKSKTSGGTTDYAAPVKGRFTISRDDSKNTLYLQMNSL KTEDTAVYYCARDHYYYPFAYWGQGTLVTVSSASTKGPSVFPLA PSSKSTSGGTAALGCLVKDYFPEPVTVSWNSGALTSGVHTFPAV LQSSGLYSLSSVVTVPSSSLGTQTYICNVNHKPSNTKVDKRVEP KSC |
| SEQ ID NO: 266 | DNA Heavy Chain | CAAGTGCAGCTGGTGGAATCTGGCGGCGGACTGGTCAAGCCTGG CGGTAGCCTGAGACTGTCTTGCGCCGCCTCCGGCTTCACCTTCT CCTCCAACGCCATGCACTGGGTCCGACAGGCCCCTGGCAAGGGC CTGGAGTGGGTCGGACGGATCAAGTCCAAGACCTCCGGCGGCAC CACCGACTACGCTGCCCCTGTGAAGGGCCGGTTCACCATCTCCC GGGACGACTCCAAGAACACCCTGTACCTGCAGATGAACTCCCTG AAAACCGAGGACACCGCCGTGTACTACTGCGCCAGGGACCACTA CTACTACCCCTTCGCCTACTGGGGCCAGGGCACCCTGGTCACCG TGTCCTCTGCTAGCACCAAGGGCCCCTCCGTGTTCCCTCTGGCC CCTTCCAGCAAGTCTACCTCTGGCGGCACCGCTGCTCTGGGCTG CCTGGTGAAGGACTACTTCCCTGAGCCTGTGACAGTGTCCTGGA ACTCTGGCGCCCTGACCTCCGGCGTGCACACCTTCCCTGCCGTG CTGCAGTCCTCCGGCCTGTACTCCCTGTCCTCCGTGGTGACAGT GCCTTCCTCCAGCCTGGGCACCCAGACCTATATCTGCAACGTGA ACCACAAGCCTTCCAACACCAAGGTGGACAAGCGGGTGGAGCCT AAGTCATGC |
| SEQ ID NO: 267 (Combined) | LCDR1 | RASQSIRYNLA |
| SEQ ID NO: 268 (Combined) | LCDR2 | AASSLQS |
| SEQ ID NO: 269 (Combined) | LCDR3 | HQYIAKPIT |
| SEQ ID NO: 270 (Kabat) | LCDR1 | RASQSIRYNLA |
| SEQ ID NO: 271 (Kabat) | LCDR2 | AASSLQS |
| SEQ ID NO: 272 (Kabat) | LCDR3 | HQYIAKPIT |
| SEQ ID NO: 273 (Chothia) | LCDR1 | SQSIRYN |
| SEQ ID NO: 274 (Chothia) | LCDR2 | AAS |
| SEQ ID NO: 275 (Chothia) | LCDR3 | YIAKPI |
| SEQ ID NO: 276 (IMGT) | LCDR1 | QSIRYN |
| SEQ ID NO: 277 (IMGT) | LCDR2 | AAS |
| SEQ ID NO: 278 (IMGT) | LCDR3 | HQYIAKPIT |
| SEQ ID NO: 279 | VL | DIQMTQSPSSLSASVGDRVTITCRASQSIRYNLAWYQQKPGKAP KLLIYAASSLQSGVPSRFSGSGSGTDFTLTISSLQPEDFATYYC HQYIAKPITFGQGTKVEIK |
| SEQ ID NO: 280 | DNA VL | GACATCCAGATGACCCAGAGCCCCTCCAGCCTGTCCGCCTCCGT GGGCGACAGAGTGACCATCACCTGTCGGGCCTCCCAGTCCATCC GGTACAACCTGGCCTGGTATCAGCAGAAGCCCGGCAAGGCCCCT AAGCTGCTGATCTACGCCGCCAGCTCCCTGCAGTCCGGCGTGCC CTCCAGATTCTCCGGCTCTGGCTCCGGCACCGACTTCACCCTGA CCATCTCCAGCCTGCAGCCCGAGGACTTCGCCACCTACTACTGC CACCAGTATATCGCCAAGCCCATCACCTTCGGCCAGGGCACCAA AGTGGAAATCAAG |
| SEQ ID NO: 281 | Light Chain | DIQMTQSPSSLSASVGDRVTITCRASQSIRYNLAWYQQKPGKAP KLLIYAASSLQSGVPSRFSGSGSGTDFTLTISSLQPEDFATYYC HQYIAKPITFGQGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| SEQ ID NO: 282 | DNA Light Chain | GACATCCAGATGACCCAGAGCCCCTCCAGCCTGTCCGCCTCCGT GGGCGACAGAGTGACCATCACCTGTCGGGCCTCCCAGTCCATCC GGTACAACCTGGCCTGGTATCAGCAGAAGCCCGGCAAGGCCCCT AAGCTGCTGATCTACGCCGCCAGCTCCCTGCAGTCCGGCGTGCC CTCCAGATTCTCCGGCTCTGGCTCCGGCACCGACTTCACCCTGA CCATCTCCAGCCTGCAGCCCGAGGACTTCGCCACCTACTACTGC CACCAGTATATCGCCAAGCCCATCACCTTCGGCCAGGGCACCAA AGTGGAAATCAAGCGTACGGTGGCCGCTCCCAGCGTGTTCATCT |

TABLE 2-continued

| Examples of anti-FXI/FXIa Antibody Binding Agents (e.g., anti-idiotype antibody and Fab fragments | | |
|---|---|---|
| | description | DNA or amino acid sequence |
| | | TCCCCCCCAGCGACGAGCAGCTGAAGAGCGGCACCGCCAGCGTG GTGTGCCTGCTGAACAACTTCTACCCCCGGGAGGCCAAGGTGCA GTGGAAGGTGGACAACGCCCTGCAGAGCGGCAACAGCCAGGAGA GCGTCACCGAGCAGGACAGCAAGGACTCCACCTACAGCCTGAGC AGCACCCTGACCCTGAGCAAGGCCGACTACGAGAAGCATAAGGT GTACGCCTGCGAGGTGACCCACCAGGGCCTGTCCAGCCCCGTGA CCAAGAGCTTCAACAGGGGCGAGTGC |
| | | IDT9 |
| SEQ ID NO: 283 (Combined) | HCDR1 | GYTFTNYYVH |
| SEQ ID NO: 284 (Combined) | HCDR2 | WINPYNGNTNYAQKFQG |
| SEQ ID NO: 285 (Combined) | HCDR3 | GASSIRMSYYLDV |
| SEQ ID NO: 286 (Kabat) | HCDR1 | NYYVH |
| SEQ ID NO: 287 (Kabat) | HCDR2 | WINPYNGNTNYAQKFQG |
| SEQ ID NO: 288 (Kabat) | HCDR3 | GASSIRMSYYLDV |
| SEQ ID NO: 289 (Chothia) | HCDR1 | GYTFTNY |
| SEQ ID NO: 290 (Chothia) | HCDR2 | NPYNGN |
| SEQ ID NO: 291 (Chothia) | HCDR3 | GASSIRMSYYLDV |
| SEQ ID NO: 292 (IMGT) | HCDR1 | GYTFTNYY |
| SEQ ID NO: 293 (IMGT) | HCDR2 | INPYNGNT |
| SEQ ID NO: 294 (IMGT) | HCDR3 | ARGASSIRMSYYLDV |
| SEQ ID NO: 295 | VH | QVQLVQSGAEVKKPGASVKVSCKASGYTFTNYYVHWVRQAPGQG LEWMGWINPYNGNTNYAQKFQGRVTMTRDTSISTAYMELSRLRS EDTAVYYCARGASSIRMSYYLDVWGQGTLVTVSS |
| SEQ ID NO: 296 | DNA VH | CAAGTGCAGCTGGTGCAGTCTGGCGCTGAAGTGAAGAAACCTGG CGCCTCCGTGAAAGTGTCCTGCAAGGCCTCCGGCTACACCTTCA CCAACTACTACGTGCACTGGGTCCGACAGGCCCCAGGCCAGGGC CTGGAGTGGATGGGCTGGATCAACCCCTACAACGGCAACACCAA CTACGCCCAGAAATTCCAGGGCAGAGTGACCATGACCCGGGACA CCTCCATCTCCACCGCCTACATGGAACTGTCCCGGCTGCGGAGC GAGGACACCGCCGTGTACTACTGTGCCAGAGGCGCCTCCTCCAT CCGGATGTCCTACTACCTGGACGTGTGGGGCCAGGGCACCCTGG TCACCGTGTCCTCT |
| SEQ ID NO: 297 | Heavy Chain | QVQLVQSGAEVKKPGASVKVSCKASGYTFTNYYVHWVRQAPGQG LEWMGWINPYNGNTNYAQKFQGRVTMTRDTSISTAYMELSRLRS EDTAVYYCARGASSIRMSYYLDVWGQGTLVTVSSASTKGPSVFP LAPSSKSTSGGTAALGCLVKDYFPEPVTVSWNSGALTSGVHTFP AVLQSSGLYSLSSVVTVPSSSLGTQTYICNVNHKPSNTKVDKRV EPKSC |
| SEQ ID NO: 298 | DNA Heavy Chain | CAAGTGCAGCTGGTGCAGTCTGGCGCTGAAGTGAAGAAACCTGG CGCCTCCGTGAAAGTGTCCTGCAAGGCCTCCGGCTACACCTTCA CCAACTACTACGTGCACTGGGTCCGACAGGCCCCAGGCCAGGGC CTGGAGTGGATGGGCTGGATCAACCCCTACAACGGCAACACCAA CTACGCCCAGAAATTCCAGGGCAGAGTGACCATGACCCGGGACA CCTCCATCTCCACCGCCTACATGGAACTGTCCCGGCTGCGGAGC GAGGACACCGCCGTGTACTACTGTGCCAGAGGCGCCTCCTCCAT CCGGATGTCCTACTACCTGGACGTGTGGGGCCAGGGCACCCTGG TCACCGTGTCCTCTGCTAGCACCAAGGGCCCCTCCGTGTTCCCT CTGGCCCCTTCCAGCAAGTCTACCTCTGGCGGCACCGCTGCTCT GGGCTGCCTGGTGAAGGACTACTTCCCTGAGCCTGTGACAGTGT CCTGGAACTCTGGCGCCCTGACCTCCGGCGTGCACACCTTCCCT GCCGTGCTGCAGTCCTCCGGCCTGTACTCCCTGTCCTCCGTGGT GACAGTGCCTTCCTCCAGCCTGGGCACCCAGACCTATATCTGCA ACGTGAACCACAAGCCTTCCAACACCAAGGTGGACAAGCGGGTG GAGCCTAAGTCATGC |
| SEQ ID NO: 299 (Combined) | LCDR1 | RASQSISNYLN |
| SEQ ID NO: 300 (Combined) | LCDR2 | AASNLQS |
| SEQ ID NO: 301 (Combined) | LCDR3 | FQYTHSPAT |

TABLE 2-continued

Examples of anti-FXI/FXIa Antibody Binding Agents (e.g., anti-idiotype antibody and Fab fragments

| | description | DNA or amino acid sequence |
|---|---|---|
| SEQ ID NO: 302 (Kabat) | LCDR1 | RASQSISNYLN |
| SEQ ID NO: 303 (Kabat) | LCDR2 | AASNLQS |
| SEQ ID NO: 304 (Kabat) | LCDR3 | FQYTHSPAT |
| SEQ ID NO: 305 (Chothia) | LCDR1 | SQSISNY |
| SEQ ID NO: 306 (Chothia) | LCDR2 | AAS |
| SEQ ID NO: 307 (Chothia) | LCDR3 | YTHSPA |
| SEQ ID NO: 308 (IMGT) | LCDR1 | QSISNY |
| SEQ ID NO: 309 (IMGT) | LCDR2 | AAS |
| SEQ ID NO: 310 (IMGT) | LCDR3 | FQYTHSPAT |
| SEQ ID NO: 311 | VL | DIQMTQSPSSLSASVGDRVTITCRASQSISNYLNWYQQKPGKAP KLLIYAASNLQSGVPSRFSGSGSGTDFTLTISSLQPEDFATYYC FQYTHSPATFGQGTKVEIK |
| SEQ ID NO: 312 | DNA VL | GACATCCAGATGACCCAGAGCCCCTCCAGCCTGTCCGCCTCCGT GGGCGACAGAGTGACCATCACCTGTCGGGCCTCCCAGTCCATCT CCAACTACCTGAACTGGTATCAGCAGAAGCCCGGCAAGGCCCCT AAGCTGCTGATCTACGCCGCCTCCAACCTGCAGTCCGGCGTGCC CTCCAGATTCTCCGGCTCTGGCTCCGGCACCGACTTCACCCTGA CCATCTCCAGCCTGCAGCCCGAGGACTTCGCCACCTACTACTGC TTCCAGTACACCCACAGCCCCGCCACCTTCGGCCAGGGCACCAA AGTGGAAATCAAG |
| SEQ ID NO: 313 | Light Chain | DIQMTQSPSSLSASVGDRVTITCRASQSISNYLNWYQQKPGKAP KLLIYAASNLQSGVPSRFSGSGSGTDFTLTISSLQPEDFATYYC FQYTHSPATFGQGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| SEQ ID NO: 314 | DNA Light Chain | GACATCCAGATGACCCAGAGCCCCTCCAGCCTGTCCGCCTCCGT GGGCGACAGAGTGACCATCACCTGTCGGGCCTCCCAGTCCATCT CCAACTACCTGAACTGGTATCAGCAGAAGCCCGGCAAGGCCCCT AAGCTGCTGATCTACGCCGCCTCCAACCTGCAGTCCGGCGTGCC CTCCAGATTCTCCGGCTCTGGCTCCGGCACCGACTTCACCCTGA CCATCTCCAGCCTGCAGCCCGAGGACTTCGCCACCTACTACTGC TTCCAGTACACCCACAGCCCCGCCACCTTCGGCCAGGGCACCAA AGTGGAAATCAAGCGTACGGTGGCCGCTCCCAGCGTGTTCATCT TCCCCCCCAGCGACGAGCAGCTGAAGAGCGGCACCGCCAGCGTG GTGTGCCTGCTGAACAACTTCTACCCCCGGGAGGCCAAGGTGCA GTGGAAGGTGGACAACGCCCTGCAGAGCGGCAACAGCCAGGAGA GCGTCACCGAGCAGGACAGCAAGGACTCCACCTACAGCCTGAGC AGCACCCTGACCCTGAGCAAGGCCGACTACGAGAAGCATAAGGT GTACGCCTGCGAGGTGACCCACCAGGGCCTGTCCAGCCCCGTGA CCAAGAGCTTCAACAGGGGCGAGTGC |
| | | IDT10 |
| SEQ ID NO: 315 (Combined) | HCDR1 | GYTFTNYYVH |
| SEQ ID NO: 316 (Combined) | HCDR2 | WINPYSGNTNYAQKFQG |
| SEQ ID NO: 317 (Combined) | HCDR3 | GASSIRMSYYLDV |
| SEQ ID NO: 318 (Kabat) | HCDR1 | NYYVH |
| SEQ ID NO: 319 (Kabat) | HCDR2 | WINPYSGNTNYAQKFQG |
| SEQ ID NO: 320 (Kabat) | HCDR3 | GASSIRMSYYLDV |
| SEQ ID NO: 321 (Chothia) | HCDR1 | GYTFTNY |
| SEQ ID NO: 322 (Chothia) | HCDR2 | NPYSGN |
| SEQ ID NO: 323 (Chothia) | HCDR3 | GASSIRMSYYLDV |
| SEQ ID NO: 324 (IMGT) | HCDR1 | GYTFTNYY |
| SEQ ID NO: 325 (IMGT) | HCDR2 | INPYSGNT |

TABLE 2-continued

Examples of anti-FXI/FXIa Antibody Binding Agents (e.g., anti-idiotype antibody and Fab fragments

| | description | DNA or amino acid sequence |
|---|---|---|
| SEQ ID NO: 326 (IMGT) | HCDR3 | ARGASSIRMSYYLDV |
| SEQ ID NO: 327 | VH | QVQLVQSGAEVKKPGASVKVSCKASGYTFTNYYVHWVRQAPGQG LEWMGWINPYSGNTNYAQKFQGRVTMTRDTSISTAYMELSRLRS EDTAVYYCARGASSIRMSYYLDVWGQGTLVTVSS |
| SEQ ID NO: 328 | DNA VH | CAAGTGCAGCTGGTGCAGTCTGGCGCTGAAGTGAAGAAACCTGG CGCCTCCGTGAAAGTGTCCTGCAAGGCCTCCGGCTACACCTTCA CCAACTACTACGTGCACTGGGTCCGACAGGCCCCAGGCCAGGGC CTGGAGTGGATGGGCTGGATCAACCCCTACTCCGGCAACACCAA CTACGCCCAGAAATTCCAGGGCAGAGTGACCATGACCCGGGACA CCTCCATCTCCACCGCCTACATGGAACTGTCCCGGCTGCGGAGC GAGGACACCGCCGTGTACTACTGTGCCAGAGGCGCCTCCTCCAT CCGGATGTCCTACTACCTGGACGTGTGGGGCCAGGGCACCCTGG TCACCGTGTCCTCT |
| SEQ ID NO: 329 | Heavy Chain | QVQLVQSGAEVKKPGASVKVSCKASGYTFTNYYVHWVRQAPGQG LEWMGWINPYSGNTNYAQKFQGRVTMTRDTSISTAYMELSRLRS EDTAVYYCARGASSIRMSYYLDVWGQGTLVTVSSASTKGPSVFP LAPSSKSTSGGTAALGCLVKDYFPEPVTVSWNSGALTSGVHTFP AVLQSSGLYSLSSVVTVPSSSLGTQTYICNVNHKPSNTKVDKRV EPKSC |
| SEQ ID NO: 330 | DNA Heavy Chain | CAAGTGCAGCTGGTGCAGTCTGGCGCTGAAGTGAAGAAACCTGG CGCCTCCGTGAAAGTGTCCTGCAAGGCCTCCGGCTACACCTTCA CCAACTACTACGTGCACTGGGTCCGACAGGCCCCAGGCCAGGGC CTGGAGTGGATGGGCTGGATCAACCCCTACTCCGGCAACACCAA CTACGCCCAGAAATTCCAGGGCAGAGTGACCATGACCCGGGACA CCTCCATCTCCACCGCCTACATGGAACTGTCCCGGCTGCGGAGC GAGGACACCGCCGTGTACTACTGTGCCAGAGGCGCCTCCTCCAT CCGGATGTCCTACTACCTGGACGTGTGGGGCCAGGGCACCCTGG TCACCGTGTCCTCTGCTAGCACCAAGGGCCCCTCCGTGTTCCCT CTGGCCCCTTCCAGCAAGTCTACCTCTGGCGGCACCGCTGCTCT GGGCTGCCTGGTGAAGGACTACTTCCCTGAGCCTGTGACAGTGT CCTGGAACTCTGGCGCCCTGACCTCCGGCGTGCACACCTTCCCT GCCGTGCTGCAGTCCTCCGGCCTGTACTCCCTGTCCTCCGTGGT GACAGTGCCTTCCTCCAGCCTGGGCACCCAGACCTATATCTGCA ACGTGAACCACAAGCCTTCCAACACCAAGGTGGACAAGCGGGTG GAGCCTAAGTCATGC |
| SEQ ID NO: 331 (Combined) | LCDR1 | RASQSISNYLN |
| SEQ ID NO: 332 (Combined) | LCDR2 | AASNLQS |
| SEQ ID NO: 333 (Combined) | LCDR3 | FQYTHSPAT |
| SEQ ID NO: 334 (Kabat) | LCDR1 | RASQSISNYLN |
| SEQ ID NO: 335 (Kabat) | LCDR2 | AASNLQS |
| SEQ ID NO: 336 (Kabat) | LCDR3 | FQYTHSPAT |
| SEQ ID NO: 337 (Chothia) | LCDR1 | SQSISNY |
| SEQ ID NO: 338 (Chothia) | LCDR2 | AAS |
| SEQ ID NO: 339 (Chothia) | LCDR3 | YTHSPA |
| SEQ ID NO: 340 (IMGT) | LCDR1 | QSISNY |
| SEQ ID NO: 341 (IMGT) | LCDR2 | AAS |
| SEQ ID NO: 342 (IMGT) | LCDR3 | FQYTHSPAT |
| SEQ ID NO: 343 | VL | DIQMTQSPSSLSASVGDRVTITCRASQSISNYLNWYQQKPGKAP KLLIYAASNLQSGVPSRFSGSGSGTDFTLTISSLQPEDFATYYC FQYTHSPATFGQGTKVEIK |
| SEQ ID NO: 344 | DNA VL | GACATCCAGATGACCCAGAGCCCCTCCAGCCTGTCCGCCTCCGT GGGCGACAGAGTGACCATCACCTGTCGGGCCTCCCAGTCCATCT CCAACTACCTGAACTGGTATCAGCAGAAGCCCGGCAAGGCCCCT AAGCTGCTGATCTACGCCGCCTCCAACCTGCAGTCCGGCGTGCC CTCCAGATTCTCCGGCTCTGGCTCCGGCACCGACTTCACCCTGA CCATCTCCAGCCTGCAGCCCGAGGACTTCGCCACCTACTACTGC TTCCAGTACACCCACAGCCCCGCCACCTTCGGCCAGGGCACCAA AGTGGAAATCAAG |

TABLE 2-continued

Examples of anti-FXI/FXIa Antibody Binding Agents (e.g., anti-idiotype antibody and Fab fragments

| | description | DNA or amino acid sequence |
|---|---|---|
| SEQ ID NO: 345 | Light Chain | DIQMTQSPSSLSASVGDRVTITCRASQSISNYLNWYQQKPGKAP<br>KLLIYAASNLQSGVPSRFSGSGSGTDFTLTISSLQPEDFATYYC<br>FQYTHSPATFGQGTKVEIKRTVAAPSVFIFPPSDEQLKSGTASV<br>VCLLNNFYPREAKVQWKVDNALQSGNSQESVTEQDSKDSTYSLS<br>STLTLSKADYEKHKVYACEVTHQGLSSPVTKSFNRGEC |
| SEQ ID NO: 346 | DNA Light Chain | GACATCCAGATGACCCAGAGCCCCTCCAGCCTGTCCGCCTCCGT<br>GGGCGACAGAGTGACCATCACCTGTCGGGCCTCCCAGTCCATCT<br>CCAACTACCTGAACTGGTATCAGCAGAAGCCCGGCAAGGCCCCT<br>AAGCTGCTGATCTACGCCGCCTCCAACCTGCAGTCCGGCGTGCC<br>CTCCAGATTCTCCGGCTCTGGCTCCGGCACCGACTTCACCCTGA<br>CCATCTCCAGCCTGCAGCCCGAGGACTTCGCCACCTACTACTGC<br>TTCCAGTACACCCACAGCCCCGCCACCTTCGGCCAGGGCACCAA<br>AGTGGAAATCAAGCGTACGGTGGCCGCTCCCAGCGTGTTCATCT<br>TCCCCCCCAGCGACGAGCAGCTGAAGAGCGGCACCGCCAGCGTG<br>GTGTGCCTGCTGAACAACTTCTACCCCCGGGAGGCCAAGGTGCA<br>GTGGAAGGTGGACAACGCCCTGCAGAGCGGCAACAGCCAGGAGA<br>GCGTCACCGAGCAGGACAGCAAGGACTCCACCTACAGCCTGAGC<br>AGCACCCTGACCCTGAGCAAGGCCGACTACGAGAAGCATAAGGT<br>GTACGCCTGCGAGGTGACCCACCAGGGCCTGTCCAGCCCCGTGA<br>CCAAGAGCTTCAACAGGGGCGAGTGC |
| | Combined CDR Consensus sequences | |
| SEQ ID NO: 347 | HCDR1 | GFTFXSAAVH |
| SEQ ID NO: 348 | HCDR2 | RIKSKAXGGTTDYAAPVKG |
| SEQ ID NO: 349 | HCDR2 | RIKSKXXGGTTDYAAPVKG |
| SEQ ID NO: 357 | HCDR2 | RIKSKAXXGTTDYAAPVKG |
| SEQ ID NO: 358 | HCDR2 | RIKSKXXXGTTDYAAPVKG |
| SEQ ID NO: 350 | HCDR3 | DSPSISSYSIPYFSGMDV |
| SEQ ID NO: 351 | LCDR1 | RASQGIRAWLN |
| SEQ ID NO: 352 | LCDR1 | RASQXIXXXLN |
| SEQ ID NO: 353 | LCDR2 | AASSLQS |
| SEQ ID NO: 359 | LCDR2 | AASXLQS |
| SEQ ID NO: 354 | LCDR3 | HQYITHPPT |
| SEQ ID NO: 355 | LCDR3 | HQYIXXPXT |
| | Kabat CDR Consensus sequences | |
| SEQ ID NO: 356 | HCDR1 | SAAVH |
| SEQ ID NO: 348 | HCDR2 | RIKSKAXGGITDYAAPVKG |
| SEQ ID NO: 349 | HCDR2 | RIKSKXXGGITDYAAPVKG |
| SEQ ID NO: 357 | HCDR2 | RIKSKAXXGTTDYAAPVKG |
| SEQ ID NO: 358 | HCDR2 | RIKSKXXXGTTDYAAPVKG |
| SEQ ID NO: 350 | HCDR3 | DSPSISSYSIPYFSGMDV |
| SEQ ID NO: 351 | LCDR1 | RASQGIRAWLN |
| SEQ ID NO: 352 | LCDR1 | RASQXIXXXLN |
| SEQ ID NO: 353 | LCDR2 | AASSLQS |
| SEQ ID NO: 359 | LCDR2 | AASXLQS |
| SEQ ID NO: 354 | LCDR3 | HQYITHPPT |
| SEQ ID NO: 355 | LCDR3 | HQYIXXPXT |

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), or Lefranc et al., (2003) Dev. Comp. Immunol., 27, 55-77 ("IMGT" numbering scheme). Other methods for delineating the CDR regions may alternatively be used. For example, the CDR definitions of both Kabat and Chothia may be combined ("Combined" system).

For example, under Kabat, the CDR amino acid residues of an antibody in the heavy chain variable domain (VH) are numbered 31-35 (HCDR1), 50-66 (HCDR2), and 99-111 (HCDR3); and the CDR amino acid residues in the light chain variable domain (VL) are numbered 22-35 (LCDR1), 51-57 (LCDR2), and 90-100 (LCDR3). Under Chothia the CDR amino acids in the VH are numbered 26-32 (HCDR1), 52-57 (HCDR2), and 99-111 (HCDR3); and the amino acid residues in VL are numbered 25-33 (LCDR1), 51-53 (LCDR2), and 92-99 (LCDR3). By combining the CDR definitions of both Kabat and Chothia, the "Combined" CDRs consist of amino acid residues 26-35 (HCDR1), 50-66 (HCDR2), and 99-108 (HCDR3) in human VH and amino acid residues 24-38 (LCDR1), 54-60 (LCDR2), and 93-101 (LCDR3) in human VL. As another example, under IMGT, the CDR amino acid residues in the heavy chain variable domain (VH) are numbered 26-33 (HCDR1), 51-58 (HCDR2), and 97-108 (HCDR3); and the CDR amino acid residues in the light chain variable domain (VL) are numbered 27-36 (LCDR1), 54-56 (LCDR2), and 93-101 (LCDR3). Table 2 provides exemplary Kabat, Chothia, Combined, and IMGT HCDR1, HCDR2, HCDR3, LCDR1, LCDR2, and LCDR3 for anti-FXI/FXIa antibody binding agents (e.g., antibodies), e.g., IDT1-IDT10.

Since each of the antibodies disclosed in Table 2, can bind to anti-FXI/FXIa antibody NOV1401, and antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and matched), although each antibody preferably contains a VH CDR1, 2 and 3 and a VL CDR1, 2 and 3 to create other FXI and/or FXIa binding molecules provided herein. Such "mixed and matched" anti-FXI/FXIa antibody binding agents can be tested using the binding assays known in the art and those described in the Examples (e.g., ELISAs, SET, BIACORE™ assays). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for antibodies provided herein. In addition to the foregoing, in one aspect, binding agents provided herein may be antigen-binding fragments of antibodies and can comprise a VH CDR1, 2, and 3, or a VL CDR 1, 2, and 3, wherein the fragment binds to an anti-FXI/FXIa antibody, such as NOV1401, as a single variable domain.

In particular aspects, provided herein is a binding agent (e.g., anti-idiotype antibody and fragments thereof, such as Fab fragment) which specifically binds a target anti-FXI/FXIa antibody, wherein the binding agent inhibits an anti-coagulant activity of the target anti-FXI/FXIa antibody, wherein the target anti-FXI/FXIa antibody is antibody NOV1401 (comprising a VH comprising the amino acid sequence of SEQ ID NO: 12 and a VL comprising the amino acid sequence of SEQ ID NO: 23), and wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein:

a. the HCDR1 comprises the amino acid sequence of SEQ ID NO: 27, 59, 91, 123, 155, 187, 219, 251, 283, or 315;
b. the HCDR2 comprises the amino acid sequence of SEQ ID NO: 28, 60, 92, 124, 156, 188, 220, 252, 284, or 316;
c. the HCDR3 comprises the amino acid sequence of SEQ ID NO: 29, 61, 93, 125, 157, 189, 221, 253, 285, or 317;
d. the LCDR1 comprises the amino acid sequence of SEQ ID NO: 43, 75, 107, 139, 171, 203, 235, 267, 299, or 331;
e. the LCDR2 comprises the amino acid sequence of SEQ ID NO: 44, 76, 108, 140, 172, 204, 236, 268, 300, or 332; and
f. the LCDR3 comprises the amino acid sequence of SEQ ID NO: 45, 77, 109, 141, 173, 205, 237, 269, 301, or 333.

In particular aspects, provided herein is a binding agent (e.g., anti-idiotype antibody and fragments thereof, such as Fab fragment) which specifically binds a target anti-FXI/FXIa antibody, wherein the binding agent inhibits an anti-coagulant activity of the target anti-FXI/FXIa antibody, wherein the target anti-FXI/FXIa antibody is antibody NOV1401 (comprising a VH comprising the amino acid sequence of SEQ ID NO: 12 and a VL comprising the amino acid sequence of SEQ ID NO: 23), and wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein:

a. the HCDR1 comprises the amino acid sequence of SEQ ID NO: 30, 62, 94, 126, 158, 190, 222, 254, 286, or 318;
b. the HCDR2 comprises the amino acid sequence of SEQ ID NO: 31, 63, 95, 127, 159, 191, 223, 255, 287, or 319;
c. the HCDR3 comprises the amino acid sequence of SEQ ID NO: 32, 64, 96, 128, 160, 192, 224, 256, 288, or 320;
d. the LCDR1 comprises the amino acid sequence of SEQ ID NO: 46, 78, 110, 142, 174, 206, 238, 270, 302, or 334;
e. the LCDR2 comprises the amino acid sequence of SEQ ID NO: 47, 79, 111, 143, 175, 207, 239, 271, 303, or 335; and
f. the LCDR3 comprises the amino acid sequence of SEQ ID NO: 48, 80, 112, 144, 176, 208, 240, 272, 304, or 336.

In particular aspects, provided herein is a binding agent (e.g., anti-idiotype antibody and fragments thereof, such as Fab fragment) which specifically binds a target anti-FXI/FXIa antibody, wherein the binding agent inhibits an anti-coagulant activity of the target anti-FXI/FXIa antibody, wherein the target anti-FXI/FXIa antibody is antibody NOV1401 (comprising a VH comprising the amino acid sequence of SEQ ID NO: 12 and a VL comprising the amino acid sequence of SEQ ID NO: 23), and wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein a. the HCDR1 comprises the amino acid sequence GFTF-X1-SAAVH (SEQ ID NO: 347), wherein X1 is any amino acid or is S or Q;
b. the HCDR2 comprises the amino acid sequence RIK-SKA-X4-X5-GTTDYAAPVKG (SEQ ID NO: 357), RIKSK-X3-X4-X5-GTTDYAAPVKG (SEQ ID NO: 358), RIKSK-X3-X4-GGTTDYAAPVKG (SEQ ID NO: 349) or RIKSKA-X4-GGTTDYAAPVKG (SEQ ID NO: 348), wherein X3 is any amino acid or is T or A, X4 is any amino acid or is S or D, and X5 is any amino acid or is G or A;
c. the HCDR3 comprises the amino acid sequence DSP-SISSYSIPYFSGMDV (SEQ ID NO: 350);
d. the LCDR1 comprises the amino acid sequence RASQ-GIRAWLN (SEQ ID NO: 351) or RASQ-X6-I-X7-X8-X9-LN (SEQ ID NO: 352), wherein X6 is any amino acid or is S or G, X7 is any amino acid or is R or S, X8 is any amino acid or is A or N, and X9 is any amino acid or is W or Y;
e. the LCDR2 comprises the amino acid sequence AASS-LQS (SEQ ID NO: 353); and f. the LCDR3 comprises the amino acid sequence HQYITHPPT (SEQ ID NO: 354) or HQYI-X10-X11-P-X12-T (SEQ ID NO: 355), wherein X10 is any amino acid or is T or A, X11 is any amino acid or is H or K, and X12 is any amino acid or is P or I.

In particular aspects, provided herein is a binding agent (e.g., anti-idiotype antibody and fragments thereof, such as Fab fragment) which specifically binds a target anti-FXI/FXIa antibody, wherein the binding agent inhibits an anticoagulant activity of the target anti-FXI/FXIa antibody, wherein the target anti-FXI/FXIa antibody is antibody NOV1401 (comprising a VH comprising the amino acid sequence of SEQ ID NO: 12 and a VL comprising the amino acid sequence of SEQ ID NO: 23), and wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein a. the HCDR1 comprises the amino acid sequence GFTF-X1-SAAVH (SEQ ID NO: 347), wherein X1 is S or Q;
b. the HCDR2 comprises the amino acid sequence RIKSKA-X4-X5-GTTDYAAPVKG (SEQ ID NO: 357), wherein X4 is S or D and X5 is G or A;
c. the HCDR3 comprises the amino acid sequence DSPSISSYSIPYFSGMDV (SEQ ID NO: 350);
d. the LCDR1 comprises the amino acid sequence RASQGIRAWLN (SEQ ID NO: 351);
e. the LCDR2 comprises the amino acid sequence AASSLQS (SEQ ID NO: 353); and
f. the LCDR3 comprises the amino acid sequence HQYITHPPT (SEQ ID NO: 354).

In particular aspects, provided herein is a binding agent (e.g., anti-idiotype antibody and fragments thereof, such as Fab fragment) which specifically binds a target anti-FXI/FXIa antibody, wherein the binding agent inhibits an anticoagulant activity of the target anti-FXI/FXIa antibody, wherein the target anti-FXI/FXIa antibody is antibody NOV1401 (comprising a VH comprising the amino acid sequence of SEQ ID NO: 12 and a VL comprising the amino acid sequence of SEQ ID NO: 23), and wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein a. the HCDR1 comprises the amino acid sequence SAAVH (SEQ ID NO: 356);
b. the HCDR2 comprises the amino acid sequence RIKSKA-X4-X5-GTTDYAAPVKG (SEQ ID NO: 357), RIKSK-X3-X4-X5-GTTDYAAPVKG (SEQ ID NO: 358), RIKSK-X3-X4-GGTTDYAAPVKG (SEQ ID NO: 349) or RIKSKA-X4-GGTTDYAAPVKG (SEQ ID NO: 348), wherein X3 is any amino acid or is T or A, X4 is any amino acid or is S or D, and X5 is any amino acid or is G or A;
c. the HCDR3 comprises the amino acid sequence DSPSISSYSIPYFSGMDV (SEQ ID NO: 350);
d. the LCDR1 comprises the amino acid sequence RASQGIRAWLN (SEQ ID NO: 351) or RASQ-X6-I-X7-X8-X9-LN (SEQ ID NO: 352), wherein X6 is any amino acid or is S or G, X7 is any amino acid or is R or S, X8 is any amino acid or is A or N, and X9 is any amino acid or is W or Y;
e. the LCDR2 comprises the amino acid sequence AASSLQS (SEQ ID NO: 353); and
f. the LCDR3 comprises the amino acid sequence HQYITHPPT (SEQ ID NO: 354) or HQYI-X10-X11-P-X12-T (SEQ ID NO: 355), wherein X10 is any amino acid or is T or A, X11 is any amino acid or is H or K, and X12 is any amino acid or is P or I.

In particular aspects, provided herein is a binding agent (e.g., anti-idiotype antibody and fragments thereof, such as Fab fragment) which specifically binds a target anti-FXI/FXIa antibody, wherein the binding agent inhibits an anticoagulant activity of the target anti-FXI/FXIa antibody, wherein the target anti-FXI/FXIa antibody is antibody NOV1401 (comprising a VH comprising the amino acid sequence of SEQ ID NO: 12 and a VL comprising the amino acid sequence of SEQ ID NO: 23), wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein a. the HCDR1 comprises the amino acid sequence SAAVH (SEQ ID NO: 356);
b. the HCDR2 comprises the amino acid sequence RIKSKA-X4-X5-GTTDYAAPVKG (SEQ ID NO: 357), wherein X4 is S or D and X5 is G or A;
c. the HCDR3 comprises the amino acid sequence DSPSISSYSIPYFSGMDV (SEQ ID NO: 350);
d. the LCDR1 comprises the amino acid sequence RASQGIRAWLN (SEQ ID NO: 351);
e. the LCDR2 comprises the amino acid sequence AASSLQS (SEQ ID NO: 353); and
f. the LCDR3 comprises the amino acid sequence HQYITHPPT (SEQ ID NO: 354).

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 91, the HCDR2 comprises the amino acid sequence of SEQ ID NO: 92, the HCDR3 comprises the amino acid sequence of SEQ ID NO: 93, the LCDR1 comprises the amino acid sequence of SEQ ID NO: 107, the LCDR2 comprises the amino acid sequence of SEQ ID NO: 108, and the LCDR3 comprises the amino acid sequence of SEQ ID NO: 109.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 94, the HCDR2 comprises the amino acid sequence of SEQ ID NO: 95, the HCDR3 comprises the amino acid sequence of SEQ ID NO: 96, the LCDR1 comprises the amino acid sequence of SEQ ID NO: 110, the LCDR2 comprises the amino acid sequence of SEQ ID NO: 111, and the LCDR3 comprises the amino acid sequence of SEQ ID NO: 112.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 97, the HCDR2 comprises the amino acid sequence of SEQ ID NO: 98, the HCDR3 comprises the amino acid sequence of SEQ ID NO: 99, the LCDR1 comprises the amino acid sequence of SEQ ID NO: 113, the LCDR2 comprises the amino acid sequence of SEQ ID NO: 114, and the LCDR3 comprises the amino acid sequence of SEQ ID NO: 115.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 100, the HCDR2 comprises the amino acid sequence of SEQ ID NO: 101, the HCDR3 comprises the amino acid sequence of SEQ ID NO: 102, the LCDR1 comprises the amino acid sequence of SEQ ID NO: 116, the LCDR2 comprises the amino acid sequence of SEQ ID NO: 117, and the LCDR3 comprises the amino acid sequence of SEQ ID NO: 118.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 27, the HCDR2 comprises the amino acid sequence of SEQ ID NO: 28, the HCDR3 comprises the amino acid sequence of SEQ ID NO: 29, the LCDR1 comprises the amino acid sequence of SEQ ID NO: 43, the LCDR2 comprises the amino acid sequence of SEQ ID NO: 44, and the LCDR3 comprises the amino acid sequence of SEQ ID NO: 45.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 30, the HCDR2 comprises the amino acid sequence of SEQ ID NO: 31, the HCDR3 comprises the amino acid sequence of SEQ ID NO: 32, the LCDR1 comprises the amino acid sequence of SEQ ID NO: 46, the LCDR2 comprises the amino acid sequence of SEQ ID NO: 47, and the LCDR3 comprises the amino acid sequence of SEQ ID NO: 48.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 33, the HCDR2 comprises the amino acid sequence of SEQ ID NO: 34, the HCDR3 comprises the amino acid sequence of SEQ ID NO: 35, the LCDR1 comprises the amino acid sequence of SEQ ID NO: 49, the LCDR2 comprises the amino acid sequence of SEQ ID NO: 50, and the LCDR3 comprises the amino acid sequence of SEQ ID NO: 51.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 36, the HCDR2 comprises the amino acid sequence of SEQ ID NO: 37, the HCDR3 comprises the amino acid sequence of SEQ ID NO: 38, the LCDR1 comprises the amino acid sequence of SEQ ID NO: 52, the LCDR2 comprises the amino acid sequence of SEQ ID NO: 53, and the LCDR3 comprises the amino acid sequence of SEQ ID NO: 54.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 59, the HCDR2 comprises the amino acid sequence of SEQ ID NO: 60, the HCDR3 comprises the amino acid sequence of SEQ ID NO: 61, the LCDR1 comprises the amino acid sequence of SEQ ID NO: 75, the LCDR2 comprises the amino acid sequence of SEQ ID NO: 76, and the LCDR3 comprises the amino acid sequence of SEQ ID NO: 77.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 62, the HCDR2 comprises the amino acid sequence of SEQ ID NO: 63, the HCDR3 comprises the amino acid sequence of SEQ ID NO: 64, the LCDR1 comprises the amino acid sequence of SEQ ID NO: 78, the LCDR2 comprises the amino acid sequence of SEQ ID NO: 79, and the LCDR3 comprises the amino acid sequence of SEQ ID NO: 80.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 65, the HCDR2 comprises the amino acid sequence of SEQ ID NO: 66, the HCDR3 comprises the amino acid sequence of SEQ ID NO: 67, the LCDR1 comprises the amino acid sequence of SEQ ID NO: 81, the LCDR2 comprises the amino acid sequence of SEQ ID NO: 82, and the LCDR3 comprises the amino acid sequence of SEQ ID NO: 83.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 68, the HCDR2 comprises the amino acid sequence of SEQ ID NO: 69, the HCDR3 comprises the amino acid sequence of SEQ ID NO: 70, the LCDR1 comprises the amino acid sequence of SEQ ID NO: 84, the LCDR2 comprises the amino acid sequence of SEQ ID NO: 85, and the LCDR3 comprises the amino acid sequence of SEQ ID NO: 86.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 123, the HCDR2 comprises the amino acid sequence of SEQ ID NO: 124, the HCDR3 comprises the amino acid sequence of SEQ ID NO: 125, the LCDR1 comprises the amino acid sequence of SEQ ID NO: 139, the LCDR2 comprises the amino acid sequence of SEQ ID NO: 140, and the LCDR3 comprises the amino acid sequence of SEQ ID NO: 141.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 126, the HCDR2 comprises the amino acid sequence of SEQ ID NO: 127, the HCDR3 comprises the amino acid sequence of SEQ ID NO: 128, the LCDR1 comprises the amino acid sequence of SEQ ID NO: 142, the LCDR2 comprises the amino acid sequence of SEQ ID NO: 143, and the LCDR3 comprises the amino acid sequence of SEQ ID NO: 144.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 129, the HCDR2 comprises the amino acid sequence of SEQ ID NO: 130, the HCDR3 comprises the amino acid sequence of SEQ ID NO: 131, the LCDR1 comprises the amino acid sequence of SEQ ID NO: 145, the LCDR2 comprises the amino acid sequence of SEQ ID NO: 146, and the LCDR3 comprises the amino acid sequence of SEQ ID NO: 147.

In particular aspects, provided herein is a binding agent (e.g., anti-idiotype antibody and fragments thereof, such as Fab fragment) which specifically binds a target anti-FXI/

FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 132, the HCDR2 comprises the amino acid sequence of SEQ ID NO: 133, the HCDR3 comprises the amino acid sequence of SEQ ID NO: 134, the LCDR1 comprises the amino acid sequence of SEQ ID NO: 148, the LCDR2 comprises the amino acid sequence of SEQ ID NO: 149, and the LCDR3 comprises the amino acid sequence of SEQ ID NO: 150.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 155, the HCDR2 comprises the amino acid sequence of SEQ ID NO: 156, the HCDR3 comprises the amino acid sequence of SEQ ID NO: 157, the LCDR1 comprises the amino acid sequence of SEQ ID NO: 171, the LCDR2 comprises the amino acid sequence of SEQ ID NO: 172, and the LCDR3 comprises the amino acid sequence of SEQ ID NO: 173.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 158, the HCDR2 comprises the amino acid sequence of SEQ ID NO: 159, the HCDR3 comprises the amino acid sequence of SEQ ID NO: 160, the LCDR1 comprises the amino acid sequence of SEQ ID NO: 174, the LCDR2 comprises the amino acid sequence of SEQ ID NO: 175, and the LCDR3 comprises the amino acid sequence of SEQ ID NO: 176.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 161, the HCDR2 comprises the amino acid sequence of SEQ ID NO: 162, the HCDR3 comprises the amino acid sequence of SEQ ID NO: 163, the LCDR1 comprises the amino acid sequence of SEQ ID NO: 177, the LCDR2 comprises the amino acid sequence of SEQ ID NO: 178, and the LCDR3 comprises the amino acid sequence of SEQ ID NO: 179.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 164, the HCDR2 comprises the amino acid sequence of SEQ ID NO: 165, the HCDR3 comprises the amino acid sequence of SEQ ID NO: 166, the LCDR1 comprises the amino acid sequence of SEQ ID NO: 180, the LCDR2 comprises the amino acid sequence of SEQ ID NO: 181, and the LCDR3 comprises the amino acid sequence of SEQ ID NO: 182.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 187, the HCDR2 comprises the amino acid sequence of SEQ ID NO: 188, the HCDR3 comprises the amino acid sequence of SEQ ID NO: 189, the LCDR1 comprises the amino acid sequence of SEQ ID NO: 203, the LCDR2 comprises the amino acid sequence of SEQ ID NO: 204, and the LCDR3 comprises the amino acid sequence of SEQ ID NO: 205.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 190, the HCDR2 comprises the amino acid sequence of SEQ ID NO: 191, the HCDR3 comprises the amino acid sequence of SEQ ID NO: 192, the LCDR1 comprises the amino acid sequence of SEQ ID NO: 206, the LCDR2 comprises the amino acid sequence of SEQ ID NO: 207, and the LCDR3 comprises the amino acid sequence of SEQ ID NO: 208.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 193, the HCDR2 comprises the amino acid sequence of SEQ ID NO: 194, the HCDR3 comprises the amino acid sequence of SEQ ID NO: 195, the LCDR1 comprises the amino acid sequence of SEQ ID NO: 209, the LCDR2 comprises the amino acid sequence of SEQ ID NO: 210, and the LCDR3 comprises the amino acid sequence of SEQ ID NO: 211.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 196, the HCDR2 comprises the amino acid sequence of SEQ ID NO: 197, the HCDR3 comprises the amino acid sequence of SEQ ID NO: 198, the LCDR1 comprises the amino acid sequence of SEQ ID NO: 212, the LCDR2 comprises the amino acid sequence of SEQ ID NO: 213, and the LCDR3 comprises the amino acid sequence of SEQ ID NO: 214.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 219, the HCDR2 comprises the amino acid sequence of SEQ ID NO: 220, the HCDR3 comprises the amino acid sequence of SEQ ID NO: 221, the LCDR1 comprises the amino acid sequence of SEQ ID NO: 235, the LCDR2 comprises the amino acid sequence of SEQ ID NO: 236, and the LCDR3 comprises the amino acid sequence of SEQ ID NO: 237.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 222, the HCDR2 comprises the amino acid sequence of SEQ ID NO: 223, the HCDR3 comprises the amino acid sequence of SEQ ID NO: 224, the LCDR1 comprises the amino acid sequence of SEQ ID NO: 238, the LCDR2 comprises the amino acid sequence of SEQ ID NO: 239, and the LCDR3 comprises the amino acid sequence of SEQ ID NO: 240.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 225, the HCDR2 comprises the amino acid sequence of SEQ ID NO: 226, the HCDR3 comprises the amino acid sequence of SEQ ID NO: 227, the LCDR1 comprises the amino acid sequence of SEQ ID NO: 241, the LCDR2 comprises the amino acid sequence of SEQ ID NO: 242, and the LCDR3 comprises the amino acid sequence of SEQ ID NO: 243.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 228, the HCDR2 comprises the amino acid sequence of SEQ ID NO: 229, the HCDR3 comprises the amino acid sequence of SEQ ID NO: 230, the LCDR1 comprises the amino acid sequence of SEQ ID NO: 244, the LCDR2 comprises the amino acid sequence of SEQ ID NO: 245, and the LCDR3 comprises the amino acid sequence of SEQ ID NO: 246.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 251, the HCDR2 comprises the amino acid sequence of SEQ ID NO: 252, the HCDR3 comprises the amino acid sequence of SEQ ID NO: 253, the LCDR1 comprises the amino acid sequence of SEQ ID NO: 267, the LCDR2 comprises the amino acid sequence of SEQ ID NO: 268, and the LCDR3 comprises the amino acid sequence of SEQ ID NO: 269.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 254, the HCDR2 comprises the amino acid sequence of SEQ ID NO: 255, the HCDR3 comprises the amino acid sequence of SEQ ID NO: 256, the LCDR1 comprises the amino acid sequence of SEQ ID NO: 270, the LCDR2 comprises the amino acid sequence of SEQ ID NO: 271, and the LCDR3 comprises the amino acid sequence of SEQ ID NO: 272.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 257, the HCDR2 comprises the amino acid sequence of SEQ ID NO: 258, the HCDR3 comprises the amino acid sequence of SEQ ID NO: 259, the LCDR1 comprises the amino acid sequence of SEQ ID NO: 273, the LCDR2 comprises the amino acid sequence of SEQ ID NO: 274, and the LCDR3 comprises the amino acid sequence of SEQ ID NO: 275.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 260, the HCDR2 comprises the amino acid sequence of SEQ ID NO: 261, the HCDR3 comprises the amino acid sequence of SEQ ID NO: 262, the LCDR1 comprises the amino acid sequence of SEQ ID NO: 276, the LCDR2 comprises the amino acid sequence of SEQ ID NO: 277, and the LCDR3 comprises the amino acid sequence of SEQ ID NO: 278.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 283, the HCDR2 comprises the amino acid sequence of SEQ ID NO: 284, the HCDR3 comprises the amino acid sequence of SEQ ID NO: 285, the LCDR1 comprises the amino acid sequence of SEQ ID NO: 299, the LCDR2 comprises the amino acid sequence of SEQ ID NO: 300, and the LCDR3 comprises the amino acid sequence of SEQ ID NO: 301.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 286, the HCDR2 comprises the amino acid sequence of SEQ ID NO: 287, the HCDR3 comprises the amino acid sequence of SEQ ID NO: 288, the LCDR1 comprises the amino acid sequence of SEQ ID NO: 302, the LCDR2 comprises the amino acid sequence of SEQ ID NO: 303, and the LCDR3 comprises the amino acid sequence of SEQ ID NO: 304.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 289, the HCDR2 comprises the amino acid sequence of SEQ ID NO: 290, the HCDR3 comprises the amino acid sequence of SEQ ID NO: 291, the LCDR1 comprises the amino acid sequence of SEQ ID NO: 305, the LCDR2 comprises the amino acid sequence of SEQ ID NO: 306, and the LCDR3 comprises the amino acid sequence of SEQ ID NO: 307.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 292, the HCDR2 comprises the amino acid sequence of SEQ ID NO: 293, the HCDR3 comprises the amino acid sequence of SEQ ID NO: 294, the LCDR1 comprises the amino acid sequence of SEQ ID NO: 308, the LCDR2 comprises the amino acid sequence of SEQ ID NO: 309, and the LCDR3 comprises the amino acid sequence of SEQ ID NO: 310.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 315, the HCDR2 comprises the amino acid sequence of SEQ ID NO: 316, the HCDR3 comprises the amino acid sequence of SEQ ID NO: 317, the LCDR1 comprises the amino acid sequence of SEQ ID NO: 331, the LCDR2 comprises the amino acid sequence of SEQ ID NO: 332, and the LCDR3 comprises the amino acid sequence of SEQ ID NO: 333.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 318, the HCDR2 comprises the amino acid sequence of SEQ ID NO: 319, the HCDR3 comprises the amino acid sequence of SEQ ID NO: 320, the LCDR1 comprises the amino acid sequence of SEQ ID NO: 334, the LCDR2 comprises the amino acid sequence of SEQ ID NO: 335, and the LCDR3 comprises the amino acid sequence of SEQ ID NO: 336.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 321, the HCDR2 comprises the amino acid sequence of SEQ ID NO: 322, the HCDR3 comprises the amino acid sequence of SEQ ID NO: 323, the LCDR1 comprises the amino acid sequence of SEQ ID NO: 337, the LCDR2 comprises the amino acid sequence of SEQ ID NO: 338, and the LCDR3 comprises the amino acid sequence of SEQ ID NO: 339.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein the HCDR1 comprises the amino acid sequence of SEQ ID NO: 324, the HCDR2 comprises the amino acid sequence of SEQ ID NO: 325, the HCDR3 comprises the amino acid sequence of SEQ ID NO: 326, the LCDR1 comprises the amino acid sequence of SEQ ID NO: 340, the LCDR2 comprises the amino acid sequence of SEQ ID NO: 341, and the LCDR3 comprises the amino acid sequence of SEQ ID NO: 342.

Since each of the binding agents (e.g., antibodies) disclosed in Table 2, can bind to anti-FXI/FXIa antibody NOV1401, the VH, VL, full length light chain, and full length heavy chain sequences (amino acid sequences and the nucleotide sequences encoding the amino acid sequences) can be "mixed and matched" to create other anti-FXI/FXIa antibody binding agents. Such "mixed and matched" anti-FXI/FXIa antibody binding agents can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a VH and a VL, wherein the VH comprises the amino acid sequence of SEQ ID NO: 39, 71, 103, 135, 167, 199, 231, 263, 295, or 327, and the VL comprises the amino acid sequence of SEQ ID NO: 55, 87, 119, 151, 183, 215, 247, 279, 311, or 343.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a VH and a VL, wherein the VH comprises the amino acid sequence of SEQ ID NO: 39 and the VL comprises the amino acid sequence of SEQ ID NO: 55.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a VH and a VL, and wherein the VH comprises the amino acid sequence of SEQ ID NO: 71 and the VL comprises the amino acid sequence of SEQ ID NO: 87.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a VH and a VL, and wherein the VH comprises the amino acid sequence of SEQ ID NO: 103 and the VL comprises the amino acid sequence of SEQ ID NO: 119.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a VH and a VL, and wherein the VH comprises the amino acid sequence of SEQ ID NO: 135 and the VL comprises the amino acid sequence of SEQ ID NO: 151.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a VH and a VL, and wherein the VH comprises the amino acid sequence of SEQ ID NO: 167 and the VL comprises the amino acid sequence of SEQ ID NO: 183.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a VH and a VL, and wherein the VH comprises the amino acid sequence of SEQ ID NO: 199 and the VL comprises the amino acid sequence of SEQ ID NO: 215.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a VH and a VL, and wherein the VH comprises the amino acid sequence of SEQ ID NO: 231 and the VL comprises the amino acid sequence of SEQ ID NO: 247.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a VH and a VL, and wherein the VH comprises the amino acid sequence of SEQ ID NO: 263 and the VL comprises the amino acid sequence of SEQ ID NO: 279.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a VH and a VL, and wherein the VH comprises the amino acid sequence of SEQ ID NO: 295 and the VL comprises the amino acid sequence of SEQ ID NO: 311.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a VH and a VL, and wherein the VH comprises the amino acid sequence of SEQ ID NO: 327 and the VL comprises the amino acid sequence of SEQ ID NO: 343.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a heavy chain and a light chain, wherein the heavy chain comprises the amino acid sequence of SEQ ID NO: 41, 73, 105, 137, 169, 201, 233, 265, 297, or 329, and the light chain comprises the amino acid sequence of SEQ ID NO: 57, 89, 121, 153, 185, 217, 249, 281, 313, or 345.

In particular aspects, provided herein is a binding agent (e.g., anti-idiotype antibody and fragments thereof, such as Fab fragment) which specifically binds a target anti-FXI/

FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a heavy chain and a light chain, and wherein the heavy chain comprises the amino acid sequence of SEQ ID NO: 41 and the light chain comprises the amino acid sequence of SEQ ID NO: 57.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a heavy chain and a light chain, and wherein the heavy chain comprises the amino acid sequence of SEQ ID NO: 73 and the light chain comprises the amino acid sequence of SEQ ID NO: 89.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a heavy chain and a light chain, and wherein the heavy chain comprises the amino acid sequence of SEQ ID NO: 105 and the light chain comprises the amino acid sequence of SEQ ID NO: 121.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a heavy chain and a light chain, and wherein the heavy chain comprises the amino acid sequence of SEQ ID NO: 137 and the light chain comprises the amino acid sequence of SEQ ID NO: 153.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a heavy chain and a light chain, and wherein the heavy chain comprises the amino acid sequence of SEQ ID NO: 169 and the light chain comprises the amino acid sequence of SEQ ID NO: 185.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a heavy chain and a light chain, and wherein the heavy chain comprises the amino acid sequence of SEQ ID NO: 201 and the light chain comprises the amino acid sequence of SEQ ID NO: 217.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a heavy chain and a light chain, and wherein the heavy chain comprises the amino acid sequence of SEQ ID NO: 233 and the light chain comprises the amino acid sequence of SEQ ID NO: 249.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a heavy chain and a light chain, and wherein the heavy chain comprises the amino acid sequence of SEQ ID NO: 265 and the light chain comprises the amino acid sequence of SEQ ID NO: 281.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a heavy chain and a light chain, and wherein the heavy chain comprises the amino acid sequence of SEQ ID NO: 297 and the light chain comprises the amino acid sequence of SEQ ID NO: 313.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a heavy chain and a light chain, and wherein the heavy chain comprises the amino acid sequence of SEQ ID NO: 329 and the light chain comprises the amino acid sequence of SEQ ID NO: 345.

In certain aspects, provided herein is a binding agent (e.g., anti-idiotype antibody and fragments thereof, such as Fab fragment) which specifically binds a target anti-FXI/FXIa antibody, such as NOV1401 (e.g., comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody Fab fragment of antibody IDT1, IDT2, IDT3, IDT4, IDT5, IDT6, IDT7, IDT8, IDT9, or IDT10, for example, as set forth in Table 2.

In certain aspects, provided herein is a binding agent (e.g., anti-idiotype antibody and fragments thereof, such as Fab fragment) which specifically binds a target anti-FXI/FXIa antibody, such as NOV1401 (e.g., comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody Fab fragment of antibody IDT1, IDT2, IDT3, IDT4, IDT5, IDT6, IDT7, IDT8, IDT9, or IDT10, for example, as set forth in Table 2, and is a recombinant, monoclonal human antibody.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody.

A human antibody that is "the product of" or "derived from" a particular human germline immunoglobulin sequence may contain amino acid differences as compared to the germline sequence, due to, for example, naturally occurring somatic mutations or intentional introduction of site-directed mutations. However, in specific aspects, in the VH or VL framework regions, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene.

In specific aspects, typically, a recombinant human antibody will display no more than 10 amino acid differences from the amino acid sequence encoded by the human germline immunoglobulin gene in the VH or VL framework regions. In certain cases, the human antibody may display no more than 5, or even no more than 4, 3, 2, or 1 amino acid difference from the amino acid sequence encoded by the germline immunoglobulin gene. Examples of human germline immunoglobulin genes include, but are not limited to the variable domain germline fragments described here, as well as DP47 and DPK9.

Homologous Antibodies

In another aspect, the present disclosure provides a binding agent comprising amino acid sequences that are homologous to sequences described in Table 2, wherein the binding agent binds to an anti-FXI/FXIa antibody, and retains the desired functional properties (e.g., reversal of one or more anticoagulant effects) of those antibodies described in Table 2 such as any one of antibodies IDT1-IDT10. In specific aspects, such homologous antibodies retain the CDR amino acid sequences described in Table 2 (e.g., Kabat CDRs, Chothia CDRs, IMGT CDRs, or Combined CDRs).

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a VH and a VL, and wherein the VH and VL comprise amino acid sequences that are at least 80%, at least 85%, at least 90%, at least 91%, at least 92%, at least 93%, at least 94%, at least 95%, at least 96%, at least 97%, at least 98% or at least 99% identical to the VH and VL sequences selected from Table 2. In a further specific aspect, the differences in amino acid sequence in the VL and/or VH of the binding agent is not within the complementarity determining regions.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a VH and a VL, and wherein the VH comprises an amino acid sequence that is at least 90% or at least 95% identical to the amino acid sequence of SEQ ID NO: 39 and the VL comprises an amino acid sequence that is at least 90% or at least 95% identical to the amino acid sequence of SEQ ID NO: 55. In a further specific aspect, the differences in amino acid sequence in the VL and/or VH of the binding agent is not within the complementarity determining regions.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a VH and a VL, and wherein the VH comprises an amino acid sequence that is at least 90% or at least 95% identical to the amino acid sequence of SEQ ID NO: 71 and the VL comprises the amino acid sequence of SEQ ID NO: 87. In a further specific aspect, the differences in amino acid sequence in the VL and/or VH of the binding agent is not within the complementarity determining regions.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a VH and a VL, and wherein the VH comprises an amino acid sequence that is at least 90% or at least 95% identical to the amino acid sequence of SEQ ID NO: 103 and the VL comprises the amino acid sequence of SEQ ID NO: 119. In a further specific aspect, the differences in amino acid sequence in the VL and/or VH of the binding agent is not within the complementarity determining regions.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a VH and a VL, and wherein the VH comprises an amino acid sequence that is at least 90% or at least 95% identical to the amino acid sequence of SEQ ID NO: 135 and the VL comprises an amino acid sequence that is at least 90% or at least 95% identical to the amino acid sequence of SEQ ID NO: 151. In a further specific aspect, the differences in amino acid sequence in the VL and/or VH of the binding agent is not within the complementarity determining regions.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a VH and a VL, and wherein the VH comprises an amino acid sequence that is at least 90% or at least 95% identical to the amino acid sequence of SEQ ID NO: 167 and the VL comprises an amino acid sequence that is at least 90% or at least 95% identical to the amino acid sequence of SEQ ID NO: 183. In a further specific aspect, the differences in amino acid sequence in the VL and/or VH of the binding agent is not within the complementarity determining regions.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a VH and a VL, and wherein the VH comprises an amino acid sequence that is at least 90% or at least 95% identical to the amino acid sequence of SEQ ID NO: 199 and the VL comprises an amino acid sequence that is at least 90% or at least 95% identical to the amino acid sequence of SEQ ID NO: 215. In a further specific aspect, the differences in amino acid sequence in the VL and/or VH of the binding agent is not within the complementarity determining regions.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a VH and a VL, and wherein the VH comprises an amino acid sequence that is at least 90% or at least 95% identical to the amino acid sequence of SEQ ID NO: 231 and the VL comprises an amino acid sequence that is at least 90% or at least 95% identical to the amino acid sequence of SEQ ID NO: 247. In a further specific aspect, the differences in amino acid sequence in the VL and/or VH of the binding agent is not within the complementarity determining regions.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a VH and a VL, and wherein the VH comprises an amino acid sequence that is at least 90% or at least 95% identical to the amino acid sequence of SEQ ID NO: 263 and the VL comprises an amino acid sequence that is at least 90% or at least 95% identical to the amino acid sequence of SEQ ID NO: 279. In a further specific aspect, the differences in amino acid sequence in the VL and/or VH of the binding agent is not within the complementarity determining regions.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a VH and a VL, and wherein the VH comprises an amino acid sequence that is at least 90% or at least 95% identical to the amino acid sequence of SEQ ID NO: 295 and the VL comprises an amino acid sequence that is at least 90% or at least 95% identical to the amino acid sequence of SEQ ID NO: 311. In a further specific aspect, the differences in amino acid sequence in the VL and/or VH of the binding agent is not within the complementarity determining regions.

In particular aspects, provided herein is a binding agent (e.g., anti-idiotype antibody and fragments thereof, such as Fab fragment) which specifically binds a target anti-FXI/FXIa antibody (e.g., NOV1401 comprising a VH comprising the amino acid sequence of SEQ ID NO: 12 and a VL comprising the amino acid sequence of SEQ ID NO: 23), wherein the binding agent inhibits an anticoagulant activity of the target anti-FXI/FXIa antibody, wherein the binding agent is an antibody or antigen-binding fragment thereof comprising a VH and a VL, and wherein the VH comprises an amino acid sequence that is at least 90% or at least 95% identical to the amino acid sequence of SEQ ID NO: 327 and the VL comprises an amino acid sequence that is at least 90% or at least 95% identical to the amino acid sequence of SEQ ID NO: 343. In a further specific aspect, the differences in amino acid sequence in the VL and/or VH of the binding agent is not within the complementarity determining regions.

As used herein, the percent identity between the two sequences is a function of the number of identical positions shared by the sequences (i.e., % identity equals number of identical positions/total number of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

Additionally or alternatively, the protein sequences of the present invention can further be used as a "query sequence" to perform a search against public databases to, for example, identify related sequences. For example, such searches can be performed using the BLAST program (version 2.0) of Altschul, et al., 1990 J. Mol. Biol. 215:403-10.

The present disclosure also provides a binding agent (e.g., anti-idiotype antibody and fragments thereof, such as Fab fragment) which specifically binds a target anti-FXI/FXIa antibody (e.g., NOV1401), wherein the binding agent is an antibody or antigen-binding fragment thereof comprising (or alternatively, consisting of) a VH amino acid sequence listed in Table 2, wherein no more than about 1, 2, 3, 4, 5, 6, 7, 8, 9, 10, 11, 12, 13, 14, 15, 16, 17, 18, 19, or 20 amino acids in a framework sequence (for example, a sequence which is not a CDR) have been mutated (wherein a mutation is, as various non-limiting examples, an addition, substitution or deletion).

The present disclosure also provides a binding agent (e.g., anti-idiotype antibody and fragments thereof, such as Fab fragment) which specifically binds a target anti-FXI/FXIa antibody (e.g., NOV1401), wherein the binding agent is an antibody or antigen-binding fragment thereof comprising (or alternatively, consisting of) a VL amino acid sequence listed in Table 2, wherein no more than about 1, 2, 3, 4, 5, 6, 7, 8, 9, 10, 11, 12, 13, 14, 15, 16, 17, 18, 19, or 20 amino acids in a framework sequence (for example, a sequence which is not a CDR) have been mutated (wherein a mutation is, as various non-limiting examples, an addition, substitution or deletion).

Antibodies with Conservative Modifications

In certain aspects, the present disclosure relates to a binding agent, which is an antibody or antigen-binding fragment thereof (e.g., Fab fragment) that specifically binds to an anti-FXI/FXIa antibody such as NOV1401, wherein the binding agent comprises VH comprising CDR1, CDR2, and CDR3 sequences and a VL comprising CDR1, CDR2, and CDR3 sequences, wherein one or more of these CDR sequences have specified amino acid sequences based on the antibodies described herein, such as those described in Table 2, or conservative modifications thereof, and wherein the binding agents retain the desired functional properties (e.g., reversing one or more anticoagulant effects of an anti-FXI/FXIa antibody) of the binding agents described herein, e.g., binding agents IDT1, IDT2, IDT3, IDT4, IDT5, IDT6, IDT7, IDT8, IDT9, or IDT10.

In specific aspects, a binding agent described herein, which is an antibody or antigen-binding fragment thereof (e.g., Fab fragment) that specifically binds to an anti-FXI/FXIa antibody such as NOV1401, comprises VH comprising CDR1, CDR2, and CDR3 sequences and a VL comprising CDR1, CDR2, and CDR3 sequences set forth in Table 2 with one, two, three, or more conservative modifications in one or more CDRs, and wherein the binding agents retain the desired functional properties (e.g., binding to anti-FXI/FXIa antibody and/or reversing one or more anticoagulant effects of an anti-FXI/FXIa antibody) of the binding agents described herein, e.g., binding agents IDT1, IDT2, IDT3, IDT4, IDT5, IDT6, IDT7, IDT8, IDT9, or IDT10.

In further specific aspects, provided herein is a binding agent (e.g., anti-idiotype antibody) which specifically binds a target anti-FXI/FXIa antibody such as NOV1401, wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3 selected from those set forth in Table 2 and conservative modifications thereof, and (2) a VL comprising complementarity determining regions LCDR1, LCDR2, and LCDR3 selected from those set forth in Table 2 and conservative modifications thereof. In a particular aspect, the binding agent (e.g., anti-idiotype antibody) comprises Combined HCDR1, HCDR2, and HCDR3 selected from those set forth in Table 2 and conservative modifications thereof, and Combined LCDR1, LCDR2, and LCDR3 selected from those set forth in Table 2 and conservative modifications thereof. In a particular aspect, the binding agent (e.g., anti-idiotype antibody) comprises Kabat HCDR1, HCDR2, and HCDR3 selected from those set forth in Table 2 and conservative modifications thereof, and Kabat LCDR1, LCDR2, and LCDR3 selected from those set forth in Table 2 and conservative modifications thereof. In a particular aspect, the binding agent (e.g., anti-idiotype antibody) comprises Chothia HCDR1, HCDR2, and HCDR3 selected from those set forth in Table 2 and conservative modifications thereof, and Chothia LCDR1, LCDR2, and LCDR3 selected from those set forth in Table 2 and conservative modifications thereof. In a particular aspect, the binding agent (e.g., anti-idiotype antibody) comprises IMGT HCDR1, HCDR2, and HCDR3 selected from those set forth in Table 2 and conservative modifications thereof, and IMGT LCDR1, LCDR2, and LCDR3 selected from those set forth in Table 2 and conservative modifications thereof.

In particular aspects, provided herein is a binding agent (e.g., anti-idiotype antibody and fragments thereof, such as Fab fragment) which specifically binds a target anti-FXI/FXIa antibody such as NOV1401, wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein:

a. the HCDR1 comprises the amino acid sequence of SEQ ID NO: 27, 59, 91, 123, 155, 187, 219, 251, 283, or 315, or conservative modifications thereof;
b. the HCDR2 comprises the amino acid sequence of SEQ ID NO: 28, 60, 92, 124, 156, 188, 220, 252, 284, or 316, or conservative modifications thereof;
c. the HCDR3 comprises the amino acid sequence of SEQ ID NO: 29, 61, 93, 125, 157, 189, 221, 253, 285, or 317, or conservative modifications thereof;
d. the LCDR1 comprises the amino acid sequence of SEQ ID NO: 43, 75, 107, 139, 171, 203, 235, 267, 299, or 331, or conservative modifications thereof;
e. the LCDR2 comprises the amino acid sequence of SEQ ID NO: 44, 76, 108, 140, 172, 204, 236, 268, 300, or 332, or conservative modifications thereof; and
f. the LCDR3 comprises the amino acid sequence of SEQ ID NO: 45, 77, 109, 141, 173, 205, 237, 269, 301, or 333, or conservative modifications thereof.

In particular aspects, provided herein is a binding agent (e.g., anti-idiotype antibody and fragments thereof, such as Fab fragment) which specifically binds a target anti-FXI/FXIa antibody such as NOV1401, wherein the binding agent inhibits an anticoagulant activity of the target anti-FXI/FXIa antibody, wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein:

a. the HCDR1 comprises the amino acid sequence of SEQ ID NO: 30, 62, 94, 126, 158, 190, 222, 254, 286, or 318, or conservative modifications thereof;
b. the HCDR2 comprises the amino acid sequence of SEQ ID NO: 31, 63, 95, 127, 159, 191, 223, 255, 287, or 319, or conservative modifications thereof;
c. the HCDR3 comprises the amino acid sequence of SEQ ID NO: 32, 64, 96, 128, 160, 192, 224, 256, 288, or 320, or conservative modifications thereof;
d. the LCDR1 comprises the amino acid sequence of SEQ ID NO: 46, 78, 110, 142, 174, 206, 238, 270, 302, or 334, or conservative modifications thereof;
e. the LCDR2 comprises the amino acid sequence of SEQ ID NO: 47, 79, 111, 143, 175, 207, 239, 271, 303, or 335, or conservative modifications thereof; and
f. the LCDR3 comprises the amino acid sequence of SEQ ID NO: 48, 80, 112, 144, 176, 208, 240, 272, 304, or 336, or conservative modifications thereof.

The present disclosure also provides a binding agent (e.g., anti-idiotype antibody and fragments thereof, such as Fab fragment) which specifically binds a target anti-FXI/FXIa antibody (e.g., NOV1401), wherein the binding agent is an antibody or antigen-binding fragment thereof comprising (or alternatively, consisting of) a VH amino acid sequence listed in Table 2, wherein no more than about 1, 2, 3, 4, 5, 6, 7, 8, 9, 10, 11, 12, 13, 14, 15, 16, 17, 18, 19, or 20 amino acids in a framework sequence (for example, a sequence which is not a CDR) have conservative modifications.

The present disclosure also provides a binding agent (e.g., anti-idiotype antibody and fragments thereof, such as Fab fragment) which specifically binds a target anti-FXI/FXIa antibody (e.g., NOV1401), wherein the binding agent is an antibody or antigen-binding fragment thereof comprising (or alternatively, consisting of) a VL amino acid sequence listed in Table 2, wherein no more than about 1, 2, 3, 4, 5, 6, 7, 8, 9, 10, 11, 12, 13, 14, 15, 16, 17, 18, 19, or 20 amino acids in a framework sequence (for example, a sequence which is not a CDR) have conservative modifications.

Binding Agents that Bind to the Same Epitope

The present disclosure provides binding agents that bind to the same epitope of an anti-FXI/FXIa antibody, such as NOV1401, as one of the binding agents (e.g., antibodies) described in Table 2 (e.g., any one of IDT1, IDT2, IDT3, IDT4, IDT5, IDT6, IDT7, IDT8, IDT9, and IDT10). Additional binding agents can therefore be identified based on their ability to compete (e.g., to competitively inhibit the binding of, in a statistically significant manner, by binding to the same or overlapping epitope) with other binding agents described herein in anti-FXI/FXIa binding assays (such as those described in the Examples Section).

The ability of a test binding agent to inhibit the binding of reference binding agent described herein, such as antibody IDT3, to an anti-FXI/FXIa antibody such as NOV1401 demonstrates that the test binding agent can compete with that reference binding agent for binding to an anti-FXI/FXIa antibody such as NOV1401; such binding agent may, according to non-limiting theory, bind to the same or a related (e.g., a structurally similar or spatially proximal) epitope on the anti-FXI/FXIa antibody such as NOV1401 as the reference binding agent with which it competes. In a certain embodiment, the binding agent that binds to the same epitope on an anti-FXI/FXIa antibody, such as NOV1401, as a binding agent provided herein (e.g., antibody IDT3) is a human monoclonal antibody. Such human monoclonal antibodies can be prepared and isolated as described herein.

As used herein, a binding agent (e.g., antibody) "competes" for binding when the competing binding agent (e.g., antibody) binds to the same anti-FXI/FXIa antibody epitope as a reference binding agent (e.g., any one of antibodies IDT1-IDT10) and inhibits anti-FXI/FXIa antibody binding of the reference binding agent by more than 40% or 50% (for example, 60%, 70%, 80%, 85%, 90%, 95%, 98% or 99%) in the presence of an equimolar concentration of competing binding agent. This may be determined, for instance, in a competitive binding assay, by any of the methods well known to those of skill in the art.

As used herein, a binding agent (e.g., antibody or antigen binding fragment thereof) does not "compete" with a reference binding agent provided herein (e.g., anyone of antibody IDT1-IDT10) unless said competing binding agent (e.g., antibody or antigen binding fragment thereof) binds the same epitope, or an overlapping epitope, within an anti-FXI/FXIa antibody, such as NOV1401, as a reference binding agent provided herein (e.g., any one of antibodies IDT1-IDT10). As used herein, a competing binding agent (e.g., antibody or antigen binding fragment thereof) does not include one which (i) sterically blocks a reference binding agent provided herein (e.g., any one of antibodies IDT1-IDT10) from binding its target (e.g., if said competing binding agent binds to a nearby, non-overlapping epitope and physically prevents a reference binding agent provided herein from binding its target); and/or (ii) binds to a different, non-overlapping epitope within the anti-FXI/FXIa antibody and induces a conformational change to the anti-FXI/FXIa antibody such that said anti-FXI/FXIa antibody can no longer be bound by a reference binding agent provided herein in a way that would occur absent said conformational change.

Engineered and Modified Antibodies

Binding agents (e.g., anti-FXI/FXIa antibody binding agent) provided herein which are antibodies can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i. e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.)

Framework sequences can be obtained from public DNA databases or published references that include germline antibody gene sequences. For example, germline DNA sequences for human heavy and light chain variable region genes can be found in the "VBase" human germline sequence database (available on the world wide web at mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. Mol. Biol. 227:776-798; and Cox, J. P. L. et al., 1994 Eur. J Immunol. 24:827-836; the contents of each of which are expressly incorporated herein by reference.

An example of framework sequences for use in antibodies of the present disclosure are those that are structurally similar to the framework sequences used by selected antibodies described herein, e.g., consensus sequences and/or framework sequences used by monoclonal antibodies of the invention. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al). Frameworks that can be utilized as scaffolds on which to build the antibodies and antigen binding fragments described herein include, but are not limited to VH1A, VH1B, VH3, Vk1, Vl2, and Vk2. Additional frameworks are known in the art and may be found, for example, in the vBase data base on the world wide web at vbase.mrc-cpe.cam.ac.uk/index.php?&MMN_position=1:1.

Accordingly, in specific aspects, the present disclosure relates to binding agents, such as isolated antibodies which bind an anti-FXI/FXIa antibody such as NOV1401, comprising a heavy chain variable region comprising an amino acid sequence selected from the group consisting of SEQ ID NOs: 39, 71, 103, 135, 167, 199, 231, 263, 295, and 327, or an amino acid sequence having one, two, three, four or five amino acid substitutions, deletions or additions in the framework region of such sequences, and further comprising a light chain variable region comprising an amino acid sequence selected from the group consisting of SEQ ID NOs: 55, 87, 119, 151, 183, 215, 247, 279, 311, and 343, or an amino acid sequence having one, two, three, four or five amino acid substitutions, deletions or additions in the framework region of such sequences.

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples Section. Conservative modifications (as discussed above) can be introduced. The mutations may be amino acid substitutions, additions or deletions. Moreover, typically no more than one, two, three, four or five residues within a CDR region are altered.

Accordingly, in specific aspects, provided herein are affinity matured variants of antibody IDT1, IDT2, IDT3, IDT4, IDT5, IDT6, IDT7, IDT8, IDT9, or IDT10, wherein the affinity matured variant has higher affinity for the anti-FXI/FXIa antibody NOV1401 than the parental, and is capable of reversing one or more anticoagulant effects of NOV1401. In particular aspects, provided herein is In particular aspects, provided herein is a binding agent (e.g., anti-idiotype antibody and fragments thereof, such as Fab fragment) which specifically binds a target anti-FXI/FXIa antibody, wherein the binding agent inhibits an anticoagulant activity of the target anti-FXI/FXIa antibody, wherein the target anti-FXI/FXIa antibody is antibody NOV1401 (comprising a VH comprising the amino acid sequence of SEQ ID NO: 12 and a VL comprising the amino acid sequence of SEQ ID NO: 23), and wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein:

a. the HCDR1 comprises the amino acid sequence of SEQ ID NO: 27, 59, 91, 123, 155, 187, 219, 251, 283, or 315, or an amino acid sequence thereof having one, two, three, four or five amino acid substitutions, deletions or additions;
b. the HCDR2 comprises the amino acid sequence of SEQ ID NO: 28, 60, 92, 124, 156, 188, 220, 252, 284, or 316, or an amino acid sequence thereof having one, two, three, four or five amino acid substitutions, deletions or additions;
c. the HCDR3 comprises the amino acid sequence of SEQ ID NO: 29, 61, 93, 125, 157, 189, 221, 253, 285, or 317, or an amino acid sequence thereof having one, two, three, four or five amino acid substitutions, deletions or additions;
d. the LCDR1 comprises the amino acid sequence of SEQ ID NO: 43, 75, 107, 139, 171, 203, 235, 267, 299, or 331, or an amino acid sequence thereof having one, two, three, four or five amino acid substitutions, deletions or additions;
e. the LCDR2 comprises the amino acid sequence of SEQ ID NO: 44, 76, 108, 140, 172, 204, 236, 268, 300, or 332, or an amino acid sequence thereof having one, two, three, four or five amino acid substitutions, deletions or additions; and
f. the LCDR3 comprises the amino acid sequence of SEQ ID NO: 45, 77, 109, 141, 173, 205, 237, 269, 301, or 333, or an amino acid sequence thereof having one, two, three, four or five amino acid substitutions, deletions or additions.

In particular aspects, provided herein is a binding agent (e.g., anti-idiotype antibody and fragments thereof, such as Fab fragment) which specifically binds a target anti-FXI/FXIa antibody, wherein the binding agent inhibits an anticoagulant activity of the target anti-FXI/FXIa antibody, wherein the target anti-FXI/FXIa antibody is antibody NOV1401 (comprising a VH comprising the amino acid sequence of SEQ ID NO: 12 and a VL comprising the amino acid sequence of SEQ ID NO: 23), and wherein the binding agent is an antibody or antigen-binding fragment thereof comprising (1) a VH comprising complementarity determining regions HCDR1, HCDR2, and HCDR3, and (2) a VL comprising complementarity determining regions LCDR1, LCDR2, and LCDR3; wherein:

a. the HCDR1 comprises the amino acid sequence of SEQ ID NO: 30, 62, 94, 126, 158, 190, 222, 254, 286, or 318, or an amino acid sequence thereof having one, two, three, four or five amino acid substitutions, deletions or additions;

b. the HCDR2 comprises the amino acid sequence of SEQ ID NO: 31, 63, 95, 127, 159, 191, 223, 255, 287, or 319, or an amino acid sequence thereof having one, two, three, four or five amino acid substitutions, deletions or additions;

c. the HCDR3 comprises the amino acid sequence of SEQ ID NO: 32, 64, 96, 128, 160, 192, 224, 256, 288, or 320, or an amino acid sequence thereof having one, two, three, four or five amino acid substitutions, deletions or additions;

d. the LCDR1 comprises the amino acid sequence of SEQ ID NO: 46, 78, 110, 142, 174, 206, 238, 270, 302, or 334, or an amino acid sequence thereof having one, two, three, four or five amino acid substitutions, deletions or additions;

e. the LCDR2 comprises the amino acid sequence of SEQ ID NO: 47, 79, 111, 143, 175, 207, 239, 271, 303, or 335, or an amino acid sequence thereof having one, two, three, four or five amino acid substitutions, deletions or additions; and f. the LCDR3 comprises the amino acid sequence of SEQ ID NO: 48, 80, 112, 144, 176, 208, 240, 272, 304, or 336, or an amino acid sequence thereof having one, two, three, four or five amino acid substitutions, deletions or additions.

Grafting Antigen-Binding Domains into Alternative Frameworks or Scaffolds

With respect to anti-FXI/FXIa antibody binding agents provided herein which are antibodies, a wide variety of antibody/immunoglobulin frameworks or scaffolds can be employed so long as the resulting polypeptide includes at least one binding region which specifically binds to a target anti-FXI/FXIa antibody. Such frameworks or scaffolds include the 5 main idiotypes of human immunoglobulins, or fragments thereof, and include immunoglobulins of other animal species, preferably having humanized aspects. Single heavy-chain antibodies such as those identified in camelids are of particular interest in this regard.

In one aspect, the present disclosure pertains to generating non-immunoglobulin based antibodies using non-immunoglobulin scaffolds onto which CDRs such as those described in Table 2 can be grafted. Known or future non-immunoglobulin frameworks and scaffolds may be employed, as long as they comprise a binding region specific for the target anti-FXI/FXIa antibody such as NOV1401. Known non-immunoglobulin frameworks or scaffolds include, but are not limited to, fibronectin (Compound Therapeutics, Inc., Waltham, Mass.), ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (Scil Proteins GmbH, Halle, Germany).

The fibronectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel $\alpha$-helices and a $\beta$-turn. Binding of the variable regions is mostly optimized by using ribosome display.

Avimers are derived from natural A-domain containing protein such as LRP-1. These domains are used by nature for protein-protein interactions and in human over 250 proteins are structurally based on A-domains. Avimers consist of a number of different “A-domain” monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of *Pieris Brassicae* has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

In specific aspects, the present disclosure provides fully human antibodies that specifically bind to a target anti-FXI/FXIa antibody such as NOV1401. Compared to the chimeric or humanized antibodies, human antibodies have further reduced antigenicity when administered to human subjects.

Bispecific Molecules and Multivalent Antibodies

In another aspect, the present disclosure features bispecific or multispecific molecules comprising an antibody or a fragment thereof which specifically binds a target anti-FXI/FXIa antibody such as NOV1401 and reverses one or more anticoagulant effects. An antibody provided herein, or antigen-binding regions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present disclosure includes bispecific molecules comprising at least one first binding specificity for a target anti-FXI/FXIa antibody such as NOV1401, and a second binding specificity for a second target epitope. For example, the second target epitope is another epitope of an anti-FXI/FXIa antibody different from the first target epitope.

Additionally, for aspects in which the bispecific molecule is multi-specific, the molecule can further include a third binding specificity, in addition to the first and second target epitope.

In one aspect, bispecific molecules of the present disclosure comprise as a binding specificity at least one antibody, or an antibody fragment thereof, including, e.g., a Fab, Fab', F(ab')2, Fv, or a single chain Fv. The antibody may also be a light chain or heavy chain dimer, or any minimal fragment thereof such as a Fv or a single chain construct as described in Ladner et al. U.S. Pat. No. 4,946,778.

Diabodies are bivalent, bispecific molecules in which VH and VL domains are expressed on a single polypeptide chain, connected by a linker that is too short to allow for pairing between the two domains on the same chain. The VH and VL domains pair with complementary domains of another chain, thereby creating two antigen binding sites (see e.g., Holliger et al., 1993 Proc. Natl. Acad. Sci. USA 90:6444-6448; Poljak et al., 1994 Structure 2:1121-1123). Diabodies can be produced by expressing two polypeptide chains with either the structure VHA-VLB and VHB-VLA (VH-VL configuration), or VLA-VHB and VLB-VHA (VL-VH configuration) within the same cell. Most of them can be expressed in soluble form in bacteria. Single chain diabodies (scDb) are produced by connecting the two diabody-forming polypeptide chains with linker of approximately 15 amino acid residues (see Holliger and Winter, 1997 Cancer Immunol. Immunother., 45(3-4):128-30; Wu et al., 1996 Immunotechnology, 2(1):21-36). scDb can be expressed in bacteria in soluble, active monomeric form (see Holliger and Winter, 1997 Cancer Immunol. Immunother., 45(34): 128-30; Wu et al., 1996 Immunotechnology, 2(1):21-36; Pluckthun and Pack, 1997 Immunotechnology, 3(2): 83-105; Ridgway et al., 1996 Protein Eng., 9(7):617-21). A diabody can be fused to Fc to generate a "di-diabody" (see Lu et al., 2004 J. Biol. Chem., 279(4):2856-65).

Other antibodies which can be employed in the bispecific molecules are murine, chimeric and humanized monoclonal antibodies.

Bispecific molecules can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al., 1984 J. Exp. Med. 160:1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')2 or ligand x Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In another aspect, the present invention provides multivalent compounds comprising at least two identical or different antigen-binding portions of the antibodies of the invention binding to FXIa. The antigen-binding portions can be linked together via protein fusion or covalent or non-covalent linkage. Alternatively, methods of linkage have been described for the bispecfic molecules. Tetravalent compounds can be obtained for example by cross-linking antibodies of the antibodies of the invention with an antibody that binds to the constant regions of the antibodies of the invention, for example the Fc or hinge region.

Trimerizing domain are described for example in Borean patent EP 1 012 280B1. Pentamerizing modules are described for example in PCT/EP97/05897.

Antibody Conjugates and Fusions

In specific aspects, the present disclosure provides binding agents, which are antibodies or fragments thereof that specifically bind to a target anti-FXI/FXIa antibody (e.g., such as NOV1401), and that are recombinantly fused or chemically conjugated (including both covalent and non-covalent conjugations) to a heterologous protein or polypeptide (or fragment thereof. In a particular aspect, a heterologous protein is a polypeptide of at least 10, at least 20, at least 30, at least 40, at least 50, at least 60, at least 70, at least 80, at least 90 or at least 100 amino acids) is used to generate fusion proteins. In particular aspects, the present disclosure provides binding agents that are fusion proteins comprising an antigen-binding fragment of an antibody described herein (e.g., a Fab fragment, Fd fragment, Fv fragment, F(ab)2 fragment, a VH domain, a VH CDR, a VL domain or a VL CDR) and a heterologous protein, polypeptide, or peptide. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to a FXIa protein may be recombined with one or more components, motifs, sections, parts, domains, fragments, etc. of one or more heterologous molecules.

Moreover, the antibodies or fragments thereof can be fused to marker sequences, such as a peptide to facilitate purification. In particular embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

In other aspects, binding agents such as antibodies described herein or fragments thereof are conjugated to a compound, for example, a diagnostic or detectable agent. In one aspect, such antibodies or fragments thereof are conjugated by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine (131I, 125I, 123I, and 121I,), carbon (14C), sulfur (35S), tritium (3H), indium (115In, 113In, 112In, and 111In,), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142 Pr, 105Rh, 97Ru, 68Ge, 57Co, 65Zn, 85Sr, 32P, 153Gd, 169Yb, 51Cr, 54Mn, 75Se, 113Sn, and 117Tin; and positron emitting metals using various positron emission tomographies, and nonradioactive paramagnetic metal ions.

Further, an antibody or fragment thereof may be conjugated to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity.

Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Methods of Producing Antibodies

Provided herein are nucleic acid molecules (e.g., substantially purified nucleic acid molecules) which encode polypeptides of binding agents described herein, vectors (e.g., expression vectors) comprising the same, host cells comprising such vectors or nucleic acid molecules, and methods of producing binding agents described herein, e.g., antibodies or antigen-binding fragment thereof, such as Fab fragments, which specifically binds an anti-FXI/FXIa antibody, e.g., NOV1401.

In specific aspects, provided herein is a vector (e.g., expression vector) comprising a polynucleotide described herein (e.g., Table 2).

In certain aspects, provided herein is a host cell comprising a vector described herein or a polynucleotide described herein. In specific aspects, the host cell is a eukaryotic cell. In certain aspects, the host cell is a mammalian cell (e.g., non-human mammalian cell, such as CHO cells). In particular aspects, a host cell comprises (i) a vector or polynucleotide comprising nucleotide sequences encoding a VH or a heavy chain and (ii) a vector or polynucleotide comprising nucleotide sequences encoding a VL or a light chain. In specific aspects, a first host cell comprises a vector or polynucleotide comprising nucleotide sequences encoding a VH or a heavy chain and a second host cell comprises a vector or polynucleotide comprising nucleotide sequences encoding a VL or a light chain.

In particular aspects, provided herein is a method of producing a binding agent, e.g., an antibody or antigen-binding fragment (e.g., Fab fragment) that binds an anti-FXI/FXIa antibody, such as NOV1401, comprising the step of culturing a host cell described herein under conditions suitable for expression of the binding agent.

In certain aspects, the method of producing an anti-FXI/FXIa antibody or fragment thereof further comprises purifying the anti-FXI/FXIa antibody or fragment thereof.

Nucleic Acids Encoding Binding Agents

The present disclosure provides polynucleotides comprising nucleotide sequences encoding binding agents described herein. In specific aspects, the present disclosure provides polynucleotides comprising nucleic acid sequences that encode the VH, VL, full length heavy chain, and/or full length light chain of antibodies described herein that specifically bind to a target anti-FXI/FXIa antibody, for example, antibodies IDT1, IDT2, IDT3, IDT4, IDT5, IDT6, IDT7, IDT8, IDT9, and IDT10. Such nucleic acid sequences can be optimized for expression in mammalian cells (for example, see Table 2).

In specific aspects where a binding agent is an antibody or antigen-binding fragment thereof, provided herein is a polynucleotide comprising nucleotide sequences encoding a VL, VH or a VL and VH of an anti-FXI/FXIa antibody binding agent described herein, e.g., antibody IDT1, IDT2, IDT3, IDT4, IDT5, IDT6, IDT7, IDT8, IDT9, or IDT10. In one aspect, a polynucleotide provided herein comprises a nucleotide sequence encoding a VL of an anti-FXI/FXIa antibody binding agent described herein, e.g., antibody IDT1, IDT2, IDT3, IDT4, IDT5, IDT6, IDT7, IDT8, IDT9, or IDT10. In one aspect, a polynucleotide provided herein comprises a nucleotide sequence encoding a VH of an anti-FXI/FXIa antibody binding agent described herein, e.g., antibody IDT1, IDT2, IDT3, IDT4, IDT5, IDT6, IDT7, IDT8, IDT9, or IDT10. In one aspect, a polynucleotide provided herein comprises a nucleotide sequence encoding a VH and a VL of an anti-FXI/FXIa antibody binding agent described herein, e.g., antibody IDT1, IDT2, IDT3, IDT4, IDT5, IDT6, IDT7, IDT8, IDT9, or IDT10.

In specific aspects where a binding agent is an antibody or antigen-binding fragment thereof, provided herein is a polynucleotide comprising nucleotide sequences encoding a heavy chain, a light chain, or a heavy chain and a light chain of an anti-FXI/FXIa antibody binding agent described herein, e.g., antibody IDT1, IDT2, IDT3, IDT4, IDT5, IDT6, IDT7, IDT8, IDT9, or IDT10. In one aspect, a polynucleotide provided herein comprises a nucleotide sequence encoding a heavy chain of an anti-FXI/FXIa antibody binding agent described herein, e.g., antibody IDT1, IDT2, IDT3, IDT4, IDT5, IDT6, IDT7, IDT8, IDT9, or IDT10. In one aspect, a polynucleotide provided herein comprises a nucleotide sequence encoding a light chain of an anti-FXI/FXIa antibody binding agent described herein, e.g., antibody IDT1, IDT2, IDT3, IDT4, IDT5, IDT6, IDT7, IDT8, IDT9, or IDT10. In one aspect, a polynucleotide provided herein comprises a nucleotide sequence encoding a heavy chain and a light chain of an anti-FXI/FXIa antibody binding agent described herein, e.g., antibody IDT1, IDT2, IDT3, IDT4, IDT5, IDT6, IDT7, IDT8, IDT9, or IDT10.

In particular aspects, provided herein is a polynucleotide comprising one or more nucleotide sequences set forth in Table 2, for example, a polynucleotide comprising the nucleotide sequence of SEQ ID NO: 40, 72, 104, 136, 168, 200, 232, 264, 296, or 328 encoding a VH; and a comprising the nucleotide sequence of SEQ ID NO: 56, 88, 120, 152, 184, 216, 248, 280, 312, or 344 encoding a VL.

In particular aspects, provided herein is a polynucleotide comprising one or more nucleotide sequences set forth in Table 2, for example, a polynucleotide comprising the nucleotide sequence of SEQ ID NO: 42, 74, 106, 138, 170, 202, 234, 266, 298, or 330 encoding a heavy chain; and a comprising the nucleotide sequence of SEQ ID NO: 58, 90, 122, 154, 186, 218, 250, 282, 314, or 346 encoding a light chain.

In certain aspects, polynucleotides provided herein comprise nucleotide sequences that are substantially identical (e.g., at least 65%, 80%, 80%, 90%, 95%, 98%, or 99%) to the nucleotide sequences of those identified in Table 2, for example, SEQ ID NO: 40, 72, 104, 136, 168, 200, 232, 264, 296, or 328 encoding a VH; and SEQ ID NO: 56, 88, 120, 152, 184, 216, 248, 280, 312, or 344 encoding a VL. When expressed from appropriate expression vectors, polypeptides encoded by these polynucleotides are capable of binding to an anti-FXI/FXIa antibody, such as antibody NOV1401.

Also provided in the present disclosure are polynucleotides which encode at least one CDR region and usually all three CDR regions from a heavy or light chain variable region of a binding agent described herein (e.g., Table 2), e.g., binding agent which is an antibody or antigen-binding fragment thereof that binds an anti-FXI/FXIa antibody. In other aspects, some polynucleotides encode all or substantially all of the variable region sequence of a heavy chain and/or a light chain of a binding agent described herein (e.g., Table 2), e.g., binding agent which is an antibody or antigen-binding fragment thereof that binds an anti-FXI/FXIa antibody. In specific aspects, provided herein are polynucleotides which can encode both a variable region and a constant region of an antibody, e.g., an antibody or antigen-binding fragment thereof that binds an anti-FXI/FXIa antibody. Because of the degeneracy of the code, a variety of nucleic acid sequences will encode each of the immunoglobulin amino acid sequences.

Polynucleotide sequences can be produced by de novo solid-phase DNA synthesis or by PCR mutagenesis of an existing sequence (e.g., sequences as described herein) encoding a binding agent, e.g., a binding agent which is an antibody or antigen-binding fragment there of (e.g., Fab fragment) that binds an anti-FXI/FXIa-antibody. Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the present disclosure are expression vectors and host cells for producing a binding agent described herein, e.g., a binding agent which is an antibody or antigen-binding fragment there of (e.g., Fab fragment) that binds an anti-FXI/FXIa-antibody. Various expression vectors can be employed to express the polynucleotides encoding the FXIa-binding antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of polynucleotides and polypeptides in mammalian (e.g., human) cells include pThioHis A, B & C, pcDNA3.1/His, pEBVHis A, B & C, (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding a binding agent described herein, e.g., a binding agent which is an antibody or antigen-binding fragment there of (e.g., Fab fragment) that binds an anti-FXI/FXIa-antibody, such as NOV1401. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of a binding agent, e.g., a binding agent which is an antibody or antigen-binding fragment there of (e.g., Fab fragment) that binds an anti-FXI/FXIa-antibody, such as NOV1401. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted anti-FXI/FXIa-antibody binding agent sequences. In specific aspects, inserted anti-FXI/FXIa-antibody binding agent sequences are linked to a signal sequences before inclusion in the vector. Vectors to be used to receive sequences encoding anti-FXI/FXIa-antibody binding agent (e.g., antibody NOV1401 binding agent) light and heavy chain variable domains, and in certain aspects, also encode constant regions or parts thereof. Such vectors allow expression of the variable regions as fusion proteins with the constant regions thereby leading to production of intact antibodies or fragments thereof. Typically, such constant regions are human.

Host cells for harboring and expressing an anti-FXI/FXIa-antibody binding agent (e.g., antibody NOV1401 binding agent) can be either prokaryotic or eukaryotic. *E. coli* is one prokaryotic host useful for cloning and expressing the polynucleotides of the present disclosure. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express FXIa-binding polypeptides of the present disclosure. Insect cells in combination with baculovirus vectors can also be used.

In some specific embodiments, mammalian host cells are used to express and produce anti-FXI/FXIa-antibody binding agent (e.g., antibody NOV1401 binding agent) polypeptides of the present disclosure. These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, and transformed B-cells. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences.

These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express FXIa-binding antibody chains or binding fragments can be prepared using expression vectors of the present disclosure which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Framework or Fc Engineering

Engineered antibodies of the present disclosure include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the present disclosure.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the present disclosure may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the present disclosure may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one aspect, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another aspect, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcal protein A (SpA) binding relative to native Fc-hinge domain SpA binding. This approach is described in further detail in U.S. Pat. No. 6,165,745 by Ward et al.

In another aspect, the antibody is modified to increase its biological half-life. Various approaches are possible. For example, one or more of the mutations as described in U.S. Pat. No. 6,277,375 to Ward can be used. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other aspects, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another aspect, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another aspect, one or more amino acid residues are altered to thereby alter the ability of the antibody to fix complement. This approach is described further in PCT Publication WO 94/29351 by Bodmer et al.

In a specific aspect, a binding agent described herein (e.g., binding agent described in Table 2), for example, a binding agent which is an antibody or antigen-binding fragment thereof (e.g., Fab fragment) that binds an anti-FXI/FXIa-antibody (such as antibody NOV1401) comprises a human IgG (e.g., IgG1) Fc region comprising amino acid substitutions, D265A and/or P329A, to reduce the likelihood for ADCC or CDC caused by any surface-associated FXI. These Alanine substitutions have been shown to reduce ADCC and CDC (see, e.g., Idosugie et al., J. Immunol. 164:4178-4184, 2000; Shields et al., J. Biol. Chem. 276:6591-6604, 2001).

In yet another aspect, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al., 2001 J. Biol. Chen. 276:6591-6604).

In still another aspect, the glycosylation of an antibody is modified. For example, an aglycoslated antibody can be made (i.e., the antibody lacks glycosylation). Glycosylation can be altered to, for example, increase the affinity of the antibody for "antigen." Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the present disclosure to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1, 4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

Methods of Engineering Altered Antibodies

As discussed above, binding agents described herein, for example, binding agents which are antibodies or antigen-binding fragment thereof (e.g., Fab fragment) that bind an anti-FXI/FXIa-antibody, such as NOV1401, and that VH and VL sequences or full length heavy and light chain sequences provided herein (e.g., Table 2) can be used to create new anti-FXI/FXIa-antibody binding agents (e.g., antibody NOV1401 binding agents) by modifying full length heavy chain and/or light chain sequences, VH and/or VL sequences, or the constant region(s) attached thereto. Thus, in another aspect of the present disclosure, the structural features of an anti-FXI/FXIa-antibody binding agent of the present disclosure are used to create structurally related anti-FXI/FXIa-antibody binding agents that retain at least one functional property of the antibodies of the present disclosure, such as binding to an anti-FXI/FXIa antibody, e.g., NOV1401, and also reversing one or more activities of an anti-FXI/FXIa antibody, e.g., reversing one or more anticoagulant activities of an anti-FXI/FXIa antibody.

For example, one or more CDR regions of the antibodies of the present disclosure, or mutations thereof, can be combined recombinantly with known framework regions and/or other CDRs to create additional, recombinantly-engineered, anti-FXI/FXIa antibody-binding agents (e.g., antibody NOV1401 binding agent) of the present disclosure, as discussed above. Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another aspect, the present disclosure provides a method for preparing an anti-FXI/FXIa antibody binding agent (e.g., antibody NOV1401 binding agent) optimized for expression in a mammalian cell consisting of: a full length heavy chain antibody sequence having a sequence selected from those provided in Table 2; and a full length light chain antibody sequence having a sequence selected from those provided in Table 2; altering at least one amino acid residue within the full length heavy chain antibody sequence and/or the full length light chain antibody sequence to create at least one altered antibody sequence; and expressing the altered antibody sequence as a protein. In one embodiment, the alteration of the heavy or light chain is in the framework region of the heavy or light chain.

The altered antibody sequence can also be prepared by screening antibody libraries having fixed CDR3 sequences or minimal essential binding determinants as described in US2005/0255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the functional properties of anti-FXI/FXIa-antibody binding agents (e.g., antibody NOV1401 binding agents) described herein, which functional properties include, but are not limited to, specifically binding an anti-FXI/FXIa antibody (e.g., antibody NOV1401), for example, and contacting the one or more CDR amino acid residues of the anti-FXI/FXIa; inhibiting binding of a target anti-FXI/FXIa antibody (e.g., antibody NOV1401) to human FXI and/or FXIa; inhibiting the ability of a target anti-FXI/FXIa antibody (e.g., antibody NOV1401) to block the activity of FXIa; and inhibiting or reversing one or more anticoagulant effects of a target anti-FXI/FXIa antibody (e.g., antibody NOV1401).

In certain embodiments of the methods of engineering antibodies of the present disclosure, mutations can be introduced randomly or selectively along all or part of an anti-FXI/FXIa antibody binding agent coding sequence and the resulting modified anti-FXI/FXIa antibody binding agents can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

In certain aspects of the present disclosure anti-FXI/FXIa antibody binding agents (e.g., antibody NOV1401 binding agent) have been engineered to remove sites of deamidation. Deamidation is known to cause structural and functional changes in a peptide or protein. Deamindation can result in decreased bioactivity, as well as alterations in pharmacokinetics and antigenicity of the protein pharmaceutical. (*Anal Chem.* 2005 Mar. 1; 77(5):1432-9).

In certain aspects of the present disclosure anti-FXI/FXIa antibody binding agents (e.g., antibody NOV1401 binding agent) described herein have been engineered to increase pI and improve their drug-like properties. The pI of a protein is a key determinant of the overall biophysical properties of a molecule. Antibodies and polypeptides that have low pIs have been known to be less soluble, less stable, and prone to aggregation. Further, the purification of antibodies and polypeptides with low pI is challenging and can be problematic especially during scale-up for clinical use. Increasing the pI of binding agents, such as antibodies, or Fabs, of the present disclosure improved their solubility, enabling the antibodies to be formulated at higher concentrations (>100 mg/ml). Formulation of the antibodies at high concentrations (e.g. >100 mg/ml) offers the advantage of being able to administer higher doses of the antibodies, which in turn may enable reduced dosing frequency, a significant advantage for treatment of chronic diseases including thrombotic and/or thromboembolic disorders. Higher pIs may also increase the FcRn-mediated recycling of the IgG version of the antibody thus enabling the drug to persist in the body for a longer duration, requiring fewer injections. Finally, the overall stability of the antibodies is significantly improved due to the higher pI resulting in longer shelf-life and bioactivity in vivo. In specific aspects, the pI of an anti-FXI/FXIa antibody binding agent is greater than or equal to 8.2.

The functional properties of the altered antibodies can be assessed using standard assays available in the art and/or described herein, such as those set forth in the Examples (e.g., ELISAs, aPTT assay, TGA assay).

Prophylactic and Therapeutic Uses

The present disclosure relates to methods for reversing (e.g., partially reversing) or decreasing the anticoagulant effect of an anti-FXI/FXIa antibody (e.g., antibody NOV1401) in a patient being treated with the anti-FXI/FXIa antibody or antigen-binding fragment thereof, comprising administering an effective amount of a binding agent provided herein, e.g., a binding agent (e.g., antibody or antigen-binding fragment thereof, such as a Fab fragment) which binds an anti-FXI/FXIa antibody and is capable of reversing one or more anticoagulant effects. In specific aspects, reversal of the anticoagulant effects of an anti-FXI/FXIa antibody may be needed by a patient for emergency surgery/urgent procedures and in life-threatening or uncontrolled bleeding. In particular aspects, a patient is being treated with an anti-FXI/FXIa antibody to manage, treat, prevent, or reduce the risk of a thromboembolic disease or disorder, for example reducing the risk of stroke or thrombosis (e.g., systemic embolism) in patients with atrial fibrillation (e.g., non-valvular atrial fibrillation), chronic kidney disease, such as end stage renal failure (ESRD) undergoing hemodialysis. In further specific aspects, the patient has a demonstrated high risk of bleeding. In specific aspects, non-limiting examples of anti-FXI/FXIa antibody binding agents for use in these methods include antibodies (e.g., anti-idiotype antibodies) and antigen-binding fragments, such as Fab fragments, described herein, e.g., in Table 2, for example, antibodies IDT1, IDT2, IDT3, IDT4, IDT5, IDT6, IDT7, IDT8, IDT9, and IDT10; antibodies comprising VH CDRs and VL CDRs of such antibodies; antibodies that bind the same epitope(s) within target antibody NOV1401 as such antibodies.

In certain aspects, the present disclosure relates to methods for reducing clotting time in a subject administered an anti-FXI/FXIa antibody (e.g., antibody NOV1401), comprising administering an effective amount of a binding agent provided herein, e.g., a binding agent (e.g., anti-idiotype antibody or antigen-binding fragment thereof, such as a Fab fragment) which binds the anti-FXI/FXIa antibody and is capable of inhibiting binding of the anti-FXI/FXIa antibody to human FXI/FXIa.

In specific aspects, the present disclosure relates to methods for managing bleeding or bleeding risk or for reducing bleeding or bleeding risk in a patient being treated with an anti-FXI/FXIa antibody (e.g., antibody NOV1401), comprising administering an effective amount of a binding agent provided herein, e.g., a binding agent (e.g., antibody or antigen-binding fragment thereof, such as a Fab fragment) which binds an anti-FXI/FXIa antibody and is capable of reversing one or more anticoagulant effects. In specific aspects, reversal of the anticoagulant effects of an anti-FXI/FXIa antibody may be needed by a patient for emergency surgery/urgent procedures and in life-threatening or uncontrolled bleeding. In particular aspects, a patient is being treated with an anti-FXI/FXIa antibody to manage, treat, prevent, or reduce the risk of a thromboembolic disease or disorder, for example reducing the risk of stroke or thrombosis (e.g., systemic embolism) in patients with atrial fibrillation (e.g., non-valvular atrial fibrillation), chronic kidney disease, such as end stage renal failure (ESRD) undergoing hemodialysis. In further specific aspects, the patient has a demonstrated high risk of bleeding. In specific aspects, non-limiting examples of anti-FXI/FXIa antibody binding agents for use in these methods include antibodies (e.g., anti-idiotype antibodies and fragments thereof such as Fabs) and antigen-binding fragments, such as Fab fragments, described herein, e.g., in Table 2, for example, antibodies IDT1, IDT2, IDT3, IDT4, IDT5, IDT6, IDT7, IDT8, IDT9, and IDT10; antibodies comprising VH CDRs and VL CDRs of such antibodies; antibodies that bind the same epitope(s) within target antibody NOV1401 as such antibodies.

In a particular aspect, provided herein are methods of managing bleeding or bleeding risk in a patient treated or administered an anti-FXI antibody described herein (e.g., antibody described in Table 1 such as NOV1401 or an anti-FXI antibody comprising HCDRs and LCDRs of NOV1401), comprising the step of administering to the patient in need thereof, an anti-idiotype antibody, or antigen binding fragment thereof (e.g., Fab), of the anti-FXI antibody, wherein the anti-idiotype or antigen binding fragment thereof (e.g., Fab) specifically binds to the anti-FXI antibody and blocks the anti-FXI antibody from binding to FXI. In specific embodiments, an anti-idiotype antibody or antigen binding fragment thereof (e.g., Fab) reverses the effects of an anti-FXI antibody described herein to mitigate bleeding risks, for example during urgent major surgery or trauma.

In specific aspects, an anti-idiotype antibody or antigen binding fragment thereof (e.g., Fab) reverses or inhibits an anti-FXI antibody's anti-coagulant effects. In particular aspects, the anti-idiotype antibody or antigen binding fragment thereof (e.g., Fab) is administered to a patient in need thereof to temporarily reverse the anti-coagulant effect of an anti-FXI antibody described herein (e.g., antibody described in Table 1 such as NOV1401 or an anti-FXI antibody comprising HCDRs and LCDRs of NOV1401).

In a particular aspect, provided herein are methods of managing bleeding or bleeding risk in a patient treated or administered an anti-FXI antibody such as NOV1401 (e.g., SEQ ID NOs: 14 and 25), comprising the step of administering to the patient in need thereof, an anti-idiotype antibody, or antigen binding fragment thereof (e.g., Fab), of the anti-FXI antibody such as NOV1401 (e.g., SEQ ID NOs: 14 and 25), wherein the anti-idiotype, or antigen binding fragment thereof (e.g., Fab), specifically binds to the antigen-binding region of an anti-FXI antibody such as NOV1401 (e.g., SEQ ID NOs: 14 and 25) and blocks the anti-FXI antibody from binding to FXI and/or FXIa. In a specific embodiment, the anti-idiotype antibody, or antigen binding fragment thereof (e.g., Fab), of an anti-FXI antibody such as NOV1401 (e.g., SEQ ID NOs: 14 and 25) reverses or inhibits one or more of the anti-coagulant effects of the anti-FXI antibody (e.g., NOV1401). In certain embodiments, a temporary reversal or inhibition of one or more of the anti-coagulant effects of the anti-FXI antibody (e.g., NOV1401) is achieved. In specific embodiments, following the temporary reversal or inhibition of the anti-FXI antibody (e.g., NOV1401), the anti-FXI antibody (e.g., NOV1401) is again administered to the patient.

As used herein, the terms "effective amount" or "therapeutically effective amount" refer to an amount of a therapy (e.g., a binding agent provided herein such as an anti-idiotype antibody that binds an anti-FXI/FXIa antibody (e.g., NOV1401) or a pharmaceutical composition provided herein) which is sufficient to reduce and/or ameliorate the severity and/or duration of a given condition, disorder, or disease and/or a symptom related thereto. These terms also encompass an amount necessary for the reduction, slowing, or amelioration of the advancement or progression of a given condition, disorder, or disease, reduction, slowing, or amelioration of the recurrence, development or onset of a given condition, disorder or disease, and/or to improve or enhance the prophylactic or therapeutic effect(s) of another therapy (e.g., a therapy other than an anti-FXI/FXIa antibody binding agent provided herein). In some aspects, "effective amount" as used herein also refers to the amount of an antibody described herein to achieve a specified result, for example, reduction or reversal in one or more anticoagulant effects (e.g., aPTT prolongation, and reduction in the amount of thrombin in a thrombin generation assay (TGA) in human plasma) of a target anti-FXI/FXIa antibody; and reduction in, or blocking, binding of a target anti-FXI/FXIa antibody to FXI/FXIa.

In specific aspects, a patient, who may be in need of, or may benefit from, the methods described herein (e.g., methods for reversing anticoagulant effects with anti-FXI/FXIa antibody binding agents), has been treated with an anti-FXI/FXIa antibody (e.g., antibody NOV1401) to manage, treat, prevent, or reduce the risk of a thromboembolic disease or disorder, e.g., thrombic stroke, atrial fibrillation, stroke prevention in atrial fibrillation (SPAF), deep vein thrombosis, venous thromboembolism, pulmonary embolism, acute coronary syndromes (ACS), ischemic stroke, acute limb ischemia, chronic thromboembolic pulmonary hypertension, or systemic embolism. In further specific aspects, the patient has a demonstrated high risk of bleeding.

In other aspects, a patient, who may be in need of, or may benefit from, the methods described herein (e.g., methods for reversing anticoagulant effects with anti-FXI/FXIa antibody binding agents), has been treated with an anti-FXI/FXIa antibody (e.g., antibody NOV1401) for treatment of acute VTE, primary and extended secondary prevention of VTE, prevention of major adverse thromboembolic events in patient undergoing dialysis (with or without AF), prevention of major cardiovascular and cerebral events (MACCE) in patients with CAD undergoing PCI and receiving single or dual antiplatelet therapy, post-acute coronary syndromes (ACS) patients, heparin induced thrombocytopenia (HIT), prevention of thromboembolic events in heart failure patients and secondary stroke prevention.

In specific aspects, one of the following groups of subjects is being treated with an anti-FXI/FXIa antibody (e.g., antibody NOV1401) and may be in need of, or benefit from, the methods described herein (e.g., methods for reversing anticoagulant effects with anti-FXI/FXIa antibody binding agents):

- Subjects with indications for chronic anticoagulation therapy (e.g., AF, left ventricular thrombus, prior cardioembolic stroke)
- subjects at intermediate-to-high risk for major bleeding;
- subjects undergoing elective or primary percutaneous coronary intervention (PCI) with stenting which may be require to receive dual antiplatelet therapy (aspirin and P2Y12 receptor antagonists) to prevent stent thrombosis.

In specific aspects, a subject, who may be in need of, or benefit from, the methods described herein (e.g., methods for reversing anticoagulant effects with anti-FXI/FXIa antibody binding agents), has been treated with an anti-FXI/FXIa antibody (e.g., antibody NOV1401) to manage, treat, prevent, or reduce the risk of one of the following conditions:

- thromboembolism in subjects with suspected or confirmed cardiac arrhythmia such as paroxysmal, persistent or permanent atrial fibrillation or atrial flutter;
- stroke prevention in atrial fibrillation (SPAF), a subpopulation of which is AF patients undergoing percutaneous coronary interventions (PCI);
- acute venous thromboembolic events (VTE) treatment and extended secondary VTE prevention in patients at high risk for bleeding;
- cerebral and cardiovascular events in secondary prevention after transient ischemic attack (TIA) or non-disabling stroke and prevention of thromboembolic events in heart failure with sinus rhythm;
- clot formation in left atrium and thromboembolism in subjects undergoing cardioversion for cardiac arrhythmia;
- thrombosis before, during and after ablation procedure for cardiac arrhythmia;
- venous thrombosis, this includes but not exclusively, treatment and secondary prevention of deep or superficial veins thrombosis in the lower members or upper member, thrombosis in the abdominal and thoracic veins, sinus thrombosis and thrombosis of jugular veins;
- thrombosis on any artificial surface in the veins like catheter or pacemaker wires;
- pulmonary embolism in patients with or without venous thrombosis;
- Chronic Thromboembolic Pulmonary Hypertension (CTEPH);
- arterial thrombosis on ruptured atherosclerotic plaque, thrombosis on intra-arterial prosthesis or catheter and thrombosis in apparently normal arteries, this includes but not exclusively acute coronary syndromes, ST elevation myocardial infarction, non ST elevation myocardial infarction, unstable angina, stent thrombosis, thrombosis of any artificial surface in the arterial system and thrombosis of pulmonary arteries in subjects with or without pulmonary hypertension;
- thrombosis and thromboembolism in patients undergoing percutaneous coronary interventions (PCI);
- cardioembolic and cryptogenic strokes;
- thrombosis in patients with invasive and non-invasive cancer malignancies;
- thrombosis over an indwelling catheter;
- thrombosis and thromboembolism in severely ill patients;
- cardiac thrombosis and thromboembolism, this includes but not exclusively cardiac thrombosis after myocardial infarction, cardiac thrombosis related to condition such as cardiac aneurysm, myocardial fibrosis, cardiac enlargement and insufficiency, myocarditis and artificial surface in the heart;
- thromboembolism in patients with valvular heart disease with or without atrial fibrillation;
- thromboembolism over valvular mechanic or biologic prostheses;
- injuries or trauma in patients who had native or artificial cardiac patches, arterial or venous conduit tubes after heart repair of simple or complex cardiac malformations;
- venous thrombosis and thromboembolism after knee replacement surgery, hip replacement surgery, and orthopedic surgery, thoracic or abdominal surgery;
- arterial or venous thrombosis after neurosurgery including intracranial and spinal cord interventions;
- congenital or acquired thrombophilia including but not exclusively factor V Leiden, prothrombin mutation, antithrombin III, protein C and protein S deficiencies, factor XIII mutation, familial dysfibrinogenemia, congenital deficiency of plasminogen, increased levels of factor XI, sickle cell disease, antiphospholipid syndrome, autoimmune disease, chronic bowel disease, nephrotic syndrome, hemolytic uremia, myeloproliferative disease, disseminated intra vascular coagulation, paroxysmal nocturnal hemoglobinuria and heparin induced thrombopenia;
- thrombosis and thromboembolism in chronic kidney disease;
- thrombosis and thromboembolism in end stage renal disease (ESRD);
- thrombosis and thromboembolism in patients with chronic kidney disease or ESRD undergoing hemodialysis; and
- thrombosis and thromboembolism in patients undergoing hemodialysis and/or extra-corporal membrane oxygenation.

In a specific aspect, an anti-FXI/FXIa antibody binding agent is for use in methods of reducing bleeding or bleeding risk, or managing bleeding or bleeding risk, in a patient being treated or administered an anti-FXI/FXIa antibody (e.g., antibody NOV1401) to reduce the risk of stroke and/or systemic embolism, wherein the patient has non-valvular atrial fibrillation.

In a specific aspect, an anti-FXI/FXIa antibody binding agent is for use in methods of reducing bleeding or bleeding risk, or managing bleeding or bleeding risk, in a patient being treated or administered an anti-FXI/FXIa antibody (e.g., antibody NOV1401) to reduce the risk of stroke and/or systemic embolism, wherein the patient has non-valvular atrial fibrillation with a demonstrated high risk of bleeding.

In a specific aspect, an anti-FXI/FXIa antibody binding agent is for use in methods of reducing bleeding or bleeding risk, or managing bleeding or bleeding risk, in a patient being treated or administered an anti-FXI/FXIa antibody (e.g., antibody NOV1401) to reduce the risk of stroke and/or systemic embolism, wherein the patient has ESRD and is undergoing dialysis.

In a specific aspect, an anti-FXI/FXIa antibody binding agent is for use in methods of reducing bleeding or bleeding risk, or managing bleeding or bleeding risk, in a patient being treated or administered an anti-FXI/FXIa antibody (e.g., antibody NOV1401) to reduce the risk of stroke and/or systemic embolism, wherein the patient has non-valvular atrial fibrillation and ESRD and is undergoing dialysis.

In specific aspects, a subject, who may be in need of, or benefit from, the methods described herein (e.g., methods for reversing anticoagulant effects with anti-FXI/FXIa antibody binding agents), has been treated with an anti-FXI/FXIa antibody (e.g., antibody NOV1401) in combination with other agents for the prevention, treatment, or improvement of thromboembolic disorders. For example, statin therapies may be used in combination with the FXIa antibodies and antigen binding fragments of the present disclosure for the treatment of patients with thrombotic and/or thromboembolic disorders. Such subjects undergoing combination therapy may be in need of, or benefit from, the methods described herein (e.g., methods for reversing anticoagulant effects with anti-FXI/FXIa antibody binding agents).

In a specific aspect, provided herein are methods of reducing bleeding or bleeding risk, or managing bleeding or bleeding risk, in a patient being treated or administered an anti-FXI/FXIa antibody (e.g., antibody NOV1401), said method comprises administering a binding agent which specifically binds to the anti-FXI/FXIa antibody (e.g., antibody NOV1401), and reverses an anticoagulant effect of the anti-FXI/FXIa antibody. In particular aspects, the bleeding or bleeding risk is associated with trauma, surgery, or post-delivery. In another particular aspect, the bleeding or bleeding risk is associated with emergency surgery or urgent procedures. In other particular aspects, the bleeding is life-threatening or uncontrolled. In specific aspects, the binding agent is an antibody, such as an anti-idiotype antibody which specifically binds an anti-FXI/FXIa antibody (e.g., NOV1401). In additional specific aspects, the binding agent is an anti-idiotype antibody which specifically binds to one or more epitopes within the variable regions of an anti-FXI/FXIa antibody (e.g., NOV1401). In more specific aspects, the binding agent is a Fab fragment of an anti-idiotype antibody which specifically binds to an anti-FXI/FXIa antibody (e.g., NOV1401). In particular aspects, the binding agent is an anti-idiotype antibody or antigen-binding fragment thereof comprising amino acid sequences selected from Table 2. In particular aspects, the binding agent is an anti-idiotype antibody or antigen-binding fragment thereof, such as a Fab fragment, comprising VH and VL amino acid sequences of antibody IDT1, IDT2, IDT3, IDT4, IDT5, IDT6, IDT7, IDT8, IDT9, or IDT10, as set forth in Table 2. In particular aspects, the binding agent is an anti-idiotype antibody or antigen-binding fragment thereof, such as a Fab fragment, comprising VH and VL amino acid sequences of antibody IDT2, IDT3, IDT4, or IDT5, as set forth in Table 2. In particular aspects, the binding agent is an anti-idiotype antibody or antigen-binding fragment thereof, such as a Fab fragment, comprising VH and VL amino acid sequences of antibody IDT1 or IDT3, as set forth in Table 2.

In specific aspects, bleeding is typically associated with, but not limited to, trauma, surgery, menstruation or post-delivery. Therefore, under these circumstances, a subject, who has been treated with an anti-FXI/FXIa antibody (e.g., NOV1401), may be in need of quick and effective therapy, such as an anti-FXI/FXIa antibody binding agent described herein, to reduce bleeding or to reduce bleeding risk. In specific aspects, prolonged bleeding may occur after a major trauma or after surgery, such as surgery involving organs with high fibrinolytic area such as buccal, nasal, genital or urinary mucosa. Tooth extraction, tonsillectomy and ablation of the uterus or prostate are more non-limiting examples of surgeries that entail a high risk of bleeding. In specific aspects, concomitant use of antiplatelets, other anticoagulants and fibrinolytic agents can increase the risk of bleeding.

In certain aspects, a temporary reversal or inhibition of one or more of the anticoagulant effects of an anti-FXI antibody (e.g., antibody NOV1401) is desired. In a particular aspect, provided herein are methods of reducing or managing bleeding or bleeding risk in a patient treated or administered an anti-FXI/FXIa antibody such as antibody NOV1401, comprising the step of administering to the patient in need thereof, a binding agent described herein, such as antibody IDT1, IDT2, IDT3, IDT4, IDT5, IDT6, IDT7, IDT8, IDT9, or IDT10 or a Fab fragment thereof, once or twice, over a period of time (e.g., 1 hour to 24 hours or to 48 hours), followed by administering the anti-FXI/FXIa antibody, wherein a temporary reversal or inhibition of one or more of the anticoagulant effects of the anti-FXI antibody is achieved.

In certain aspects, an anti-FXI/FXIa antibody binding agent described herein can be administered in combination with another anticoagulant reversal therapy. Non-limiting examples of conventional strategies for reversing anticoagulant effects include (i) fluid replacement using colloids, crystalloids, human plasma or plasma proteins such as albumin; or (ii) transfusion with packed red blood or whole blood. Examples of therapies for reversal of the effects of anticoagulants, for example, in cases of severe emergency, include, but are not limited to, prohemostasis blood components such as fresh frozen plasma (FFP), prothrombin complex concentrates (PCC) and activated PCC [(APCC); e.g. factor VIII inhibitor bypass activity (FEIBA)] and recombinant activated factor VII (rFVIIa).

In specific aspects, the present disclosure relates to methods for reversing the anticoagulant effect of an anti-FXI/FXIa antibody (e.g., antibody NOV1401) in a patient being treated with the anti-FXI/FXIa antibody or antigen-binding fragment thereof, comprising (i) administering to the patient an effective amount of a binding agent provided herein, e.g., a binding agent (e.g., antibody or antigen-binding fragment thereof, such as a Fab fragment) which binds an anti-FXI/FXIa antibody and is capable of reversing one or more anticoagulant effects; and (ii) administering to the patient another anticoagulant reversal therapy, such as fresh frozen plasma (FFP), prothrombin complex concentrates (PCC), activated PCC or recombinant activated factor VII (rFVIIa). In specific aspects, the present disclosure relates to methods for reversing the anticoagulant effect of an anti-FXI/FXIa antibody (e.g., antibody NOV1401) in a patient being treated with the anti-FXI/FXIa antibody or antigen-binding fragment thereof, comprising (i) administering to the patient an effective amount of a binding agent provided herein, e.g., a binding agent (e.g., antibody or antigen-binding fragment thereof, such as a Fab fragment) which binds an anti-FXI/FXIa antibody and is capable of reversing one or more anticoagulant effects; and (ii) administering to the patient fresh frozen plasma (FFP). In specific aspects, such method achieves homeostasis.

In certain aspects, provided herein is a method of managing bleeding in a patient being treated with an anti-FXI antibody provided herein (e.g., an antibody described in Table 1, such as, an anti-FXI antibody comprising VL CDRs and VHCDRs of NOV1401), said method comprises temporarily reversing of the anticoagulant effect for a sufficient time to manage the bleeding. In specific embodiments, the step of reversing of the anticoagulant effect comprises (i) fluid replacement using colloids, crystalloids, human plasma or plasma proteins such as albumin; or (ii) transfusion with packed red blood or whole blood. In specific aspects, therapeutic agents for reversal of the effect of anticoagulants, for example, in cases of severe emergency, include, but are not limited to, prohemostasis blood components such as fresh frozen plasma (FFP), prothrombin complex concentrates (PCC) and activated PCC (APCC) (e.g. factor VIII inhibitor bypass activity (FEIBA)), and recombinant activated factor VII (rFVIIa). In one particular aspect, a regimen may comprise administration of rFVIIa at a dose of 30 μg/kg followed by administration of rFVIIa at a dose of 15-30 μg/kg every 2-4 hours for 24-48 hours in addition to tranexamic acid 1 g every 6 hours for 5 to 7 days may have potential to recover hemostasis and stop bleeding in subjects treated with an anti-FXI antibody (e.g., NOV1401 or an antibody comprising VL CDRs and VH CDRs of NOV1401) who are undergoing major surgery and in patients with an active non-accessible bleeding site. For instance, Riddell et al reported experience in 4 patients with severe FXI deficiency without inhibitor undergoing surgery (Riddell et al., 2011, Thromb. Haemost., 106: 521-527); patients were administered rFVIIa 30 μg/kg and tranexamic acid 1 g i.v. at induction of anesthesia. Subsequent bolus doses of rFVIIa 15-30 μg/kg were administered at 2 to 4 hourly intervals as guided by rotational thromboelastometry (ROTEM) results. In specific examples, patients were treated with rFVIIa at above mentioned doses for 24-48 hours. In particular examples, tranexamic acid 1 g every six-hourly was continued for five days. In this small series, rFVIIa at doses as low as 15-30 μg/kg in combination with tranexamic acid was safe and effective in correcting the hemostatic defect in severe FXI deficiency in this study. In another study comprising 4 patients with severe FXI deficiency with inhibitor (autologous neutralizing FXI antibodies usually acquired after transfusion or administration of blood products to patients with severe FXI deficiency) who experienced 5 surgeries, the authors (Livnat et al., 2009, Thromb. Haemost.; 102: 487-492) applied the following protocol: 1 g of tranexamic acid orally two hours before surgery, then patients received immediately prior to the interventions another 1 g tranexamic acid i.v. Recombinant FVIIa at doses ranging from 15 to 30 μg/kg was infused at the completion of surgery. Subsequently, oral tranexamic acid 1 g was given every 6 hour for at least 7 days. Fibrin glue was sprayed at the bed of the extirpated gallbladder in one patient. This protocol secured normal hemostasis in patients with severe FXI deficiency with inhibitor. In one aspect, fibrin glue can be used to restore local hemostasis during dental surgery in patients with FXI deficiency (Bolton-Maggs (2000) Haemophilia; 6 (S1):100-9). In a certain embodiment with respect to methods to manage bleeding in patients being treated with an anti-FXI antibody provided herein (e.g., NOV1401), a regimen consisting of tranexamic acid 1 g every 6 hours for 5 to 7 days associated with the use of fibrin glue could be used to establish local hemostasis in subjects undergoing minor surgery and in subjects with accessible bleeding site, including oral and nasal bleeding events.

In certain aspects, provided herein is a method of managing bleeding or bleeding risk in a patient being treated with an anti-FXI/FXIa antibody provided herein (e.g., an antibody described in Table 1, such as, NOV1401 or an anti-FXI/FXIa antibody comprising VL CDRs and VHCDRs of NOV1401), said method comprising administering to the patient an anticoagulant reversal therapy capable of reversing (e.g., partially reversing) the anticoagulant effects of the anti-FXI/FXIa antibody. In specific aspects, the anticoagulant reversal therapy capable of reversing the anticoagulant effect of the anti-FXI/FXIa antibody is rFVIIa (recombinant Factor VIIa), emicizumab (ACE910), tranexamic acid, Fresh Frozen Plasma (FFP), Hemoeleven, Prothrombin Complex Concentrate (PCC), Activated PCC, or FEIBA (a FVIII inhibitor complex). In specific aspects, the anticoagulant reversal therapy is administered alone, or in combination with a binding agent provided herein (e.g., binding agent described in Table 2).

In specific aspects, the present disclosure relates to methods for reversing (e.g., partially reversing) the anticoagulant effect of an anti-FXI/FXIa antibody (e.g., an anti-FXI/FXIa antibody described in Table 1 such as antibody NOV1401 or an anti-FXI/FXIa antibody comprising VH CDRs and VL CDRs of NOV1401) in a patient being treated with the anti-FXI/FXIa antibody or antigen-binding fragment thereof, comprising administering to the patient an anticoagulant reversal therapy, such as rFVIIa (recombinant Factor VIIa), emicizumab (ACE910), tranexamic acid, Fresh Frozen Plasma (FFP), Hemoeleven, Prothrombin Complex Concentrate (PCC), Activated PCC, or FEIBA (a FVIII inhibitor complex).

In specific aspects, the present disclosure relates to methods for reversing the anticoagulant effect of an anti-FXI/FXIa antibody (e.g., an anti-FXI/FXIa antibody described in Table 1 such as antibody NOV1401 or an anti-FXI/FXIa antibody comprising VH CDRs and VL CDRs of NOV1401) in a patient being treated with the anti-FXI/FXIa antibody or antigen-binding fragment thereof, comprising (i) administering to the patient an effective amount of a binding agent provided herein, e.g., a binding agent (e.g., antibody or antigen-binding fragment thereof, such as a Fab fragment) which binds an anti-FXI/FXIa antibody and is capable of reversing one or more anticoagulant effects; and (ii) administering to the patient another anticoagulant reversal therapy, such as rFVIIa (recombinant Factor VIIa), emicizumab (ACE910), tranexamic acid, Fresh Frozen Plasma (FFP), Hemoeleven, Prothrombin Complex Concentrate (PCC), Activated PCC, or FEIBA (a FVIII inhibitor complex).

In specific aspects, the risk of thromboembolic events including stroke, systemic embolism, coronary or peripheral artery thrombosis, venous thrombosis and pulmonary embolism increases with presence of predisposing factors such as thrombophilia, vessel wall damage and stasis. Evaluation of medical history, familiar antecedents and associated comorbidities can help to stratify patients according to their thromboembolic risks. In patients with atrial fibrillation, several scoring systems e.g., CHADS2 and CHA2DS2-VASc have been developed to assess stroke risk. Each was developed based on data from randomized trials, and clinical and epidemiologic cohort studies, and translated a weighted, multivariate formula of stroke risk factors to a simplified, easy-to-use mnemonic device, algorithm, calculator, or online tool. The CHADS2 risk score was used stratification tool to predict thromboembolic risk in atrial fibrillation patients (Lip (2011) Am J Med; 124(2):111-4; Camm et al (2012) Eur Heart J; 33: 2719-2747); however, accumulated evidence shows that CHA2DS2-VASc is at least as good as or possibly better than, scores such as CHADS2 in identifying patients who develop stroke and thromboembolism and definitively better at identifying 'truly low-risk' patients with atrial fibrillation. The CHA2DS2-VASc score is presently recommended by Guidelines (Camm et al (2012) Eur Heart J 33, 2719-2747; January et al, AHA/ACC/HRS Atrial Fibrillation Guideline; J Am Coll Cardiol 2014; 64:2246-80) to guide the decision with regard to patients who should benefit of anticoagulant therapy and also to identify low risk patients in whom anticoagulation therapy is not warranted.

Bleeding risk assessment tools specific to the atrial fibrillation patients e.g., HAS-BLED, ATRIA, HEMORR2HAGES; ORBIT and ABC risk score were developed to predict the bleeding risk in patients with atrial fibrillation. Unfortunately, as the bleeding risk is tightly correlated with the stroke risk, those risk score were of rather limited value to guide therapeutic decisions to use vitamin K antagonists such as warfarin or NOACS. However, bleeding risk scores may become of considerable help to identify patients who can benefit of a new therapy with a reduced bleeding risk e.g. anti-FXI/FXIa antibody (e.g., antibody NOV1401).

In certain aspects, subjects with a bleeding risk, for example a demonstrated high risk of bleeding, may be identified by previous medical history of bleeding, for example, bleeding during or after surgery or bleeding when treated with an anticoagulant (e.g. Warfarin). In addition, subjects with a bleeding risk, for example a demonstrated high risk of bleeding, may be identified by in vitro/ex vivo assays known in the art, for example, assays with a subject's plasma measuring aPTT and other biomarkers of the extrinsic coagulation pathways, such as prothrombin time (PT) and thrombin time (TT).

In particular aspects, subjects with moderate to high risk for stroke and systemic embolism have a CHA2DS2VASc risk score ≥2. In further particular aspects, subjects with a HAS BLED risk score ≥3 is characterized as having a high risk of bleeding (see Gallego, et al., (2012) Carc Arrhythm Electrophysiol.; 5:312-318, and Friberg et al., (2012) Circulation.; 125:2298-2307).

In specific aspects, a subject being treated by the methods provided herein is a human subject at least 18 years old. In another aspect, a subject being treated by the methods provided herein is a human subject at least 50 years old. In another aspect, a subject being treated by the methods provided herein is a human subject at least 55 years old. In another aspect, a subject being treated by the methods provided herein is a human subject at least 60 years old. In another aspect, a subject being treated by the methods provided herein a human subject is at least 65 years old.

In particular aspects, a subject being treated by the methods provided herein (e.g., methods for treating VTE or for secondary prevention of VTE) is between the age of 2 and 18 years old. In particular aspects, a subject being treated by the methods provided herein (e.g., methods for treating VTE or for secondary prevention of VTE) is between the age of 12 and 18 years old. In particular aspects, a subject being treated by the methods provided herein (e.g., methods for treating VTE or for secondary prevention of VTE) is a child at least 2 years old and under 18 years old. In particular aspects, a subject being treated by the methods provided herein (e.g., methods for treating VTE or for secondary prevention of VTE) is a child at least 12 years old and under 18 years old.

In specific aspects, a subject (e.g., human subject) being treated by the methods provided herein has a body mass index (BMI) that is greater than or equal to 18 $kg/m^2$. In another aspect, a subject being treated by the methods provided herein has a BMI that is greater than or equal to 30 $kg/m^2$. In another aspect, a subject being treated by the methods provided herein has a BMI that is greater than or equal to 35 $kg/m^2$. In another aspect, a subject being treated by the methods provided herein has a BMI that is greater than or equal to 40 $kg/m^2$.

In certain aspects, methods for reversing the anticoagulant effects of an anti-FXI/FXIa antibody (e.g., antibody NOV1401) with an anti-FXI/FXIa antibody binding agent described herein, results in (i) reduction or reversal in aPTT prolongation as determined with aPTT assays with human plasma; (ii) reduction in the amount of thrombin in a thrombin generation assay (TGA) amount of thrombin in a thrombin generation assay (TGA) in human plasma; and/or (iii) reduction or reversal of bleeding or bleeding risk. In specific aspects, reversal of the anticoagulant effects is less than 100%, but is sufficient to achieve a clinically beneficial outcome, e.g., reduction or stop in bleeding.

In certain aspects, methods for reversing the anticoagulant effect of an anti-FXI/FXIa antibody (e.g., antibody NOV1401) with an anti-FXI/FXIa antibody binding agent described herein, results in reduction or reversal in aPTT prolongation as determined with aPTT assays with human plasma, by at least 10%, at least 20%, at least 30%, at least 40%, at least 50%, at least 60%, at least 70%, at least 80%, or at least 90%.

Pharmaceutical Compositions

The present disclosure provides pharmaceutical compositions comprising anti-FXI/FXIa antibody-binding agents described herein (e.g., antibody described in Table 2 and Fab fragments thereof) formulated together with a pharmaceutically acceptable carrier. The compositions can additionally contain one or more other therapeutic agents that are suitable for treating or preventing, for example, thromboembolic disorders (e.g., thrombotic disorders). Pharmaceutically acceptable carriers enhance or stabilize the composition, or can be used to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present disclosure can be administered by a variety of methods known in the art. The route and/or mode of administration vary depending upon the desired results. It is preferred that administration be intravenous, intramuscular, intraperitoneal, or subcutaneous, or administered proximal to the site of the target. The pharmaceutically acceptable carrier should be suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

In specific aspects, a composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the present disclosure can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the FXIa-binding antibody is employed in the pharmaceutical compositions of the present disclosure. The FXIa-binding antibodies are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present disclosure can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present disclosure employed, thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician can start doses of the antibodies of the present disclosure employed in the pharmaceutical composition at levels lower than that required to achieve the desired therapeutic effect and gradually increase the dosage until the desired effect is achieved. In general, effective doses of the compositions of the present disclosure, for the treatment of a thrombotic and/or thromboembolic disorders described herein vary depending upon many different factors, including means of administration, target site, physiological state of the patient, other medications administered, and whether treatment is prophylactic or therapeutic. Treatment dosages need to be titrated to optimize safety and efficacy. For systemic administration with an antibody, the dosage ranges from about 0.01 to 15 mg/kg of the host body weight. For administration with an antibody, the dosage may range from 0.1 mg to 5 mg. For example, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, or 5.0 mg/kg.

In a certain aspect, an anti-FXI/FXIa antibody binding agent described herein is administered, for example by i.v. or s.c. route, at a dose in the range of 5 mg to 600 mg.

In a certain aspect, an anti-FXI/FXIa antibody binding agent described herein is administered, for example by i.v. or s.c. route, at a dose of approximately 5 mg, 10 mg, 15 mg, 20 mg, 30 mg, 40 mg, 50 mg, 60 mg, 90 mg, 100 mg, 120 mg, 150 mg, 180 mg, 200 mg, 210 mg, 240 mg, 250 mg, 270 mg, 300 mg, 330 mg, 350 mg, 360 mg, 390 mg, 400 mg, 420 mg, 450 mg, 480 mg, 500 mg, 510 mg, 540 mg, 550 mg, 570 mg, or 600 mg.

In particular aspects, an antibody is usually administered on multiple occasions. Intervals between single dosages can be weekly, biweekly, monthly or yearly. Intervals can also be irregular as indicated by measuring blood levels of antibody in the patient. In addition alternative dosing intervals can be determined by a physician and administered monthly or as necessary to be efficacious. In some methods of systemic administration, dosage is adjusted to achieve a plasma antibody concentration of 1-1000 μg/ml and in some methods 25-500 μg/ml. Alternatively, antibody can be administered as a sustained release formulation, in which case less frequent administration is required. Dosage and frequency vary depending on the half-life of the antibody in the patient. In general, humanized antibodies show longer half life than that of chimeric antibodies and nonhuman antibodies. The dosage and frequency of administration can vary depending on whether the treatment is prophylactic or therapeutic. In certain aspects for prophylactic applications, a relatively low dosage is administered at relatively infrequent intervals over a long period of time. Some patients continue to receive treatment for the rest of their lives. In certain aspects for therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

In specific aspects, an anti-FXI/FXIa binding agent described herein is administered for a temporary duration or period of time when reversal of anticoagulant effects of an anti-FXI/FXIa antibody is desired. In specific aspects, an anti-FXI/FXIa binding agent described herein is administered once, few times, for a temporary duration or period of time (e.g., 1 hour to 24 hours or to 48 hours but generally not exceeding 7 days) when reversal of anticoagulant effects of an anti-FXI/FXIa antibody is desired to achieve homeostasis.

EXAMPLES

The following examples are provided to further illustrate the present disclosure but not to limit its scope. Other variants of the present disclosure will be readily apparent to one of ordinary skill in the art and are encompassed by the appended claims.

Example 1

Human Fab Phage Library Panning

Phage Display Panning

Antibodies against NOV1401 were generated by the selection of clones that bound to NOV1401 using as a source of antibody a commercially available phage display library, the Morphosys HuCAL PLATINUM® library. The phagemid library is based on the HuCAL® concept (Knappik et al., 2000, J Mol Biol 296: 57-86) and employs the CysDisplay™ technology for displaying the Fab on the phage surface (WO01/05950). For the isolation of anti-NOV1401 antibodies a solid phase panning strategy was employed with direct coating of NOV1401 to a Maxisorp™ (Nunc) 96 well plate followed by three rounds of panning with increasing washing stringency.

Subcloning and Microexpression of Selected Fab Fragments

To facilitate rapid expression of soluble Fab, the Fab encoding inserts of the selected HuCAL PLATINUM® phage were subcloned from pMORPH® 30 display vector into pMORPH® x11 expression vector pMORPH® x11_FH.

For initial screening and characterization an overnight cultures of individual Fab-expressing *E. coli* clones were lysed using 2×BBS solution (400 mM Boric acid, 300 mM Sodium chloride, 5 mM EDTA) supplemented with 2.5 mg/mL lysozyme. Fab containing *E. coli* lysates were used for ELISA screening.

ELISA Screening

Using ELISA screening, single Fab clones were identified from panning output for binding to NOV1401. Fabs were tested using Fab containing crude *E. coli* lysates.

For identification of NOV1401 binding Fab fragments Maxisorp™ (Nunc) 384 well plates were directly coated with 5 ug/ml NOV1401. After blocking of plates with Superblock®, Fab-containing *E. coli* lysates were added. Binding of Fabs was detected by F(ab)2 specific goat anti-human IgG conjugated to alkaline phosphatase (diluted 1:5000) using Attophos fluorescence substrate (Roche, catalogue #11681982001). Fluorescence emission at 535 nm was recorded with excitation at 430 nm.

Engineering to Remove Potential Deamidation Sites

In order to remove potential liabilities in long term storage potential deamidation sites (Asn-Gly or Asn-Ser) were removed by replacing asparagine to serine or glutamine. Genes including the altered amino acids were generated via gene synthesis.

Expression and Purification of HuCAL® Fab Fragments

Expression of Fab fragments was performed in *E. coli* TG1 F-cells. Cultures were incubated at 37° C. until the OD600 reached a value of 0.5. Fab expression was induced by addition of IPTG to a final concentration of 0.75 mM and cultures were further incubated o/n at 30° C. and 180 rpm. Cells were harvested and disrupted. His6-tagged Fab fragments were isolated via IMAC and gel filtration and protein concentrations were determined by UV-spectrophotometry at 280 nm.

Example 2

Binding Data

Surface Plasmon Resonance (SPR) Binding Analysis of Anti-NOV1401 Fab Binding to NOV1401

SPR binding experiments were performed on a ProteOn XPR36 instrument (Bio-Rad Laboratories, Inc.) in PBS/T buffer (50 mM phosphate, 150 mM NaCl, pH 7.4, 0.005% v/v Tween-20) at 25° C. NOV1401 ('Ligand') was immobilized onto an activated ProteOn GLC sensor chip (Bio-Rad Laboratories, Inc.) using standard amine coupling procedures as described by the manufacturer. Briefly, NOV1401 was injected at a concentration of 10 µg/ml in 20 mM sodium acetate, pH 5.0 and at a flow rate of 30 µl/min for 10 min. Unreacted groups were blocked by injecting 1 M ethanolamine.

For kinetic studies anti-NOV1401 Fabs ('Analytes') were diluted in PBS/T buffer to generate a dilution series with concentrations ranging from 0.125-4 nM. Fabs were injected onto surfaces with immobilized NOV1401 at a flow rate of 100 µL/min and sensorgrams were recorded for association and dissociation times of 220 s and 1800 s, respectively. Blank surfaces were used for background corrections. There was no need to regenerate surfaces since the ProteOn protein interaction array system allows to run up to six binding experiments on an identical surface in parallel.

Data processing and analysis including kon, koff, and $K_D$ determination were performed with the ProteOn Manager™ software version 3.1.0.6. Sensorgrams were fitted by applying a Langmuir 1:1 binding model (Rmax set at global) and dissociation constants were calculated from kon and koff. Table 3 shows the dissociation constants for 10 anti-NOV1401 Fab determined by SPR.

TABLE 3

Summary of SPR binding data

| Anti-NOV1401 | Average $K_D$ [nM] | StDEV [nM] | n |
|---|---|---|---|
| IDT1 | 0.44 | 0.02 | 2 |
| IDT2 | 0.23 | NA | 1 |
| IDT3 | 0.24 | 0.02 | 2 |
| IDT4 | 0.31 | 0.02 | 2 |
| IDT5 | 0.35 | 0.04 | 2 |
| IDT6 | 10.08 | 0.13 | 2 |
| IDT7 | 0.33 | 0.01 | 2 |
| IDT8 | 2.15 | 0.15 | 2 |
| IDT9 | 1.92 | 0.00 | 2 |
| IDT10 | 5.97 | 0.03 | 2 |

Solution Equilibrium Titration (SET) Binding Analysis of Anti-NOV1401 Fab Binding to NOV1401

14 serial (2×) dilutions of NOV1401 were prepared in sample buffer (PBS pH 7.4 containing 0.5% (w/v) BSA and 0.02% Tween 20) and a constant concentration of the anti-NOV1401 Fab was added to each NOV1401 concentration ranging from 40 pM to 240 pM. Optimal constant anti-NOV1401 Fab concentrations and optimal starting concentrations for NOV1401 dilution series were determined in pilot experiments. A starting concentration of 10 nM NOV1401 was used for weaker binders ($K_D$~1 nM or higher) and a starting concentration of 2 nM was used for stronger binders ($K_D$<0.2 nM).

30 µl/well of each dilution mix was distributed in duplicates to a 384-well polypropylene Eppendorf microplate (MTP). Sample buffer served as negative control and a sample containing no antigen as positive control (Bmax). The plate was sealed and incubated overnight at RT on a plate shaker. A streptavidin (SA) plate from Pierce® (pre-blocked Streptavidin High Binding Capacity 384-Well Plate, #15505) was coated by adding 30 µl/well of 0.5 µg/ml biotinylated NOV1401 diluted in PBS, sealed and incubated for 2 h at RT on a MTP shaker.

After incubation and three times washing with PBST (PBS containing 0.05% Tween 20) 30 µl/well of the NOV1401/anti-NOV1401 Fab preparation was transferred from the polypropylene MTP to the NOV1401-coated SA plate and incubated for 30 min at RT on a MTP shaker. After three additional wash steps, 30 µl of 0.5 µg/ml detection antibody (Goat anti-human Kappa LC-HRP, BETHYL # A80-115P) diluted in sample buffer was added to each well and incubated for 1 h at RT with shaking. After washing the plate again three times, 30 µl of detection reagent (Lumi-GLO Peroxidase Chemiluminescent Substrate, KPL #54-61-01) was added to each well. Electrochemiluminescence (ECL) signals were generated and detected immediately with a luminescence imager (SpectraMax M5, Molecular Devices, LLC).

Average ECL-signals were calculated from duplicate measurements within each assay. Data were baseline adjusted by subtracting the lowest value from all data points and plotted against the corresponding antigen concentration. $K_D$ values were determined by fitting the plot with the following non-linear curve fitting model for 1:1 binding according to Haenel et al 2005:

$$y = B_{max} - \left(\frac{B_{max}}{2[Fab]}\left([Fab] + x + K_D - \sqrt{([Fab] + x + K_D)^2 - 4x[Fab]}\right)\right)$$

where y is the blank-subtracted ECL signal, [Fab] is the applied Fab concentration, x is the applied total soluble antigen (here NOV1401), Bmax is the blank-subtracted ECL signal for x=0, and $K_D$ is the dissociation constant.

The SET results for nine anti-NOV1401 Fabs are summarized in Table 4 and representative binding response curves are shown in FIG. 1. SET data could not be fit for IDT6 and have not been included.

TABLE 4

Summary of SET results for anti-NOV1401 antibodies

| Antidote | Average $K_D$ (nM) | Stdev | n |
|---|---|---|---|
| IDT1 | 0.11 | 0.01 | 2 |
| IDT2 | 0.10 | 0.003 | 3 |
| IDT3 | 0.10 | 0.01 | 2 |
| IDT4 | 0.97 | 0.04 | 2 |
| IDT5 | 0.14 | 0.02 | 3 |
| IDT7 | 0.96 | 0.01 | 2 |
| IDT8 | 0.16 | 0.02 | 3 |
| IDT9 | 0.68 | 0.05 | 2 |
| IDT10 | 1.19 | 0.09 | 2 |

Example 3

SPR Binding Competition

SPR experiments were performed in principle as described in Example 2 with the following changes. Human plasma-derived FXIa was used as ligand and immobilized on an activated ProteOn GLC sensor chip (Bio-Rad Laboratories, Inc.) using standard amine coupling procedures as described and by injecting FXIa at a concentration of 10 μg/ml in 20 mM sodium acetate, pH 5.0 and at a flow rate of 30 μl/min for 10 min.

For binding competition studies NOV1401 and three mixture of NOV1401 with anti-NOV1401 Fab at molar ratios of 1:1, 1:2, and 1:10 were prepared in PBS/T buffer and injected in simultaneously onto surfaces with immobilized FXI at a flow rate of 100 μL/min. Sensorgrams were recorded for association and dissociation times of 220 s and 1800 s, respectively. Blank surfaces were used for background corrections.

NOV1401/anti-NOV1401 Fab mixtures yielded significantly lower binding responses to immobilized FXIa than NOV1401 alone with a 1/10 mixture (NOV1401/anti-NOV1401 Fab) showing no binding to FXIa. As the response units (RUs) in SPR are directly proportional to the mass bound to the chip, increasing concentrations of anti-NOV1401 Fab seems to prevent NOV1401 from binding to FXIa indicating that anti-NOV1401 can bind to NOV1401 and block NOV1401 from binding to FXIa.

Figure 2:
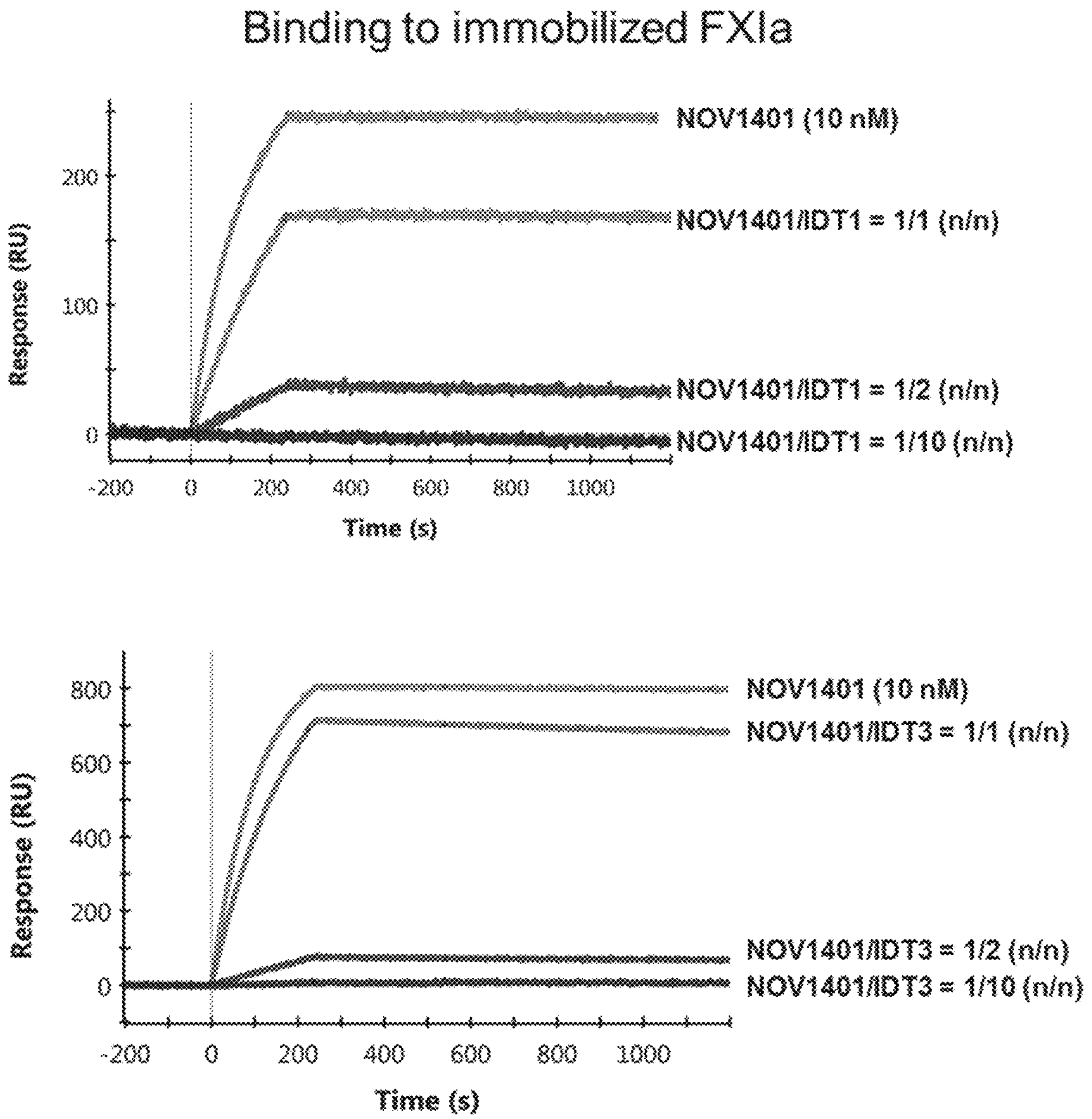
FIG. 2 shows representative SPR response curves for binding of NOV1401 and three NOV1401/anti-NOV1401 mixtures to immobilized FXIa. Increasing concentrations of anti-NOV1401 reduce binding of NOV1401 to FXIa with a 10 fold molar excess completely blocking the binding. These data indicate that anti-NOV1401 is capable to bind to and block NOV1401 from interacting with FXIa. Anti-NOV1401 alone did not show any binding to immobilized FXIa (not shown).

FIG. 2 shows two representative examples for anti-NOV1401 Fabs (IDT1, IDT3). Anti-NOV1401 Fabs clearly reduce NOV1401 binding to its antigen FXIa, therefore compete with FXIa for binding to NOV1401. Added to a NOV1401 solution at 10× molar excess (5× molar excess per NOV1401 binding sites), anti-NOV1401 Fab completely prevents NOV1401 from binding to FXIa, indicating that anti-NOV1401 Fabs are capable of neutralizing free NOV1401 in solution.

Example 4

Reversal of the Anticoagulant Activity of NOV1401

Effects of anti-NOV1401 Fabs on the anticoagulant activity of NOV1401 was tested by using the activated partial thromboplastin time (aPTT) assay and the thrombin generation assay (TGA).

aPTT Assay:

Lyophilized normal human plasma 'Coagulation Control N' (Cat #5020050) was purchased from Technoclone GmbH (Vienna, Austria). It was pooled from citrated plasma of selected healthy donors. The clotting time obtained with this normal plasma reflects normal concentrations of the coagulation factors involved in clotting. The lyophilized plasma was stored at 4° C. Prior to its use, the plasma was re-suspended in 1 mL of distilled water by carefully rotating the vial and then keeping it for 10 minutes at room temperature.

The intrinsic pathway triggering Dapttin TC (Cat #5035090) was purchased from Technoclone GmbH (Vienna, Austria), containing phospholipid, sulfatide, and silicate. The lyophilized trigger was reconstituted in distilled water with the volume indicated on the vial.

Calcium Chloride (Fluka, Cat #21115) was prepared in distillated water at a stock concentration of 25 mM. Phosphate Buffered Saline (PBS, Life Technologies, Cat #10010-023) was used as antibody dilution buffer.

The measurements of the clotting time were performed in a ball coagulometer model MC10 (Merlin medical, Germany), which is a semi-automated mechanical clot detection system. The system utilizes a special cuvette in which a stainless steel ball is distributed (Merlin medical, Cat # Z05100).

The cuvette is placed into the measuring well of the ball coagulometer. After the sample, plasma, and trigger are added to the cuvette, the measuring well rotates slowly causing the cuvette to rotate along its longitudinal axis. Because the cuvette is positioned at a slight angle, gravity and inertia always position the ball at the lowest point of the cuvette. Exactly opposite the ball-position is a magnetic sensor. After an appropriate incubation period, a timer is started with the addition of the calcium chloride solution. As coagulation takes place, fibrin strands form in the reaction mixture. The fibrin strands pull the ball away from its inertia position that triggers an impulse in the magnetic sensor. This impulse electronically stops the timer.

Serial dilutions of NOV1401 were prepared in PBS. The reconstituted human blood plasma, trigger reagent (Dapttin), calcium chloride were warmed up in a water bath at 37° C. for 10 minutes.

The assay was performed exclusively in specialized cuvettes containing a stainless steel ball. The pipetting scheme is outlined in Table 5.

TABLE 5

Pipetting scheme for measuring NOV1401 activity in aPTT assay

| Assay step | Solution | aPTT assay Volume [μL] |
|---|---|---|
| 1 | antibody dilution or diluent | 50 |
| 2 | human blood plasma | 50 |
| 3 | Dapttin | 50 |
| 4 | | Incubate 3 minutes at 37° C. under rotation |
| 5 | 25 mM Calcium Chloride | 50 |
| 6 | Immediately start the timer | |
| 7 | The timer stops when the clot is formed | |

The samples were measured in duplicates at a temperature of 37° C. in the Merlin ball coagulometer described above.

The clot formation was timed for each concentration of NOV1401 and plotted versus the corresponding antibody concentrations. The resulting dose-response curve was fitted using the non-linear regression program GraphPad Prism (GraphPad Software Inc., La Jolla, Calif., USA). From fitting the dose response curve the NOV1401 concentration for doubling of the initial clotting time (sample containing plasma without antibody), also described as '2×aPTT', was determined.

Anti-NOV1401 Fabs Block the Anticoagulant Activity of NOV1401:

To determine if anti-NOV1401 Fabs can block NOV1401's ability to prolong clotting times in the aPTT assay, several NOV1401/anti-NOV1401 Fab mixtures in PBS were generated where the NOV1401 concentration was kept constant at a value required for 2×aPTT which was determined in a separate experiment as described above. Anti-NOV1401 Fab was added at equimolar amount (1/1) or at molar excess, typically 1/3 or 1/5, and 1/10 (n/n). The pipetting scheme is shown in Table 6.

TABLE 6

Pipetting scheme for measuring the effect of anti-NOV1401 Fab on NOV1401 activity in the aPTT assay.

| Assay step | Solution | aPTT assay Volume [μL] |
|---|---|---|
| 1 | NOV1401 or diluent | 25 |
| 2 | Antidote or control Ig | 25 |
| 3 | | Incubate 10 minutes |

TABLE 6-continued

| Pipetting scheme for measuring the effect of anti-NOV1401 Fab on NOV1401 activity in the aPTT assay. | | |
|---|---|---|
| Assay step | Solution | aPTT assay Volume [μL] |
| 4 | Human blood plasma | 50 |
| 5 | Dapttin | 50 |
| 6 | | Incubate 3 minutes at 37° C. under rotation |
| 7 | 25 mM Calcium Chloride | 50 |
| 8 | Immediately start the timer | |
| 9 | The timer stops when the clot is formed | |

The samples were measured in duplicates at a temperature of 37° C. in the Merlin ball coagulometer described above.

Figure 3:
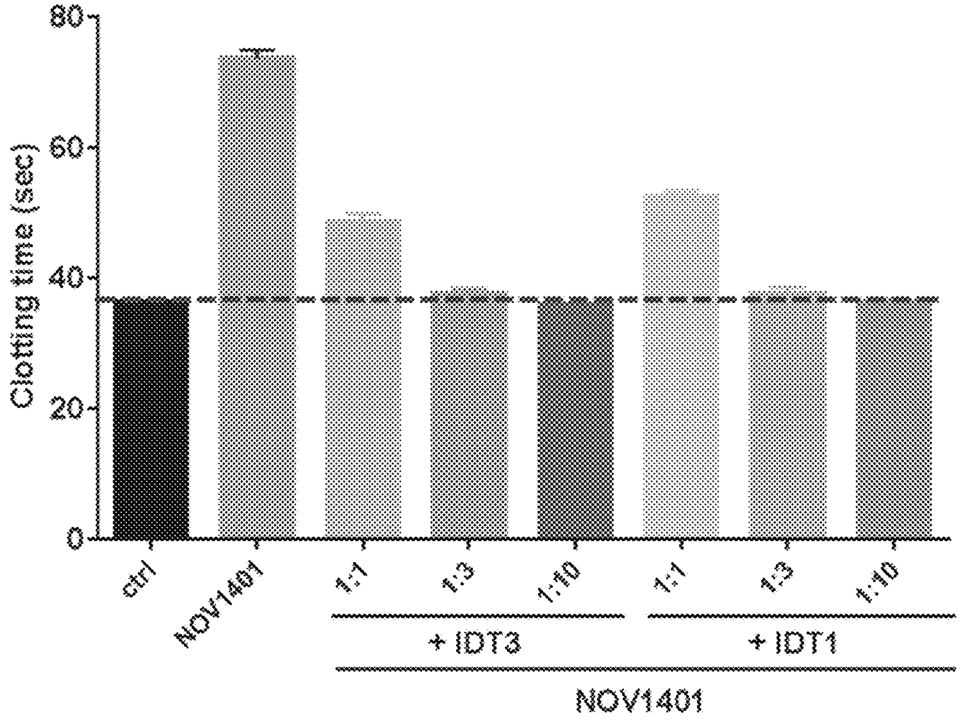
FIG. 3 shows aPTT assay results for two representative anti-NOV1401 Fabs when NOV1401 was preincubated for 10 min with anti-NOV1401 before FXI-containing human plasma was added and the intrinsic pathway of the coagulation cascade was triggered. Both anti-NOV1401 Fabs block the aPTT prolonging effect of NOV1401 in a concentration-dependent manner, i.e. inhibit the effect of NOV1401. 100% inhibition (dotted line) was achieved at 3× molar access of anti-NOV1401.

The results for two anti-NOV1401 Fabs—IDT1 and IDT3—are shown in FIG. 3. At a constant NOV1401 concentration of 0.096 μM increasing amounts of NOV1401 Fab block the effect of NOV1401 on coagulation as measured in the aPTT assay. A three times molar excess of IDT1 or IDT3 (1.5× molar excess per binding site) was sufficient to completely inhibit the effect of NOV1401 on aPTT.

These data confirm and extend the results from SPR competition experiments as they suggest that anti-NOV1401 Fabs block the function of NOV1401 when pre-mixed with NOV1401. Together these results suggest that anti-NOV1401 Fabs are capable to prevent free NOV1401 from binding to FXI and blocking the effects of FXI.

Anti-NOV1401 Fabs Partially Reverse the Anticoagulant Activity of NOV1401:

To determine if anti-NOV1401 Fabs can reverse NOV1401's ability to prolong clotting times in the aPTT, NOV1401 was preincubated with FXI-containing human plasma for 5 min before anti-NOV1401 Fab was added. As in the blocking experiment the concentration of NOV1401 was kept constant a value required for 2×aPTT determined separately in a dose response experiment as described above.

Anti-NOV1401 Fab was added at equimolar amount (1/1) or at molar excess, typically ⅓ and 1/10 (n/n). The pipetting scheme is shown in Table 7.

TABLE 7

| Pipetting scheme for measuring reversal of the effects of NOV1401 on aPTT by anti-NOV1401 Fab. | | |
|---|---|---|
| Assay step | Solution | aPTT assay Volume [μL] |
| 1 | Human blood plasma | 50 |
| 2 | NOV1401 or diluent | 25 |
| 3 | | Incubate 5 minutes |
| 4 | Antidote or control Ig | 25 |
| 5 | | Incubate 10 minutes |
| 6 | Dapttin | 50 |
| 7 | | Incubate 3 minutes at 37° C. under rotation |
| 8 | 25 mM Calcium Chloride | 50 |
| 9 | Immediately start the timer | |
| 10 | The timer stops when the clot is formed | |

The samples were measured in duplicates at a temperature of 37° C. in the Merlin ball coagulometer described above. The reversal percentage of NOV1401 clotting time was determined for each anti-NOV1401 Fab using the following equation:

Percentage reversal=(NOV1401 clotting time−antidote clotting time)/(NOV1401 clotting time−initial clotting time)*100.

Figure 4:
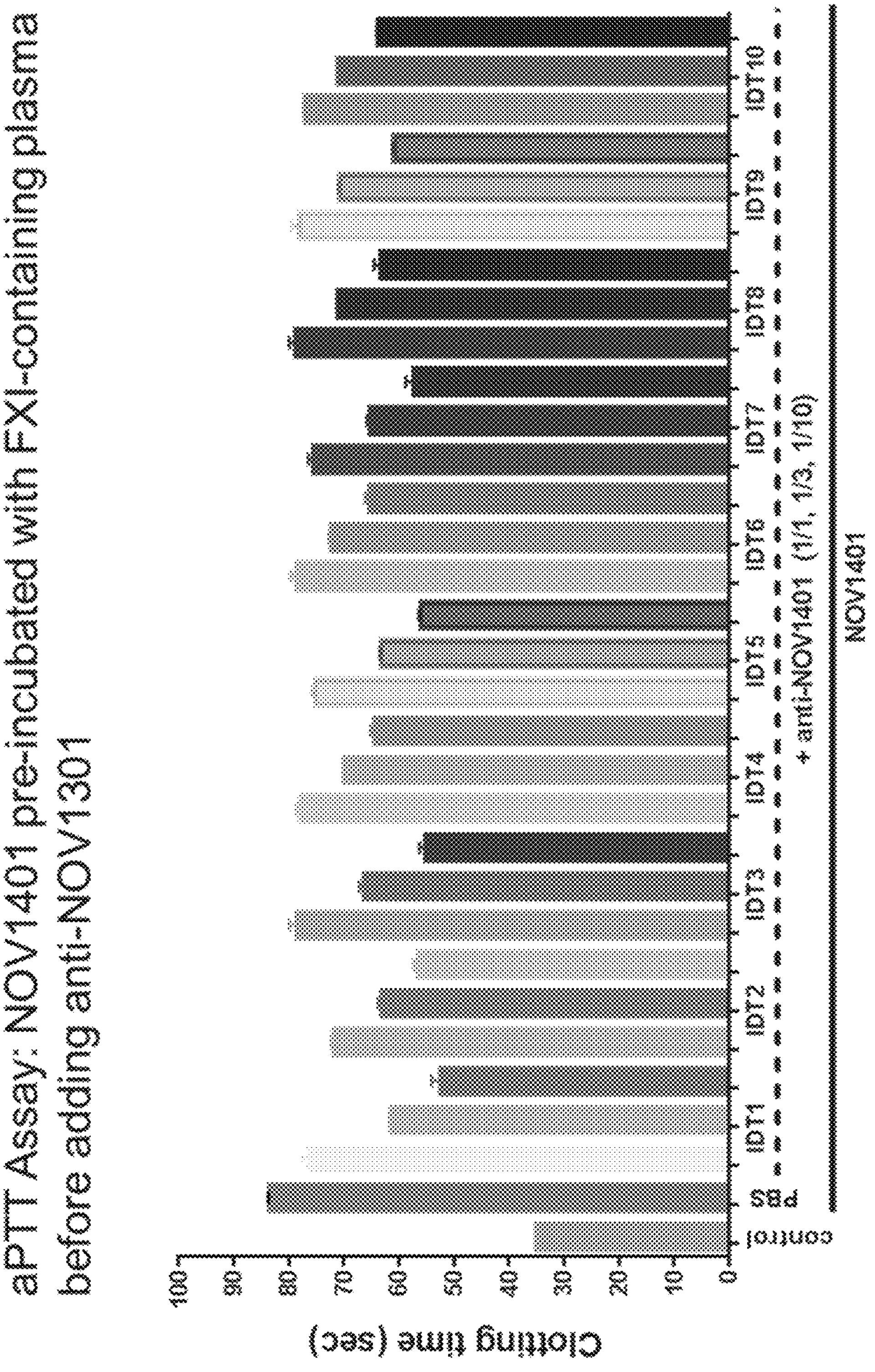
FIG. 4 shows aPTT assay results for 10 anti-NOV1401 Fabs when NOV1401 was pre-incubated for 5 min with FXI-containing human plasma before anti-NOV1401 Fab was added and the intrinsic pathway of the coagulation cascade was triggered. All 10 anti-NOV1401 show a concentration-dependent partial reversal of the effects of NOV1401 on aPTT.

The results for all 10 anti-NOV1401 Fabs are shown in FIG. 4. At a constant NOV1401 concentration of 0.096 μM increasing amounts of anti-NOV1401 Fab added after NOV1401 was incubated with FXI containing human plasma partially reverse the effect of NOV1401 on coagulation as measured in the aPTT assay. While all anti-NOV1401 show some reversal, the degree of reversal at a given concentration varies and a maximum reversal of 55-65% was observed at 10× molar excess. The reversal percentages for all anti-NOV1401 Fabs are summarized in Table 8. These results suggest that anti-NOV1401 Fabs are capable of reversing, at least partially reversing, the anticoagulant effects of NOV1401 as measured in the aPTT assay.

TABLE 8

Summary of aPTT reversal data for anti-NOV1401 antibodies

| anti-NOV1401 | NOV1401/anti NOV1401 ratio (n/n) | | |
|---|---|---|---|
| Fab | 1/10 | 1/3 | 1/1 |
| IDT1 | 64% | 45% | 12 |
| IDT2 | 55% | 42% | 21 |
| IDT3 | 58% | 35% | 9 |
| IDT4 | 39% | 27% | 10 |
| IDT5 | 56% | 42% | 17 |
| IDT6 | 38% | 22% | 9 |
| IDT7 | 54% | 37% | 16 |
| IDT8 | 42% | 25% | 8 |
| IDT9 | 46% | 25% | 10 |
| IDT10 | 40% | 25% | 12 |

Thrombin Generation Assay:

To confirm the reversal of NOV1401 anticoagulant activity observed in the aPTT assay in another functional assay, the TGA was employed to measure thrombin generated through the thrombin feedback loop, which depends on the activity of FXIa.

For the TGA lyophilized normal human plasma (Coagulation control N) was purchased from Technoclone GmbH (Cat #5020040) and reconstituted in distilled water in a volume suggested by the manufacturer.

The substrate solution was prepared using the fluorogenic substrate Z-Gly-Gly-Arg-AMC from Technoclone GmbH (Cat #5006230). Aliquots of the lyophilized substrate were kept at 4° C. The substrate was dissolved freshly in the volume of distilled water indicated on the vial 20 minutes prior its use in the assay. The reconstituted substrate solution contains the fluorogenic peptide at a concentration of 1 mM and CaCl2 at a concentration of 15 mM.

The trigger reagent 'platelet poor plasma (PPP)-reagent low' was purchased from Thrombinoscope (Cat # TS31.00) and reconstituted in distilled water as indicated on the vial. PPP-reagent low' contains a mixture of phospholipids and tissue factor at very low concentration. The reagent was 8-fold diluted in 80 mM Tris/HCl at pH7.4, 0.05% (w/v) CHAPS immediately before use.

The samples were aliquoted and measured in 96 well black/clear bottom plates purchased from Costar (product no 3603). For automation transfer samples were placed in V-bottom 96 well plate (Costar, 3894) and transferred using a CyBio automation system (Analytik Jena US, Woburn, Mass., USA).

The reconstituted human blood plasma, trigger reagent 'PPP-reagent low' and substrate were pre-warmed for 10 minutes in a water bath at 37° C. Serial 1:3 antibody dilutions in PBS were prepared in a 96 well plate starting with a NOV1401 concentration of 5 μM (5× the highest final concentration of 1 μM) for a total of 8 dilutions. 222 μl of trigger reagent was mixed with 1108 μl of substrate solution to generate the 10+50 trigger reagent substrate mix. 80 μl per well was added into a V-bottom 96 well plate for later transfer using an automation system. The plate was kept at 37° C. The reagents were added according to the scheme given in Table 9.

TABLE 9

Pipetting scheme for TGA with NOV1401

| Assay step | Solution | Volume [ul] |
|---|---|---|
| 1 | Antibody solutions (8 dilutions) | 20 |
| 2 | Plasma stock solution | 20 |
| 5 minutes incubation at 37° C. in a thermomixer at 300 rpm. | | |
| 3 | Trigger reagent/substrate mixture | 10 + 50 |

Trigger/substrate mixtures were transferred using automation. After adding the mixtures, excitation and emission at 360 nm at 460 nm, respectively, were recorded immediately using a Synergy Neo instrument (BioTek Instrument Inc., Winooski, Vt., USA). The samples were measured in duplicates at a temperature of 37° C. in the plate reader for 90 minutes at intervals of 55 seconds.

To generate peak thrombin concentration values data were processed using the TGA evaluation software file provided by Technoclone. To generate plots for peak thrombin concentration vs antibody concentration data were fit using GraphPad software. These data were fit to a non-linear regression model in the GraphPad Prism5 software (GraphPad Software Inc., La Jolla, Calif., USA). The IC50 value was determined using the built-in four-parameter dose-response curve equation (variable slope): y=Bottom+(Top−Bottom)/(1+10^((Log IC50−x)*Hillslope)) where y is the maximal concentration of thrombin formed at the inhibitor concentration, x, and top and bottom represent the concentration of thrombin without inhibitor and at the highest concentration of inhibitor, respectively.

NOV1401 dose-dependently reduces thrombin in the TGA and the $IC_{50}$ value determined by this method was used as the concentration of NOV1401 in reversal experiments with anti-NOV1401 Fabs.

Anti-NOV1401 Fab Partially Reverses the Effect of NOV1401 on Thrombin Generation in the TGA:

To determine if anti-NOV1401 Fabs can reverse NOV1401's ability to reduce thrombin generation in the TGA, NOV1401 was preincubated with FXI-containing human plasma for 5 min before anti-NOV1401 Fab was added. The concentration of NOV1401 was kept constant at the $IC_{50}$ value determined separately in a dose response experiment as described above. Anti-NOV1401 Fab was added at equimolar amount (1/1) or at molar excess, typically ⅓ and 1/10 (n/n). The pipetting scheme is shown in Table 10.

TABLE 10

Pipetting scheme for measuring the reversal of the effects of NOV1401 on TGA by anti-NOV1401 Fab.

| Assay step | Solution | Volume [uL] |
|---|---|---|
| 1 | NOV1401 solution or PBS | 10 |
| 2 | Antidote or control IgG | 10 |

TABLE 10-continued

Pipetting scheme for measuring the reversal of the effects of NOV1401 on TGA by anti-NOV1401 Fab.

| Assay step | Solution | Volume [uL] |
|---|---|---|
| 10 minutes incubation at 37° C. | | |
| 3 | Plasma stock solution | 20 |
| 5 minutes incubation at 37° C. in a thermomixer at 300 rpm. | | |
| 4 | Trigger reagent/substrate mixture | 10 50 |

The maximum concentrations of thrombin generated for each assay conditions are plotted and the percentage reversal was determined using the following equation:

$$y=(A-B)/(C-B)*100.$$

where y is the percentage reversal, A the thrombin concentration for assay conditions with anti-NOV1401, B is the thrombin concentration for assay conditions without anti-NOV1401, C is the initial thrombin concentration.

Figure 5:
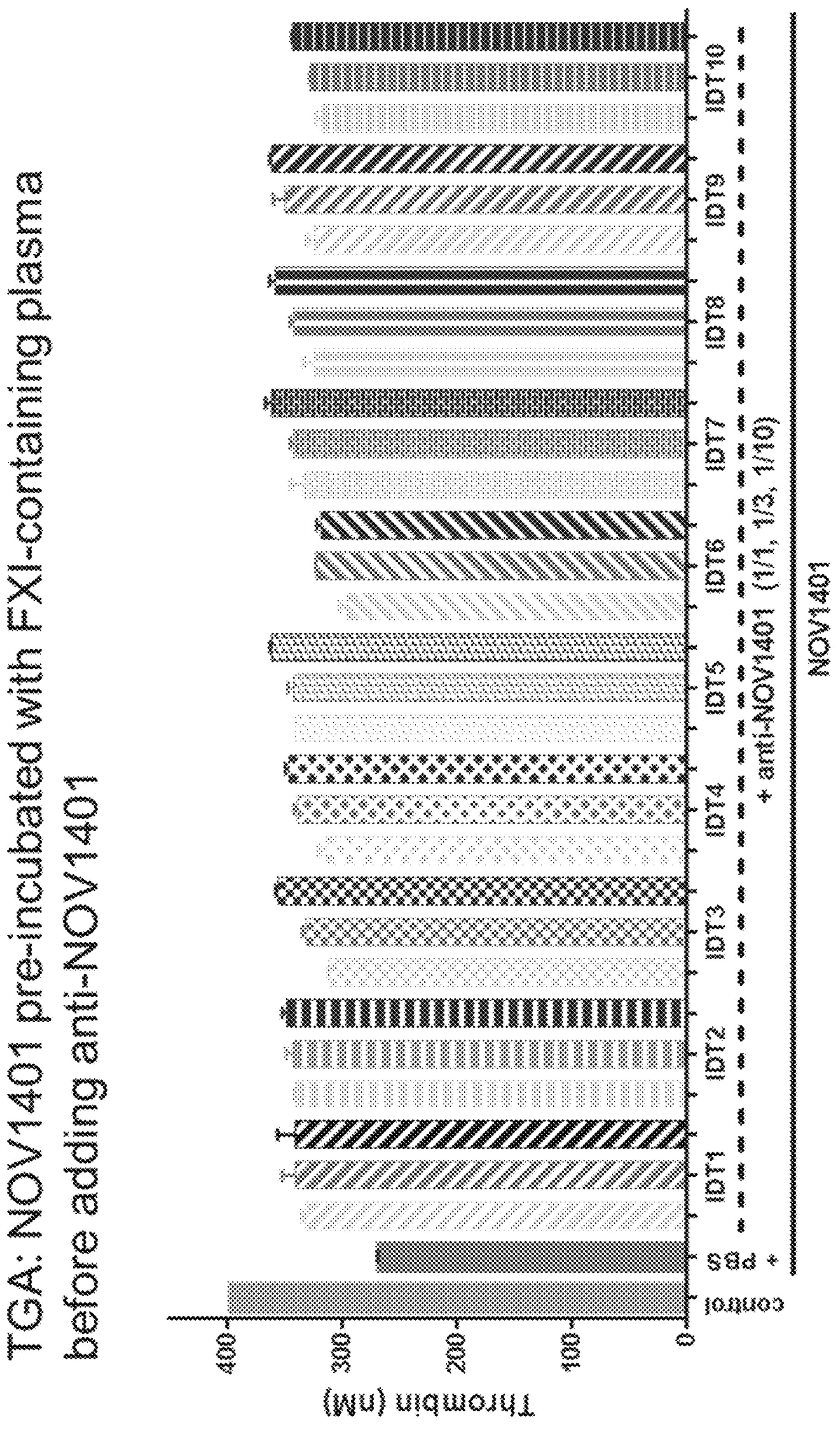
FIG. 5 shows TGA results for 10 anti-NOV1401 Fabs when NOV1401 was pre-incubated for 5 min with FXI-containing human plasma before anti-NOV1401 Fab was added and the thrombin feedback loop was triggered. The TGA was conducted at a constant concentration for NOV1401 of 0.05 which corresponds to the $IC_{50}$ value determined in a separate experiment. All 10 anti-NOV1401 Fabs show a concentration-dependent partial reversal of the effects of NOV1401 on thrombin generation.

The results for all 10 anti-NOV1401 Fabs are shown in FIG. 5. At a constant NOV1401 concentration of 0.05 μM increasing amounts of anti-NOV1401 Fab added after NOV1401 was incubated with FXI-containing human plasma led to an increase in thrombin concentration, hence reversing (e.g., at least partially reversing) the effect of NOV1401 on thrombin generation in the TGA. While all anti-NOV1401 show some reversal, the degree of reversal at a given concentration varies and a maximum reversal of 37-72% was observed at 10× molar excess. The reversal percentages for all anti-NOV1401 Fabs are summarized in Table 11. These results suggest that anti-NOV1401 Fabs can reverse (e.g., at least partially reverse) the reduction of thrombin by NOV1401 in the TGA.

TABLE 11

Summary of TGA reversal data for anti-NOV1401 antibodies

| anti-NOV1401 Fab | NOV1401/anti NOV1401 ratio (n/n) | | |
|---|---|---|---|
| | 1/10 | 1/3 | 1/1 |
| IDT1 | 55% | 55% | 49% |
| IDT2 | 61% | 57% | 55% |
| IDT3 | 67% | 47% | 31% |
| IDT4 | 60% | 53% | 33% |
| IDT5 | 72% | 56% | 55% |
| IDT6 | 37% | 41% | 18% |
| IDT7 | 71% | 66% | 50% |
| IDT8 | 69% | 56% | 41% |
| IDT9 | 72% | 61% | 41% |
| IDT10 | 57% | 45% | 37% |

Anti-NOV1401 Fabs Acutely Reverses the Anticoagulant Effects of NOV1401 in Cynomolgus Monkeys:

To test if an anti-NOV1401 Fab can reverse NOV1401's ability to prolong clotting times in vivo we administered a single 3 mg/kg subcutaneous dose of NOV1401 to cynomolgus monkeys on study day one followed by two i.v. doses of IDT3 on study day 4 and 5, respectively. A dose of 3 mg/kg s.c. was chosen for NOV1401 since it has been demonstrated that this dose leads to sustained aPTT prolongation in cynomolgus monkeys. Based on our in vitro experiments with human plasma, anti-NOV1401 Fab was administered in molar excess, for example, IDT3 was administered i.v. at 10 mg/kg followed by 30 mg/kg in one animal and at 30 mg/kg followed by 90 mg/kg in a second animal. Additional animals (N=2) were also administered NOV1401 only (one dose of 3 mg/kg s.c. on study day one), or IDT3 only (two i.v. doses of 30 mg/kg and 90 mg/kg on study day 4 and 5, respectively).

For ex-vivo aPTT analysis, blood samples were collected into sodium citrate coagulation tubes on study day 3, and 30 min, 2 hours, 8 hours and 12 hours post IDT3 dose on study days 4 and 5. Additional samples were collected on study days 6, 7, 8, and 9. All blood samples were centrifuged; plasma samples were obtained and frozen at approximately −70° C. or below.

In animals treated with NOV1401 alone, a single subcutaneous dose of 3 mg/kg prolonged aPTT by 1.7 to 1.8× throughout the end of the study demonstrating that NOV1401 has potent anticoagulant effects in cynomolgus monkeys and confirming earlier studies.

Figure 6:
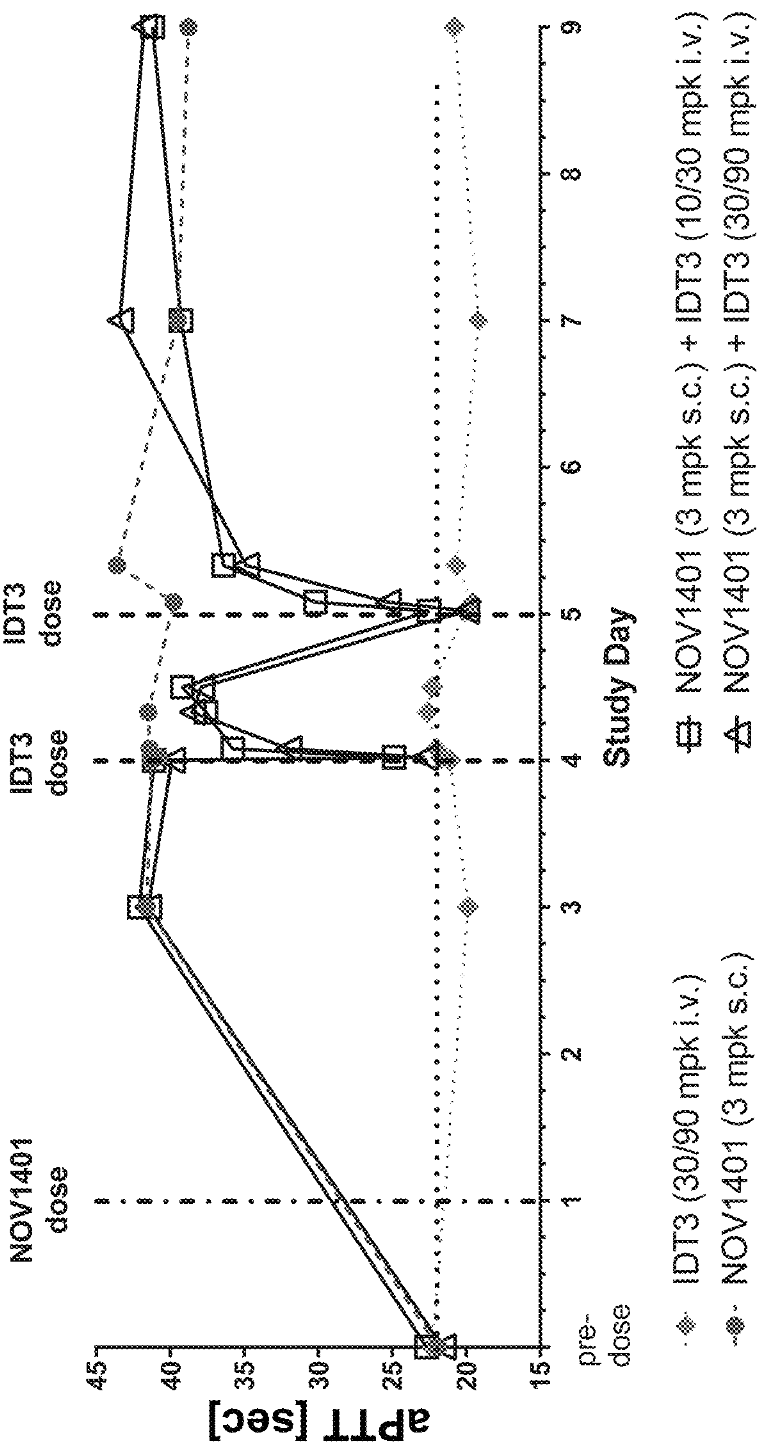
FIG. 6 shows ex-vivo aPTT assay results from blood/plasma samples of cynomolgus monkeys treated with a single 3 mg/kg subcutaneous dose of NOV1401 on study day one followed by two i.v. doses of IDT3 on study days 4 and 5, respectively.

In animals that were dosed at 10 mg/kg i.v. with IDT3 three days after NOV1401, aPTT was normalized immediately and had reached baseline levels at the earliest time point of 30 min after dosing (FIG. 6). After 8-12 hours, the aPTT prolongating effect of NOV1401 had returned close to maximum levels, but was reduced again to baseline after a second dose of 30 mg/kg was administered. Very similar effects were observed when IDT3 was dosed at 30 mg/kg and 90 mg/kg. The higher doses seem to extend the reversal effect. No effect on aPTT was observed in animals that were only administered IDT3 at 30 mg/kg and 90 mg/kg (FIG. 6).

These data suggest that anti-NOV1401 Fabs such as IDT3 are able to acutely reverse the effects of MAA868 on aPTT in vivo and anti-NOV1401 Fabs provided herein such as IDT3 can serve as an effective reversal agent for anti-FXI/FXIa antibody NOV1401, for example in cases when quick neutralization of anti-FXI/FXIa antibody NOV1401 be needed. These data also indicate that the acute reversal observed in vivo in this monkey study correlates with the partial reversal observed in the in vitro experiments with human plasma, such as the aPTT assays described herein.

INCORPORATION BY REFERENCE

All references cited herein, including patents, patent applications, papers, publications, text books, and the like, and the references cited therein, to the extent that they are not already, are hereby incorporated herein by reference in their entirety.

EQUIVALENTS

The foregoing written specification is considered to be sufficient to enable one skilled in the art to practice the present disclosure. The foregoing description and examples detail certain preferred embodiments of the present disclosure and describe the best mode contemplated by the inventors. It will be appreciated, however, that no matter how detailed the foregoing may appear in text, the present disclosure may be practiced in many ways and the present disclosure should be construed in accordance with the appended claims and any equivalents thereof.

The invention claimed is:

1. A binding agent which specifically binds a target antibody that binds human Factor XI (FXI) and/or Factor XIa (FXIa) within the catalytic domain, wherein the target antibody comprises (i) a heavy chain variable region (VH) comprising complementarity determining regions HCDR1, HCDR2 and HCDR3 of a VH comprising the amino acid sequence of SEQ ID NO: 12 and (ii) a light chain variable region (VL) comprising complementarity determining regions LCDR1, LCDR2, and LCDR3 of a VL comprising the amino acid sequence of SEQ ID NO: 23, and wherein the binding agent is an antibody or antigen-binding fragment wherein:

a) the HCDR1 comprises the amino acid sequence of SEQ ID NO: 91, the HCDR2 comprises the amino acid sequence of SEQ ID NO: 92, the HCDR3 comprises the amino acid sequence of SEQ ID NO: 93, the LCDR1 comprises the amino acid sequence of SEQ ID NO: 107, the LCDR2 comprises the amino acid sequence of SEQ ID NO: 108, and the LCDR3 comprises the amino acid sequence of SEQ ID NO: 109;

b) the HCDR1 comprises the amino acid sequence of SEQ ID NO: 94, the HCDR2 comprises the amino acid sequence of SEQ ID NO: 95, the HCDR3 comprises the amino acid sequence of SEQ ID NO: 96, the LCDR1 comprises the amino acid sequence of SEQ ID NO: 110, the LCDR2 comprises the amino acid sequence of SEQ ID NO: 111, and the LCDR3 comprises the amino acid sequence of SEQ ID NO: 112;

c) the HCDR1 comprises the amino acid sequence of SEQ ID NO: 97, the HCDR2 comprises the amino acid sequence of SEQ ID NO: 98, the HCDR3 comprises the amino acid sequence of SEQ ID NO: 99, the LCDR1 comprises the amino acid sequence of SEQ ID NO: 113, the LCDR2 comprises the amino acid sequence of SEQ ID NO: 114, and the LCDR3 comprises the amino acid sequence of SEQ ID NO: 115; or d) the HCDR1 comprises the amino acid sequence of SEQ ID NO: 100, the HCDR2 comprises the amino acid sequence of SEQ ID NO: 101, the HCDR3 comprises the amino acid sequence of SEQ ID NO: 102, the LCDR1 comprises the amino acid sequence of SEQ ID NO: 116, the LCDR2 comprises the amino acid sequence of SEQ ID NO: 117, and the LCDR3 comprises the amino acid sequence of SEQ ID NO: 118.

2. The binding agent of claim 1, wherein the VH comprises the amino acid sequence of SEQ ID NO: 103 and the VL comprises the amino acid sequence of SEQ ID NO: 119.

3. The binding agent of claim 1, wherein the heavy chain comprises the amino acid sequence of SEQ ID NO: 105 and the light chain comprises the amino acid sequence of SEQ ID NO: 121.

4. The binding agent of claim 1 wherein the binding agent is an antibody Fab fragment.

5. The binding agent of claim 1 wherein the binding agent is a monoclonal human antibody.

6. A pharmaceutical composition comprising the binding agent of claim 1.

7. A method for reversing the anticoagulant effect of an anti-FXI/FXIa antibody in a patient being treated with the anti-FXI/FXIa antibody or antigen-binding fragment thereof, comprising administering an effective amount of the binding agent of claim 1 to a patient in need thereof, wherein the anti-FXI/FXIa antibody comprises (i) a heavy chain variable region (VH) comprising complementarity determining regions HCDR1, HCDR2 and HCDR3 of a VH comprising the amino acid sequence of SEQ ID NO: 12 and (ii) a light chain variable region (VL) comprising complementarity determining regions LCDR1, LCDR2, and LCDR3 of a VL comprising the amino acid sequence of SEQ ID NO: 23.

8. The method of claim 7, wherein the anti-FXI/FXIa antibody or antigen-binding fragment thereof comprises (i) a heavy chain comprising the amino acid sequence of SEQ ID NO: 14 and a light chain comprising the amino acid sequence of SEQ ID NO: 25.

9. The method of claim 7, wherein the anti-FXI/FXIa antibody or antigen-binding fragment thereof comprises (i) a VH comprising the amino acid sequence of SEQ ID NO: 12 and (ii) a VL comprising the amino acid sequence of SEQ ID NO: 23.

10. The method of claim 7, wherein the method further comprises applying one or more of the following to the patient: (i) fluid replacement using colloids, crystalloids, human plasma or plasma proteins such as albumin; (ii) transfusion with packed red blood or whole blood; or (iii) administration of fresh frozen plasma (FFP), prothrombin complex concentrates (PCC), activated PCC (APCC), such as, factor VIII inhibitor, and/or recombinant, activated factor VII.

11. The method of claim 7, wherein the patient has a. atrial fibrillation;

b. suspected or confirmed cardiac arrhythmia such as paroxysmal, persistent or permanent atrial fibrillation or atrial flutter;

c. Chronic Thromboembolic Pulmonary Hypertension (CTEPH);

d. valvular heart disease with or without atrial fibrillation;

e. pulmonary hypertension;

f. congenital or acquired thrombophilia, factor V Leiden, prothrombin mutation, antithrombin III, protein C and protein S deficiencies, factor XIII mutation, familial dysfibrinogenemia, congenital deficiency of plasminogen, increased levels of factor XI, sickle cell disease, antiphospholipid syndrome, autoimmune disease, chronic bowel disease, nephrotic syndrome, hemolytic uremia, myeloproliferative disease, disseminated intra vascular coagulation, paroxysmal nocturnal hemoglobinuria or heparin induced thrombopenia; or g. chronic kidney disease.

12. The method of claim 7, wherein reversal of the anticoagulant effect of the anti-FXI/FXIa antibody or antigen-binding fragment thereof is for emergency surgery/urgent procedures and in life-threatening or uncontrolled bleeding.

13. An anti-idiotype antibody that specifically binds to an anti-FXI/FXIa antibody, wherein the anti-idiotype antibody comprises the binding agent of claim 1.

14. The anti-idiotype antibody of claim 13, wherein the anti-idiotype antibody reverses or inhibits the anti-FXI/FXIa antibody's anticoagulant effects.

15. A method of managing bleeding or bleeding risk in a patient treated with or administered an anti-FXI/FXIa antibody, comprising the step of administering to the patient in need thereof the anti-idiotype antibody of claim 13, wherein the anti-FXI/FXIa antibody comprises (i) a heavy chain variable region (VH) comprising complementarity determining regions HCDR1, HCDR2 and HCDR3 of a VH comprising the amino acid sequence of SEQ ID NO: 12 and (ii) a light chain variable region (VL) comprising complementarity determining regions LCDR1, LCDR2, and LCDR3 of a VL comprising the amino acid sequence of SEQ ID NO: 23.

16. The binding agent of claim 1, wherein:

a. the HCDR1 comprises the amino acid sequence of SEQ ID NO: 91;

b. the HCDR2 comprises the amino acid sequence of SEQ ID NO: 92;

c. the HCDR3 comprises the amino acid sequence of SEQ ID NO: 93;

d. the LCDR1 comprises the amino acid sequence of SEQ ID NO: 107;

e. the LCDR2 comprises the amino acid sequence of SEQ ID NO: 108; and f. the LCDR3 comprises the amino acid sequence of SEQ ID NO: 109.

17. The binding agent of claim 1, wherein:

a. the HCDR1 comprises the amino acid sequence of SEQ ID NO: 94;

b. the HCDR2 comprises the amino acid sequence of SEQ ID NO: 95;

c. the HCDR3 comprises the amino acid sequence of SEQ ID NO: 96;

d. the LCDR1 comprises the amino acid sequence of SEQ ID NO: 110;

e. the LCDR2 comprises the amino acid sequence of SEQ ID NO: 111; and f. the LCDR3 comprises the amino acid sequence of SEQ ID NO: 112.

* * * * *

UNITED STATES PATENT AND TRADEMARK OFFICE

CERTIFICATE OF CORRECTION

PATENT NO. : 10,647,780 B2
APPLICATION NO. : 15/604556
DATED : May 12, 2020
INVENTOR(S) : Stefan Ewert It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 197 days.

Signed and Sealed this
Tenth Day of January, 2023

Katherine Kelly Vidal

Katherine Kelly Vidal
*Director of the United States Patent and Trademark Office*